United States Patent [19]
Pasteris

[11] Patent Number: 4,842,639
[45] Date of Patent: Jun. 27, 1989

[54] PHENYL-SUBSTITUTED SULFONAMIDES

[75] Inventor: Robert J. Pasteris, Wilmington, Del.

[73] Assignee: E. I. Du Pont de Nemours and Company, Wilmington, Del.

[21] Appl. No.: 911,428

[22] Filed: Sep. 25, 1986

Related U.S. Application Data

[63] Continuation-in-part of Ser. No. 716,351, Mar. 29, 1985, abandoned, which is a continuation-in-part of Ser. No. 663,555, Oct. 22, 1984, abandoned, which is a continuation-in-part of Ser. No. 607,989, May 7, 1984, abandoned.

[51] Int. Cl.$^4$ .................. C07D 251/52; C07D 251/46; C07D 417/12; A01N 43/66
[52] U.S. Cl. ............................................ 71/91; 71/90; 71/93; 71/86; 71/87; 544/49; 544/198; 544/197; 544/206; 544/207; 544/208; 544/209; 544/211; 544/212; 544/113; 544/195; 544/83
[58] Field of Search ................... 71/93, 90, 91, 86, 87; 544/49, 198, 197, 207, 206, 209, 208, 212, 211, 113, 195, 83

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/92 |
| 4,369,320 | 1/1983 | Levitt et al. | 544/320 |
| 4,465,506 | 8/1984 | Welch | 71/92 |
| 4,492,596 | 1/1985 | Pasteris | 71/90 |
| 4,502,882 | 3/1985 | Carter | 71/93 |
| 4,514,211 | 4/1985 | Rorer | 71/92 |
| 4,586,950 | 5/1986 | Pasteris | 71/93 |
| 4,589,911 | 5/1986 | Ehrenfreund et al. | 544/212 |
| 4,609,398 | 9/1986 | Nicholson et al. | |
| 4,620,870 | 11/1986 | Pasteris | 71/90 |
| 4,634,465 | 1/1987 | Ehrenfreund et al. | 544/209 |

FOREIGN PATENT DOCUMENTS

| | | |
|---|---|---|
| 83/5165 | 1/1984 | South Africa . |
| 83/7434 | 4/1984 | South Africa . |

*Primary Examiner*—John M. Ford

[57] ABSTRACT

This invention relates to novel condensed ring sulfonylureas and their use as herbicides and growth regulants.

35 Claims, No Drawings

PHENYL-SUBSTITUTED SULFONAMIDES

BACKGROUND OF THE INVENTION

This invention relates to novel condensed ring sulfonylureas and their use as herbicides and growth regulants.

U.S. Pat. No. 4,127,405 teaches compounds which are useful for controlling weeds in wheat having the formula:

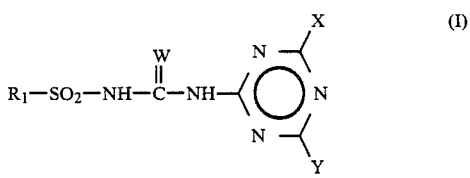

wherein
$R_1$ is

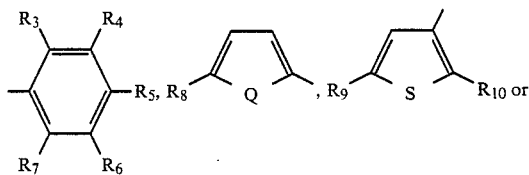

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

U.S. Pat. No. 4,169,719 discloses herbicidal benzenesulfonylureas.

Herbicidal indanesulfonylureas are taught in U.S. Pat. No. 4,465,506.

Herbicidal quinolinesulfonylureas are described in U.S. Pat. No. 4,369,329, issued Jan. 18, 1983.

Herbicidal benzofuran, benzothiophene, benzopyran and benzothiopyran sulfonylureas are disclosed in EP-A-No. 79,683, published May 25, 1983.

EP-A-No. 82,681, published June 29, 1983, discloses herbicidal 1,3-benzodioxole and 1,4-benzodioxanesulfonylureas.

South African Patent Application No. 83/5165 discloses herbicidal sulfonylureas of the general structure shown below:

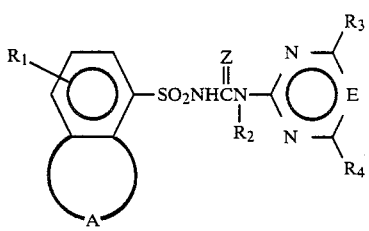

wherein
A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group.

South African Patent Application No. 83/7434 discloses herbicidal sulfonamides of formula

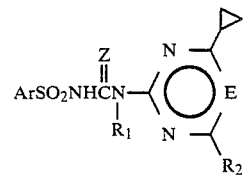

where
Ar is

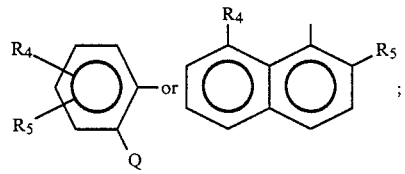

and $R_2$ is halogen, $C_1$–$C_3$ alkyl, $C_1$–$C_3$ haloalkyl, $C_1$–$C_3$ alkoxy, $C_1$–$C_3$ haloalkoxy, amino, $C_1$–$C_3$ alkylamino, di($C_1$–$C_3$ alkyl)amino, $C_3$–$C_6$ cycloalkyl or $C_2$–$C_6$ alkoxyalkyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I, agriculturally suitable compositions containing them, and their method-of-use as preemergent or postemergent herbicides or as plant growth regulants.

$$J-SO_2NHCNA \overset{W}{\underset{R}{\parallel}} \quad I$$

wherein
J is

[Structures J-1 through J-12 shown]

n is 0 or 1;
W is O or S;
$W_1$ is S;
$W_2$ is O or S;
R is H or $CH_3$;
$R_1$ is H, $C_1$-$C_6$ alkyl, $C_1$-$C_6$ haloalkyl, halogen, nitro, $C_1$-$C_6$ alkoxy, $SO_2NR_aR_b$, $C_1$-$C_6$ alkylthio, $C_1$-$C_6$ alkylsulfinyl, $C_1$-$C_6$ alkylsulfonyl, CN, $CO_2R_c$, $C_1$-$C_6$ haloalkoxy, $C_1$-$C_6$ haloalkylthio, $NH_2$, $C_1$-$C_6$ alkylamino, di($C_1$-$C_6$ alkyl)amino, $Si(CH_3)_2(C_1$-$C_4$ alkyl), $Si(CH_3)_2$-phenyl or $C_1$-$C_3$ alkyl substituted with $C_1$-$C_3$ alkoxy, $C_1$-$C_3$ alkylthio, $C_1$-$C_3$ alkylsulfinyl, $C_1$-$C_3$ alkylsulfonyl, $SO_2NR_dR_e$, $NO_2$, CN, $CO_2R_f$, $C_1$-$C_3$ haloalkoxy or $C_1$-$C_3$ haloalkylthio;
$R_a$ is H, $C_1$-$C_4$ alkyl, $C_1$-$C_3$ cyanoalkyl, methoxy or ethoxy;
$R_b$ is H, $C_1$-$C_4$ alkyl or $C_3$-$C_4$ alkenyl; or
$R_a$ and $R_b$ may be taken together as —$(CH_2)_3$—, —$(CH_2)_4$—, —$(CH_2)_5$— or —$CH_2CH_2OCH_2CH_2$—;
$R_c$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, $C_5$-$C_6$ cycloalkyl, $C_4$-$C_7$ cycloalkylalkyl or $C_2$-$C_4$ alkoxyalkyl;

$R_d$ is $C_1$-$C_3$ alkyl;

$R_e$ is H or $C_1$-$C_3$ alkyl;

$R_f$ is $C_1$-$C_3$ alkyl;

$R_1'$ is H, $C_1$-$C_3$ alkyl, $C_1$-$C_3$ alkoxy, $C_1$-$C_3$ haloalkoxy, $C_1$-$C_3$ haloalkyl, $C_1$-$C_3$ alkylthio, $C_1$-$C_3$ haloalkylthio, amino, $C_1$-$C_3$ alkylamino, di($C_1$-$C_3$ alkyl)amino, halogen or $NO_2$;

$R_2$ is H, $R_{11}'$, $SR_{11}'$, $SO_2R_{11}$, $OR_{11}'$, $C(O)R_{11}$, $C(O)OR_{11}'$, $(C(O))_2OR_{11}'$, $(CO)_2R_{11}'$, $C(O)NR_{12}R_{18}$, $C(O)NRA$, $C(S)SR_{11}'$, $NH_2$, $NR_{12}R_{18}$, OH, CN, $P(O)R_{13}R_{14}$, $P(S)R_{13}R_{14}$, $Si(CH_3)_2R_{15}$, L or C(O)L;

$R_3$ is H or $CH_3$;

$R_4$ is $C_1$-$C_4$ alkyl;

$R_5$ is H or $C_1$-$C_4$ alkyl;

$R_6$ is H or $CH_3$;

$R_7$ is $C_1$-$C_4$ alkyl, Cl or Br;

A is

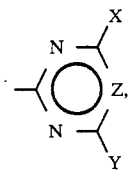 A-1

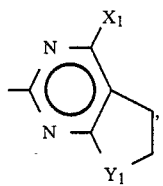 A-2

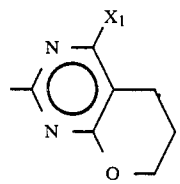 A-3

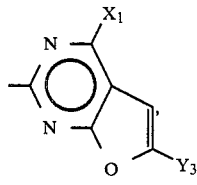 A-4

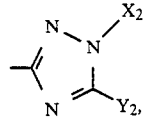 A-5

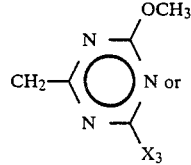 A-6

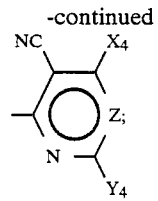 A-7

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, F, Cl, Br, $C_2$-$C_5$ alkoxyalkyl, $C_2$-$C_5$ alkoxyalkoxy, amino, $C_1$-$C_3$ alkylamino, amino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, azido, cyano,

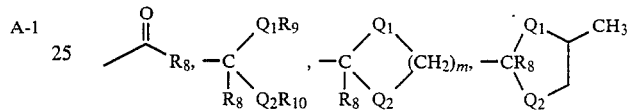

or $N(OCH_3)CH_3$;

m is 2 or 3;

$Q_1$ and $Q_2$ are independently O or S;

$R_8$ is H or $C_1$-$C_3$ alkyl;

$R_9$ and $R_{10}$ are independently $C_1$-$C_3$ alkyl;

Z is CH, N, $CCH_3$, $CC_2H_5$, CCl or CBr;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $OCH_3$, $OC_2H_5$, $SCH_3$, $SC_2H_5$, $CH_3$ or $CH_2CH_3$;

$X_3$ is $CH_3$ or $OCH_3$;

$Y_3$ is H or $CH_3$;

$Y_4$ is $CH_3$, $OCH_3$, $OC_2H_5$ or Cl;

$X_4$ is $CH_3$, $OCH_3$, $OC_2H_5$, $CH_2OCH_3$ or Cl;

$R_{11}$ is $C_1$-$C_{10}$ alkyl, $C_3$-$C_{10}$ alkoxyalkoxyalkyl, $C_2$-$C_{10}$ alkenyl, $C_4$-$C_{10}$ alkenylalkenyl, $C_3$-$C_{10}$ epoxyalkyl, $C_2$-$C_{10}$ alkynyl, $C_4$-$C_{10}$ alkynylalkynyl, $C_4$-$C_{10}$ alkynylalkenyl, $C_3$-$C_6$ cycloalkyl, $C_4$-$C_7$ cycloalkylalkyl or

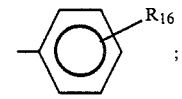

;

when $R_{11}$ is $C_3$-$C_6$ cycloalkyl or $C_4$-$C_7$ cycloalkylalkyl it may optionally be substituted by $C_1$-$C_4$ alkyl, 1 to 3 atoms of Cl or F or 1 Br; when $R_{11}$ is $C_1$-$C_{10}$ alkyl, $C_2$-$C_{10}$ alkenyl or $C_2$-$C_{10}$ alkynyl it may optionally be substituted by one or more halogens and/or by $(R_{17})_{m'}$, where when $m'$ is 2, the values of $R_{17}$ may be identical or different;

$R_{11}'$ is $C_1$-$C_{10}$ alkyl, $C_3$-$C_{10}$ alkoxyalkoxyalkyl, $C_3$-$C_{10}$ alkenyl, $C_5$-$C_{10}$ alkenylalkenyl, $C_3$-$C_{10}$ epoxyalkyl, $C_3$-$C_{10}$ alkynyl, $C_5$-$C_{10}$ alkynylalkynyl, $C_5$-$C_{10}$ alkynylalkenyl, $C_3$-$C_6$ cycloalkyl, $C_4$-$C_7$ cycloalkylalkyl or

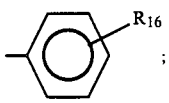

when $R_{11}'$ is $C_3$-$C_6$ cycloalkyl or $C_4$-$C_7$ cycloalkylalkyl it may be optionally substituted by $C_1$-$C_4$ alkyl, 1 to 3 atoms of Cl or F or 1Br; when $R_{11}'$ is $C_1$-$C_{10}$ alkyl, $C_3$-$C_{10}$ alkenyl or $C_3$-$C_{10}$ alkynyl, it may optionally be substituted by one or more halogens and/or by $(R_{17})_{m'}$, where when $m'$ is 2, the values of $R_{17}$ may be identical or different;

$m'$ is 1 or 2;

$R_{12}$ is H or $C_1$-$C_4$ alkyl;

$R_{13}$ and $R_{14}$ are independently $C_1$-$C_4$ alkyl, $C_1$-$C_4$ alkoxy or $C_1$-$C_4$ alkylthio;

$R_{15}$ is $C_1$-$C_{10}$ alkyl, benzyl or

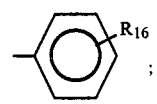

$R_{16}$ is H, F, Cl, Br, $CH_3$, $OCH_3$, $NO_2$, CN, $SCH_3$, $SO_2CH_3$ or $CF_3$;

$R_{17}$ is $OR_{18}$, $OC(O)R_{18}$, $P^+R_9R_{10}R_{15}$, $P^+(C_6H_5)_3$, $OC(O)NR_{12}R_{18}$, $OSO_2R_{18}'$, $OP(O)R_{13}R_{14}$, $P(O)R_{13}R_{14}$ $OP(S)R_{13}R_{14}$, $P(S)R_{13}R_{14}$, $OSi(CH_3)_2R_{15}$, $Si(CH_3)_2R_{15}$, $SR_{18}$, $SOR_{18}'$, $SO_2R_{18}'$, SCN, CN, $SP(O)R_{13}R_{14}$, $SP(S)R_{13}R_{14}$, $N^+R_{12}R_{15}R_{18}$, $NR_{12}R_{18}$, $NR_{12}C(O)R_{18}$, $NR_{12}C(O)OR_{18}'$, $NR_{12}C(O)NR_{12}R_{18}$, $NR_{12}SO_2R_{18}'$, $NR_{12}P(O)R_{13}R_{14}$, $NR_{12}P(S)R_{13}R_{14}$, $NO_2$, $C(O)R_{18}$, $C(O)OR_{18}$, $C(O)NR_{12}R_{18}$, $SeR_{18}$, naphthyl, L,

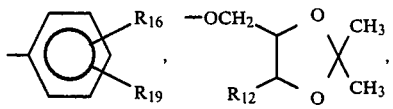

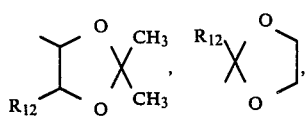

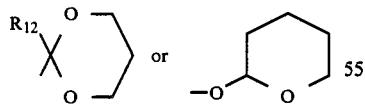

$R_{18}$ is H, $C_1$-$C_{10}$ alkyl, $C_1$-$C_{10}$ haloalkyl, $C_2$-$C_{10}$ alkenyl, $C_2$-$C_{10}$ alkynyl, $C_3$-$C_6$ cycloalkyl or

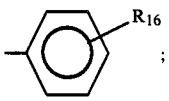

$R_{18}'$ is $C_1$-$C_{10}$ alkyl, $C_1$-$C_{10}$ haloalkyl, $C_3$-$C_{10}$ alkenyl, $C_3$-$C_{10}$ alkynyl, $C_3$-$C_6$ cycloalkyl or $R_{19}$ is H, F, Cl, Br, $CH_3$,

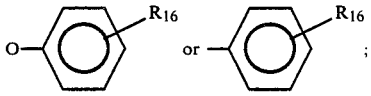

and

L is a 5- or 6-membered aromatic heterocyclic, a 5- or 6-membered dihydroaromatic heterocycle or a 5- or 6-membered tetrahydroaromatic heterocycle which contains 1–4 heteroatoms selected from 0–1 oxygen atoms, 0–1 sulfur atoms wherein sulfur may take the form of S, SO or $SO_2$, and/or 0–4 nitrogen atoms, with the proviso that oxygen and sulfur are only linked to each other if the sulfur is in the form of SO or $SO_2$, and these heterocycles may optionally by substituted by 1–4 $CH_3$, 1–2 $OCH_3$, $SCH_3$, Cl, $N(CH_3)_2$ or CN or L is a 5- or 6-membered lactone, lactam or cycloalkanone which may optionally be substituted by 1–4 $CH_3$ groups;

provided that (a) when W is S, then R is H, J is $J_1$, $J_2$, $J_3$ or $J_4$; A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CF_3$, $OCH_2CH_2OCH_3$, $CH(OCH_3)_2$ or

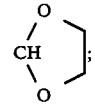

(b) when X is F, Cl or Br, then Z is CH and Y is $OCH_3$, $OC_2H_5$, $NH_2$, $NHCH_3$, $N(CH_3)_2$ or $OCF_2H$;

(c) when $R_3$ is $CH_3$, then n is O;

(d) when J is J-1 or J-2 and $R_2$ is H or $C_1$-$C_4$ alkyl, then $R_1$ and $R_1'$ are other than H, F, Cl, Br, $CH_3$, $OCH_3$, $CF_3$, $OCF_2H$, or $SCH_3$ or X is other than $CH_3$, $OCH_3$, $OCH_2CH_3$, F, Cl, Br, $OCF_2H$, $CH_2Cl$, $CH_2Br$, $CH_2F$, cyclopropyl or $CF_3$ or Y is $C_3$-$C_4$ alkyl, $C_3$-$C_4$ alkoxy, $C_4$ haloalkoxy, $C_4$ haloalkylthio, $C_3$-$C_5$ alkoxyalkyl, $C_4$-$C_5$ alkoxyalkoxy, $C_2$-$C_3$ alkylamino, di($C_2$-$C_3$ alkyl)amino, $C_4$ alkenyloxy, $C_4$ alkynyloxy, $C_3$-$C_5$ alkylthioalkyl, $C_2$-$C_4$ haloalkyl, $C_2$-$C_4$ alkynyl, $C(O)R_8$ or $N(OCH_3)CH_3$;

(e) the total number of carbon atoms in $R_2$ does not exceed 13;

(f) when X is $C_3$-$C_5$ cycloalkyl, then Y is $CH_3$, $CH_2CH_3$, $OCH_3$, $OCH_2CH_3$, $CH_2OCH_3$, $OCF_2H$, $SCF_2H$, $OCH_2CF_3$, $CF_3$, $OCH_2CH=CH_2$, $OCH_2C\equiv CH$, $NHCH_3$, $N(CH_3)_2$ or $CH(OCH_3)_2$;

(g) when $R_1$ or $R_1'$ is para to the sulfonylurea bridge then $R_1$ or $R_1'$ are H, $CH_3$, F, Cl, Br or $OCH_3$; and (h) when X or Y is $OCH_2CH_2F$ or $OCH_2CHF_2$ then $R_2$ is other than $C_5$ alkyl, $CH_3OCH_2CH_2$, $C_2H_5OCH_2CH_2$ or $C_1$-$C_4$ alkyl subsituted with 1–3 atoms of F, Cl or Br;

(i) when X or Y is $OCH_2CH_2F$, $OCH_2CHF_2$ or $OCH_2CF_3$, then the other is not di($C_1$-$C_3$ alkyl)amino $C_1$-$C_3$ alkylamino or $N(OCH_3)CH_3$;

(j) when X or Y is $OCF_2H$, then Z is CH;

(k) when $R_{17}$ and the bridging nitrogen of a cyclic sulfonamide are attached to the same carbon, then $R_{17}$ is other than OH, SH, $OC(O)R_{18}$, $OC(O)NR_{12}R_{18}$, $OSO_2R_{18'}$, $OP(O)R_{13}R_{14}$, $OSi(CH_3)_2R_{15}$, $SP(O)R_{13}R_{14}$, $SP(S)R_{13}R_{14}$, $NR_{12}R_{18}$ or $N^+R_{12}R_{15}R_{18}$;

and their agriculturally suitable salts.

In the above definitions, the term "alkyl", used either alone or in compound words such as "alkylthio" or "haloalkyl", denotes straight chain or branched alkyl, e.g. methyl, ethyl, n-propyl, 2-propyl or the different butyl, pentyl, hexyl, heptyl, octyl, nonyl or decyl isomers.

Alkoxy denotes methoxy, ethoxy, n-propyloxy, isopropyloxy and the different butyl, pentyl or hexyl isomers.

Alkenyl denotes straight chain or branched alkenes, e.g. vinyl, 1-propenyl, 2-propenyl, isopropenyl and the different butenyl, pentenyl, hexenyl, heptenyl, octenyl, nonenyl or decenyl isomers.

Alkynyl denotes straight chain or branched alkynes, e.g. ethynyl, 1-propynyl, 2-propynyl and the different butynyl, pentynyl, hexynyl, heptynyl, octynyl, nonynyl and decynyl isomers.

Alkylsulfonyl denotes methylsulfonyl, ethylsulfonyl and the different propylsulfonyl isomers.

Alkylthio, alkylsulfinyl, alkylamino, alkylsulfamoyl, etc. are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine.

The total number of carbon atoms in a substituent group is indicated by the $C_i$-$C_j$ prefix where i and j are numbers from 1 to 10. For example, $C_3$-$C_5$ alkylthioalkyl would designate $CH_2SCH_2CH_3$ through $(CH_2)_4SCH_3$ or $CH_2SC_4H_9$, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

It would be recognized by one skilled in the art that when $R_{17}$ is OH or SH, that these substituents cannot be bonded to the same carbon as another heteroatom or to an olefinic or acetylenic carbon atom.

Preferred for reasons of their higher herbicidal activity, greater plant growth regulant activity or more favorable ease of synthesis are:

1. Compounds of Formula I wherein
J is J-1 or J-4.
2. Compounds of Formula I wherein
J is J-2 or J-3.
3. Compounds of Formula I wherein
J is J-8 or J-9.
4. Compounds of Formula I wherein
J is J-5, J-6, J-7 or J-10.
5. Compounds of Formula I wherein
J is J-11 or J-12.
6. Compounds of Preferred 1 wherein
W is O;
R is H;
X is $CH_3$, $OCH_3$, $OCH_2CH_3$, Cl, F, Br, $OCF_2H$, $CH_2F$, $CF_3$ or cyclopropyl;
Y is H, $CH_3$, $OCH_3$, $OC_2H_5$, $CH_2OCH_3$, $NH_2$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $OCH_2CF_3$, CN, $N_3$, $OCH_2CH_2OCH_3$, $CH_2SCH_3$,

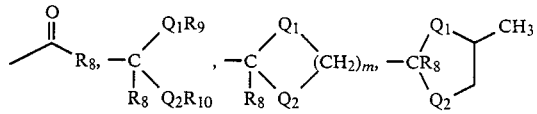

or $QCF_2T$;
Q is O or S;
T is H, CHClF, CHBrF or $CHFCF_3$.

7. Compounds of Preferred 6 wherein
$R_1$ is $C_1$-$C_3$ alkyl, $C_1$-$C_3$ alkoxy, $C_1$-$C_3$ haloalkoxy, $C_1$-$C_3$ haloalkyl, $C_1$-$C_3$ alkylthio, $C_1$-$C_3$ haloalkylthio, amino, $C_1$-$C_3$ alkylsulfinyl, $C_1$-$C_3$ alkylsulfonyl, CN, $NH_2$, $C_1$-$C_3$ alkylamino, di($C_1$-$C_3$ alkylamino) or $C_1$-$C_2$ alkyl substituted with $C_1$-$C_2$ alkoxy, $C_1$-$C_2$ alkylthio, $C_1$-$C_2$ haloalkoxy, $C_1$-$C_2$ haloalkylthio, CN or $NO_2$.

8. Compounds of Preferred 7 wherein
$R_2$ is $C_1$-$C_6$ alkyl, $C_1$-$C_6$ alkylcarbonyl, $C_1$-$C_6$ alkoxycarbonyl, $C_1$-$C_6$ alkyl substituted by 1-3 atoms of F, Cl or 1 Br, or by 1 or 2 groups selected from $C_1$-$C_2$ alkoxy, CN, $C_1$-$C_2$ alkoxycarbonyl, $C_1$-$C_2$ alkylcarbonyl, OH, $C_1$-$C_2$ alkylsulfonyl, $C_1$-$C_2$ alkylsulfonyloxy or $C_1$-$C_2$ alkylcarbonyloxy, $C_3$-$C_4$ alkenyl, $C_3$-$C_4$ haloalkenyl, $C_3$-$C_4$ alkynyl, $C_4$ alkynyl substituted by 1 atom of F or Cl, phenyl or phenyl substituted with Cl, $CF_3$, $NO_2$, CN or $SO_2CH_3$; and
$R_4$ is $CH_3$.

9. Compounds of Preferred 8 wherein
A is A-1; and
Y is $CH_3$, $C_2H_5$, $OCH_3$, $CH_2OCH_3$, $OCF_2H$ or $CH(OCH_3)_2$.

10. Compounds of Preferred 9 wherein
$R_1$ and $R_1'$ are H, Cl, $C_1$-$C_2$ alkyl, $C_1$-$C_2$ alkoxy or $C_1$-$C_2$ alkylthio.

11. Compounds of Preferred 10 wherein
J is J-1.

12. Compounds of Preferred 11 wherein
$R_1$ is H; and
Z is CH.

13. Compounds of Preferred 12 wherein
$R_2$ is $C_1$-$C_4$ haloalkyl, $C_1$-$C_3$ alkyl substituted with $C_1$-$C_2$ alkoxy, $C_1$-$C_2$ alkylthio, $C_1$-$C_2$ alkylsulfonyl or CN, $C_3$-$C_4$ alkenyl, $C_3$-$C_4$ haloalkenyl, $C_3$-$C_4$ alkynyl, $C_1$-$C_3$ alkoxycarbonyl or $C_1$-$C_3$ alkylcarbonyl.

14. Compounds of Preferred 11 wherein
$R_1$ is H;
Z is N; and
$R_2$ is $C_1$-$C_3$ alkylcarbonyl or $C_1$-$C_3$ alkoxycarbonyl.

15. Compounds of Preferred 2 wherein
W is O;
$R_1$ is H;
X is $CH_3$, $OCH_3$, $OCH_2CH_3$, Cl, F, Br, $OCF_2H$, $CH_2F$, $CF_3$ or cyclopropyl;
Y is H, $CH_3$, $OCH_3$, $OC_2H_5$, $CH_2OCH_3$, $NH_2$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $OCH_2CF_3$, CN, $N_3$, $OCH_2CH_2OCH_3$, $CH_2SCH_3$,

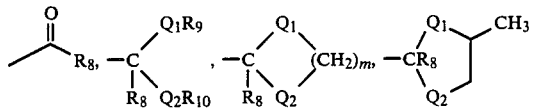

or QCF$_2$T;

$R_2$ is $C_1$-$C_6$ alkyl, $C_1$-$C_6$ alkylcarbonyl, $C_1$-$C_6$ alkoxycarbonyl, $C_1$-$C_6$ alkyl substituted by 1–3 atoms of F, Cl or 1 Br, or by 1 or 2 groups selected from $C_1$-$C_2$ alkoxy, CN, $C_1$-$C_2$ alkoxycarbonyl, $C_1$-$C_2$ alkylcarbonyl, OH, $C_1$-$C_2$ alkylthio $C_1$-$C_2$ alkylsulfonyl, $C_1$-$C_2$ alkylsulfonyloxy or $C_1$-$C_2$ alkylcarbonyloxy, $C_3$-$C_4$ alkenyl, $C_3$-$C_4$ haloalkenyl, $C_3$-$C_4$ alkynyl, $C_4$ alkynyl substituted by 1 atom of F or Cl, phenyl or phenyl substituted with Cl, CF$_3$, NO$_2$, CN or SO$_2$CH$_3$;

$R_1'$ is H, Cl, $C_1$-$C_2$ alkyl, $C_1$-$C_2$ alkoxy or $C_1$-$C_2$ alkylthio.

16. Compounds of Preferred 15 wherein
A is A-1; and
Y is CH$_3$, C$_2$H$_5$, OCH$_3$, CH$_2$OCH$_3$, OCF$_2$H or CH(OCH$_3$)$_2$.

17. Compounds of Preferred 3 wherein
W is O;
$R_1$ is H;
$R_1'$ is H;
A is A-1;
X is CH$_3$, OCH$_3$, OCH$_2$CH$_3$, Cl, F, Br, OCH$_2$H, CH$_2$F or cyclopropyl; and
Y is CH$_3$, C$_2$H$_5$, OCH$_3$, CH$_2$OCH$_3$, OCF$_2$H or CH(OCH$_3$)$_2$;

18. Compounds of Preferred 4 wherein
W is O;
$R_1$ is H;
$R_1'$ is H;
A is A-1;
X is CH$_3$, OCH$_3$, OCH$_2$CH$_3$, Cl, F, Br, OCH$_2$H, CH$_2$F or cyclopropyl; and
Y is CH$_3$, C$_2$H$_5$, OCH$_3$, CH$_2$OCH$_3$, OCF$_2$H or CH(OCH$_3$)$_2$;

19. Compounds of Preferred 5 wherein
W is O;
$R_1$ is H;
$R_1'$ is H;
A is A-1;
X is CH$_3$, OCH$_3$, OCH$_2$CH$_3$, Cl, F, Br, OCF$_2$H, CH$_2$F or cyclopropyl; and
Y is CH$_3$, C$_2$H$_5$, OCH$_3$, CH$_2$OCH$_3$, OCF$_2$H or CH(OCH$_3$)$_2$.

Specifically preferred for reasons of their highest herbicidal activity, greatest plant growth regulant activity and/or most favorable ease of synthesis are:

2,3-dihydro-N-[(4,6-dimethoxypyrimidin-2-yl)aminocarbonyl]-2-(2-methoxyethyl)-1,2-benzisothiazole-7-sulfonamide, 1,1-dioxide, m.p. 194°–197° C.;

2,3-dihydro-N-[(4,6-dimethoxypyrimidin-2-yl)aminocarbonyl]-2-(3-methylbutyl)-1,2-benzisothiazole-7-sulfonamide, 1,1-dioxide, m.p. 227°–229° C.;

2,3-dihydro-N-[(4,6-dimethoxypyrimidin-2-yl)aminocarbonyl]-2-(phenylmethyl)-1,2-benzisothiazole-7-sulfonamide, 1,1-dioxide, m.p. 216°–218° C.;

2,3-dihydro-N-[(4,6-dimethoxypyrimidin-2-yl)aminocarbonyl]-2-(2-oxopropyl)-1,2-benzisothiazole-7-sulfonamide, 1,1-dioxide, m.p. 178°–182° C.;

2,3-dihydro-N-[(4-chloro-6-methoxypyrimidin-2-yl)aminocarbonyl]-2-(2-ethoxyethyl)-1,2-benzisothiazole-7-sulfonamide, 1,1-dioxide, m.p. 193°–197° C.;

2,3-dihydro-N-[(4,6-dimethoxypyrimidin-2-yl)aminocarbonyl]-2-(2-ethoxyethyl)-1,2-benzisothiazole-7-sulfonamide, 1-1-dioxide, m.p. 203°–204° C.;

2,3-dihydro-N-[(4,6-dimethylpyrimidin-2-yl)aminocarbonyl]-2-(2-fluoroethyl)-1,2-benzisothiazole-7-sulfonamide, 1,1-dioxide, m.p. 214°–215° C.;

2,3-dihydro-N-[(4-methoxy-6-methyl-1,3,5-triazin-2-yl)aminocarbonyl]-2-(2-fluoroethyl)-1,2-benzisothiazole-7-sulfonamide, 1,1-dioxide, m.p. 190°–192° C.;

2,3-dihydro-N-[(4,6-dimethoxypyrimidin-2-yl)aminocarbonyl]-2-acetyl-1,2-benzoisothiazole-7-sulfonamide, 1,1-dioxide, m.p. 191°–193° C.;

2,3-dihydro-N-[(4,6-dimethoxypyrimidin-2-yl)aminocarbonyl]-2-(3-chloropropyl)-1,2-benzisothiazole-7-sulfonamide, 1,1-dioxide, m.p. 201°–203° C.;

2,3-dihydro-N-[(chloro-6-methoxypyrimidin-2-yl)aminocarbonyl]-2-(2-fluoroethyl)-1,2benzisoythiazole-7-sulfonamide, 1,1-dioxide, m.p. 215°–217° C.

2,3-dihydro-N-[(4,6-dimethoxypyrimidin-2-yl)aminocarbonyl]-2-(3-fluoropropyl)-1,2-benzisothiazole-7-sulfonamide, 1,1-dioxide, m.p. 199°–200° C.;

2,3-dihydro-N-[(4-chloro-6-methoxypyrimidin-2-yl)aminocarbonyl]-2-(2-chloroethyl)-1,2-benzisothiazole-7-sulfonamide, 1,1-dioxide, m.p. 219°–220° C.;

N-[(4-chloro-6-methoxypyrimidin-2-yl)aminocarbonyl]-2-(2-fluoroethyl)-2,3-dihydro-1,2-benzoisothiazole-7-sulfonamide, 1,1-dioxide, m.p. 215°–217° C.;

N-[(4-chloro-6-methoxypyrimidin-2-yl)aminocarbonyl]-2-(3-fluoropropyl)-2,3-dihydro-1,2-benzoisothiazole-7-sulfonamide, 1,1-dioxide, m.p. 222.5°–223.5° C.

DETAILED DESCRIPTION OF THE INVENTION

Synthesis

The following discussion represents a general outline for the preparation of the compounds of this invention. All of the syntheses described below are multistep with one or more methods being taught for each step. This allows for a wide variety of possible synthetic pathways to prepare a particular compound of Formula I. The proper choice of th synthetic pathway and the best ordering of the reaction sequences for each individual compound will be known to one skilled in the art.

The compounds of Formula I can be prepared by one or more of the methods described below in Equations 1 through 5.

As shown in Equation 1, many of the compounds of Formula I where J is J$_1$, J$_2$, J$_3$ and J$_4$, can be prepared by reacting a sulfonylisocyanate (W=O) or, a sulfonylisothiocyanate (W=S) of Formula II with an appropriate heterocyclic amine of Formula III. R, A and W are as previously defined.

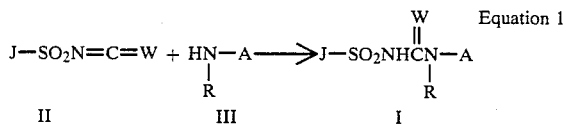

Equation 1

The reaction is carried out at 25° to 100° C. in an inert, aprotic solvent such as methylene chloride or xylene for 0.5 to 24 hours as taught in U.S. Pat. No. 4,127,405.

Many of the compounds of Formula I, where J is $J_1$, $J_2$, $J_3$ and $J_4$, W is S and R is H, (Ia) can be prepared by reacting the appropriate sulfonamide of Formula IV with a heterocyclic isothiocyanate of Formula V, as shown in Equation 2.

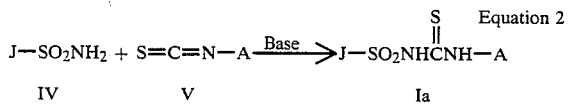

Equation 2

The reaction is carried out at 25° to 80° C. in an inert, aprotic solvent such as acetone or acetonitrile in the presence of a base such as potassium carbonate for 0.5 to 24 hours. The required heterocyclic isothiocyanates V are prepared from the corresponding amines III which would be known to one skilled in the art as taught in EPO Publication No. 35,893.

Many of the compounds of Formula I, where J is $J_1$, $J_2$, $J_3$ and $J_4$ and W is O (Ib), can be prepared by reacting a sulfonylcarbamate of Formula VI with an appropriate amine of Formula III, as shown in Equation 3.

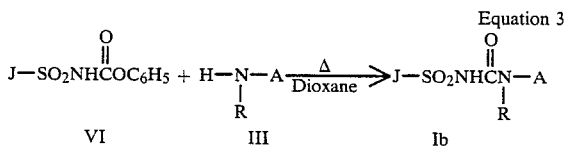

Equation 3

The reaction is carried out at 50° to 100° C. in a solvent such as dioxane for 0.5 to 24 hours. The required carbamates VII are prepared by reacting the corresponding sulfonamides IV with diphenylcarbonate in the presence of a strong base.

Compounds of Formula Ib can also be prepared, as shown in Equation 4, by reacting a heterocyclic carbamate of Formula VI with an appropriate sulfonamide of Formula IV.

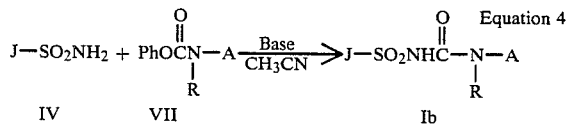

Equation 4

The reaction is carried out at 0° to 50° C. in a solvent such as acetonitrile or dioxane in the presence of a non-nucleophilic base such as DBU for 0.2 to 24 hours. The required phenylcarbamate VII are prepared by reacting the corresponding heterocyclic amines III with diphenylcarbonate or phenylchloroformate in the presence of a strong base.

Many of the compounds of Formula Ib where J is $J_1$, $J_2$, $J_3$ and $J_4$ can be prepared by reacting the sulfonamides of Formula IV with an appropriate methylcarbamate of Formula VIII in the presence of an equimolar amount of trimethylaluminum, as shown in Equation 5.

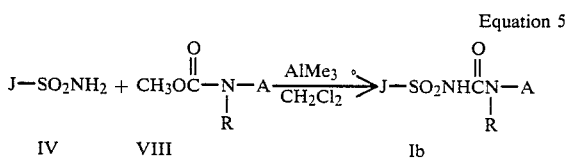

Equation 5

The reaction is carried out at 25° to 40° C. in a solvent such as methylene chloride for 10 to 96 hours under an inert atmosphere. The required carbamates VIII are prepared by reacting the corresponding amines III with dimethylcarbonate or methyl chloroformate in the presence of a strong base.

The intermediate sulfonylisocyanates (W=O) and sulfonisothiocyanates (W=S) of Formula II from Equation 1 can be prepared as shown in Equations 6 through 8.

As shown in Equation 6, many of the sulfonylisocyanates of Formula IIa where J is $J_1$, $J_2$, $J_3$ and $J_4$ can be prepared by the reaction of sulfonamides of Formula IV with phosgene, in the presence of n-butylisocyanate and a tertiary amine catalyst, at reflux in a solvent such as xylene by the method of U.S. Pat. No. 4,238,621.

Equation 6

The sulfonylisocyanates can also be prepared from the solfonamides by a two step procedure involving (a) reacting the sulfonamides with n-butylisocyanate in the presence of a base such as $K_2CO_3$ at reflux in an inert solvent such as 2-butanone forming a n-butylsulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p. 223-241, Academic Press, New York and London, W. Foerst Ed.

Alternatively, as shown in Equation 7, many of the sulfonylisocyanates of Formula IIa where J is $J_1$, $J_2$, $J_3$ and $J_4$ can be prepared by reacting the corresponding sulfonyl chlorides IX with cyanic acid salts.

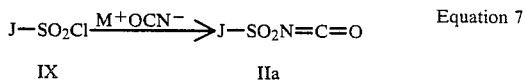

Equation 7

The reaction is carried out at 25° to 100° C. in an inert aprotic solvent such as acetonitrile for 0.5-24 hours in the presence of phosphorus pentoxide and an alkali metal salt such as lithium iodide.

Many of the sulfonylisothiocyanates of Formula IIb where J is $J_1$, $J_2$, $J_3$ and $J_4$ can be prepared, as shown in Equation 8, by contacting the sulfonamides of Formula IV with carbon disulfide in the presence of two equivalents of a strong base. The resulting salt is then reacted with phosgene according to the teachings of K. Hartke, *Arch. Pharm.*, 299, 174 (1966).

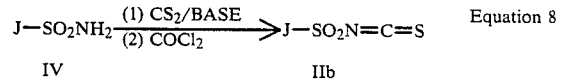

Equation 8

The sulfonamides of Formula IV where J is $J_1$, $J_2$, $J_3$ and $J_4$ of Equations 2, 4, 5, 6 and 8 as well as the other sulfonamides required to prepare the compounds of this invention can be prepared from the corresponding sulfonyl chlorides of Formula IX by contacting with either anhydrous or aqueous ammonia as shown in Equation 9.

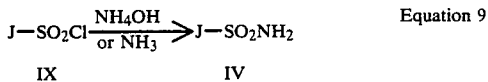

Equation 9

The preparation of sulfonamides from sulfonyl chlorides is widely reported in the literature, for reviews see: F. Hawking and J. S. Lawrence, "The Sulfonamides," H. K. Lewis and Co., London, 1950 and E. H. Northey, "The Sulfonamides and Allied Compounds," Reinhold Publishing Corp., New York, 1948.

Alternatively, many sulfonamides IV can be prepared by dealkylation of their corrresponding N-t-butyl sulfonamides X as shown in Equation 10.

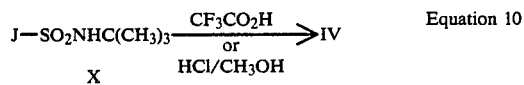

Equation 10

The reaction is carried out by contacting the N-t-butyl sulfonamide X with a strong acid such as trifluoroacetic acid or methanolic HCl at 25° to 50° C. for 0.5 to 24 hours. The N-t-butyl sulfonamides X are readily prepared by reacting sulfonylchlorides IX with t-butylamine and are useful either as an aid in purification, to enhance solubility for subsequent reactions such as Equation 12 below or to protect the sulfonamide function from competing with reactions at other parts of the molecule.

Many of the sulfonamides of Formula IVa can be prepared by functionalization of the corresponding N-unsubstituted sulfonamides of formula IVb as shown in Equation 11. $G_1-G_2$ is $CHR_3(CHR_4)_n$ and $CH=CH_4$, R' is H or $C(CH_3)_3$ and X is Cl, Br, I or other readily displaceable groups. When $R_3$ is $CH_3$ then n is O.

Equation 11

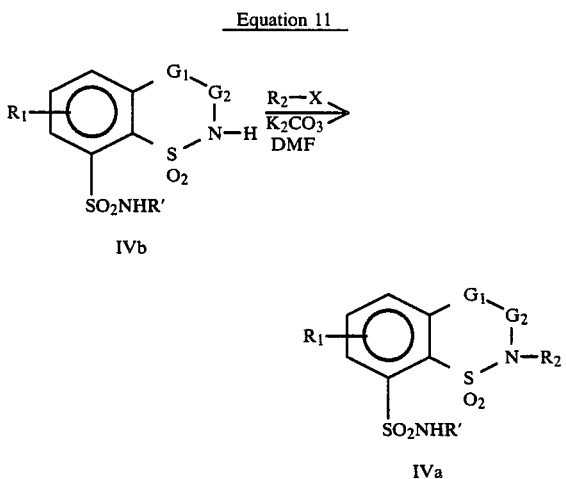

The reaction is carried out by contacting the sulfonamides IVb with the appropriate electrophile in the presence of a suitable base such as $K_2CO_3$ in an inert, polar solvent such as DMF at 0° to 100° C. for 0.5 to 24 hours. In some instances the $R_2$ function can also be introduced by Michael addition of IVb to the appropriate Michael acceptor as known to one skilled in the art.

While many of the $R_2$ groups can be introduced directly, as described above, some of the $R_2$ groups may best be prepared by standard functional group manipulations upon compounds of Formula IVa containing an appropriate $R_2$ group pecursor as will be known to one skilled in the art. Some examples of these manipulations are the preparation of IVa where $R_2$ contains an epoxide by the epoxidation of IVa where $R_2$ contains a carbon-carbon double bond, the preparation of IVa where $R_2$ contains a sulfone by the oxidation of IVa where $R_2$ contains a thioether function, the preparation of IVa where $R_2$ contains $OC(O)CH_3$ by acetylation of IVa where $R_2$ contains OH, or the preparation of IVa where $R_2$ contains $NH_2$ by the reduction of IVa where $R_2$ contains $NO_2$. This is also the case for many of the $R_1$ substituents which can be prepared by an analogous chemical manipulation known to one skilled in the art.

Many of the unsaturated sulfonamides of Formula IVc can also be prepared from the corresponding saturated sulfonamides of Formula IVd by the two-step procedure shown in Equation 12. $G_1-G_2$ is $SO_2-NR_2$, $CO-NR_5$ or $NR_5-CO$, R' is H or $C(CH_3)_3$ and R" is H or $R_4$.

Equation 12

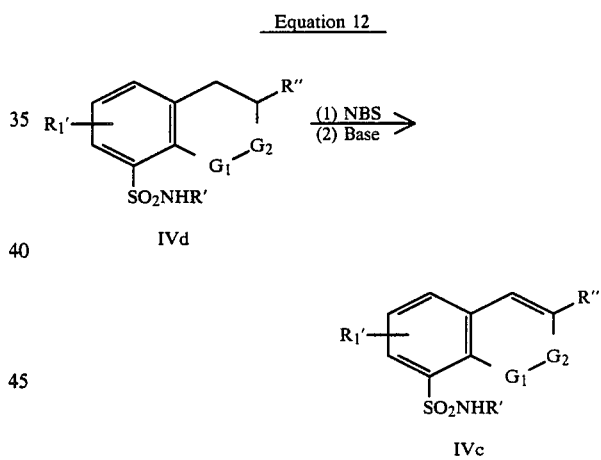

The first step involves benzylic bromination by N-bromosuccinimide to give a monobromide which is subsequently dehydrobrominated in a second step by reaction with a suitable base such as triethyl amine or potassium-t-butoxide in an inert solvent such as THF. This method has been used to prepare isocoumarins from 3,4-dihydroisocoumarins, see R. Barry, Chem. Rev., 64, 229 (1964). In cases where $R_1$ is an alkyl group, competitive bromination at this site may occur resulting in a mixture. The desired bromide may be separated at this stage, or after treatment with the base, by standard methods.

The thiocarbonylsulfonamides of Formula IV where J is $J_5$, $J_6$, $J_7$, $J_8$, $J_9$ and $J_{10}$ and where $W_1$ is S can be prepared from their corresponding oxygen analogs where $W_1$ is O as represented in Equation 13 using ring system $J_5$ as an example.

Equation 13

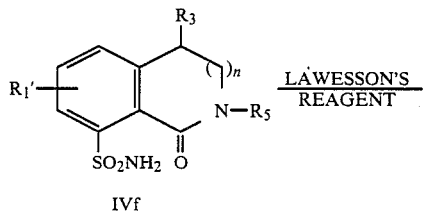
IVf

LAWESSON'S REAGENT

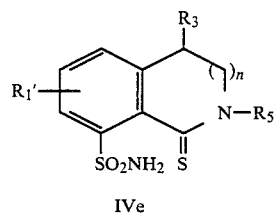
IVe

The reaction is carried out at 100° to 140° C. in a solvent such as xylene for 1.0 to 24 hours as taught by Lawesson, et al. *Bull. Chem. Soc. Belg.*, 87, 229 (1978). The corresponding oxygen carbonyl sulfonamides of ring systems $J_5$, $J_6$, $J_7$, $J_8$, $J_9$ and $J_{10}$ where $W_1$ is O can be prepared according to the methods described herein and in EPO Publication No. 107979. EPO Publication No. 107979 also describes the synthesis of indanone and tetralone sulfonamides which can be ketalized by standard methods known to one skilled in the art to give sulfonamides of Formula IV where J is J-11 and J-12.

The sulfonyl chlorides of Formula IX of Equations 7 and 9 are important intermediates for the preparation of the compounds of this invention. The syntheses of the required sulfonyl chloride intermediates where J is $J_1$, $J_2$, $J_3$ and $J_4$ are described in Equations 14 through 16. These methods can also be used to prepare the corresponding oxygen carbonyl analogs of ring systems $J_5$, $J_6$, $J_7$, $J_8$, $J_9$ and $J_{10}$ where $W_1$ is O.

As shown in Equation 14, many of the sulfonyl chlorides of Formula IX can be prepared from the corresponding amines XI.

Equation 14

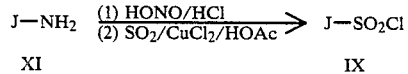

The reaction involves diazotization of the amine XI with sodium nitrite in HCl, followed by reaction of the diazonium salt with sulfur dioxide and cupric chloride in acetic acid analogous to the teachings of Yale and Sowinski, *J. Org. Chem.*, 25, 1824 (1960).

Alternatively, sulfonyl chlorides of Formula IX can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°–40° C. for 1 to 24 hours.

Many of the sulfonyl chlorides of Formula IX can also be prepared by oxidative chlorination of the corresponding thio compounds of Formula XII as shown in Equation 15. R' is H, alkyl, benzyl or carbamoyl, $R_1$ is not $SCH_3$ and J does not contain non-aromatic unsaturation.

Equation 15

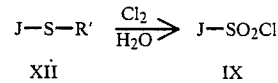

The reaction is carried out by addition of molecular chlorine or a chlorine equivalent to the thio compound in the presence of water at 0° to 80° C. in an aliphatic carboxylic acid solvent such as acetic acid or an inert organic solvent such as dichloroethane for 1 to 24 hours.

Alternatively, many of the sulfonyl chlorides of Formula IX can be prepared by the two-step sequence shown in Equation 16 starting from the thio compounds XII where R' is H (XIIa) and $R_1$ is not $SCH_3$.

Equation 16

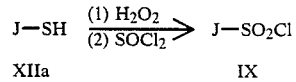

The thiol XII (R'=H) is contacted with excess hydrogen peroxide in the presence of base to give a sulfonic acid salt which in turn is converted to the desired sulfonyl chloride by contacting with a suitable reagent such as thionyl chloride or phosphorous pentachloride as known to one skilled in the art.

Some of the sulfonyl chlorides of Formula IX may best be prepared by direct chlorosulfonation depending on the substitution pattern on the ring and the nature of the substituent as will be known to one skilled in the art.

Many of the S-arylthiocarbamates of Formula XIIb (XII, R'=CON(CH$_3$)$_2$) can be prepared by the Newman-Kwart rearrangement starting with the corresponding phenols XIII as shown in Equation 17.

Equation 17

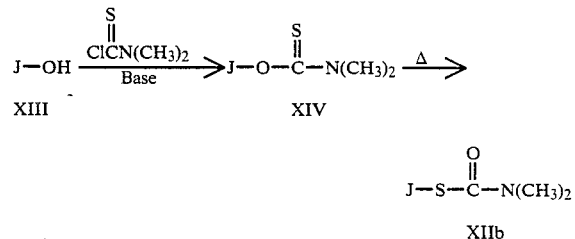

The phenol XIII is first reacted with N,N-dimethylthiocarbamoyl chloride in the presence of a base. The resulting O-aryl-N,N-dimethylthiocarbamate XIV is then heated at 150° C. to 300° C. for 2 to 24 hours as taught by Newman and Karnes *J. Org. Chem.*, 31, 3980 (1966) to give the desired S-aryl-N,N-dimethylthiocarbamate XIIb. The related thiols XIIa can be obtained by hydrolysis of the thiocarbamates XIIb.

Many of the sulfides of Formula XII where R' is alkyl or benzyl can be prepared by reacting a halocompound of Formula XV with an appropriate mercaptan in the presence of a base as shown in Equation 18. R' is alkyl or benzyl and X is F, Cl or Br.

Equation 18

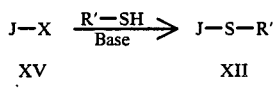

The reaction is carried out in a solvent such as DMF at 25° to 150° C. for 0.5 to 24 hours. The halocompounds XV must not contain functionality which can be attacked by a mercaptide anion as will be known to one skilled in the art. An example of this would be where J is $J_1$ and $R_2$ was a haloalkyl group. These compounds can be prepared from the corresponding sulfides XII where J is $J_1$, R' is alkyl or benzyl and $R_2$ is H by standard alkylation methods.

Many of the thiocompounds XII of Equation 15 and the chlorocompounds XV (X=Cl) of Equation 18, where J is $J_1$ and n is O, can be prepared by the reaction sequence shown in Equation 19. G is Cl or S-alkyl, $R_1$ does not contain functionality incompatible with BuLi or $BH_3$ and $R_3$ is as previously defined.

Equation 19

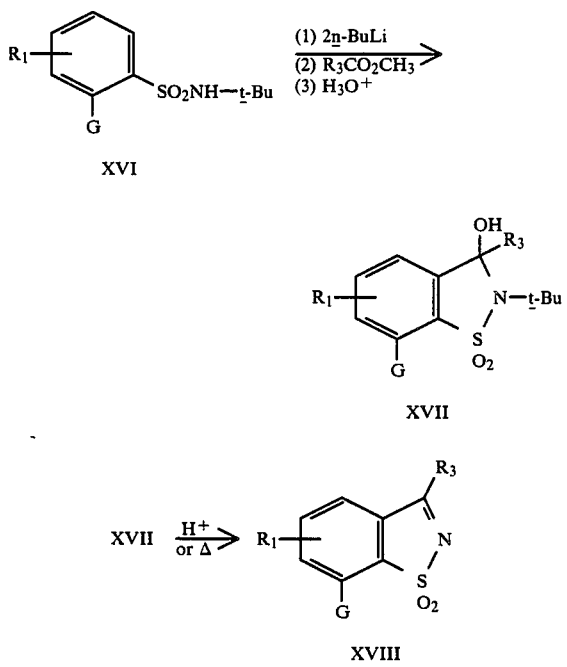

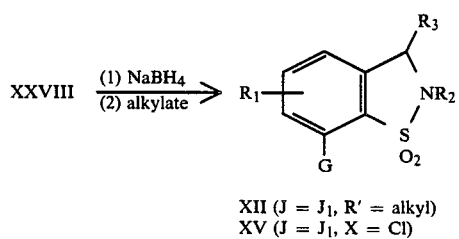

XII (J = $J_1$, R' = alkyl)
XV (J = $J_1$, X = Cl)

-continued
Equation 19

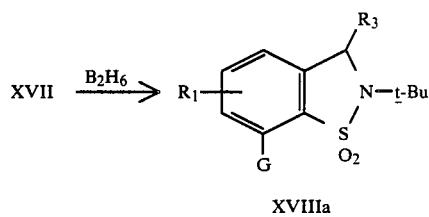

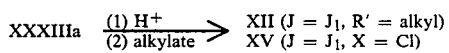

The sequence begins by contacting an apropriately substituted N-t-butylbenzenesulfonamide XVI with two equivalents of butyl lithium at 0° to 25° C. in an inert solvent such as THF for 2 to 10 hours to give a dianion according to the teachings of J. Lombardino, *J. Org. Chem.*, 36, 1843 (1971). The dianion can then be trapped with an ester or, when $R_3$ is H, with dimethylformamide at −78° to 25° C. to produce, upon aqueous acid workup, the hemiaminal XVII. The hemiaminal XVII can be de-t-butylated and dehydrated by a catalytic amount of acid such as p-toluene-sulfonic acid in a solvent such as benzene or toluene at reflux. The resulting benzisothiazole XVIII can be reduced with a reagent such as sodium borohydride in a suitable solvent such as ethanol to produce a 2,3-dihydrobenzisothiazole which is N-alkylated as described in equation II to give either XII (J=$J_1$, R'=alkyl) or XV (J=$J_1$, X=Cl) by standard methods known to one skilled in the art. Alternatively, hemiaminal XVII may be treated with diborane to produce a t-butyl-2,3-dihydrobenzisothiazole XVIIIa. Compounds XII (J=$J_1$, R'=alkyl) or XV (J=$J_1$, X=Cl) are then readily prepared as described previously by treatment of XVIIIa with trifluoroacetic acid followed by N-alkylation. If the t-butyl group in structures XVI and XVII is replaced by the appropriate $R_2$ group, the diborane reduction of the hemiaminal gives XII and XV directly.

Many of the thio compounds XII of Equation 15 and the chloro compounds XV of Equation 18, where J is $J_1$ and $J_4$ and n=1, can be prepared by the reaction sequence shown in Equation 20. G is Cl or S-alkyl, Y is H or $CH_3$, $R_1$ does not contain functionality incompatible with BuLi. R" is $C(CH_3)_3$ or functionality selected from $R_2$ which is compatible with the lithiation conditions shown as will be known to one skilled in the art and $R_4$ is H or $C_1$-$C_4$ alkyl.

Equation 20

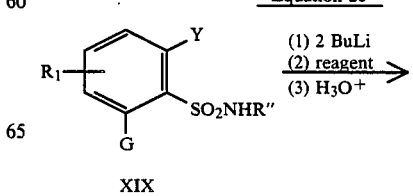

-continued
Equation 20

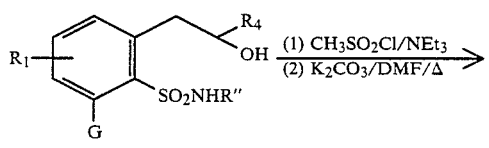

XX

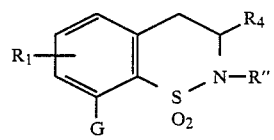

XII (J = J$_1$, J$_4$, R' = alkyl)
XV (J = J$_1$, J$_4$, X = Cl)

The reaction is carried out by reacting the N-substituted benzenesulfonamides XIX with two equivalents of n-BuLi at −78° to 25° C. in a solvent such as THF for 0.5 to 5 hours. When Y is H, an ortho-anion is formed which is trapped with an appropriate epoxide to give the hydroxy sulfonamides XX. When Y is CH$_3$, an ortho-methyl anion is produced which is reacted with an aldehyde or DMF to give alcohol XX. The alcohol can be mesylated by reaction of XX with mesyl chloride in the presence of an equivalent of a tertiary amine at 0° to 25° C. for 1 to 24 hours in a solvent such as methylene chloride. The resulting mesylate is cyclized by heating with a base such as potassium carbonate in a solvent such as DMF to produce the desired compounds XII (J=J$_1$, J$_4$, R'=alkyl) or XV (J=J$_1$, J$_4$, X=Cl). When R'' is C(CH$_3$)$_3$, contacting with acid as described in Equation 10 will give the corresponding benazisothiazine where R'' is H. This can be alkylated as described previously for the benzisothiazoles of Equation 19.

Many of the thio compounds of Formula XII, where J is J$_6$ or J$_{10}$ (W$_1$=O), can be prepared from the thioether compounds XXI shown in Equation 21. Y is H or CH$_3$, R$_1$' does not contain Br, R' is C$_2$–C$_4$alkyl, R$_6$ is H or CH$_3$ and R$_7$ is H or C$_1$–C$_4$ alkyl.

Equation 21

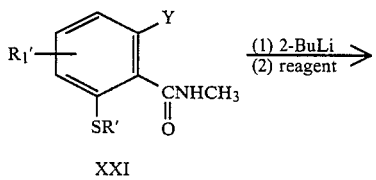

XXI

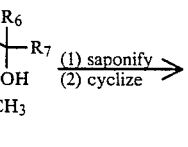

XXII

-continued
Equation 21

XII (J = J$_6$, J$_{10}$)

The reaction is carried out by reacting the N-methylcarboxamide XXI with two equivalents of n-BuLi at −78° to 25° C. in a solvent such as THF for 0.5 to 5 hours to give, when Y is H, an orthoanion which is trapped with an appropriate epoxide to give the hydroxy sulfonamides XXII as taught by Narasimkan and Bhide, *Chem. Comm.*, 1552 (1970). When Y is CH$_3$, an ortho methyl anion is produced which is reacted with an aldehyde or slowly enolizable ketones to give the amides XXII as taught by Watanabe et al. *Tetrahedron Lett.* 1647 (1982). The aides XXII are saponified by standard methods to the corresponding benzoic acids which readily cyclize upon heating in the presence of acid such as p-toluenesulfonic acid to give the desired lactones XII (J=J$_6$, J$_{10}$, R'=alkyl).

The amines of Formula XI in Equation 14, can be prepared by reduction of the corresponding nitro compounds of Formula XXI, as shown in Equation 22.

Equation 22

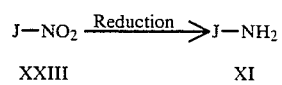

XXIII          XI

The reduction of nitro compounds to amines can be carried out by any of several known methods as described in *Preparative Organic Chemistry*, 4 Ed., p. 557–563, John Wiley and Sons, New York and London, G. Hilgetag and A. Martini Ed.

Many of the nitro compounds of Formula XXIII in Equation 22 can be prepared by the procedures outlined in Equations 23 through 30. With suitable modifications known to one skilled in the art, the general ring forming reactions outlined below for these nitro compounds XXIII can be adapted to prepare many of the phenols of Formula XIII and halocompounds of Formula XV.

As shown in Equation 23, many of the nitro compounds of Formula XXI, where J is J$_1$ (XXIIIa) can be prepared starting from the appropriately substituted nitrobenzenes of Formula XXII. R' is H or CH$_2$Cl.

Equation 23

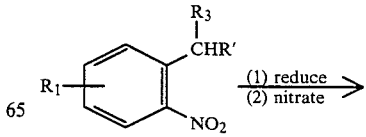

XXIV

-continued
Equation 23

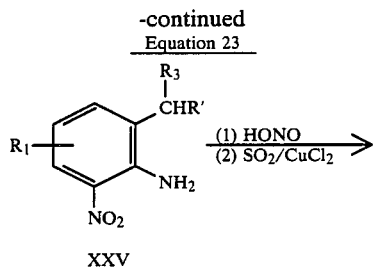

XXV

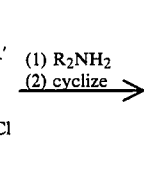

XXVI

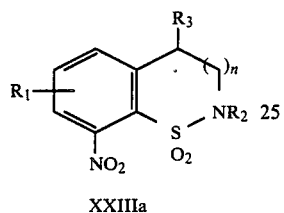

XXIIIa

The nitrobenzenes XXIV are first reduced to their corresponding amines and nitrated by standard methods to produce, in part, compounds of Formula XXV. In some instances, it may be desirable to first protect the amino group as its acetate prior to nitration as is known to one skilled in the art. The desired nitro compound XXV can be isolated by either fractional crystallization or chromatographic procedures and converted to sulfonyl chlorides XXVI by the method previously discussed in Equation 14. The intermediate sulfonyl chlorides XXVI can be converted into their correspnding sulfonamides by reaction with an appropriate amine (see Equation 9) and subsequently cyclized: (a) when R' is CH$_2$Cl, to the nitro-1,2-benzothiazines XXIIIa, where n is 1, by heating in the presence of a base such as potassium carbonate; or (b) when R' is H, by contacting the sulfonamide with NBS in a solvent such as carbon tetrachloride to give sulfonamides where R' is Br, followed by contacting this product with a base to give the nitro benzisothiazoles XXIa where n is 0. Note the discussion of Equation 12 for NBS brominations when R$_1$ is alkyl.

The procedure of Equation 23 is similar to the method taught by E. Sianesi et al., *Chem. Ber.*, 104, 1880 (1971) for the preparation of substituted 1,2-benzothiazine-1,1-dioxides. The starting nitrobenzenes XXII can be prepared by standard methods known to one skilled in the art.

Alternatively, as shown in Equation 24, many of the nitro compounds of Formula XXIIIa where n is 1 can be prepared, in part, by contacting the nitro acetamides XXVII with fuming sulfuric acid according to the method taught by H. Zenno and T. Mizutani, (*Chem. Abst.*: 72: 79122 (1970)) for the preparation of 7-nitro-1,2-benzothiazine-1,1-dioxide. The resulting benzothiazines can be isolated and subsequently alkylated by standard methods known to one skilled in the art.

Equation 24

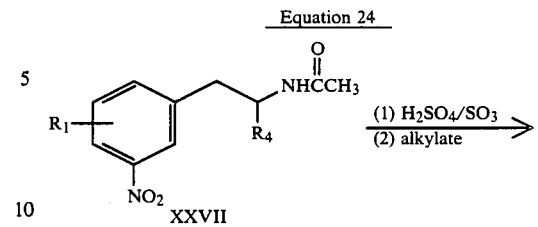

XXVII

XXIIIa (n = 1)

Many of the nitro compounds of Formula XXIIIa where n is 0 can also be prepared from the corresponding 1,2-benzisothiazoles XXVI as shown in Equation 25.

Equation 25

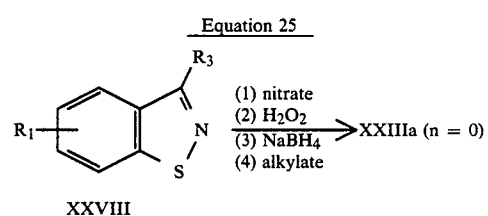

XXVIII

Nitration of XXVIII gives, in part, the 7-nitro derivative which is isolated by standard methods. The derivative is converted to its 1,1-dioxide by treatment with hydrogen peroxide. Reduction of the carbon-nitrogen double bond with NaBH$_4$ followed by alkylation of the resulting sulfonamide gives compounds XXIIIa where n is 0. The above reactions are characteristics of 1,2-benzisothiazoles XXVIII. For reviews of their synthesis and reactions, see L. L. Bambas, "The Chemistry of Heterocyclic Compounds," Vol. 4, part III, 1952, p. 223-378, and M. Davis, *Adv. Heterocyclic Chem.*, Vol. 14 (1972) p. 43-98. 1,2-Benzothiazines are also well known in the literature, for a review of their chemistry and alternate methods of their propagation see J. G. Lombardino, D. E. Kuhla, *Adv. Heterocyclic Chem.*, Vol. 28 (1981) p. 73-126.

As shown in Equation 26, many of the nitro compounds of Formula XXIII where J=J$_6$ (W$_1$=O) (XXIId) can be prepared from the appropriately substituted amines XXV. R' is H or CH$_2$Cl.

Equation 26

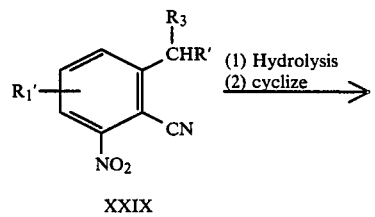

XXIX

-continued
Equation 26

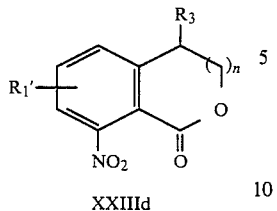

XXIIId

The nitro amines XXV, previously defined in Equation 23, can be converted into the corresponding cyano compounds XXIX by the "Sandmeyer Reaction" (T. Sandmeyer, *Chem. Ber.*, 17, 1633, 2650 (1884)). The cyano function is hydrolyzed to a carboxylic acid by methods known to one skilled in the art, and the carboxylic acids or their corresponding esters can be (a) cyclized to the nitro isocoumarins XXIIId (n=1) by heating in the presence of base when R' is CH$_2$Cl, or (b) cyclized to the nitro phthalides XXIId (n=0 when R' is H by first brominating with NBS or bromine (note discussion of Equation 12 for brominations when R$_1$' is alkyl) followed by heating in a solvent such as aqueous dioxane. The latter method is that taught by J. A. Houbion et al., *Org. Prep. and Procedures Int.*, 11, 27 (1979) for the preparation of 7-nitrophthalide (XXIIId, n=0, R$_1$'=R$_3$=H).

The procedure of Equation 26 is similar to the method of P. Banejce and D. Chaudhury, *J. Org. Chem.*, 26, 4344 (1961) for the preparation of substituted isocoumarins; similar methods can be utilized for the preparation of isocoumarins of the J$_{10}$ (W$_1$=O) type. Isocoumarins are well known in the literature, for a review of their synthesis and reactions see R. Barry, *Chem. Rev.*, 64, 229–260 (1964).

Many of the nitro compounds of Formula XXIII, where n=0 can also be prepared by reduction of the corresponding 3-nitrophthalic anhydrides with either sodium borohydride or lithium aluminum hydride in tetrahydrofuran as taught by M. Kayser and P. Morand, *Can. J. Chem.*, 58, 2848 (1980) for the preparation of 7-nitrophthalide (XXXIId; n=0, R$_1$'=H). Phthalides and phthalic anhydrides are well known in the art, for a review of their synthesis and reactions see, S. Wawzonek, *Heterocyclic Compounds*, Vol. 2, John Wiley and Sons, Inc., New York, 1951.

As shown in Equation 27, many of the nitro compounds of Formula XXIII where J is J$_5$ (W$_1$=O) (XXIIe) can be prepared from the appropriately substituted benzonitriles XXIX. R' is H or CH$_2$Cl.

Equation 27

XXIX $\xrightarrow[\text{(3) R}_5\text{NH}_2]{\substack{\text{(1) Hydrolysis} \\ \text{(2) SOCl}_2}}$

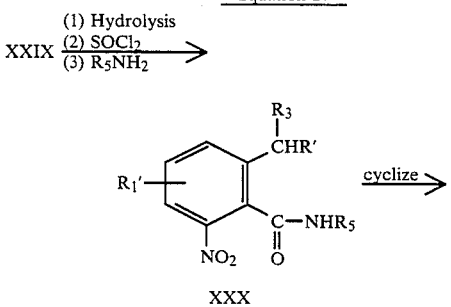

XXX

-continued
Equation 27

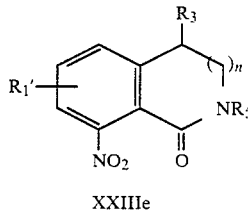

XXIIIe

The benzonitriles XXIX, previously described in Equation 26, are hydrolyzed to carboxylic acids, converted to their corresponding acid chlorides by contacting with a reagent such as thionyl chloride and subsequently reacted with the appropriate amine, by standard methods, to give the amides XXX. The intermediate amides XXX can be cyclized to the nitro compounds XXIIIe by the procedures previously described in Equation 23 for converting sulfonamides of XXVI into nitro compounds XXIIIa.

Alternatively, many of the nitro compounds of Formula XXIIIe can be prepared from the nitro compounds of Formula XXIIId as shown in Equation 28.

Equation 28

XXIIId $\xrightarrow{\text{R}_5\text{NH}_2}$

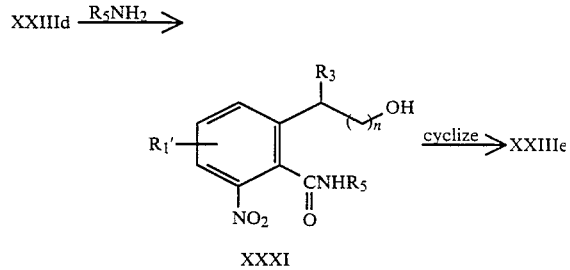

XXXI

The reactions of phthalides with amines to produce phthalimidines is well known, see C. Hollins, *The Synthesis of Nitrogen Ring Compounds*, Ernest Benn Limited. London, 1924. In these reactions, heating the phthalides (XXIIId, n=0) with an amine produces the phthalimidines (XXIIIe, n=0) directly, the intermediate alcohols XXXI (n=0) are not isolated. With the 3,4-dihydrocoumarins (XXIIId, n=1) the intermediate amide alcohols XXXI (n=1) are formed (see P. Maitte, *Colloq. Intern. Centre Natl. Rech. Sci. (Paris)*, 64, 197 (1955). *Chem. Abst.*, 55: 10426 (1961)) and can be converted to the dihydroisoquinolines XXIIIe (n=1) by first conversion to the corresponding mesylate followed by heating with a base as described above in Equation 20 for the preparation of compounds XII (J=J$_1$, R'=alkyl) and XV (J=J$_1$, X=Cl) from the sulfonamide alcohols XX. For a comprehensive review of the synthesis and reactions of dihydroisoquinolones see N. J. McCorkindale, *The Chemistry of Heterocyclic Compounds*, Vol. 38, part III, John Wiley and Sons, New York, in press.

As shown in Equation 29, many of the nitro compounds of Formula XXIII whqere J is J$_7$ (W$_1$=O) (XXIIIf) can be prepared from the appropriate substituted nitrobenzenes XXIV. R' is Br or CH$_2$Br.

Equation 29

XXIV $\xrightarrow[\text{(2) Hydrolyze}]{\text{(1) KCN}}$

-continued
Equation 29

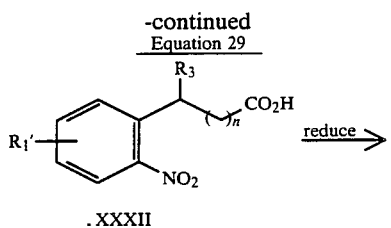

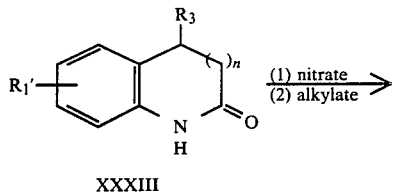

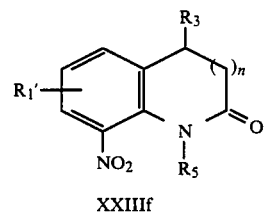

The nitrobenzenes XXIV, previously discussed in Equation 23, are reacted with potassium cyanide in a solvent such as acetone to give nitrile intermediates which are hydrolized to the corresponding carboxylic acids XXXII by standard methods known to one skilled in the art. The nitro carboxylic acids XXXII, when reduced by standard methods (see discussion of Equation 22), spontaneously cyclize to give the lactams XXXIII. For a discussion of this reaction when n is O, see W. Sumpter and F. Miller, *The Chemistry of Heterocyclic Compounds*, Vol. 32, John Wiley and Sons, New York, 1977, p. 216-217, and references cited therein. The nitro lactams XXIIIf are prepared in part from lactams XXXIII by standard nitration and alkylation procedures known to one skilled in the art.

Alternatively, many lactams XXXIII of Equation 29 can be prepared from the substituted anilines XXXIV as shown in Equation 30.

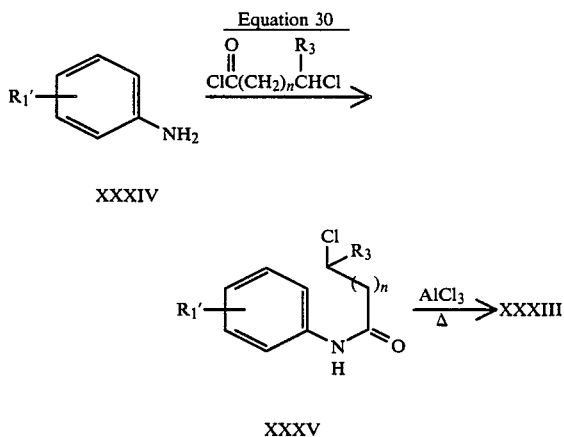

The substituted anilines XXXIV are reacted with either a chloroacetyl chloride (n=0) or β-chloropropionyl chloride (n=1, $R_3$=H) in the presence of an acid scavenger to give the chloro amides XXXV. The amides XXXV are cyclized by heating in the presence of a suitable Friedel-Crafts reagent such as $AlCl_3$ to give the lactams XXXIII. The method of Equation 30 has been widely used for the preparation of oxindoles (XXXIII, n=0; see W. Sumpter and F. Miller, loc. cit., p. 135-136 for discussion and references) and for the preparation of 3,4-dihydro-2-quinolones (XXXIII, n=1; see G. Jones, loc. cit., p. 164-168 for discussion and references). For a general review of oxindole chemistry see W. Sumpter and F. Miller, loc. cit., p. 134-153.

Many of the nitro compounds of Formula XXIII in Equation 22 where J is $J_2$, $J_3$, $J_8$ ($W_1$=O) and $J_9$ ($W_1$=O) can be prepared from the correspondiing nitro compounds of Formula XXIII where J is $J_1$ (n=1), $J_4$, $J_5$ ($W_1$=O) and $J_7$ ($W_1$=O), respectively, by the bromination-dehydrobromination sequence described above for sulfonamides IV in Equation 12.

The amines of Formula III in Equations 1 and 3 are also important intermediates for the preparation of the compounds of this invention and are described below.

The pyrimidines and triazines of Formula (IIIa) to (IIId) below are either known or can be prepared by methods obvious to one skilled in the art.

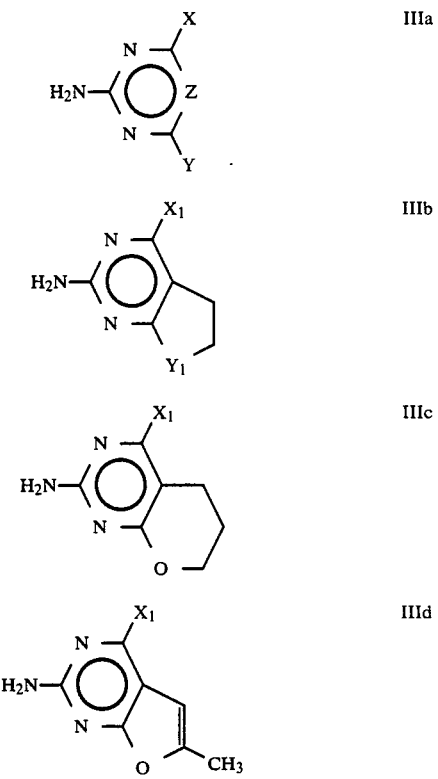

For a review of the synthesis and reactions of 2-aminopyrimidines (IIIa, Z=CR') see *The Chemistry of Heterocyclic Compounds*, Vol. 16, John Wiley and Sons, New York (1962). For a review of the synthesis and reactions of 2-amino-s-triazines (IIIa, Z=N) see *The Chemistry of Heterocyclic Compounds*, Vol. 13, John Wiley, New York (1959), F. C. Schaefer, U.S. Pat. No. 3,154,547 and F. C. Schaefer and K. R. Huffman, *J. Org. Chem.*, 28, 1812 (1963). The synthesis of the bicyclic amines IIIb and IIIc is taught in European Patent Application No. 15,683. The synthesis of bicyclic amines IIId is taught in European Patent Application No. 46,677. The synthesis of amines IIIa where X is cyclopropyl is taught in South African Patent Application No. 83/7434.

The amines of Formula III where X is $OCF_2H$, $OCH_2F$, $OCF_3$ or $CF_3$; or $X_1$ is $OCF_2H$ and/or Y is $OCH_2F$, $OCF_3$, $SCH_2F$, $SCF_3$ or $GCF_2T$ wherein G is O or S and T is H, CHClF, CHBrF or $CHFCF_3$ can be prepared by methods that would be obvious to one skilled in the art.

The pyrimidines of Formula IIIa (Z=CH) where Y is

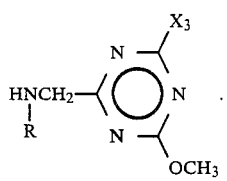

can be prepared according to the methods known to one skilled in the art.

The triazine amines of Formula IIIe where $X_3$ is $CH_3$ or $OCH_3$ and R is H or $CH_3$ can be prepared according to the teachings of European Patent Application No. 94,260.

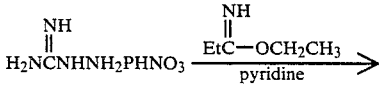
IIIe

Preparation of 3-amino-1,2,4-triazoles of Formula IIIf are known in the art and 1,2,4-triazoles are reviewed in *The Chemistry of Heterocyclic Compounds* "Triazoles 1,2,4" (John Wiley and Sons, New York, 1981). Commonly used starting materials containing nitrogein are N-aminoguanidine, hydrazine, alkylhydrazines, cyanamide, ethyl cyanoacetamidate, dimethyl cyanodithioimidocarbonate, dimethyl cyanoimidocarbonate, ethoxymethylenecyanamide, and acylhydrazines. Some literature syntheses are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); Berichte, 96, 1064 (1963).

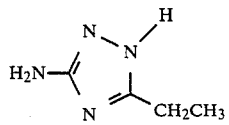

Condensation of hydrazine with ethyl N-cyanoacetimidate yields 3-amino-5-methyltriazole; *Journal of Organic Chemistry*, 28, 1816 (1963).

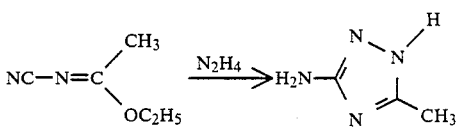

U.S. Pat. No. 2,835,581 (1958) teaches the preparation of 3-amino-5-(hydroxymethyl)triazole from N-aminoguanidine and glycolic acid.

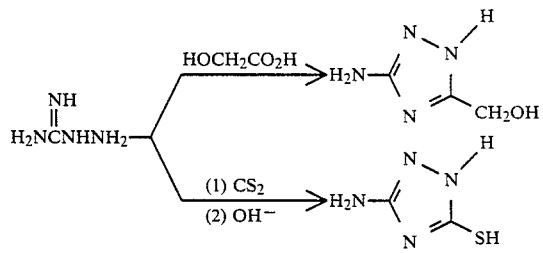

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; *Journal of Organic Chemistry*, 39, 1522 (1974).

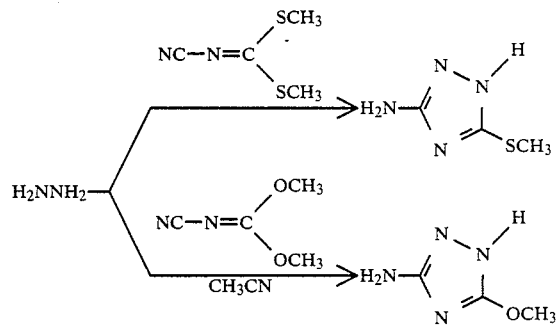

Reaction of substituted hydrazines with N-cyanothioimidocarbonates (prepared according to the procedure given in D. M. Wieland, Ph.D. Thesis, 1971, pp. 123-124) yields disubstituted aminotriazoles as shown below.

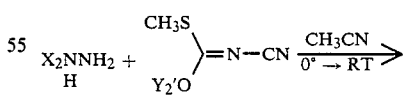

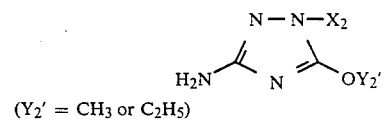

($Y_2' = CH_3$ or $C_2H_5$)

Many of the aminoheterocyclic intermediates of Formula III where R is methyl may be prepared by a two-step procedure as described for IIIg in Equation 31, wherein X, Y and Z are as previously defined.

Equation 31

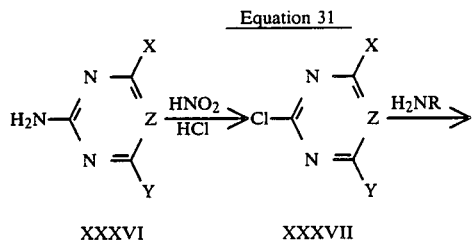

XXXVI      XXXVII

IIIg

A solution of the amine XXXVI in concentrated hydrochloric acid is treated with sodium nitrite solution and the chloro compound XXXVII is isolated in the usual manner by filtration of the acidic solution. A representative procedure is described by Bee and Rose in *J. Chem. Soc. C,* 2031 (1966), for the case in which Z=CH, and X=Y=OCH$_3$. Displacement of the chlorine of XXXVII may be accomplished by heating with an excess of methylamine in water to obtain the methylamino heterocycle (IIIg).

Quaternization of amino functionality present in the R$_2$ group of compounds of formula I are also useful as herbicides and can be prepared by standard methods known to one skilled in the art.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange my also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

EXAMPLE 1

2-t-Butyl-3-hydroxy-7-chloro-2,3-dihydro-1,2-benzisothiazole-1,1-dioxide

To a solution of 49.5 g of N-t-butyl-2-chlorobenzenesulfonamide in 875 mls of dry THF was added 262 ml of a 1.6M hexane solution of n-butyl lithium at −20° to −5° C. under an inert atmosphere. The mixture was stirred at 0° C. for 1 hour, room temperature for 2 hours, recooled to −78° C. and contacted with 38 mls of dry dimethylformamide. The mixture was allowed to warm to room temperature overnight, poured into water, acidified to a ph of ∼3 and ether extracted. The extract was washed with water and brine, dried over MgSO$_4$ and concentrated to give a yellow oil. The oil was dissolved in 50% ether in hexane solution and allowed to stand, giving, after filtration, 38 g of the title compound as colorless crystals, m.p. 139°–141° C.

90 MHz NMR (CDCl$_3$)δ: 7.7–7.2 (m, 3H, arom); 5.9 (br. d, J=11 Hz, 1H, CH; 4.2 (br. d, J=11 Hz, 1H, OH; and 1.5 (s, 9H, CH$_3$'s).

IR (nujol) 3440 cm−$^1$.

EXAMPLE 2

7-Chloro-1,2-benzisothiazole-1,1-dioxide

A solution of 37 g of 2-t-butyl-3-hydroxy-7-chloro-2,3-dihydro-1,2-benzisothiazole-1,1-dioxide and 0.2 g of tosic acid in 370 mls of benzene was refluxed through a Dean-Stark water separator for 16 hours, cooled in ice and filtered to give 18.9 g of the title compound as colorless crystals, m.p. 162°–164° C.

90 MHz NMR (CDCl$_3$)δ: 9.15 (s, 1H, CH); and 8.0–7.7 (m, 3H, arom).

IR (nujol) 1445, 1320, 1170 cm−1.

EXAMPLE 3

7-Chloro-2,3-dihydro-1,2-benzisothiazole-1,1-dioxide

A suspension of 17.9 g of 7-chloro-1,2-benzisothiazole-1,1-dioxide in 180 ml of absolute ethanol was cooled to 0° C. and treated with 3.33 g of sodium borohydride at such a rate that the temperature remained below 5° C. The mixture was warmed to room temperature for 30 minutes, recooled to 0° C. and contacted with glacial acetic acid to destroy excess hydride. The mixture was concentrated to dryness, the resulting solid suspended in water, filtered, washed with water and dried in vacuo at 50° C. for 16 hours to give 17.6 g of the title compound as a white powder, m.p. 159°–161° C.

90 MHz NMR (CDCl$_3$/DMSO-d$_6$)δ: 7.9–7.2 (m, 3H, arom); 6.9 (br, 1H, NH); and 4.4 (s, 2H, CH$_2$).

IR (nujol) 3220 cm−$^1$.

EXAMPLE 4

2-Pentyl-7-chloro-2,3-dihydro-1,2-benzisothiazole-1,1-dioxide

A suspension of 10.2 g of 7-chloro-2,3-dihydro-1,2-benzisothiazole-1,1-dioxide, 8.3 g of potassium carbonate and 7.7 ml of 1-iodopentane was refluxed in 50 ml of ethanol for 28 hours, cooled, concentrated and added to 200 ml of water. The mixture was extracted with n-BuCl, the extract washed with water and brine, dried over MgSO$_4$ and concentrated to give 13.3 g of an amber oil which was triturated with hexane to give 11.4 of the title compound as a tan powder, m.p. 46°–48° C.

90 MHz NMR (CDCl$_3$)$\delta$: 7.7-7.2 (m, 3H, arom); 4.3 (s, 2H, CH$_2$); 3.3 (t, 2H, CH$_3$); and 2.0-0.7 (m, 9H, alkyl).

IR (nujol) 1573, 1300, 1170, 1158 cm$^{-1}$.

EXAMPLE 5

2-Pentyl-7-(propylthio)-2,3-dihydro-1,2-benzisothiazole-1,1-dioxide

To a solution of 5.0 g of potassium-t-butoxide in 40 ml of dry dimethylformamide was added 4.0 ml of propyl mercaptan at $-5°$ to $0°$ C. under an inert atmosphere followed by 11.0 g of 2-pentyl-7-chloro-2,3-dihydro-1,2-benzisothiazole-1,1-dioxide. The mixture was stirred at room temperature for 16 hours, poured into water and extracted with n-butyl chloride. The extract was washed with water and brine, dried over MgSO$_4$ and concentrated to give 10.3 g of the title compound as a yellow oil.

60 MHz NMR (CDCl$_3$)$\delta$: 7.7-7.0 (m, 3H, arom); 4.3 (s, 2H, CH$_2$); 3.4-2.9 (m, 4H, CH$_2$); and 2.0-0.8 (m, 14H, alkyl).

IR (neat) 1582, 1455, 1300, 1170, 1155 cm$^{-1}$.

EXAMPLE 6

2-Pentyl-2,3-dihydro-1,2-benzisothiazole-7-sulfonamide-1,1-dioxide

A solution of 9.5 g of 2-pentyl-7-(propylthio-2,3-dihydro-1,2-benzisothiazole-1,1-dioxide in 40 ml of acetic acid containing 1.3 ml of water was contacted with 7.0 ml of liquified chlorine at $10°$ to $15°$ C. and allowed to warm to $25°$ C. The excess chlorine was removed via a stream of nitrogen gas and the solution was poured onto ice. The resulting solid was filtered, washed with water and hexane, dried, dissolved in CH$_2$Cl$_2$ and contacted with 2.0 ml of liquified ammonia at $-78°$ C. to $25°$ C. The mixture was added to 100 ml of 1N HCl and extracted with CH$_2$Cl$_2$. The extract was washed with water and brine, dried over MgSO$_4$, concentrated and slurried in ether to give 6.35 g of the title compound as a white powder, m.p. $156°-160°$ C.

60 MHz NMR (CDCl$_3$/DMSO-d$_6$)$\delta$: 8.2-7.6 (m, 3H, arom); 6.7 (b, 2H, NH$_2$); 4.4 (s, 2H, CH$_2$); 3.3 (t, 2H, CH$_2$); and 2.0-0.8 (m, 9H, alkyl).

IR (nujol) 3370, 3270, 1540, 1285 cm$^{-1}$.

EXAMPLE 7

N-[(4,6-Dimethoxypyrimidin-2-yl)-aminocarbonyl]-2-pentyl-2,3-dihydro-1,2-benzisothiazole-7-sulfonamide-1,1-dioxide A solution of 0.32 g of 2-pentyl-2,3-dihydro-1,2-benzisothiazole-7-sulfonamide-1,1-dioxide and 0.28 g of O-phenyl-N-(4,6-dimethoxypyrimidin-2-yl)carbamate in 5 ml of dry acetonitrile was treated with 0.15 ml of 1,8-diazabicyclo[5.4.0]undec-7-ene. The solution was stirred at $25°$ C. for 10 minutes, diluted with 10 ml of water, cooled to $0°$ C. and acidified with 1N HCl. The resulting precipitate was filtered, washed with water and ether and air dried to give 0.43 g of the title compound as a white powder, m.p. $197°-203°$ C.

200 MHz NMR (CDCl$_3$)$\delta$: 13.0 (b, 1H, NH); 8.34 (d, 1H, arom); 7.77 (t, 1H, arom); 7.64 (d, 1H, arom); 7.12 (b, 1H, NH); 5.77 (s, 1H, CH); 4.34 (s, 2H, CH$_2$); 4.00 (s, 6H, OCH$_3$'s); 3.24 (m, 2H, CH$_2$); 1.75 (m, 2H, CH$_2$); 1.36 (m, 4H, CH$_2$'s); and 0.88 (t, 3H, CH$_3$).

IR (nujol) 1730, 1710, 1610 cm$^{-1}$.

EXAMPLE 8

N-Methylisoindolin-1-thione-7-sulfonamide

A mixture of 0.68 g of N-methylisoindolin-1-one-7-sulfonamide, 0.61 g of Lawesson's reagent (2,4-bis(4-methoxyphenyl)-1,3-dithia-2,4-diphosphetane-2,4-disulfide) and 15 ml of xylene was heated to reflux under nitrogen for 24 hours. The mixture was allowed to cool, the solid products collected, and recrystallized from isopropanol (carbon) to give 0.31 g of the title compound as a yellow solid, m.p. $231°-232°$ C.

90 MHz NMR (CDCl$_3$/DMSO-d$_6$)$\delta$: 3.60 (s, 3H, NCH$_3$); 5.08 (s, 2H, CH$_2$); 7.28 (s, 2H, NH$_2$); and 7.5-8.3 (m, 3H, arom).

EXAMPLE 9

N-[(4,6-Dimethoxypyrimidin-2-yl)aminocarbonyl]-2-methylisoindolin-1-thione-7-sulfonamide To a mixture of 0.14 g of N-methylisoindolin-1-thione-7-sulfonamide and 0.16 g of N-(4,6-dimethoxypyrimidin-2-yl)-O-phenylcarbamate in 5 ml of acetonitrile was added dropwise 0.085 ml of DBU. The deep red solution was stirred for 30 minutes, diluted with 5 ml of water, acidified to pH 6 with 5% HCl, the solid collected, washed with water, washed with ether, and dried in vacuo to give 0.06 g of the title compound as a pale yellow solid, m.p. $202°-203.5°$ C.(d).

200 MHz NMR (CDCl$_3$)$\delta$: 3.61 (s, 3H, NCH$_3$); 3.96 (s, 6H, OCH$_3$'s); 5.28 (s, 2H, CH$_2$); 5.80 (s, 1H, pyrimidine C$_5$-H); 7.15 (broad s, 1H, NH); 7.6 (t, 1H); 8.1 (d, 1H); 8.3 (d, 1H); and 12.9 (broad s, 1H, NH).

IR (nujol) 1720 cm$^{-1}$.

Using the procedures of Examples 1 to 9 and the methods described herein, the following compounds of Tables I-V can be prepared.

TABLE Ia

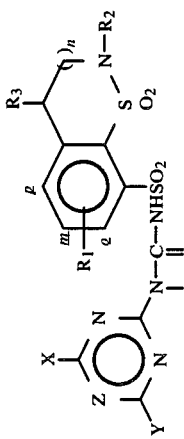

| W | n | R | R₁ | R₂ | R₃ | X | Y | Z | m.p. (°C.) |
|---|---|---|----|----|----|----|---|---|-----------|
| O | 0 | H | H | CH₂CH₂CH₂CH₂CH₃ | H | CH₃ | CH₃ | CH | 189–193 |
| O | 0 | H | H | CH₂CH₂CH₂CH₂CH₃ | H | CH₃ | OCH₃ | CH | 190–197 |
| O | 0 | H | H | CH₂CH₂CH₂CH₂CH₃ | H | OCH₃ | OCH₃ | CH | 197–203 |
| O | 0 | H | H | CH₂CH₂CH₂CH₂CH₃ | H | CH₃ | OCH₃ | N | 172–175 |
| O | 0 | H | H | CH₂CH₂CH₂CH₂CH₃ | H | Cl | OCH₃ | N | 154–158 |
| O | 0 | H | H | CH₂CH₂CH₂CH₂CH₃ | H | Br | OCH₃ | CH | 204–206 |
| O | 0 | H | H | CH₂CH₂CH(CH₃)₂ | H | CH₃ | CH₃ | CH | 204–206 |
| O | 0 | H | H | CH₂CH₂CH(CH₃)₂ | H | CH₃ | OCH₃ | CH | 202–205 |
| O | 0 | H | H | CH₂CH₂CH(CH₃)₂ | H | OCH₃ | OCH₃ | CH | 227–229 |
| O | 0 | H | H | CH₂CH₂CH(CH₃)₂ | H | CH₃ | OCH₃ | N | 176–177 |
| O | 0 | H | H | CH₂CH₂CH(CH₃)₂ | H | Cl | OCH₃ | N | 175–178 |
| O | 0 | H | H | CH₂CH₂CH(CH₃)₂ | H | Br | OCH₃ | CH | 215–218 |
| O | 0 | H | H | CH₂CH(CH₃)CH₂CH₃ | H | CH₃ | CH₃ | CH | |
| O | 0 | H | H | CH₂CH(CH₃)CH₂CH₃ | H | CH₃ | OCH₃ | CH | |
| O | 0 | H | H | CH₂CH(CH₃)CH₂CH₃ | H | OCH₃ | OCH₃ | CH | |
| O | 0 | H | H | CH₂CH(CH₃)CH₂CH₃ | H | CH₃ | OCH₃ | N | |
| O | 0 | H | H | CH₂CH(CH₃)CH₂CH₃ | H | Cl | OCH₃ | N | |
| O | 0 | H | H | CH₂CH(CH₃)CH₂CH₃ | H | Br | OCH₃ | CH | |
| O | 0 | H | H | CH(CH₃)CH₂CH₂CH₃ | H | CH₃ | CH₃ | CH | |
| O | 0 | H | H | CH(CH₃)CH₂CH₂CH₃ | H | CH₃ | OCH₃ | CH | |
| O | 0 | H | H | CH(CH₃)CH₂CH₂CH₃ | H | OCH₃ | OCH₃ | CH | |
| O | 0 | H | H | CH(CH₃)CH₂CH₂CH₃ | H | CH₃ | OCH₃ | N | |
| O | 0 | H | H | CH(CH₃)CH₂CH₂CH₃ | H | Cl | OCH₃ | N | |
| O | 0 | H | H | CH(CH₃)CH₂CH₂CH₃ | H | Br | OCH₃ | CH | |
| O | 0 | H | H | CH₂C(CH₃)₃ | H | CH₃ | CH₃ | CH | |
| O | 0 | H | H | CH₂C(CH₃)₃ | H | CH₃ | OCH₃ | CH | |
| O | 0 | H | H | CH₂Ph | H | OCH₃ | OCH₃ | CH | 194–195 |
| O | 0 | H | H | CH₂Ph | H | CH₃ | CH₃ | CH | 183–186 |
| O | 0 | H | H | CH₂Ph | H | CH₃ | OCH₃ | CH | 216–218 |
| O | 0 | H | H | CH₂Ph | H | OCH₃ | OCH₃ | CH | 180–184 |
| O | 0 | H | H | CH₂Ph | H | CH₃ | OCH₃ | N | 179–183 |
| O | 0 | H | H | CH₂Ph | H | Cl | OCH₃ | N | 205–210 |
| O | 0 | H | H | CH₂Ph | H | Br | OCH₃ | CH | |
| O | 0 | H | H | OCH₃ | H | CH₃ | CH₃ | CH | |
| O | 0 | H | H | OCH₃ | H | CH₃ | OCH₃ | CH | |
| O | 0 | H | H | OCH₂CH₃ | H | CH₃ | CH₃ | CH | |
| O | 0 | H | H | OCH₂CH₃ | H | OCH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | H | OCH₂CH₂CH₃ | H | CH₃ | OCH₃ | CH | 220-221 |
| O | 0 | H | H | OCH₂CH₂CH₃ | H | OCH₃ | OCH₃ | CH | 223-224 |
| O | 0 | H | H | OCH(CH₃)₂ | H | CH₃ | OCH₃ | CH | 210-214 |
| O | 0 | H | H | OCH(CH₃)₂ | H | OCH₃ | CH₃ | CH | 175-177 |
| O | 0 | H | H | CH₂CH=CH₂ | H | CH₃ | OCH₃ | CH | 193-195 |
| O | 0 | H | H | CH₂CH=CH₂ | H | CH₃ | OCH₃ | CH | 213-215 |
| O | 0 | H | H | CH₂CH=CH₂ | H | OCH₃ | OCH₃ | N | |
| O | 0 | H | H | CH₂CH=CH₂ | H | OCH₃ | OCH₃ | CH | 215-217 |
| O | 0 | H | H | CH₂CH=CH₂ | H | Cl | OCH₃ | CH | 219-222 |
| O | 0 | H | H | CH₂CH=CH₂ | H | Br | OCH₃ | CH | |
| O | 0 | H | H | CH₂CH=CHCH₃ | H | CH₃ | CH₃ | N | |
| O | 0 | H | H | CH₂CH=CHCH₃ | H | CH₃ | OCH₃ | CH | 216-218 |
| O | 0 | H | H | CH₂CH=CHCH₃ | H | OCH₃ | OCH₃ | CH | |
| O | 0 | H | H | CH₂CH=CHCH₃ | H | CH₃ | OCH₃ | N | |
| O | 0 | H | H | CH₂CH=CHCH₃ | H | Cl | OCH₃ | N | |
| O | 0 | H | H | CH₂CH=CHCH₃ | H | Br | OCH₃ | CH | |
| O | 0 | H | H | CH₂C(CH₃)=CH₂ | H | CH₃ | OCH₃ | CH | |
| O | 0 | H | H | CH₂C(CH₃)=CH₂ | H | CH₃ | CH₃ | CH | 202-204(d) |
| O | 0 | H | H | CH₂C(CH₃)=CH₂ | H | OCH₃ | OCH₃ | CH | 198-200(d) |
| O | 0 | H | H | CH₂C(CH₃)=CH₂ | H | CH₃ | OCH₃ | CH | 201.5-204(d) |
| O | 0 | H | H | CH₂C(CH₃)=CH₂ | H | Cl | OCH₃ | CH | |
| O | 0 | H | H | CH₂C(CH₃)=CH₂ | H | Br | OCH₃ | N | |
| O | 0 | H | H | CH₂C(CH₃)=CH₂ | H | CH₃ | OCH₃ | CH | 208-210(d) |
| O | 0 | H | H | CH(CH₃)CH=CH₂ | H | OCH₃ | OCH₃ | CH | |
| O | 0 | H | H | CH(CH₃)CH=CH₂ | H | CH₃ | CH₃ | CH | |
| O | 0 | H | H | CH₂CH₂CH=CH₂ | H | CH₃ | OCH₃ | CH | |
| O | 0 | H | H | CH₂CH₂CH=CH₂ | H | OCH₃ | OCH₃ | CH | |
| O | 0 | H | H | CH₂CH₂CH=CH₂ | H | CH₃ | OCH₃ | N | |
| O | 0 | H | H | CH₂CH₂CH=CH₂ | H | Cl | OCH₃ | CH | |
| O | 0 | H | H | CH₂CH₂CH=CH₂ | H | Br | OCH₃ | CH | |
| O | 0 | H | H | CH₂C(Cl)=CH₂ | H | CH₃ | OCH₃ | CH | 216-217 |
| O | 0 | H | H | CH₂C(Cl)=CH₂ | H | CH₃ | OCH₃ | CH | 215-216 |
| O | 0 | H | H | CH₂C(Cl)=CH₂ | H | OCH₃ | OCH₃ | CH | 217-218 |
| O | 0 | H | H | CH₂C(Cl)=CH₂ | H | Cl | OCH₃ | N | |
| O | 0 | H | H | CH₂C(Cl)=CH₂ | H | OCH₃ | OCH₃ | N | |
| O | 0 | H | H | CH₂CH=CH—CH₂Cl | H | CH₃ | OCH₃ | CH | |

TABLE Ia-continued

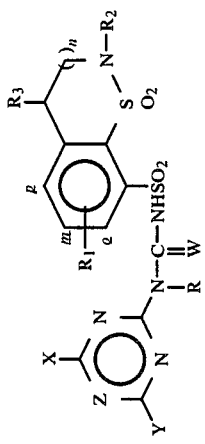

| W | n | R | R₁ | R₂ | R₃ | X | Y | Z | m.p. (°C.) |
|---|---|---|----|----|----|---|---|---|-----------|
| O | O | H | H | CH₂CH=CH—CH₂Cl | H | OCH₃ | OCH₃ | CH | |
| O | O | H | H | CH₂C(F)=CHF | H | CH₃ | OCH₃ | CH | |
| O | O | H | H | CH₂C(F)=CHF | H | OCH₃ | OCH₃ | CH | |
| O | O | H | H | CH₂C≡CH | H | CH₃ | OCH₃ | CH | 211-213 |
| O | O | H | H | CH₂C≡CH | H | OCH₃ | OCH₃ | CH | 194-196 |
| O | O | H | H | CH₂C≡C—CH₃ | H | CH₃ | OCH₃ | CH | |
| O | O | H | H | CH₂C≡C—CH₃ | H | OCH₃ | OCH₃ | CH | |
| O | O | H | H | CH₂CH₂C≡CH | H | CH₃ | OCH₃ | CH | |
| O | O | H | H | CH₂CH₂C≡CH | H | OCH₃ | OCH₃ | CH | |
| O | O | H | H | CH(CH₃)C≡CH | H | CH₃ | OCH₃ | CH | |
| O | O | H | H | CH(CH₃)C≡CH | H | OCH₃ | OCH₃ | CH | |
| O | O | H | H | CH₂C≡CCH₂Cl | H | CH₃ | OCH₃ | CH | |
| O | O | H | H | CH₂C≡CCH₂Cl | H | OCH₃ | OCH₃ | CH | |
| O | O | H | H | CH₂C≡CCH₂OH | H | CH₃ | OCH₃ | CH | |
| O | O | H | H | CH₂C≡CCH₂OH | H | OCH₃ | OCH₃ | CH | |
| O | O | H | H | CF₂H | H | CH₃ | CH₃ | CH | |
| O | O | H | H | CF₂H | H | CH₃ | OCH₃ | CH | |
| O | O | H | H | CF₂H | H | OCH₃ | OCH₃ | CH | |
| O | O | H | H | CF₂H | H | OCH₃ | OCH₃ | N | |
| O | O | H | H | CF₂H | H | Cl | OCH₃ | CH | |
| O | O | H | H | CF₂H | H | Br | OCH₃ | CH | |
| O | O | H | H | CF₂CF₂H | H | CH₃ | OCH₃ | CH | 215-216 |
| O | O | H | H | CF₂CF₂H | H | OCH₃ | OCH₃ | CH | 218-219 |
| O | O | H | H | CH₂CF₃ | H | CH₃ | CH₃ | CH | 198-199 |
| O | O | H | H | CH₂CF₃ | H | CH₃ | OCH₃ | CH | 168-170 |
| O | O | H | H | CH₂CF₃ | H | OCH₃ | OCH₃ | CH | 158-163 |
| O | O | H | H | CH₂CF₃ | H | OCH₃ | OCH₃ | N | 211-213 |
| O | O | H | H | CH₂CF₃ | H | Cl | OCH₃ | CH | |
| O | O | H | H | CH₂CF₃ | H | Br | OCH₃ | CH | |
| O | O | H | H | CH₂CH₂F | H | CH₃ | CH₃ | CH | 214-215 |
| O | O | H | H | CH₂CH₂F | H | CH₃ | OCH₃ | CH | 218-219 |
| O | O | H | H | CH₂CH₂F | H | OCH₃ | OCH₃ | CH | 212-214 |
| O | O | H | H | CH₂CH₂F | H | OCH₃ | OCH₃ | N | 190-192 |
| O | O | H | H | CH₂CH₂F | H | Cl | OCH₃ | CH | 195-196 |
| O | O | H | H | CH₂CH₂F | H | Br | OCH₃ | CH | 215-217 |
| O | O | H | H | CH₂CH₂Cl | H | CH₃ | CH₃ | CH | 204-205 |
| O | O | H | H | CH₂CH₂Cl | H | CH₃ | OCH₃ | CH | 216-217 |
| O | O | H | H | CH₂CH₂Cl | H | OCH₃ | OCH₃ | CH | 206-208 |

TABLE Ia-continued

| W | n | R | R1 | R2 | R3 | X | Y | Z | m.p. (°C.) |
|---|---|---|----|----|----|---|---|---|------------|
| O | 0 | H | H | CH2CH2Cl | H | CH3 | OCH3 | N | 127-128 |
| O | 0 | H | H | CH2CH2Cl | H | OCH3 | OCH3 | N | 132-133 |
| O | 0 | H | H | CH2CH2Cl | H | Cl | OCH3 | CH | 219-220 |
| O | 0 | H | H | CH2CH2Cl | H | Br | CH3 | CH | 215-216 |
| O | 0 | H | H | CH2CH2Br | H | CH3 | OCH3 | CH | 211-212 |
| O | 0 | H | H | CH2CH2Br | H | CH3 | OCH3 | CH | 210-212 |
| O | 0 | H | H | CH2CH2Br | H | OCH3 | OCH3 | N | 168-171 |
| O | 0 | H | H | CH2CH2Br | H | OCH3 | OCH3 | CH | 121-123 |
| O | 0 | H | H | CH2CH2Br | H | Cl | OCH3 | CH | 222-224 |
| O | 0 | H | H | CH2CH2Br | H | Br | OCH3 | CH | |
| O | 0 | H | H | CH2CH(Cl)CH2Cl | H | CH3 | OCH3 | CH | |
| O | 0 | H | H | CH2CH(Cl)CH2Cl | H | OCH3 | OCH3 | CH | |
| O | 0 | H | H | CH2CH(Br)CH2Br | H | CH3 | OCH3 | CH | |
| O | 0 | H | H | CH2CH(Br)CH2Br | H | OCH3 | OCH3 | CH | |
| O | 0 | H | H | CH2CCl3 | H | CH3 | OCH3 | CH | 228-230 |
| O | 0 | H | H | CH2CCl3 | H | OCH3 | OCH3 | CH | 234-236 |
| O | 0 | H | H | CH2CH(OH)CH3 | H | CH3 | OCH3 | CH | 228-230 |
| O | 0 | H | H | CH2CH(OH)CH3 | H | OCH3 | OCH3 | CH | 189-193 |
| O | 0 | H | H | CH2CH2CH2OH | H | CH3 | CH3 | CH | 173-176 |
| O | 0 | H | H | CH2CH2CH2OH | H | OCH3 | OCH3 | CH | 199-203 |
| O | 0 | H | H | CH2CN | H | CH3 | OCH3 | CH | 231-235 |
| O | 0 | H | H | CH2CN | H | OCH3 | OCH3 | CH | |
| O | 0 | H | H | CH2CH2CN | H | CH3 | OCH3 | CH | |
| O | 0 | H | H | CH2CH2CN | H | CH3 | OCH3 | CH | |
| O | 0 | H | H | CH2CH2CN | H | OCH3 | OCH3 | CH | |
| O | 0 | H | H | CH2CH2CN | H | Cl | OCH3 | CH | |
| O | 0 | H | H | CH2CH2CN | H | Br | OCH3 | CH | |
| O | 0 | H | H | CH2CH(CH3)CN | H | CH3 | CH3 | CH | 185-187 |
| O | 0 | H | H | CH2CH(CH3)CN | H | OCH3 | OCH3 | CH | 184-186 |
| O | 0 | H | H | CH2CH2CH2CN | H | CH3 | OCH3 | CH | |
| O | 0 | H | H | CH2OCH3 | H | CH3 | OCH3 | CH | 171-175 |
| O | 0 | H | H | CH2OCH3 | H | OCH3 | OCH3 | N | 194-197 |
| O | 0 | H | H | CH2CH2OCH3 | H | CH3 | OCH3 | N | |
| O | 0 | H | H | CH2CH2OCH3 | H | CH3 | OCH3 | | |
| O | 0 | H | H | CH2CH2OCH3 | H | OCH3 | OCH3 | | |

TABLE Ia-continued

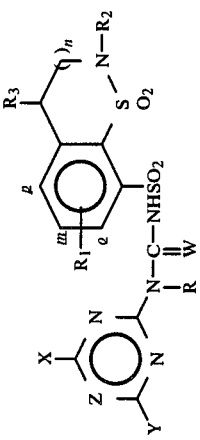

| W | n | R | R₁ | R₂ | R₃ | X | Y | Z | m.p. (°C.) |
|---|---|---|----|----|----|---|---|---|------------|
| O | 0 | H | H | CH₂CH₂OCH₃ | H | Cl | OCH₃ | CH | |
| O | 0 | H | H | CH₂CH₂OCH₃ | H | Br | OCH₃ | CH | |
| O | 0 | H | H | CH₂CH₂OCH₃ | H | CH₃ | OCH₃ | CH | 195–198 |
| O | 0 | H | H | CH₂CH₂OCH₃ | H | OCH₃ | OCH₃ | CH | 193–194 |
| O | 0 | H | H | CH₂CH₂OCH₃ | H | CH₃ | CH₃ | CH | 203–204 |
| O | 0 | H | H | CH₂CH₂OCH₃ | H | CH₃ | OCH₃ | CH | 193–195 |
| O | 0 | H | H | CH₂CH₂OCH₃ | H | CH₃ | OCH₃ | N | 187–189 |
| O | 0 | H | H | CH₂CH₂OCH₃ | H | OCH₃ | OCH₃ | CH | 193–197 |
| O | 0 | H | H | CH₂CH₂OCH₃ | H | Cl | OCH₃ | CH | |
| O | 0 | H | H | CH₂CH(OCH₃)₂ | H | Br | OCH₃ | CH | |
| O | 0 | H | H | CH₂CH(OCH₃)₂ | H | CH₃ | CH₃ | CH | |
| O | 0 | H | H | CH₂CH(OCH₃)₂ | H | CH₃ | OCH₃ | CH | |
| O | 0 | H | H | CH₂CH(OCH₃)₂ | H | OCH₃ | OCH₃ | CH | |
| O | 0 | H | H | CH₂CH(OCH₃)₂ | H | CH₃ | OCH₃ | N | |
| O | 0 | H | H | CH₂CH(OCH₃)₂ | H | OCH₃ | OCH₃ | N | |
| O | 0 | H | H | CH₂CH(OCH₂CH₃)₂ | H | Cl | OCH₃ | CH | |
| O | 0 | H | H | CH₂CH(OCH₂CH₃)₂ | H | Br | OCH₃ | CH | |
| O | 0 | H | H | CH₂CH(OCH₂CH₃)₂ | H | CH₃ | CH₃ | CH | |
| O | 0 | H | H | CH₂CH(OCH₂CH₃)₂ | H | CH₃ | OCH₃ | CH | |
| O | 0 | H | H | CH₂CH(OCH₂CH₃)₂ | H | OCH₃ | OCH₃ | CH | |
| O | 0 | H | H | CH₂CH(OCH₂CH₃)₂ | H | CH₃ | OCH₃ | N | |
| O | 0 | H | H | CH₂CH(OCH₂CH₃)₂ | H | OCH₃ | OCH₃ | N | |
| O | 0 | H | H | CH₂CH(CH₃)OCH₃ | H | Cl | OCH₃ | CH | |
| O | 0 | H | H | CH₂CH(CH₃)OCH₃ | H | Br | OCH₃ | CH | |
| O | 0 | H | H | CH₂CH(CH₃)OCH₃ | H | CH₃ | CH₃ | CH | |
| O | 0 | H | H | CH₂CH(CH₃)OCH₃ | H | CH₃ | OCH₃ | CH | |
| O | 0 | H | H | CH₂CH(CH₃)OCH₃ | H | OCH₃ | OCH₃ | CH | |
| O | 0 | H | H | CH₂CH(CH₃)OCH₃ | H | CH₃ | OCH₃ | N | |
| O | 0 | H | H | CH₂CH(CH₃)OCH₃ | H | OCH₃ | OCH₃ | N | |
| O | 0 | H | H | CH₂CH(CH₃)CH₂OCH₃ | H | Cl | OCH₃ | CH | |
| O | 0 | H | H | CH₂CH(CH₃)CH₂OCH₃ | H | Br | OCH₃ | CH | |
| O | 0 | H | H | CH₂CH(CH₃)CH₂OCH₃ | H | CH₃ | CH₃ | CH | |
| O | 0 | H | H | CH₂SCH₃ | H | CH₃ | OCH₃ | CH | 189–190 |
| O | 0 | H | H | CH₂SCH₃ | H | OCH₃ | OCH₃ | CH | 192–193 |
| O | 0 | H | H | CH₂CH₂SCH₃ | H | CH₃ | CH₃ | CH | 200–201 |
| O | 0 | H | H | CH₂CH₂SCH₃ | H | CH₃ | OCH₃ | CH | 163–164 |
| O | 0 | H | H | CH₂CH₂SCH₃ | H | CH₃ | OCH₃ | N | 168–169 |
| O | 0 | H | H | CH₂CH₂SCH₃ | H | OCH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | O | H | H | CH₂CH₂SCH₃ | H | Cl | OCH₃ | CH | 210-211 |
| O | O | H | H | CH₂CH₂SCH₃ | H | Br | OCH₃ | CH | |
| O | O | H | H | CH₂CH₂SCH₂CH₃ | H | CH₃ | OCH₃ | CH | 175-180 |
| O | O | H | H | CH₂CH₂SCH₂CH₃ | H | OCH₃ | OCH₃ | CH | 178-184 |
| O | O | H | H | CH₂CH₂SO₂CH₂CH₃ | H | CH₃ | OCH₃ | CH | 188-192 |
| O | O | H | H | CH₂CH₂SO₂CH₂CH₃ | H | OCH₃ | OCH₃ | CH | 161-164 |
| O | O | H | H | CH₂CO₂CH₃ | H | CH₃ | CH₃ | CH | 128-130 |
| O | O | H | H | CH₂CO₂CH₃ | H | CH₃ | OCH₃ | CH | |
| O | O | H | H | CH₂CO₂CH₃ | H | OCH₃ | OCH₃ | CH | |
| O | O | H | H | CH₂CO₂CH₃ | H | CH₃ | OCH₃ | N | |
| O | O | H | H | CH₂CO₂CH₃ | H | OCH₃ | OCH₃ | N | |
| O | O | H | H | CH₂CO₂CH₃ | H | Cl | OCH₃ | CH | 179-180 |
| O | O | H | H | CH₂CO₂CH₃ | H | Br | OCH₃ | CH | 173-176 |
| O | O | H | H | CH₂CO₂CH₂CH₃ | H | CH₃ | OCH₃ | CH | 214-218 |
| O | O | H | H | CH₂CO₂CH₂CH₃ | H | OCH₃ | OCH₃ | CH | 215-217 |
| O | O | H | H | CH₂CH₂CO₂CH₃ | H | CH₃ | OCH₃ | CH | |
| O | O | H | H | CH₂CH₂CO₂CH₃ | H | OCH₃ | OCH₃ | CH | |
| O | O | H | H | CH₂CH(CH₃)CO₂CH₃ | H | CH₃ | OCH₃ | CH | |
| O | O | H | H | CH₂CH(CH₃)CO₂CH₃ | H | OCH₃ | OCH₃ | CH | |
| O | O | H | H | CH₂CH₂N(CH₃)₂ | H | CH₃ | OCH₃ | CH | 195-197 |
| O | O | H | H | CH₂CH₂N(CH₃)₂ | H | OCH₃ | OCH₃ | CH | 196-198 |
| O | O | H | H | CH₂N(CH₃)₂ | H | CH₃ | OCH₃ | CH | 223-224 |
| O | O | H | H | CH₂N(CH₃)₂ | H | OCH₃ | OCH₃ | CH | 191-193 |
| O | O | H | H | CH₂CH₂N(CH₃)CH₂CH₃ | H | CH₃ | OCH₃ | CH | 205-206 |
| O | O | H | H | CH₂CH₂N(CH₃)CH₂CH₃ | H | OCH₃ | OCH₃ | CH | 160-161 |
| O | O | H | H | CH₂N(CH₂CH₃)₂ | H | CH₃ | OCH₃ | CH | 205-206 |
| O | O | H | H | CH₂N(CH₂CH₃)₂ | H | OCH₃ | OCH₃ | CH | 198-199 |
| O | O | H | H | CH₂Si(CH₃)₃ | H | CH₃ | OCH₃ | CH | |
| O | O | H | H | CH₂Si(CH₃)₃ | H | OCH₃ | OCH₃ | CH | |
| O | O | H | H | C(=O)CH₃ | H | CH₃ | OCH₃ | CH | |
| O | O | H | H | C(=O)CH₃ | H | OCH₃ | OCH₃ | CH | |
| O | O | H | H | C(=O)CH₂CH₃ | H | CH₃ | OCH₃ | CH | |
| O | O | H | H | C(=O)CH₂CH₃ | H | OCH₃ | OCH₃ | CH | |
| O | O | H | H | C(=O)CH₂CH₂CH₃ | H | CH₃ | OCH₃ | CH | |
| O | O | H | H | C(=O)CH₂CH₂CH₃ | H | OCH₃ | OCH₃ | CH | |
| O | O | H | H | SO₂CH₃ | H | CH₃ | OCH₃ | CH | |
| O | O | H | H | SO₂CH₃ | H | OCH₃ | OCH₃ | CH | |
| O | O | H | H | SO₂CH₂CH₂CH₃ | H | CH₃ | OCH₃ | CH | |
| O | O | H | H | SO₂CH₂CH₂CH₃ | H | OCH₃ | OCH₃ | CH | |
| O | O | H | H | cyclopropyl | H | CH₃ | OCH₃ | CH | |
| O | O | H | H | cyclopropyl | H | OCH₃ | OCH₃ | CH | |

TABLE Ia-continued

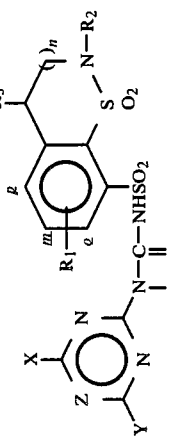

| W | n | R | R₁ | R₂ | R₃ | X | Y | Z | m.p. (°C.) |
|---|---|---|---|---|---|---|---|---|---|
| O | 0 | H | H | cyclopropyl | H | CH₃ | OCH₃ | N | 168-170 |
| O | 0 | H | H | cyclopentyl | H | CH₃ | OCH₃ | CH | 186-189 |
| O | 0 | H | H | cyclopentyl | H | OCH₃ | OCH₃ | CH | 182-183 |
| O | 0 | H | H | cyclopentyl | H | CH₃ | OCH₃ | N | 233-235 |
| O | 0 | H | H | cyclopentyl | H | Cl | OCH₃ | CH | 222-224 |
| O | 0 | H | H | cyclohexyl | H | OCH₃ | OCH₃ | CH | 224-227 |
| O | 0 | H | H | cyclohexyl | H | CH₃ | CH₃ | CH | 222°d |
| O | 0 | H | H | CH₂—cyclopropyl | H | CH₃ | OCH₃ | CH | 166-169 |
| O | 0 | H | H | CH₂—cyclopropyl | H | OCH₃ | OCH₃ | CH | 221-223 |
| O | 0 | H | H | CH₂—cyclopropyl | H | CH₃ | OCH₃ | N | 193-196 |
| O | 0 | H | H | CH₂—cyclopropyl | H | Cl | OCH₃ | CH | 204-206 |
| O | 0 | H | H | CH₂—cyclopropyl | H | Cl | OCH₃ | CH | 215-217 |
| O | 0 | H | H | CH₂—cyclopropyl | H | Br | CH₃ | CH | |
| O | 0 | H | H | CH₂—cyclopentyl | H | CH₃ | OCH₃ | CH | 195-198 |
| O | 0 | H | H | CH₂—cyclopentyl | H | CH₃ | OCH₃ | CH | 148-150 |
| O | 0 | H | H | CH₂—cyclopentyl | H | OCH₃ | OCH₃ | CH | 201-204 |
| O | 0 | H | H | CH₂—cyclopentyl | H | CH₃ | OCH₃ | CH | 188-191 |
| O | 0 | H | H | CH₂—cyclopentyl | H | Cl | OCH₃ | N | 168-170 |
| O | 0 | H | H | CH₂—cyclopentyl | H | Cl | OCH₃ | N | 175-178 |
| O | 0 | H | H | CH₂—cyclopentyl | H | Br | OCH₃ | N | 161-164 |
| O | 0 | H | H | CH₂—cyclohexyl | H | CH₃ | CH₃ | CH | |
| O | 0 | H | H | CH₂—cyclohexyl | H | CH₃ | OCH₃ | CH | |
| O | 0 | H | H | CH₂—cyclohexyl | H | OCH₃ | OCH₃ | CH | |
| O | 0 | H | H | ![CH₂—cyclopropyl-O] | H | CH₃ | OCH₃ | CH | |
| O | 0 | H | H | ![CH₂—cyclopropyl-O] | H | OCH₃ | OCH₃ | CH | |
| O | 0 | H | H | CH₂CHCl₂ | H | CH₃ | OCH₃ | CH | 194-197 |
| O | 0 | H | H | CH₂CHCl₂ | H | CH₃ | OCH₃ | CH | 176-183 |
| O | 0 | H | H | CH₂CH₂CH₂Cl | H | CH₃ | CH₃ | CH | 201-203 |
| O | 0 | H | H | CH₂CH₂CH₂Cl | H | CH₃ | OCH₃ | CH | 181-183 |
| O | 0 | H | H | CH₂CH₂CH₂Cl | H | OCH₃ | OCH₃ | CH | |
| O | 0 | H | H | CH₂CH₂CH₂Cl | H | CH₃ | OCH₃ | N | |

TABLE Ia-continued

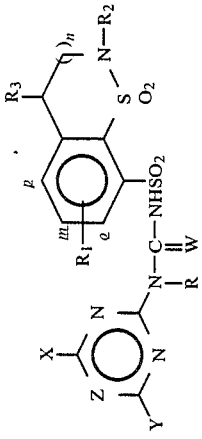

| W | n | R | R₁ | R₂ | R₃ | X | Y | Z | m.p. (°C.) |
|---|---|---|---|---|---|---|---|---|---|
| O | 0 | H | H | CH₂CH₂CH₂Cl | H | OCH₃ | OCH₃ | N | 176-178 |
| O | 0 | H | H | CH₂CH₂CH₂Cl | H | Cl | OCH₃ | CH | 186-188 |
| O | 0 | H | H | CH₂CH₂CH₂Cl | H | Br | OCH₃ | CH | |
| O | 0 | H | H | CH₂CH₂CH₂Br | H | CH₃ | CH₃ | CH | |
| O | 0 | H | H | CH₂CH₂CH₂Br | H | OCH₃ | OCH₃ | CH | |
| O | 0 | H | H | CH₂CH₂CH₂Br | H | CH₃ | OCH₃ | CH | |
| O | 0 | H | H | CH₂CH₂CH₂Br | H | Cl | OCH₃ | CH | |
| O | 0 | H | H | CH₂CH₂CH₂Br | H | OCH₃ | OCH₃ | N | |
| O | 0 | H | H | CH₂CH₂CH₂Br | H | Cl | OCH₃ | N | |
| O | 0 | H | H | CH₂CH₂CH₂Br | H | Br | OCH₃ | CH | |
| O | 0 | H | H | CH₂CH(Cl)CH₃ | H | CH₃ | OCH₃ | CH | |
| O | 0 | H | H | CH₂CH(Cl)CH₃ | H | OCH₃ | OCH₃ | CH | |
| O | 0 | H | H | CH₂Cl | H | CH₃ | CH₃ | CH | |
| O | 0 | H | H | CH₂Cl | H | CH₃ | OCH₃ | CH | |
| O | 0 | H | H | CH₂Cl | H | OCH₃ | OCH₃ | CH | |
| O | 0 | H | H | CH₂Cl | H | Cl | OCH₃ | CH | |
| O | 0 | H | H | CH₂Cl | H | Br | OCH₃ | CH | |
| O | 0 | H | H | CH₂CH₂OCH₃ | H | CH₃ | OCH₃ | CH | |
| O | 0 | H | H | CH₂CH₂OCH₃ | H | OCH₃ | OCH₃ | CH | |
| O | 0 | H | H | CH₂CH₂CH₂Cl | H | OCH₃ | OCH₃ | CH | |
| O | 0 | H | m-F | CH₂CH(CH₃)CH₂CH₃ | H | CH₃ | OCH₃ | CH | |
| O | 0 | H | m-F | CH₂CH(CH₃)CH₂CH₃ | H | OCH₃ | OCH₃ | CH | |
| O | 0 | H | m-F | CH₂CH₂OCH₃ | H | CH₃ | OCH₃ | CH | |
| O | 0 | H | m-F | CH₂CH₂OCH₃ | H | OCH₃ | OCH₃ | CH | |
| O | 0 | H | m-F | CH₂CH₂Cl | H | CH₃ | OCH₃ | CH | |
| O | 0 | H | m-F | CH₂CH₂Cl | H | OCH₃ | OCH₃ | CH | |
| O | 0 | H | m-Cl | CH₂CH(CH₃)CH₂CH₃ | H | CH₃ | OCH₃ | CH | |
| O | 0 | H | m-Cl | CH₂CH(CH₃)CH₂CH₃ | H | OCH₃ | OCH₃ | CH | |
| O | 0 | H | m-Cl | CH₂CH₂OCH₃ | H | CH₃ | OCH₃ | CH | |
| O | 0 | H | m-Cl | CH₂CH₂OCH₃ | H | OCH₃ | OCH₃ | CH | |
| O | 0 | H | m-Cl | CH₂CH₂Cl | H | CH₃ | OCH₃ | CH | |
| O | 0 | H | m-Cl | CH₂CH₂Cl | H | OCH₃ | OCH₃ | CH | |
| O | 0 | H | m-CH₃ | CH₂CH(CH₃)CH₂CH₃ | H | CH₃ | OCH₃ | CH | 163-171 |
| O | 0 | H | m-CH₃ | CH₂CH(CH₃)CH₂CH₃ | H | OCH₃ | OCH₃ | CH | 171-176 |
| O | 0 | H | m-CH₃ | CH₂CH₂OCH₃ | H | CH₃ | OCH₃ | CH | |
| O | 0 | H | m-CH₃ | CH₂CH₂OCH₃ | H | OCH₃ | OCH₃ | CH | |
| O | 0 | H | m-CH₃ | CH₂CH₂Cl | H | CH₃ | OCH₃ | CH | |
| O | 0 | H | m-CH₃ | CH₂CH₂Cl | H | OCH₃ | OCH₃ | CH | |
| O | 0 | H | m-OCH₃ | CH₂CH(CH₃)CH₂CH₃ | H | CH₃ | OCH₃ | CH | |
| O | 0 | H | m-OCH₃ | CH₂CH(CH₃)CH₂CH₃ | H | OCH₃ | OCH₃ | CH | |
| O | 0 | H | m-OCH₃ | CH₂CH₂OCH₃ | H | CH₃ | OCH₃ | CH | |
| O | 0 | H | m-OCH₃ | CH₂CH₂OCH₃ | H | OCH₃ | OCH₃ | CH | |
| O | 0 | H | m-OCH₃ | CH₂CH₂Cl | H | CH₃ | OCH₃ | CH | |
| O | 0 | H | m-OCH₃ | CH₂CH₂Cl | H | OCH₃ | OCH₃ | CH | |

TABLE Ia-continued

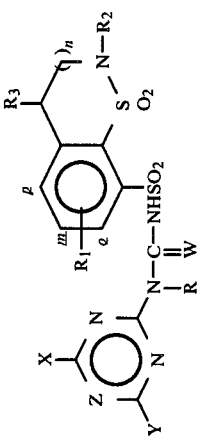

| W | n | R | R₁ | R₂ | R₃ | X | Y | Z | m.p. (°C.) |
|---|---|---|---|---|---|---|---|---|---|
| O | 0 | H | m-OCH₃ | CH₂CH(CH₃)CH₂CH₃ | H | CH₃ | OCH₃ | CH | |
| O | 0 | H | m-OCH₃ | CH₂CH(CH₃)CH₂CH₃ | H | OCH₃ | OCH₃ | CH | |
| O | 0 | H | m-CF₃ | CH₂CH₂OCH₃ | H | CH₃ | OCH₃ | CH | |
| O | 0 | H | m-CF₃ | CH₂CH₂OCH₃ | H | OCH₃ | OCH₃ | CH | |
| O | 0 | H | m-CF₃ | CH₂CH₂CH₃ | H | CH₃ | OCH₃ | CH | |
| O | 0 | H | m-CF₃ | CH₂CH₂Cl | H | OCH₃ | OCH₃ | CH | |
| O | 0 | H | m-Br | CH₂Cl | H | CH₃ | OCH₃ | CH | |
| O | 0 | H | m-CH₂CH₃ | CH₂Cl | H | OCH₃ | OCH₃ | CH | |
| O | 0 | H | m-OCH₂CH₃ | CH₂Cl | H | OCH₃ | OCH₃ | CH | |
| O | 0 | H | m-OCF₂H | CH₂Cl | H | OCH₃ | OCH₃ | CH | |
| O | 0 | H | m-SCH₃ | CH₂Cl | H | OCH₃ | OCH₃ | CH | |
| O | 0 | H | o-F | CH₂Cl | H | OCH₃ | OCH₃ | CH | |
| O | 0 | H | o-Cl | CH₂Cl | H | OCH₃ | OCH₃ | CH | |
| O | 0 | H | o-Br | CH₂Cl | H | OCH₃ | OCH₃ | CH | |
| O | 0 | H | o-CH₃ | CH₂Cl | H | OCH₃ | OCH₃ | CH | |
| O | 0 | H | o-CH₂CH₃ | CH₂Cl | H | OCH₃ | OCH₃ | CH | |
| O | 0 | H | o-OCH₃ | CH₂Cl | H | OCH₃ | OCH₃ | CH | |
| O | 0 | H | o-OCH₂CH₃ | CH₂Cl | H | OCH₃ | OCH₃ | CH | |
| O | 0 | H | o-CF₃ | CH₂Cl | H | OCH₃ | OCH₃ | CH | |
| O | 0 | H | o-OCF₂H | CH₂Cl | H | OCH₃ | OCH₃ | CH | |
| O | 0 | H | o-SCH₃ | CH₂Cl | H | OCH₃ | OCH₃ | CH | |
| O | 0 | H | m-CH₂CH₃ | CH₃ | H | CH₃ | CH₃ | CH | |
| O | 0 | H | m-CH₂CH₃ | CH₃ | H | OCH₃ | OCH₃ | CH | |
| O | 0 | H | m-CH₂CH₃ | CH₃ | H | OCH₃ | CH₃ | CH | |
| O | 0 | H | m-CH₂CH₃ | CH₃ | H | Cl | OCH₃ | CH | |
| O | 0 | H | m-CH₂CH₃ | CH₃ | H | Br | OCH₃ | CH | |
| O | 0 | H | m-CH₂CH₃ | CH₃ | H | CH₃ | OCH₃ | N | |
| O | 0 | H | m-CH₂CH₃ | CH₃ | H | OCH₃ | OCH₃ | N | |
| O | 0 | H | m-CH₂CH₃ | CH₂CH₃ | H | CH₃ | OCH₃ | N | |
| O | 0 | H | m-CH₂CH₃ | CH₂CH₃ | H | CH₃ | OCH₃ | CH | |
| O | 0 | H | m-CH₂CH₃ | CH₂CH₃ | H | OCH₃ | OCH₃ | CH | |
| O | 0 | H | m-CH₂CH₃ | CH₂CH₂CH₃ | H | CH₃ | OCH₃ | CH | |
| O | 0 | H | m-CH₂CH₃ | CH₂CH₂CH₃ | H | OCH₃ | OCH₃ | CH | |
| O | 0 | H | m-CH₂CH₃ | CH₂CH₂CH₂CH₃ | H | CH₃ | OCH₃ | CH | |
| O | 0 | H | m-CH₂CH₃ | CH(CH₃)₂ | H | CH₃ | OCH₃ | CH | |
| O | 0 | H | m-CH₂CH₃ | CH(CH₃)₂ | H | OCH₃ | OCH₃ | CH | |
| O | 0 | H | m-CH₂CH₃ | CH₂CH(CH₃)₂ | H | CH₃ | OCH₃ | CH | |
| O | 0 | H | m-OCH₂CH₃ | CH₃ | H | CH₃ | CH₃ | CH | |

TABLE Ia-continued

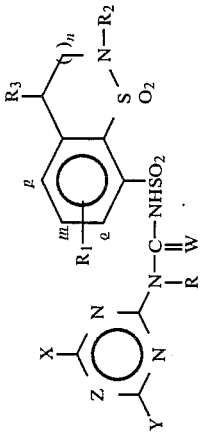

| W | n | R | R₁ | R₂ | R₃ | X | Y | Z | m.p. (°C.) |
|---|---|---|---|---|---|---|---|---|---|
| O | 0 | H | m-OCH₂CH₃ | CH₃ | H | CH₃ | OCH₃ | CH | |
| O | 0 | H | m-OCH₂CH₃ | CH₃ | H | OCH₃ | OCH₃ | CH | |
| O | 0 | H | m-OCH₂CH₃ | CH₃ | H | CH₃ | CH₃ | N | |
| O | 0 | H | m-OCH₂CH₃ | CH₃ | H | OCH₃ | OCH₃ | N | |
| O | 0 | H | m-OCH₂CH₃ | CH₃ | H | Cl | OCH₃ | N | |
| O | 0 | H | m-OCH₂CH₃ | CH₃ | H | Br | OCH₃ | CH | |
| O | 0 | H | m-OCH₂CH₃ | CH₂CH₃ | H | CH₃ | CH₃ | CH | |
| O | 0 | H | m-OCH₂CH₃ | CH₂CH₃ | H | CH₃ | OCH₃ | CH | |
| O | 0 | H | m-OCH₂CH₃ | CH₂CH₃ | H | OCH₃ | OCH₃ | CH | |
| O | 0 | H | m-OCH₂CH₃ | CH₂CH₃ | H | CH₃ | CH₃ | N | |
| O | 0 | H | m-OCH₂CH₃ | CH₂CH₃ | H | OCH₃ | OCH₃ | N | |
| O | 0 | H | m-OCH₂CH₃ | CH₂CH₃ | H | Cl | OCH₃ | N | |
| O | 0 | H | m-OCH₂CH₃ | CH₂CH₃ | H | Br | OCH₃ | CH | |
| O | 0 | H | m-OCH₂CH₃ | CH₂CH₂CH₃ | H | CH₃ | OCH₃ | CH | |
| O | 0 | H | m-OCH₂CH₃ | CH₂CH₂CH₃ | H | OCH₃ | OCH₃ | CH | |
| O | 0 | H | m-OCH₂CH₃ | CH₂CH₂CH₃ | H | CH₃ | OCH₃ | CH | |
| O | 0 | H | m-OCH₂CH₃ | CH₂CH(CH₃)₂ | H | CH₃ | OCH₃ | CH | |
| O | 0 | H | m-OCH₂CH₃ | CH₂CH(CH₃)₂ | H | OCH₃ | OCH₃ | CH | |
| O | 0 | H | m-OCH₂CH₃ | CH₂CH(CH₃)₃ | CH₃ | CH₃ | OCH₃ | CH | |
| O | 0 | H | m-OCH₂CH₃ | CH₂CH(CH₃)₃ | CH₃ | OCH₃ | OCH₃ | CH | |
| O | 0 | H | H | CH₂Cl | H | CH₃ | OCH₃ | CH | |
| O | 0 | H | H | CH₂Cl | H | OCH₃ | OCH₃ | CH | |
| O | 1 | H | H | CH₂Cl | H | CH₃ | OCH₃ | CH | |
| O | 1 | H | H | CH₂CH₂CH₂CH₃ | H | CH₃ | OCH₃ | CH | |
| O | 1 | H | H | CH₂CH₂CH₂CH₃ | H | OCH₃ | OCH₃ | CH | |
| O | 1 | H | H | CH₂CH₂CH(CH₃)₂ | H | CH₃ | OCH₃ | CH | |
| O | 1 | H | H | CH₂CH₂CH(CH₃)₂ | H | OCH₃ | OCH₃ | CH | |
| O | 1 | H | H | CH₂CH(CH₃)CH₂CH₃ | H | CH₃ | OCH₃ | CH | |
| O | 1 | H | H | CH₂CH(CH₃)CH₂CH₃ | H | OCH₃ | OCH₃ | CH | |
| O | 1 | H | H | CH(CH₃)CH₂CH₂CH₃ | H | CH₃ | OCH₃ | CH | |
| O | 1 | H | H | CH(CH₃)CH₂CH₂CH₃ | H | OCH₃ | OCH₃ | CH | |
| O | 1 | H | H | CH₂C(CH₃)₃ | H | CH₃ | OCH₃ | CH | |
| O | 1 | H | H | CH₂C(CH₃)₃ | H | OCH₃ | OCH₃ | CH | |
| O | 1 | H | H | CH₂CH₂OCH₃ | H | CH₃ | OCH₃ | CH | |
| O | 1 | H | H | CH₂CH₂OCH₃ | H | OCH₃ | OCH₃ | CH | |
| O | 1 | H | H | CH₂CH₂OCH₃ | H | CH₃ | OCH₃ | CH | |
| O | 1 | H | H | CH₂CH₂CH₂Cl | H | CH₃ | OCH₃ | CH | |
| O | 1 | H | H | CH₂CH₂CH₂Cl | H | OCH₃ | OCH₃ | CH | |
| O | 0 | H | H | CH₂CH₂CH₂Cl | H | CH₃ | OCH₃ | CH | |
| O | 1 | H | H | CH₂CH₂SCH₃ | H | CH₃ | OCH₃ | CH | |

TABLE Ia-continued

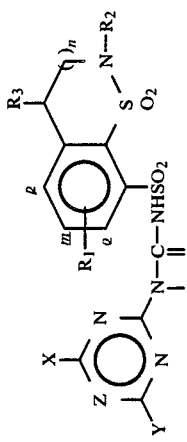

| W | n | R | R₁ | R₂ | R₃ | X | Y | Z | m.p. (°C.) |
|---|---|---|---|----|----|---|---|---|-----------|
| O | 1 | H | H | CH₂CH₂SCH₃ | H | OCH₃ | OCH₃ | CH | |
| O | 1 | H | H | CH₂C(CH₃)=CH₂ | H | OCH₃ | OCH₃ | CH | |
| O | 0 | H | H | CH₂CH₂OCH₃ | H | OCH₂CH₃ | OCH₃ | CH | |
| O | 0 | H | H | CH₂CH₂OCH₃ | H | F | OCH₃ | CH | |
| O | 0 | H | H | CH₂CH₂OCH₃ | H | OCF₂H | OCH₃ | CH | |
| O | 0 | H | H | CH₂CH₂OCH₃ | H | CH₂F | OCH₃ | CH | |
| O | 0 | H | H | CH₂CH₂OCH₃ | H | CF₃ | CF₃ | CH | |
| O | 0 | H | H | CH₂CH₂OCH₃ | H | OCH₃ | H | CH | |
| O | 0 | H | H | CH₂CH₂OCH₃ | H | CH₃ | OCH₂CH₃ | CH | |
| O | 0 | H | H | CH₂CH₂OCH₃ | H | OCH₃ | OCH₂OCH₃ | CH | |
| O | 0 | H | H | CH₂CH₂OCH₃ | H | OCH₃ | NH₂ | CH | |
| O | 0 | H | H | CH₂CH₂OCH₃ | H | OCH₃ | NHCH₃ | CH | |
| O | 0 | H | H | CH₂CH₂OCH₃ | H | OCH₃ | N(CH₃)₂ | CH | |
| O | 0 | H | H | CH₂CH₂OCH₃ | H | OCH₃ | N(OCH₃)CH₃ | CH | |
| O | 0 | H | H | CH₂CH₂OCH₃ | H | OCH₃ | CH₂CH₃ | CH | |
| O | 0 | H | H | CH₂CH₂OCH₃ | H | OCH₃ | SCH₃ | CH | |
| O | 0 | H | H | CH₂CH₂OCH₃ | H | OCH₃ | OCH₂CH=CH₂ | CH | |
| O | 0 | H | H | CH₂CH₂OCH₃ | H | OCH₃ | OCH₂C≡CH | CH | |
| O | 0 | H | H | CH₂CH₂OCH₃ | H | OCH₃ | OCH₂CF₃ | CH | |
| O | 0 | H | H | CH₂CH₂OCH₃ | H | OCH₃ | CN | CH | |
| O | 0 | H | H | CH₂CH₂OCH₃ | H | OCH₃ | N₃ | CH | |
| O | 0 | H | H | CH₂CH₂OCH₃ | H | OCH₃ | OCH₂CH₂OCH₃ | CH | |
| O | 0 | H | H | CH₂CH₂OCH₃ | H | OCH₃ | CH₂SCH₃ | CH | |
| O | 0 | H | H | CH₂CH₂OCH₃ | H | OCH₃ | OCF₂H | CH | |
| O | 0 | H | H | CH₂CH₂OCH₃ | H | OCH₃ | SCF₂H | CH | |
| O | 0 | H | H | CH₂CH₂OCH₃ | H | OCH₃ | OCF₂CHClF | CH | |
| O | 0 | H | H | CH₂CH₂OCH₃ | H | OCH₃ | OCF₂CHBrF | CH | |
| O | 0 | H | H | CH₂CH₂OCH₃ | H | OCH₃ | OCF₂CHFCF₃ | CH | |
| O | 0 | H | H | CH₂CH₂OCH₃ | H | OCH₃ | CHO | CH | |
| O | 0 | H | H | CH₂CH₂OCH₃ | H | OCH₃ | C(=O)CH₃ | CH | |
| O | 0 | H | H | CH₂CH₂OCH₃ | H | OCH₃ | C(=O)CH₂CH₃ | CH | |
| O | 0 | H | H | CH₂CH₂OCH₃ | H | OCH₃ | C(=O)CH₂CH₂CH₃ | CH | |
| O | 0 | H | H | CH₂CH₂OCH₃ | H | OCH₃ | CH(OCH₃)₂ | CH | |
| O | 0 | H | H | CH₂CH₂OCH₃ | H | OCH₃ | CH(SCH₃)₂ | CH | |
| O | 0 | H | H | CH₂CH₂OCH₃ | H | OCH₃ | CH(OCH₂CH₃)₂ | CH | |
| O | 0 | H | H | CH₂CH₂OCH₃ | H | OCH₃ | CH(SCH₂CH₂CH₃)₂ | CH | |
| O | 0 | H | H | CH₂CH₂OCH₃ | H | OCH₃ | —C—CH₃<br>OCH₃<br>SCH₃ | CH | |
| O | 0 | H | H | CH₂CH₂OCH₃ | H | OCH₃ | 1,3-dioxolan-2-yl | CH | |

TABLE 1a-continued

| W | n | R | R₁ | R₂ | R₃ | X | Y | Z | m.p. (°C.) |
|---|---|---|----|----|----|---|---|---|------------|
| O | 0 | H | H | CH₂CH₂OCH₃ | H | OCH₃ | 1,3-dioxolan-2-yl | CH | |
| O | 0 | H | H | CH₂CH₂OCH₃ | H | OCH₃ | 1,3-dithiolan-2-yl | CH | |
| O | 0 | H | H | CH₂CH₂OCH₃ | H | OCH₃ | C(OCH₃)₂CH₂CH₂CH₃ | CH | |
| O | 0 | H | H | CH₂CH₂OCH₃ | H | OCH₃ | OCH₃ | CCH₃ | |
| O | 0 | H | H | CH₂CH₂OCH₃ | H | OCH₃ | OCH₃ | CCH₂CH₃ | |
| O | 0 | H | H | CH₂CH₂OCH₃ | H | OCH₃ | OCH₃ | CCl | |
| O | 0 | H | H | CH₂CH₂OCH₃ | H | OCH₃ | OCH₃ | CBr | |
| O | 0 | H | H | (CH₂)₅CH₃ | H | CH₃ | CH₃ | CH | 195–196 |
| O | 0 | H | H | (CH₂)₅CH₃ | H | CH₃ | OCH₃ | CH | 196–197 |
| O | 0 | H | H | (CH₂)₅CH₃ | H | OCH₃ | OCH₃ | CH | 205–207 |
| O | 0 | H | H | (CH₂)₅CH₃ | H | OCH₃ | OCH₃ | N | 149–151 |
| O | 0 | H | H | (CH₂)₅CH₃ | H | Cl | OCH₃ | CH | 164–166 |
| O | 0 | H | H | (CH₂)₅CH₃ | H | Br | OCH₃ | CH | 215–218 |
| O | 0 | H | H | (CH₂)₃CH(CH₃)₂ | H | OCH₃ | OCH₃ | CH | |
| O | 0 | H | H | (CH₂)₃CH(CH₃)₂ | H | CH₃ | OCH₃ | CH | |
| O | 0 | H | H | CH₂CH₂C(CH₃)₃ | H | OCH₃ | OCH₃ | CH | |
| O | 0 | H | H | CH₂CH₂C(CH₃)₃ | H | CH₃ | OCH₃ | CH | |
| O | 0 | H | H | (CH₂)₉CH₃ | H | OCH₃ | OCH₃ | CH | 172–176 |
| O | 0 | H | H | CH₂CH₂O(CH₂)₉CH₃ | H | OCH₃ | OCH₃ | CH | |
| O | 0 | H | H | CH₂CH₂OCH₂CH₂Cl | H | OCH₃ | OCH₃ | CH | |
| O | 0 | H | H | CH₂CH₂O(CH₂)₉CF₃ | H | OCH₃ | OCH₃ | CH | |
| O | 0 | H | H | CH₂CH₂OCF₂H | H | OCH₃ | OCH₃ | CH | |
| O | 0 | H | H | CH₂CH₂S(CH₂)₉CH₃ | H | OCH₃ | OCH₃ | CH | |
| O | 0 | H | H | CH₂CH₂S(CH₂)₉CF₃ | H | OCH₃ | OCH₃ | CH | |
| O | 0 | H | H | CH₂CH₂SCF₂H | H | OCH₃ | OCH₃ | CH | |
| O | 0 | H | H | CH₂CH₂SOCH₃ | H | OCH₃ | OCH₃ | CH | |
| O | 0 | H | H | CH₂CH₂SO(CH₂)₇CH(CH₃)₂ | H | OCH₃ | OCH₃ | CH | |
| O | 0 | H | H | CH₂CH₂SOCH₂CF₃ | H | OCH₃ | OCH₃ | CH | |
| O | 0 | H | H | CH₂CH₂SO₂(CH₂)₉CH₃ | H | OCH₃ | OCH₃ | CH | |
| O | 0 | H | H | CH₂CH₂SO₂CH₂CF₃ | H | OCH₃ | CH₃ | CH | |
| O | 0 | H | H | CH₂CH₂OSO₂CH₃ | H | CH₃ | OCH₃ | CH | |
| O | 0 | H | H | CH₂CH₂OSO₂CH₃ | H | CH₃ | CH₃ | CH | |
| O | 0 | H | H | CH₂CH₂OSO₂CH₃ | H | CH₃ | OCH₃ | N | |
| O | 0 | H | H | CH₂CH₂OSO₂CH₃ | H | OCH₃ | OCH₃ | N | |
| O | 0 | H | H | CH₂CH₂OSO₂CH₃ | H | Cl | OCH₃ | CH | |
| O | 0 | H | H | CH₂CH₂OSO₂CH₃ | H | Br | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | H | CH₂CH₂OSO₂CH₂CH₃ | H | CH₃ | OCH₃ | CH | |
| O | 0 | H | H | CH₂CH₂OSO₂CH₂CH₃ | H | OCH₃ | OCH₃ | CH | |
| O | 0 | H | H | CH₂CH₂OSO₂CH₂CH₃ | H | OCH₃ | CH₃ | N | |
| O | 0 | H | H | CH₂CH₂OSO₂(CH₂)₉CH₃ | H | OCH₃ | OCH₃ | CH | |
| O | 0 | H | H | CH₂COCH₃ | H | CH₃ | CH₃ | CH | |
| O | 0 | H | H | CH₂COCH₃ | H | CH₃ | OCH₃ | CH | 178–182 |
| O | 0 | H | H | CH₂COCH₃ | H | OCH₃ | OCH₃ | CH | |
| O | 0 | H | H | CH₂COCH₃ | H | OCH₃ | OCH₃ | N | |
| O | 0 | H | H | CH₂COCH₃ | H | Cl | OCH₃ | N | |
| O | 0 | H | H | CH₂COCH₃ | H | Br | OCH₃ | CH | |
| O | 0 | H | H | CH₂COCH(CH₃)₂ | H | CH₃ | CH₃ | CH | |
| O | 0 | H | H | CH₂CO(CH₂)₉CH₃ | H | CH₃ | OCH₃ | CH | |
| O | 0 | H | H | CH₂COCH₂Cl | H | CH₃ | OCH₃ | CH | |
| O | 0 | H | H | CH₂CO(CH₂)₅CF₃ | H | OCH₃ | OCH₃ | CH | |
| O | 0 | H | H | CH₂CH₂OCO(CH₂)₉CH₃ | H | CH₃ | OCH₃ | CH | |
| O | 0 | H | H | CH₂CH₂OCOCH₃ | H | CH₃ | OCH₃ | CH | 200–201 |
| O | 0 | H | H | CH₂CH₂OCOCH₃ | H | Cl | OCH₃ | CH | 175–180 |
| O | 0 | H | H | CH₂CH₂OCOCH₃ | H | Br | OCH₃ | CH | 182–190 |
| O | 0 | H | H | CH₂CH₂OCOCH₃ | H | OCH₃ | OCH₃ | CH | |
| O | 0 | H | H | CH₂CH₂OCOCH₃ | H | OCH₃ | CH₃ | CH | |
| O | 0 | H | H | CH₂CH₂OCOCH₃ | H | OCH₃ | OCH₃ | N | 201–205 |
| O | 0 | H | H | CH₂CH₂OCOCH₃ | H | CH₃ | OCH₃ | CH | |
| O | 0 | H | H | CH₂CH₂OCOCH₃ | H | OCH₃ | OCH₃ | CH | |
| O | 0 | H | H | CH₂CH₂OCOCH₃ | H | CH₃ | OCH₃ | CH | |
| O | 0 | H | H | CH₂CH₂OCOCH₃ | H | OCH₃ | OCH₃ | CH | |
| O | 0 | H | H | CH₂CH₂OCOCH₃ | H | Cl | OCH₃ | CH | |
| O | 0 | H | H | CH₂CH₂OCOCH₃ | H | Br | OCH₃ | CH | |
| O | 0 | H | H | CH₂CH₂OCOCH₂CH₃ | H | OCH₃ | OCH₃ | CH | |
| O | 0 | H | H | CH₂CH(CH₃)OCOCH₃ | H | CH₃ | OCH₃ | CH | |
| O | 0 | H | H | CH₂CH₂OCOCH₂Cl | H | OCH₃ | OCH₃ | CH | |
| O | 0 | H | H | CH₂CH₂OCO(CH₂)₉CH₂F | H | OCH₃ | OCH₃ | CH | |
| O | 0 | H | H | CH₂CO₂(CH₂)₅CH₃ | H | CH₃ | OCH₃ | CH | |
| O | 0 | H | H | CH₂CO₂CH₂CF₃ | H | OCH₃ | OCH₃ | CH | |
| O | 0 | H | H | CH₂CO₂(CH₂)₅CH₂Br | H | OCH₃ | OCH₃ | CH | |
| O | 0 | H | H | CH₂CHO | H | OCH₃ | OCH₃ | CH | |
| O | 0 | H | H | CH₂CH₂NH₂ | H | OCH₃ | OCH₃ | CH | |
| O | 0 | H | H | CH₂CH₂NHCH₃ | H | CH₃ | OCH₃ | CH | |

TABLE Ia-continued

| W | n | R | R₁ | R₂ | R₃ | X | Y | Z | m.p. (°C.) |
|---|---|---|----|----|----|---|---|---|------------|
| O | 0 | H | H | CH₂CH₂NHCH₃ | H | OCH₃ | OCH₃ | CH | |
| O | 0 | H | H | CH₂CH₂NH(CH₂)₅CH₃ | H | OCH₃ | OCH₃ | CH | |
| O | 0 | H | H | CH₂CH₂N(CH₃)CH(CH₃)₂ | H | OCH₃ | OCH₃ | CH | |
| O | 0 | H | H | CH₂CH₂NHCOCH₃ | H | CH₃ | OCH₃ | CH | |
| O | 0 | H | H | CH₂CH₂NHCOCH₃ | H | OCH₃ | OCH₃ | CH | |
| O | 0 | H | H | CH₂CH₂NH(CH₃)COCH₃ | H | CH₃ | OCH₃ | CH | |
| O | 0 | H | H | CH₂CH₂NH(CH₃)COCH₃ | H | OCH₃ | CH₃ | CH | |
| O | 0 | H | H | CH₂CH₂OH | H | CH₃ | OCH₃ | CH | |
| O | 0 | H | H | CH₂CH₂OH | H | OCH₃ | OCH₃ | CH | |
| O | 0 | H | H | CH₂CH₂OH | H | CH₃ | OCH₃ | N | |
| O | 0 | H | H | CH₂CH₂OH | H | OCH₃ | OCH₃ | N | |
| O | 0 | H | H | CH₂CH₂OH | H | Cl | OCH₃ | CH | |
| O | 0 | H | H | CH₂CH₂OH | H | Br | OCH₃ | CH | |
| O | 0 | H | H | CH₂NO₂ | H | CH₃ | OCH₃ | CH | |
| O | 0 | H | H | CH₂NO₂ | H | OCH₃ | OCH₃ | CH | |
| O | 0 | H | H | CH₂NO₂ | H | OCH₃ | OCH₃ | N | |
| O | 0 | H | H | CH₂CH₂NO₂ | H | CH₃ | OCH₃ | CH | |
| O | 0 | H | H | CH₂CH₂NO₂ | H | OCH₃ | OCH₃ | CH | |
| O | 0 | H | H | CH₂CH₂NO₂ | H | OCH₃ | OCH₃ | N | |
| O | 0 | H | H | CH₂Si(CH₃)₂C(CH₃)₃ | H | OCH₃ | OCH₃ | CH | |
| O | 0 | H | H | 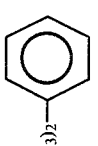 CH₂Si(CH₃)₂- | H | OCH₃ | OCH₃ | CH | |
| O | 0 | H | H | 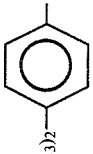 CH₂Si(CH₃)₂- | H | OCH₃ | OCH₃ | CH | |
| O | 0 | H | H | 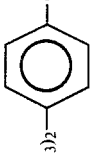 CH₂Si(CH₃)₂- | H | OCH₃ | OCH₃ | CH | |

TABLE Ia-continued

| W | n | R | R₁ | R₂ | R₃ | X | Y | Z | m.p. (°C.) |
|---|---|---|----|----|----|---|---|---|------------|
| O | 0 | H | H | CH₂Si(CH₃)₂–C₆H₄–OCH₃ | H | OCH₃ | OCH₃ | CH | |
| O | 0 | H | H | CH₂Si(CH₃)₂–C₆H₄–CH₃ | H | OCH₃ | OCH₃ | CH | |
| O | 0 | H | H | CH₂Si(CH₃)₂–C₆H₄–NO₂ | H | OCH₃ | OCH₃ | CH | |
| O | 0 | H | H | CH₂–C₆H₄–F | H | CH₃ | CH₃ | CH | 214–216 |
| O | 0 | H | H | CH₂–C₆H₄–F | H | CH₃ | OCH₃ | CH | 204–207 |
| O | 0 | H | H | CH₂–C₆H₄–F | H | OCH₃ | OCH₃ | CH | 208–210 |
| O | 0 | H | H | CH₂–C₆H₄–F | H | Cl | OCH₃ | CH | 228–230 |

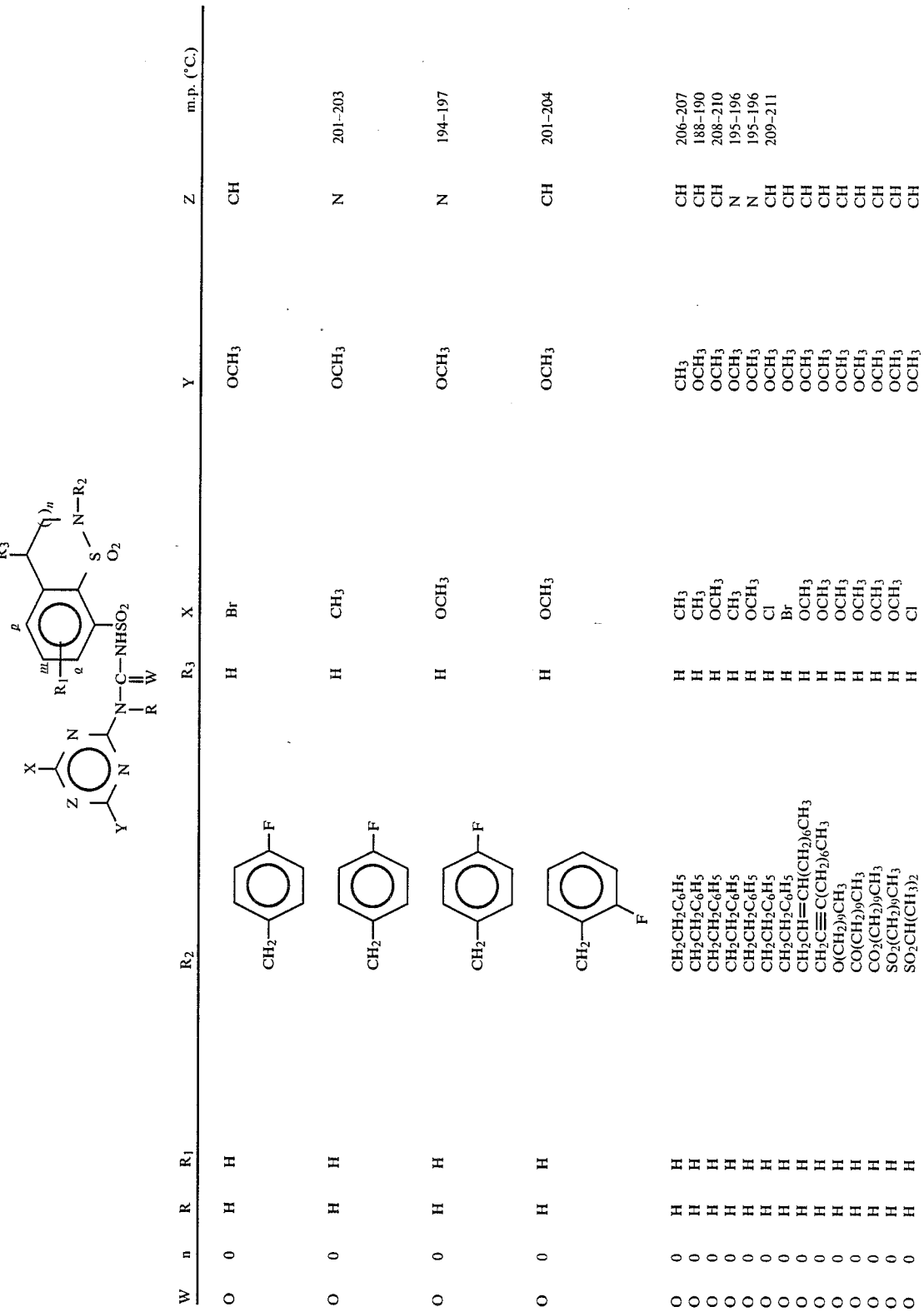

TABLE Ia-continued

| W | n | R | R₁ | R₂ | R₃ | X | Y | Z | m.p. (°C.) |
|---|---|---|---|---|---|---|---|---|---|
| O | 0 | H | H | 4-F-C₆H₄-CH₂ | H | Br | OCH₃ | CH | |
| O | 0 | H | H | 4-F-C₆H₄-CH₂ | H | CH₃ | OCH₃ | N | 201–203 |
| O | 0 | H | H | 4-F-C₆H₄-CH₂ | H | OCH₃ | OCH₃ | N | 194–197 |
| O | 0 | H | H | 2-F-C₆H₄-CH₂ | H | OCH₃ | OCH₃ | CH | 201–204 |
| O | 0 | H | H | CH₂CH₂C₆H₅ | H | CH₃ | CH₃ | CH | 206–207 |
| O | 0 | H | H | CH₂CH₂C₆H₅ | H | CH₃ | OCH₃ | CH | 188–190 |
| O | 0 | H | H | CH₂CH₂C₆H₅ | H | OCH₃ | OCH₃ | CH | 208–210 |
| O | 0 | H | H | CH₂CH₂C₆H₅ | H | CH₃ | OCH₃ | N | 195–196 |
| O | 0 | H | H | CH₂CH₂C₆H₅ | H | OCH₃ | OCH₃ | N | 195–196 |
| O | 0 | H | H | CH₂CH₂C₆H₅ | H | Cl | OCH₃ | CH | 209–211 |
| O | 0 | H | H | CH₂CH₂C₆H₅ | H | Br | OCH₃ | CH | |
| O | 0 | H | H | CH₂CH=CH(CH₂)₆CH₃ | H | OCH₃ | OCH₃ | CH | |
| O | 0 | H | H | CH₂C≡C(CH₂)₆CH₃ | H | OCH₃ | OCH₃ | CH | |
| O | 0 | H | H | O(CH₂)₉CH₃ | H | OCH₃ | OCH₃ | CH | |
| O | 0 | H | H | CO(CH₂)₉CH₃ | H | OCH₃ | OCH₃ | CH | |
| O | 0 | H | H | CO₂(CH₂)₉CH₃ | H | OCH₃ | OCH₃ | CH | |
| O | 0 | H | H | SO₂(CH₂)₉CH₃ | H | OCH₃ | OCH₃ | CH | |
| O | 0 | H | H | SO₂CH(CH₃)₂ | H | Cl | OCH₃ | CH | |

TABLE Ia-continued

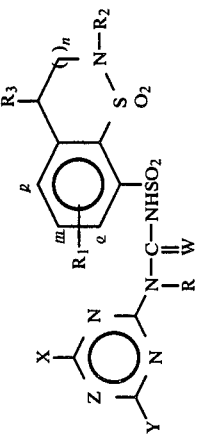

| W | n | R | R1 | R2 | R3 | X | Y | Z | m.p. (°C.) |
|---|---|---|----|----|----|---|---|---|------------|
| O | 0 | H | H | CH2C≡CC6H5 | H | OCH3 | OCH3 | CH | |
| O | 0 | H | H | COCH2Cl | H | CH3 | OCH3 | CH | |
| O | 0 | H | H | COCH2Cl | H | OCH3 | OCH3 | CH | |
| O | 0 | H | H | CO2C6H5 | H | OCH3 | OCH3 | CH | |
| O | 0 | H | H | SO2C6H5 | H | OCH3 | OCH3 | CH | 214–219 |
| O | 0 | H | H | COC6H5 | H | OCH3 | OCH3 | CH | |
| O | 0 | H | H | CH=CHCH2CH3 | H | OCH3 | CH3 | CH | |
| O | 0 | H | H | CH2CH2OCH3 | H | cyclo-propyl | CH2CH3 | CH | |
| O | 0 | H | H | CH2CH2OCH3 | H | cyclo-propyl | OCH3 | CH | |
| O | 0 | H | H | CH2CH2OCH3 | H | cyclo-propyl | OCH2CH3 | CH | |
| O | 0 | H | H | CH2CH2OCH3 | H | cyclo-propyl | CH2OCH3 | CH | |
| O | 0 | H | H | CH2CH2OCH3 | H | cyclo-propyl | OCF2H | N | |
| O | 0 | H | H | CH2CH2OCH3 | H | cyclo-propyl | SCF2H | N | |
| O | 0 | H | H | CH2CH2OCH3 | H | cyclo-propyl | OCH2CF3 | CH | |
| O | 0 | H | H | CH2CH2OCH3 | H | cyclo-propyl | CF3 | N | |
| O | 0 | H | H | CH2CH2OCH3 | H | cyclo-propyl | OCH2CH=CH2 | CH | |
| O | 0 | H | H | CH2CH2OCH3 | H | cyclo-propyl | OCH2C≡CH | N | |
| O | 0 | H | H | CH2CH2OCH3 | H | cyclo-propyl | NHCH3 | CH | |
| O | 0 | H | H | CH2CH2OCH3 | H | cyclo-propyl | N(CH3)2 | N | |
| O | 0 | H | H | CH2CH2OCH3 | H | cyclo-propyl | CH(OCH3)2 | CH | |
| O | 0 | H | H | CH2CH2CH(CH3)2 | H | cyclo-propyl | OCH3 | CH | |
| O | 0 | H | H | CH2CH2CH(CH3)2 | H | cyclo-propyl | OCH3 | N | |
| O | 0 | H | H | CH2CH=CH2 | H | cyclo-propyl | OCH3 | CH | |

TABLE Ia-continued

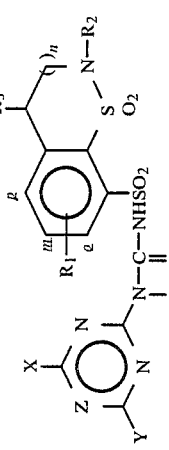

| W | n | R | R₁ | R₂ | R₃ | X | Y | Z | m.p. (°C.) |
|---|---|---|---|---|---|---|---|---|---|
| O | 0 | H | H | CH₂CH=CH₂ | H | cyclo-propyl | OCH₃ | N | |
| O | 0 | H | H | CH₂CH=CHCH₃ | H | cyclo-propyl | OCH₃ | CH | |
| O | 0 | H | H | CH₂CH=CHCH₃ | H | cyclo-propyl | OCH₃ | N | |
| O | 0 | H | H | CH₂CH₂CH₂Cl | H | cyclo-propyl | OCH₃ | CH | |
| O | 0 | H | H | CH₂CH₂CH₂Cl | H | cyclo-propyl | OCH₃ | N | |
| O | 0 | H | H | CH₂CH₂OCH₃ | H | cyclo-propyl | OCH₃ | CH | |
| O | 0 | H | H | CH₂CH₂OCH₃ | H | cyclo-propyl | OCH₃ | N | |
| O | 0 | H | H | CH₂CH=CH₂ | H | cyclo-propyl | OCH₃ | CH | |
| O | 0 | H | H | CH₂CH=CH₂ | H | cyclo-propyl | OCH₃ | N | |
| O | 0 | H | H | CH₂Si(CH₃)₃ | H | CH₃ | CH₃ | CH | 190-193 |
| O | 0 | H | H | CH₂Si(CH₃)₃ | H | Cl | OCH₃ | CH | 201-202 |
| O | 0 | H | H | CH₂Si(CH₃)₃ | H | CH₃ | OCH₃ | N | 190-193 |
| O | 0 | H | H | CH₂Si(CH₃)₃ | H | OCH₃ | OCH₃ | CH | 138-141 |
| O | 0 | H | H | (CH₂)₉CH₃ | H | CH₃ | CH₃ | CH | 167-169 |
| O | 0 | H | H | (CH₂)₉CH₃ | H | Cl | OCH₃ | CH | 159-163 |
| O | 0 | H | H | (CH₂)₉CH₃ | H | CH₃ | OCH₃ | N | 123-125 |
| O | 0 | H | H | CO₂CH₃ | H | OCH₃ | OCH₃ | CH | 141-145 |
| O | 0 | H | H | CO₂CH₃ | H | CH₃ | OCH₃ | CH | 239-241 |
| O | 0 | H | H | CO₂CH₃ | H | Cl | OCH₃ | CH | 238-241 |
| O | 0 | H | H | CH₂CH₂CO₂CH₃ | H | OCH₃ | OCH₃ | N | 217-219 |
| O | 0 | H | H | CH₂CH₂CO₂CH₃ | H | CH₃ | OCH₃ | CH | 219-220 |
| O | 0 | H | H | CH₂CH₂CO₂CH₃ | H | Cl | OCH₃ | CH | |
| O | 0 | H | H | CH₂CH₂CO₂CH₃ | H | CH₃ | OCH₃ | N | |
| O | 0 | H | H | CH₂OCH₂OCH₃ | H | OCH₃ | OCH₃ | CH | 219-223 |
| O | 0 | H | H | CH₂OCH₂OCH₃ | H | CH₃ | OCH₃ | CH | 197-199 |
| O | 0 | H | H | CH₂OCH₂OCH₃ | H | Cl | OCH₃ | N | 183-189 |
| O | 0 | H | H | CH₂OCH₂OCH₃ | H | CH₃ | OCH₃ | N | |
| O | 0 | H | H | CH₂OCH₂CH₂OCH₃ | H | OCH₃ | OCH₃ | CH | |
| O | 0 | H | H | CH₂OCH₂CH₂OCH₃ | H | CH₃ | OCH₃ | CH | |

TABLE Ia-continued

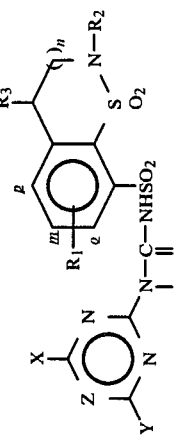

| W | n | R | R1 | R2 | R3 | X | Y | Z | m.p. (°C.) |
|---|---|---|----|----|----|----|----|----|-----|
| O | 0 | H | H | CH2CH2OCH2CH2OCH3 | H | OCH3 | OCH3 | CH | |
| O | 0 | H | H | CH2CH2OCH2CH2OCH3 | H | OCH3 | CH3 | CH | |
| O | 0 | H | H | CH(CH2CH3)2 | H | CH3 | CH3 | CH | |
| O | 0 | H | H | CH(CH2CH3)2 | H | OCH3 | OCH3 | CH | |
| O | 0 | H | H | CH(CH2CH3)2 | H | OCH3 | CH3 | CH | |
| O | 0 | H | H | CH(CH2CH3)2 | H | Cl | OCH3 | CH | |
| O | 0 | H | H | CH(CH2CH3)2 | H | CH3 | OCH3 | N | |
| O | 0 | H | H | CH(CH2CH3)2 | H | OCH3 | OCH3 | N | |
| O | 0 | H | H | CH(CH2CH3)2 | H | CH3 | CH3 | CH | 209-211 |
| O | 0 | H | H | CH(CH2CH3)2 | H | CH3 | OCH3 | CH | 219-225 |
| O | 0 | H | H | CH(CH2CH3)2 | H | OCH3 | OCH3 | CH | 223-225 |
| O | 0 | H | H | CH(CH2CH3)2 | H | Cl | OCH3 | CH | 220-223 |
| O | 0 | H | H | CH(CH2CH3)2 | CH3 | OCH3 | CH3 | N | 149-152 |
| O | 0 | H | H | CH(CH2CH3)2 | H | CH3 | CH3 | N | 139-143 |
| O | 0 | H | H | CH2CH2CH(CH3)CH2CH3 | H | OCH3 | OCH3 | CH | |
| O | 0 | H | H | CH2CH2CH(CH3)CH2CH3 | H | CH3 | OCH3 | CH | |
| O | 0 | H | H | CH2CH2CH(CH3)CH2CH3 | H | CH3 | CH3 | CH | |
| O | 0 | H | H | CH2CH2CH(CH3)CH2CH3 | H | OCH3 | CH3 | CH | |
| O | 0 | H | H | CH2CH2CH(CH3)CH2CH3 | H | Cl | OCH3 | CH | |
| O | 0 | H | H | CH2CH2CH(CH3)CH2CH3 | H | CH3 | OCH3 | N | |
| O | 0 | H | H | CH2CH2CH(CH3)CH2CH3 | H | OCH3 | OCH3 | N | |
| O | 0 | H | H | CH2CH(CH3)CH2CH2CH3 | H | OCH3 | OCH3 | CH | |
| O | 0 | H | H | CH2CH(CH3)CH2CH2CH3 | H | CH3 | OCH3 | CH | |
| O | 0 | H | H | CH2CH(CH3)CH2CH2CH3 | H | CH3 | CH3 | CH | |
| O | 0 | H | H | CH2CH(CH3)CH2CH2CH3 | H | OCH3 | CH3 | CH | |
| O | 0 | H | H | CH2CH(CH3)CH2CH2CH3 | H | Cl | OCH3 | CH | |
| O | 0 | H | H | CH2CH(CH3)CH2CH2CH3 | H | CH3 | OCH3 | N | |
| O | 0 | H | H | CH2CH(CH3)CH2CH2CH3 | H | OCH3 | OCH3 | N | |
| O | 0 | H | H | CH2OCH2CH2OCH2CH3 | H | OCH3 | OCH3 | CH | |
| O | 0 | H | H | CH2OCH2CH2OCH2CH3 | H | CH3 | OCH3 | CH | |
| O | 0 | H | H | CH2OCH2CH2OCH2CH3 | H | OCH3 | CH3 | CH | |
| O | 0 | H | H | CH2OCH2CH2OCH2CH3 | H | Cl | OCH3 | CH | |
| O | 0 | H | H | CH2OCH2CH2OCH2CH3 | H | CH3 | OCH3 | N | |
| O | 0 | H | H | CH2CH2OCH2OCH3 | H | OCH3 | OCH3 | CH | |
| O | 0 | H | H | CH2CH2OCH2OCH3 | H | CH3 | OCH3 | CH | |
| O | 0 | H | H | CH2CH2OCH2OCH3 | H | OCH3 | CH3 | CH | |
| O | 0 | H | H | CH2CH2OCH2OCH3 | H | Cl | OCH3 | CH | |
| O | 0 | H | H | CH2CH2OCH2OCH3 | H | CH3 | OCH3 | N | |
| O | 0 | H | H | CH2CH2OCH2OCH3 | H | OCH3 | OCH3 | N | |
| O | 0 | H | H | CH2CH2OCH2OCH3 | H | CH3 | CH3 | CH | |
| O | 0 | H | H | CH2CH2OCH2CHOCH3 | H | CH3 | CH3 | CH | |
| O | 0 | H | H | CH2CH2OCH2CHOCH3 | H | OCH3 | CH3 | CH | |
| O | 0 | H | H | CH2CH2CH2I | H | CH3 | CH3 | CH | |
| O | 0 | H | H | CH2CH2CH2I | H | CH3 | OCH3 | CH | |
| O | 0 | H | H | CH2CH2CH2I | H | OCH3 | OCH3 | CH | |

TABLE Ia-continued

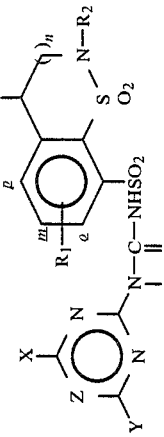

| W | n | R | R₁ | R₂ | R₃ | X | Y | Z | m.p. (°C.) |
|---|---|---|---|---|---|---|---|---|---|
| O | 0 | H | H | CH₂CH₂CH₂I | H | Cl | OCH₃ | CH | |
| O | 0 | H | H | CH₂CH₂CH₂I | H | CH₃ | OCH₃ | N | |
| O | 0 | H | H | CH₂CH₂CH₂I | H | OCH₃ | OCH₃ | N | |
| O | 0 | H | H | CH₂CH₂CH₂CH₂Cl | H | CH₃ | CH₃ | CH | |
| O | 0 | H | H | CH₂CH₂CH₂CH₂Cl | H | CH₃ | OCH₃ | CH | |
| O | 0 | H | H | CH₂CH₂CH₂CH₂Cl | H | OCH₃ | OCH₃ | CH | |
| O | 0 | H | H | CH₂CH₂CH₂CH₂Cl | H | Cl | OCH₃ | CH | |
| O | 0 | H | H | CH₂CH₂CH₂CH₂Cl | H | CH₃ | OCH₃ | N | |
| O | 0 | H | H | CH₂CH₂CH₂CH₂Cl | H | OCH₃ | OCH₃ | N | |
| O | 0 | H | H | CH₂CH₂CH₂CH₂Br | H | CH₃ | CH₃ | CH | |
| O | 0 | H | H | CH₂CH₂CH₂CH₂Br | H | CH₃ | OCH₃ | CH | |
| O | 0 | H | H | CH₂CH₂CH₂CH₂Br | H | OCH₃ | OCH₃ | CH | |
| O | 0 | H | H | CH₂CH₂CH₂CH₂Br | H | Cl | OCH₃ | CH | |
| O | 0 | H | H | CH₂CH₂CH₂CH₂Br | H | CH₃ | OCH₃ | N | |
| O | 0 | H | H | CH₂CH₂CH₂CH₂Br | H | OCH₃ | OCH₃ | N | |
| O | 0 | H | H | CH₂CH₂CH₂F | H | CH₃ | CH₃ | CH | |
| O | 0 | H | H | CH₂CH₂CH₂F | H | CH₃ | OCH₃ | CH | |
| O | 0 | H | H | CH₂CH₂CH₂F | H | OCH₃ | OCH₃ | CH | |
| O | 0 | H | H | CH₂CH₂CH₂F | H | Cl | OCH₃ | CH | |
| O | 0 | H | H | CH₂CH₂CH₂F | H | CH₃ | OCH₃ | N | |
| O | 0 | H | H | CH₂CH₂CH₂F | H | OCH₃ | OCH₃ | N | |
| O | 0 | H | H | CH₂CH₂CH₂CH₂F | H | CH₃ | CH₃ | CH | |
| O | 0 | H | H | CH₂CH₂CH₂CH₂F | H | CH₃ | OCH₃ | CH | 210-211 |
| O | 0 | H | H | CH₂CH₂CH₂CH₂F | H | OCH₃ | OCH₃ | CH | 216-217 |
| O | 0 | H | H | CH₂CH₂CH₂CH₂F | H | Cl | OCH₃ | CH | 199-200 |
| O | 0 | H | H | CH₂CH₂CH₂CH₂F | H | CH₃ | OCH₃ | N | 222-224 |
| O | 0 | H | H | CH₂CH₂CH₂CH₂F | H | OCH₃ | OCH₃ | N | 148-149 |
| O | 0 | H | H | CH₂CH₂CF₃ | H | CH₃ | CH₃ | CH | 182-184 |
| O | 0 | H | H | CH₂CH₂CF₃ | H | CH₃ | OCH₃ | CH | |
| O | 0 | H | H | CH₂CH₂CF₃ | H | OCH₃ | OCH₃ | CH | |
| O | 0 | H | H | CH₂CH₂CF₃ | H | Cl | OCH₃ | CH | |
| O | 0 | H | H | CH₂CH₂CF₃ | H | CH₃ | OCH₃ | N | |
| O | 0 | H | H | CH₂CH₂CF₃ | H | OCH₃ | OCH₃ | N | |
| O | 0 | H | H | CH₂CH₂CH₂CF₃ | H | CH₃ | CH₃ | CH | |
| O | 0 | H | H | CH₂CH₂CH₂CF₃ | H | CH₃ | OCH₃ | CH | |
| O | 0 | H | H | CH₂CH₂CH₂CF₃ | H | OCH₃ | OCH₃ | CH | |
| O | 0 | H | H | CH₂CH₂CH₂CF₃ | H | Cl | OCH₃ | CH | |
| O | 0 | H | H | CH₂CH₂CH₂CF₃ | H | CH₃ | OCH₃ | N | |
| O | 0 | H | H | CH₂CH₂CH₂CF₃ | H | OCH₃ | OCH₃ | N | |
| O | 0 | H | H | CH₂CH(CF₃)₂ | H | CH₃ | CH₃ | CH | |
| O | 0 | H | H | CH₂CH(CF₃)₂ | H | CH₃ | OCH₃ | CH | |
| O | 0 | H | H | CH₂CH(CF₃)₂ | H | OCH₃ | OCH₃ | CH | |

TABLE Ia-continued

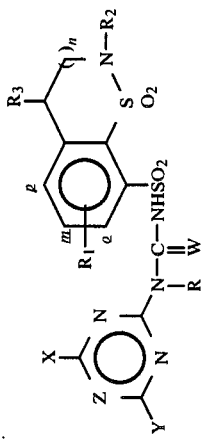

| W | n | R | R1 | R2 | R3 | X | Y | Z | m.p. (°C.) |
|---|---|---|----|----|----|---|---|---|------------|
| O | 0 | H | H | CH2OCH3 | H | CH3 | CH3 | CH | 190-192 |
| O | 0 | H | H | CH2OCH3 | H | Cl | OCH3 | CH | 172-174 |
| O | 0 | H | H | CH2OCH3 | H | OCH3 | OCH3 | N | 171-173 |
| O | 0 | H | H | CH2OCH3 | H | CH3 | OCH3 | CH | 116-119 |
| O | 0 | H | H | CH2OCH2CH3 | H | CH3 | CH3 | CH | |
| O | 0 | H | H | CH2OCH2CH3 | H | Cl | OCH3 | CH | |
| O | 0 | H | H | CH2OCH2CH3 | H | CH3 | OCH3 | CH | |
| O | 0 | H | H | CH2OCH2CH3 | H | OCH3 | OCH3 | N | |
| O | 0 | H | H | CH2CH2CH2OCH3 | H | CH3 | CH3 | CH | |
| O | 0 | H | H | CH2CH2CH2OCH3 | H | Cl | OCH3 | CH | |
| O | 0 | H | H | CH2CH2CH2OCH3 | H | CH3 | OCH3 | CH | |
| O | 0 | H | H | CH2CH2CH2OCH3 | H | OCH3 | OCH3 | N | |
| O | 0 | H | H | CH2C(OCH3)2CH3 | H | CH3 | CH3 | CH | |
| O | 0 | H | H | CH2C(OCH3)2CH3 | H | Cl | OCH3 | CH | |
| O | 0 | H | H | CH2C(OCH3)2CH3 | H | CH3 | OCH3 | CH | |
| O | 0 | H | H | CH2C(OCH3)2CH3 | H | OCH3 | OCH3 | N | |
| O | 0 | H | H | CH2C(OCH3)3CH3 | H | CH3 | CH3 | CH | |
| O | 0 | H | H | CH2CH2C(OCH3)2CH3 | H | CH3 | CH3 | CH | |
| O | 0 | H | H | CH2CH2C(OCH3)2CH3 | H | Cl | OCH3 | CH | |
| O | 0 | H | H | CH2CH2C(OCH3)2CH3 | H | CH3 | OCH3 | CH | |
| O | 0 | H | H | CH2CH2C(OCH3)2CH3 | H | OCH3 | OCH3 | N | |
| O | 0 | H | H | CH2CH2OCH2CH=CH2 | H | CH3 | CH3 | CH | |
| O | 0 | H | H | CH2CH2OCH2CH=CH2 | H | Cl | OCH3 | CH | |
| O | 0 | H | H | CH2CH2OCH2CH=CH2 | H | CH3 | OCH3 | CH | |
| O | 0 | H | H | CH2CH2OCH2CH=CH2 | H | OCH3 | OCH3 | N | |
| O | 0 | H | H | CH2CH2OCH2C=CH2 | H | CH3 | CH3 | CH | |
| O | 0 | H | H | CH2CH2OCH2C=CH2 | H | Cl | OCH3 | CH | |
| O | 0 | H | H | CH2CH2OCH2C=CH2 | H | CH3 | OCH3 | CH | |
| O | 0 | H | H | CH2CH2OCH2C=CH2 | H | OCH3 | OCH3 | N | |
| O | 0 | H | H | CH2CH2OCH=CH2 | H | CH3 | CH3 | CH | |
| O | 0 | H | H | CH2CH2OCH=CH2 | H | OCH3 | OCH3 | CH | |
| O | 0 | H | H | (2-cyclopentoxy)ethyl | H | CH3 | CH3 | CH | |
| O | 0 | H | H | (2-cyclopentoxy)ethyl | H | OCH3 | OCH3 | CH | |
| O | 0 | H | H | phenoxymethyl | H | CH3 | CH3 | CH | |
| O | 0 | H | H | phenoxymethyl | H | OCH3 | OCH3 | CH | |
| O | 0 | H | H | 2-phenoxyethyl | H | CH3 | CH3 | CH | |
| O | 0 | H | H | 2-phenoxyethyl | H | OCH3 | OCH3 | CH | |
| O | 0 | H | H | (4-chlorophenoxy)methyl | H | OCH3 | OCH3 | CH | |
| O | 0 | H | H | (4-bromophenoxy)methyl | H | OCH3 | OCH3 | CH | |
| O | 0 | H | H | (4-methylphenoxy)methyl | H | OCH3 | OCH3 | CH | |
| O | 0 | H | H | (4-nitrophenoxy)methyl | H | OCH3 | OCH3 | CH | |
| O | 0 | H | H | CH2CH2OCH2C=CH2(CH2)6CH3 | H | OCH3 | OCH3 | CH | |

TABLE Ia-continued

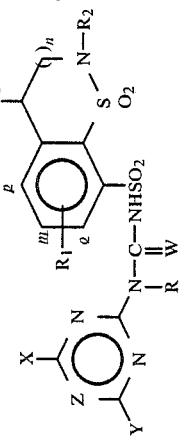

| W | n | R | R₁ | R₂ | R₃ | X | Y | Z | m.p. (°C.) |
|---|---|---|---|---|---|---|---|---|---|
| O | 0 | H | H | CH₂CH₂OCH₂C=CH(CH₂)₆CH₃ | H | OCH₃ | OCH₃ | CH | |
| O | 0 | H | H | CH₂CH₂OC(O)CH₂CH=CH₂ | H | OCH₃ | OCH₃ | CH | |
| O | 0 | H | H | CH₂CH₂OC(O)C=CCH₃ | H | OCH₃ | OCH₃ | CH | |
| O | 0 | H | H | CH₂CH₂OC(O)(cyclopropyl) | H | OCH₃ | OCH₃ | CH | |
| O | 0 | H | H | CH₂CH₂OC(O)C₆H₅ | H | OCH₃ | OCH₃ | CH | |
| O | 0 | H | H | CH₂CH₂OC(O)C₆H₅ | H | CH₃ | OCH₃ | CH | |
| O | 0 | H | H | CH₂CH₂OC(O)NHCH₃ | H | OCH₃ | OCH₃ | CH | |
| O | 0 | H | H | CH₂CH₂OC(O)NHCH₃ | H | CH₃ | OCH₃ | CH | |
| O | 0 | H | H | CH₂CH₂OC(O)NHCH₃ | H | OCH₃ | OCH₃ | CH | |
| O | 0 | H | H | CH₂CH₂OC(O)N(CH₃)₂ | H | OCH₃ | OCH₃ | CH | |
| O | 0 | H | H | CH₂CH₂OC(O)NH(CH₂)₃CH₃ | H | CH₃ | OCH₃ | CH | |
| O | 0 | H | H | CH₂CH₂OC(O)NHC₆H₅ | H | CH₃ | OCH₃ | CH | |
| O | 0 | H | H | CH₂CH₂OSO₂CF₃ | H | OCH₃ | OCH₃ | CH | |
| O | 0 | H | H | CH₂CH₂OSO₂C₆H₅ | H | CH₃ | CH₃ | CH | |
| O | 0 | H | H | CH₂CH₂OP(O)(OCH₃)₂ | H | CH₃ | OCH₃ | CH | |
| O | 0 | H | H | CH₂CH₂OP(O)(OCH₂CH₂CH₂CH₂) | H | OCH₃ | OCH₃ | CH | |
| O | 0 | H | H | CH₂P(O)(OCH₃)₂ | H | Cl | OCH₃ | CH | |
| O | 0 | H | H | CH₂P(O)(OCH₃)₂ | H | CH₃ | OCH₃ | N | |
| O | 0 | H | H | CH₂P(O)(OCH₃)₂ | H | CH₃ | OCH₃ | CH | |
| O | 0 | H | H | CH₂P(O)(OCH₃)₂ | H | OCH₃ | OCH₃ | CH | |
| O | 0 | H | H | CH₂CH₂OCO₂CH₃ | H | CH₃ | CH₃ | CH | |
| O | 0 | H | H | CH₂CH₂OCO₂CH₃ | H | CH₃ | OCH₃ | CH | |
| O | 0 | H | H | CH₂CH₂OCO₂CH₃ | H | CH₃ | OCH₃ | N | |
| O | 0 | H | H | CH₂CH₂OCO₂CH₃ | H | Cl | OCH₃ | CH | |
| O | 0 | H | H | CH₂CH₂OCO₂CH₃ | H | OCH₃ | OCH₃ | CH | |
| O | 0 | H | H | CH₂CH₂OCO₂CH₂CH₃ | H | CH₃ | OCH₃ | CH | |
| O | 0 | H | H | CH₂CH₂OCO₂CH₂CH₃ | H | CH₃ | OCH₃ | N | |
| O | 0 | H | H | CH₂CH₂OCO₂CH₂CH₃ | H | Cl | OCH₃ | CH | |
| O | 0 | H | H | CH₂CH₂OCO₂CH₂CH₃ | H | OCH₃ | OCH₃ | CH | |
| O | 0 | H | H | CH₂CH₂OCO₂CH₂CH₂CH₃ | H | CH₃ | OCH₃ | CH | |
| O | 0 | H | H | CH₂CH₂OCO₂CH₂CH₂CH₃ | H | CH₃ | OCH₃ | N | |
| O | 0 | H | H | CH₂CH₂OCO₂C₆H₅ | H | CH₃ | OCH₃ | CH | |
| O | 0 | H | H | CH₂CH₂OP(S)(OCH₃)₂ | H | OCH₃ | OCH₃ | CH | |
| O | 0 | H | H | CH₂CH₂OP(S)(CH₃)₂ | H | OCH₃ | OCH₃ | CH | |
| O | 0 | H | H | CH₂CH₂OSi(CH₃)₃ | H | CH₃ | CH₃ | CH | |
| O | 0 | H | H | CH₂CH₂OSi(CH₃)₃ | H | CH₃ | OCH₃ | CH | |
| O | 0 | H | H | CH₂CH₂OSi(CH₃)₃ | H | OCH₃ | OCH₃ | N | |
| O | 0 | H | H | CH₂CH₂OSi(CH₃)₃ | H | Cl | OCH₃ | CH | |
| O | 0 | H | H | CH₂CH₂OSi(CH₃)₃ | H | CH₃ | OCH₃ | N | |
| O | 0 | H | H | CH₂CH₂OSi(CH₃)₂C(CH₃)₃ | H | CH₃ | OCH₃ | CH | |

TABLE Ia-continued

| W | n | R | R1 | R2 | R3 | X | Y | Z | m.p. (°C.) |
|---|---|---|----|----|----|---|---|---|------------|
| O | 0 | H | H | CH2CH2OSi(CH3)2C(CH3)3 | H | OCH3 | OCH3 | CH | |
| O | 0 | H | H | CH2CH2OSi(CH3)2C(CH2)9CH3 | H | OCH3 | OCH3 | CH | |
| O | 0 | H | H | CH2CH2OSi(CH3)2C6H5 | H | OCH3 | OCH3 | CH | |
| O | 0 | H | H | CH2CH2OSi(CH3)2CH2C6H5 | H | OCH3 | CH3 | CH | |
| O | 0 | H | H | CH2CH2OH | H | CH3 | OCH3 | CH | |
| O | 0 | H | H | CH2CH2OH | H | OCH3 | OCH3 | CH | |
| O | 0 | H | H | CH2CH2OH | H | OCH3 | OCH3 | N | |
| O | 0 | H | H | CH2CH2OH | H | Cl | CH3 | CH | |
| O | 0 | H | H | CH2CH2OH | H | OCH3 | CH3 | N | |
| O | 0 | H | H | CH2CH2OC(O)CH3 | H | OCH3 | OCH3 | CH | |
| O | 0 | H | H | CH2CH2OSi(CH3)3 | H | OCH3 | OCH3 | CH | |
| O | 0 | H | H | CH2CH2OSO2CH3 | H | OCH3 | OCH3 | CH | |
| O | 0 | H | H | CH2SO2CH3 | H | CH3 | CH3 | CH | |
| O | 0 | H | H | CH2SO2CH3 | H | OCH3 | OCH3 | CH | |
| O | 0 | H | H | CH2SO2CH3 | H | Cl | OCH3 | CH | |
| O | 0 | H | H | CH2CH2SOCH2CH3 | H | CH3 | CH3 | CH | |
| O | 0 | H | H | CH2CH2SOCH2CH3 | H | OCH3 | OCH3 | CH | |
| O | 0 | H | H | CH2CH2SO2CH2CH3 | H | CH3 | CH3 | CH | |
| O | 0 | H | H | CH2CH2SO2CH2CH3 | H | OCH3 | OCH3 | CH | |
| O | 0 | H | H | CH2SC6H5 | H | CH3 | CH3 | CH | |
| O | 0 | H | H | CH2SC6H5 | H | OCH3 | OCH3 | CH | |
| O | 0 | H | H | CH2SC6H5 | H | Cl | OCH3 | CH | |
| O | 0 | H | H | CH2SC6H5 | H | CH3 | OCH3 | CH | |
| O | 0 | H | H | CH2SO2C6H5 | H | CH3 | CH3 | CH | |
| O | 0 | H | H | CH2SO2C6H5 | H | OCH3 | OCH3 | CH | |
| O | 0 | H | H | CH2SO2C6H5 | H | Cl | OCH3 | CH | |
| O | 0 | H | H | CH2SO2C6H5 | H | CH3 | OCH3 | CH | |
| O | 0 | H | H | CH2SCN | H | CH3 | CH3 | N | |
| O | 0 | H | H | CH2SCN | H | OCH3 | OCH3 | N | |
| O | 0 | H | H | CH2CH2SCN | H | CH3 | OCH3 | CH | |
| O | 0 | H | H | CH2CH2SCN | H | OCH3 | OCH3 | CH | |
| O | 0 | H | H | CH2CN | H | CH3 | OCH3 | CH | 193–195 |
| O | 0 | H | H | CH2CN | H | OCH3 | OCH3 | CH | 230–234 |
| O | 0 | H | H | CH2CN | H | CH3 | CH3 | CH | 238–241 |
| O | 0 | H | H | CH2CN | H | Cl | OCH3 | CH | |
| O | 0 | H | H | CH2CN | H | CH3 | OCH3 | N | |
| O | 0 | H | H | CH2CN | H | OCH3 | OCH3 | N | |
| O | 0 | H | H | CH2CH2SP(O)(OCH3)2 | H | OCH3 | CH3 | CH | |
| O | 0 | H | H | CH2CH2SP(S)(OCH3)2 | H | OCH3 | OCH3 | CH | |

TABLE Ia-continued

| W | n | R | R1 | R2 | R3 | X | Y | Z | m.p. (°C) |
|---|---|---|----|----|----|---|---|---|-----------|
| O | 0 | H | H | CH2P(S)2(OCH3)2 | H | OCH3 | OCH3 | CH | |
| O | 0 | H | H | CH2NH2 | H | CH3 | CH3 | CH | |
| O | 0 | H | H | CH2NH2 | H | OCH3 | OCH3 | CH | |
| O | 0 | H | H | CH2NHCH2CH2CH3 | H | OCH3 | OCH3 | CH | |
| O | 0 | H | H | CH2N(CH3)3Cl⊖ | H | OCH3 | OCH3 | CH | |
| O | 0 | H | H | CH2CH2N(CH3)3I⊖ | H | OCH3 | OCH3 | CH | |
| O | 0 | H | H | CH2CH2NHCO2CH3 | H | OCH3 | OCH3 | CH | |
| O | 0 | H | H | CH2CH2NHC(O)NHCH3 | H | CH3 | OCH3 | CH | |
| O | 0 | H | H | CH2CH2NHC(O)NHCH3 | H | OCH3 | OCH3 | CH | |
| O | 0 | H | H | CH2CH2NHSO2CH3 | H | CH3 | CH3 | CH | |
| O | 0 | H | H | CH2CH2NHSO2CH3 | H | OCH3 | OCH3 | CH | |
| O | 0 | H | H | CH2CH2NHSO2CH3 | H | CH3 | OCH3 | CH | |
| O | 0 | H | H | CH2CH2NHSO2CH3 | H | OCH3 | OCH3 | CH | |
| O | 0 | H | H | CH2CH2NHSO2CH3 | H | Cl | OCH3 | CH | |
| O | 0 | H | H | CH2CH2NHP(O)(OCH3)2 | H | OCH3 | OCH3 | CH | |
| O | 0 | H | H | CH2CH2NHP(S)(OCH3)2 | H | OCH3 | OCH3 | CH | |
| O | 0 | H | H | CH2NO2 | H | CH3 | CH3 | N | |
| O | 0 | H | H | CH2NO2 | H | OCH3 | OCH3 | CH | |
| O | 0 | H | H | CH2CH2NO2 | H | CH3 | CH3 | N | |
| O | 0 | H | H | CH2CH2NO2 | H | CH3 | OCH3 | CH | |
| O | 0 | H | H | CH2CH2NO2 | H | OCH3 | OCH3 | CH | |
| O | 0 | H | H | CH2C(O)C6H5 | H | CH3 | CH3 | N | |
| O | 0 | H | H | CH2C(O)C6H5 | H | CH3 | OCH3 | CH | |
| O | 0 | H | H | CH2C(O)C6H5 | H | OCH3 | OCH3 | CH | |
| O | 0 | H | H | CH2C(O)C6H5 | H | Cl | OCH3 | CH | |
| O | 0 | H | H | CH2C(O)C6H5 | H | CH3 | OCH3 | CH | 193–199 |
| O | 0 | H | H | CH2CH2C(O)C6H5 | H | OCH3 | OCH3 | CH | |
| O | 0 | H | H | CH2CH2C(O)C6H5 | H | CH3 | OCH3 | CH | |
| O | 0 | H | H | CH2CO2CH2CH3 | H | CH3 | CH3 | N | |
| O | 0 | H | H | CH2CO2CH2CH3 | H | OCH3 | OCH3 | N | |
| O | 0 | H | H | CH2CO2CH2CH3 | H | CH3 | OCH3 | CH | |
| O | 0 | H | H | CH2CO2CH2CH3 | H | OCH3 | OCH3 | CH | |
| O | 0 | H | H | CH2CO2CH2CH3 | H | Cl | OCH3 | CH | |
| O | 0 | H | H | CH2CO2C6H5 | H | CH3 | CH3 | N | |
| O | 0 | H | H | CH2CO2C6H5 | H | CH3 | OCH3 | CH | 164–166 |
| O | 0 | H | H | CH2CO2C6H5 | H | OCH3 | OCH3 | CH | |

TABLE Ia-continued

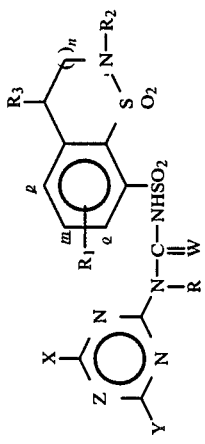

| W | n | R | R₁ | R₂ | R₃ | X | Y | Z | m.p. (°C.) |
|---|---|---|---|---|---|---|---|---|---|
| O | 0 | H | H | CH₂CO₂C₆H₅ | H | Cl | OCH₃ | CH | |
| O | 0 | H | H | CH₂CO₂C₆H₅ | H | CH₃ | OCH₃ | N | |
| O | 0 | H | H | CH₂CO₂C₆H₅ | H | OCH₃ | OCH₃ | CH | |
| O | 0 | H | H | CH₂CH₂CO₂CH₂CH₃ | H | CH₃ | OCH₃ | CH | |
| O | 0 | H | H | CH₂CH₂CO₂CH₂CH₃ | H | OCH₃ | OCH₃ | CH | |
| O | 0 | H | H | CH₂CH₂CO₂C₆H₅ | H | CH₃ | OCH₃ | CH | |
| O | 0 | H | H | CH₂CH₂CO₂C₆H₅ | H | OCH₃ | OCH₃ | CH | |
| O | 0 | H | H | CH₂CO₂C(CH₃)₃ | H | CH₃ | CH₃ | CH | 168–172 |
| O | 0 | H | H | CH₂CO₂C(CH₃)₃ | H | CH₃ | OCH₃ | CH | 178–180 |
| O | 0 | H | H | CH₂CO₂C(CH₃)₃ | H | OCH₃ | OCH₃ | CH | 156–159 |
| O | 0 | H | H | CH₂CO₂C(CH₃)₃ | H | Cl | OCH₃ | CH | |
| O | 0 | H | H | CH₂CO₂C(CH₃)₃ | H | CH₃ | OCH₃ | N | |
| O | 0 | H | H | CH₂CO₂C(CH₃)₃ | H | OCH₃ | OCH₃ | N | |
| O | 0 | H | H | CH₂CO₂H | H | CH₃ | CH₃ | CH | |
| O | 0 | H | H | CH₂CO₂H | H | CH₃ | OCH₃ | CH | |
| O | 0 | H | H | CH₂CO₂H | H | OCH₃ | OCH₃ | CH | |
| O | 0 | H | H | CH₂CO₂H | H | Cl | OCH₃ | CH | |
| O | 0 | H | H | CH₂CO₂H | H | CH₃ | OCH₃ | N | |
| O | 0 | H | H | CH₂CO₂H | H | OCH₃ | OCH₃ | N | |
| O | 0 | H | H | CH₂CH(CH₃)CN | H | CH₃ | CH₃ | CH | |
| O | 0 | H | H | CH₂CH(CH₃)CN | H | CH₃ | OCH₃ | CH | |
| O | 0 | H | H | CH₂CH(CH₃)CN | H | OCH₃ | OCH₃ | CH | |
| O | 0 | H | H | CH₂CH(CH₃)CN | H | Cl | OCH₃ | CH | |
| O | 0 | H | H | CH₂CH(CH₃)CN | H | CH₃ | OCH₃ | N | |
| O | 0 | H | H | CH₂CH(CH₃)CN | H | OCH₃ | OCH₃ | N | |
| O | 0 | H | H | CH₂C(O)NHCH₃ | H | CH₃ | OCH₃ | CH | |
| O | 0 | H | H | CH₂C(O)NHCH₃ | H | OCH₃ | OCH₃ | CH | |
| O | 0 | H | H | CH₂C(O)N(CH₃)₂ | H | CH₃ | OCH₃ | CH | |
| O | 0 | H | H | CH₂C(O)N(CH₃)₂ | H | OCH₃ | OCH₃ | CH | |
| O | 0 | H | H | (1-naphthyl)methyl | H | CH₃ | OCH₃ | CH | 163–169 |
| O | 0 | H | H | (1-naphthyl)methyl | H | OCH₃ | OCH₃ | CH | 220–228 |
| O | 0 | H | H | (2-naphthyl)methyl | H | CH₃ | OCH₃ | CH | |
| O | 0 | H | H | (2-naphthyl)methyl | H | OCH₃ | OCH₃ | CH | |
| O | 0 | H | H | (2-methylpyridinium)- methyl iodide | H | OCH₃ | OCH₃ | CH | |
| O | 0 | H | H | (2-methylpyridinium)- methyl iodide | H | OCH₃ | CH₃ | CH | 172–174 |
| O | 0 | H | H | pyridin-2-ylmethyl | H | CH₃ | CH₃ | CH | |
| O | 0 | H | H | pyridin-2-ylmethyl | H | CH₃ | OCH₃ | CH | |
| O | 0 | H | H | pyridin-2-ylmethyl | H | Cl | OCH₃ | CH | |
| O | 0 | H | H | pyridin-2-ylmethyl | H | CH₃ | OCH₃ | N | |
| O | 0 | H | H | pyridin-2-ylmethyl | H | OCH₃ | OCH₃ | N | |

TABLE Ia-continued

| W | n | R | R₁ | R₂ | R₃ | X | Y | Z | m.p. (°C.) |
|---|---|---|----|----|----|----|---|---|---|
| O | 0 | H | H | pyridin-3-ylmethyl | H | CH₃ | CH₃ | CH | |
| O | 0 | H | H | pyridin-3-ylmethyl | H | CH₃ | OCH₃ | CH | |
| O | 0 | H | H | pyridin-3-ylmethyl | H | OCH₃ | OCH₃ | CH | |
| O | 0 | H | H | pyridin-3-ylmethyl | H | Cl | OCH₃ | CH | |
| O | 0 | H | H | pyridin-3-ylmethyl | H | CH₃ | OCH₃ | N | |
| O | 0 | H | H | pyridin-3-ylmethyl | H | OCH₃ | OCH₃ | N | |
| O | 0 | H | H | pyridin-4-ylmethyl | H | CH₃ | CH₃ | CH | |
| O | 0 | H | H | pyridin-4-ylmethyl | H | CH₃ | OCH₃ | CH | |
| O | 0 | H | H | pyridin-4-ylmethyl | H | OCH₃ | OCH₃ | CH | |
| O | 0 | H | H | pyridin-4-ylmethyl | H | Cl | OCH₃ | CH | |
| O | 0 | H | H | pyridin-4-ylmethyl | H | CH₃ | OCH₃ | N | |
| O | 0 | H | H | pyridin-4-ylmethyl | H | OCH₃ | OCH₃ | N | |
| O | 0 | H | H | thien-2-ylmethyl | H | CH₃ | CH₃ | CH | |
| O | 0 | H | H | thien-2-ylmethyl | H | CH₃ | OCH₃ | CH | |
| O | 0 | H | H | thien-2-ylmethyl | H | OCH₃ | OCH₃ | CH | |
| O | 0 | H | H | thien-2-ylmethyl | H | Cl | OCH₃ | CH | |
| O | 0 | H | H | thien-2-ylmethyl | H | CH₃ | OCH₃ | N | |
| O | 0 | H | H | thien-2-ylmethyl | H | OCH₃ | OCH₃ | N | |
| O | 0 | H | H | thien-3-ylmethyl | H | CH₃ | CH₃ | CH | |
| O | 0 | H | H | thien-3-ylmethyl | H | CH₃ | OCH₃ | CH | |
| O | 0 | H | H | thien-3-ylmethyl | H | OCH₃ | OCH₃ | CH | |
| O | 0 | H | H | thien-3-ylmethyl | H | Cl | OCH₃ | CH | |
| O | 0 | H | H | thien-3-ylmethyl | H | CH₃ | OCH₃ | N | |
| O | 0 | H | H | thien-3-ylmethyl | H | OCH₃ | OCH₃ | N | |
| O | 0 | H | H | (5-methylthien-2-yl)methyl | H | CH₃ | CH₃ | CH | |
| O | 0 | H | H | (5-methylthien-2-yl)methyl | H | CH₃ | OCH₃ | CH | |
| O | 0 | H | H | (5-methylthien-2-yl)methyl | H | OCH₃ | OCH₃ | CH | |
| O | 0 | H | H | (5-chlorothien-2-yl)methyl | H | CH₃ | CH₃ | CH | |
| O | 0 | H | H | (5-chlorothien-2-yl)methyl | H | CH₃ | OCH₃ | CH | |
| O | 0 | H | H | (5-chlorothien-2-yl)methyl | H | OCH₃ | OCH₃ | CH | |
| O | 0 | H | H | (5-cyanothien-2-yl)methyl | H | CH₃ | CH₃ | CH | |
| O | 0 | H | H | (5-cyanothien-2-yl)methyl | H | CH₃ | OCH₃ | CH | |
| O | 0 | H | H | (5-cyanothien-2-yl)methyl | H | OCH₃ | OCH₃ | CH | |
| O | 0 | H | H | furan-2-ylmethyl | H | CH₃ | CH₃ | CH | |
| O | 0 | H | H | furan-2-ylmethyl | H | CH₃ | OCH₃ | CH | |
| O | 0 | H | H | (5-methylfuran-2-yl)methyl | H | CH₃ | OCH₃ | CH | |
| O | 0 | H | H | (5-methylfuran-2-yl)methyl | H | OCH₃ | OCH₃ | CH | |
| O | 0 | H | H | furan-3-ylmethyl | H | CH₃ | OCH₃ | CH | |
| O | 0 | H | H | furan-3-ylmethyl | H | OCH₃ | OCH₃ | CH | |
| O | 0 | H | H | (4,5-dihydrofuran-2-yl)methyl | H | CH₃ | OCH₃ | CH | |
| O | 0 | H | H | (4,5-dihydrofuran-2-yl)methyl | H | OCH₃ | OCH₃ | CH | |
| O | 0 | H | H | (1H—pyrrol-1-yl)methyl | H | CH₃ | OCH₃ | CH | |
| O | 0 | H | H | (1H—pyrrol-1-yl)methyl | H | OCH₃ | OCH₃ | CH | |
| O | 0 | H | H | (1H—pyrrol-2-yl)methyl | H | CH₃ | OCH₃ | CH | |

TABLE Ia-continued

| W | n | R | R₁ | R₂ | R₃ | X | Y | Z | m.p. (°C.) |
|---|---|---|----|----|----|---|---|---|------------|
| O | 0 | H | H | (1H—pyrrol-2-yl)methyl | H | OCH₃ | OCH₃ | CH | |
| O | 0 | H | H | (1-methyl-1H—pyrrol-3-yl)methyl | H | CH₃ | OCH₃ | CH | |
| O | 0 | H | H | (1-methyl-1H—pyrrol-3-yl)methyl | H | OCH₃ | OCH₃ | CH | |
| O | 0 | H | H | oxazol-2-ylmethyl | H | CH₃ | OCH₃ | CH | |
| O | 0 | H | H | oxazol-2-ylmethyl | H | OCH₃ | OCH₃ | CH | |
| O | 0 | H | H | thiazol-2-ylmethyl | H | CH₃ | OCH₃ | CH | |
| O | 0 | H | H | thiazol-2-ylmethyl | H | OCH₃ | OCH₃ | CH | |
| O | 0 | H | H | (4,5-dihydro-4,4-dimethyl-oxazol-2-yl)methyl | H | CH₃ | OCH₃ | CH | |
| O | 0 | H | H | (4,5-dihydro-4,4-dimethyl-oxazol-2-yl)methyl | H | OCH₃ | OCH₃ | CH | |
| O | 0 | H | H | isoxazol-3-ylmethyl | H | CH₃ | OCH₃ | CH | |
| O | 0 | H | H | isoxazol-3-ylmethyl | H | OCH₃ | OCH₃ | CH | |
| O | 0 | H | H | (1,2,4-oxadiazol-3-yl)methyl | H | CH₃ | OCH₃ | CH | |
| O | 0 | H | H | (1,2,4-oxadiazol-3-yl)methyl | H | OCH₃ | OCH₃ | CH | |
| O | 0 | H | H | (5-methyl-1,2,4-oxadiazol-3-yl)methyl | H | CH₃ | OCH₃ | CH | |
| O | 0 | H | H | (5-methyl-1,2,4-oxadiazol-3-yl)methyl | H | OCH₃ | OCH₃ | CH | |
| O | 0 | H | H | (5-methyl-1,3,4-oxadiazol-2-yl)methyl | H | CH₃ | OCH₃ | CH | |
| O | 0 | H | H | (5-methyl-1,3,4-oxadiazolo-2-yl)methyl | H | OCH₃ | OCH₃ | CH | |
| O | 0 | H | H | 1H—pyrazol-1-ylmethyl | H | CH₃ | OCH₃ | CH | |
| O | 0 | H | H | 1H—pyrazol-1-ylmethyl | H | CH₃ | OCH₃ | CH | |
| O | 0 | H | H | 4H—pyrazol-1-ylmethyl | H | CH₃ | OCH₃ | CH | |
| O | 0 | H | H | 1H—1,2,4,triazol-1-ylmethyl | H | OCH₃ | OCH₃ | CH | |
| O | 0 | H | H | 1H—1,2,4,triazol-1-ylmethyl | H | OCH₃ | OCH₃ | CH | |
| O | 0 | H | H | (1-methyl-1H—imidazol-2-yl)methyl | H | CH₃ | OCH₃ | CH | |
| O | 0 | H | H | (1-methyl-1H—imidazol-2-yl)methyl | H | OCH₃ | OCH₃ | CH | |
| O | 0 | H | H | (1-methyl-1H-1,2,4-triazol-5-yl)methyl | H | CH₃ | OCH₃ | CH | |
| O | 0 | H | H | (1-methyl-1H-1,2,4-triazol-5-yl)methyl | H | OCH₃ | OCH₃ | CH | |
| O | 0 | H | H | (4,5-dihydro-1,4,4-trimethyl-1H—imidazol-2-yl)methyl | H | CH₃ | OCH₃ | CH | |
| O | 0 | H | H | (4,5-dihydro-1,4,4-trimethyl-1H—imidazol-2-yl)methyl | H | OCH₃ | OCH₃ | CH | |
| O | 0 | H | H | (1,2,5-thiadiazol-3-yl)methyl | H | CH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | H | (1,2,5-thiadiazol-3-yl)methyl | H | OCH₃ | OCH₃ | CH | |
| O | 0 | H | H | 4-(2,6-dimethylmorpholino)methyl | H | CH₃ | OCH₃ | CH | |
| O | 0 | H | H | 4-(2,6-dimethylmorpholino)methyl | H | OCH₃ | OCH₃ | CH | |
| O | 0 | H | H | (4,6-dimethoxy-1,3,5-triazin-2-yl)methyl | H | CH₃ | OCH₃ | CH | |
| O | 0 | H | H | (4,6-dimethoxy-1,3,5-triazin-2-yl)methyl | H | OCH₃ | OCH₃ | CH | |
| O | 0 | H | H | (4-dimethylamino-6-methylthio-1,3,5-triazin-2-yl)methyl | H | CH₃ | OCH₃ | CH | |
| O | 0 | H | H | (4-dimethylamino-6-methylthio-1,3,5-triazin-2-yl)methyl | H | OCH₃ | OCH₃ | CH | |
| O | 0 | H | H | (cyclopentanon-2-yl)methyl | H | CH₃ | CH₃ | CH | |
| O | 0 | H | H | (cyclopentanon-2-yl)methyl | H | CH₃ | OCH₃ | CH | |
| O | 0 | H | H | (cyclopentanon-2-yl)methyl | H | OCH₃ | OCH₃ | CH | |
| O | 0 | H | H | (cyclopentanon-2-yl)methyl | H | Cl | OCH₃ | CH | |
| O | 0 | H | H | (cyclopentanon-2-yl)methyl | H | CH₃ | OCH₃ | N | |
| O | 0 | H | H | (cyclopentanon-2-yl)methyl | H | OCH₃ | OCH₃ | N | |
| O | 0 | H | H | γ-butyryllactone-2-yl)methyl | H | CH₃ | CH₃ | CH | |
| O | 0 | H | H | γ-butyryllactone-2-yl)methyl | H | CH₃ | OCH₃ | CH | |
| O | 0 | H | H | γ-butyryllactone-2-yl)methyl | H | OCH₃ | OCH₃ | CH | |
| O | 0 | H | H | γ-butyryllactone-2-yl)methyl | H | Cl | OCH₃ | N | |
| O | 0 | H | H | γ-butyryllactone-2-yl)methyl | H | CH₃ | OCH₃ | N | |
| O | 0 | H | H | γ-butyryllactone-3-yl)methyl | H | OCH₃ | OCH₃ | CH | |
| O | 0 | H | H | γ-butyryllactone-3-yl)methyl | H | CH₃ | CH₃ | CH | |
| O | 0 | H | H | γ-butyryllactone-3-yl)methyl | H | CH₃ | OCH₃ | CH | |
| O | 0 | H | H | γ-butyryllactone-3-yl)methyl | H | OCH₃ | OCH₃ | CH | |
| O | 0 | H | H | γ-butyryllactone-3-yl)methyl | H | Cl | OCH₃ | CH | |
| O | 0 | H | H | γ-butyryllactone-3-yl)methyl | H | CH₃ | OCH₃ | N | |

TABLE Ia-continued

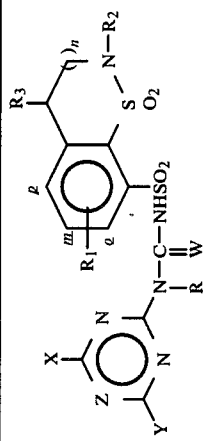

| W | n | R | R₁ | R₂ | R₃ | X | Y | Z | m.p. (°C.) |
|---|---|---|---|---|---|---|---|---|---|
| O | 0 | H | H | γ-butyryllactone-3-yl)methyl | H | OCH₃ | OCH₃ | N | |
| O | 0 | H | H | cyclohexanon-2-yl)methyl | H | CH₃ | CH₃ | CH | |
| O | 0 | H | H | (cyclohexanon-2-yl)methyl | H | CH₃ | OCH₃ | CH | |
| O | 0 | H | H | (cyclohexanon-2-yl)methyl | H | OCH₃ | OCH₃ | CH | |
| O | 0 | H | H | (cyclohexanon-2-yl)methyl | H | Cl | OCH₃ | CH | |
| O | 0 | H | H | (cyclohexanon-2-yl)methyl | H | CH₃ | OCH₃ | N | |
| O | 0 | H | H | (cyclohexanon-2-yl)methyl | H | OCH₃ | OCH₃ | N | |
| O | 0 | H | H | 2-chloro-6-fluorobenzyl | H | OCH₃ | OCH₃ | CH | |
| O | 0 | H | H | 4-methylthiobenzyl | H | OCH₃ | OCH₃ | CH | |
| O | 0 | H | H | 4-methylsulfonylbenzyl | H | OCH₃ | OCH₃ | CH | |
| O | 0 | H | H | 1,1'-biphenylmethyl | H | OCH₃ | OCH₃ | CH | |
| O | 0 | H | H | 3-phenoxybenzyl | H | OCH₃ | OCH₃ | CH | |
| O | 0 | H | H | 2-[4-(2,2-dimethyl-1,3-dioxolan-2-yl)methyl]ethyl | H | OCH₃ | OCH₃ | CH | |
| O | 0 | H | H | 4-(2,2-dimethyl-1,3-dioxolan-2-yl)methoxy | H | OCH₃ | OCH₃ | CH | |
| O | 0 | H | H | (2-methyl-1,3-dioxolan-2-yl)methyl | H | CH₃ | OCH₃ | CH | |
| O | 0 | H | H | (2-methyl-1,3-dioxolan-2-yl)methyl | H | OCH₃ | OCH₃ | CH | |
| O | 0 | H | H | 2-(2-methyl-1,3-dioxolan-2-yl)ethyl | H | CH₃ | OCH₃ | CH | |
| O | 0 | H | H | 2-(2-methyl-1,3-dioxolan-2-yl)ethyl | H | OCH₃ | OCH₃ | CH | |
| O | 0 | H | H | (1,3-dioxolan-2-yl)methyl | H | CH₃ | OCH₃ | CH | |
| O | 0 | H | H | (1,3-dioxolan-2-yl)methyl | H | OCH₃ | OCH₃ | CH | |
| O | 0 | H | H | 2-(1,3-dioxolan-2-yl)methyl | H | CH₃ | OCH₃ | CH | |
| O | 0 | H | H | 2-(1,3-dioxolan-2-yl)methyl | H | OCH₃ | OCH₃ | CH | |
| O | 0 | H | H | (1,3-dioxolan-2-yl)methyl | H | CH₃ | OCH₃ | CH | |
| O | 0 | H | H | (1,3-dioxolan-2-yl)methyl | H | OCH₃ | OCH₃ | CH | |
| O | 0 | H | H | 2-(2-tetrahydropyranyloxy)ethyl | H | CH₃ | OCH₃ | CH | |
| O | 0 | H | H | 2-(2-tetrahydropyranyloxy)ethyl | H | OCH₃ | OCH₃ | CH | |
| O | 0 | H | H | CH₂C(CH₃)=NOH | H | CH₃ | OCH₃ | CH | |
| O | 0 | H | H | CH₂C(CH₃)=NOH | H | OCH₃ | OCH₃ | CH | |
| O | 0 | H | H | CH₂CHC(CH₃)=NOH | H | CH₃ | OCH₃ | CH | |
| O | 0 | H | H | CH₂CHC(CH₃)=NOH | H | OCH₃ | OCH₃ | CH | |
| O | 0 | H | H | CH₂C(CH₃)(CN)OSi(CH₃)₃ | H | OCH₃ | OCH₃ | CH | |
| O | 0 | H | H | CH(C₆H₅)₂ | H | CH₃ | OCH₃ | CH | |

TABLE Ia-continued

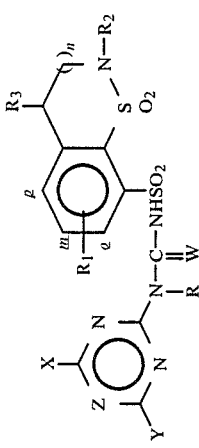

| W | n | R | R1 | R2 | R3 | X | Y | Z | m.p. (°C.) |
|---|---|---|----|----|----|---|---|---|-----------|
| O | 0 | H | H | CH(C6H5)2 | H | OCH3 | OCH3 | CH | |
| O | 0 | H | H | CH(CN)2 | H | CH3 | OCH3 | CH | |
| O | 0 | H | H | CH(CN)2 | H | OCH3 | OCH3 | CH | |
| O | 0 | H | H | C(Cl)=CHCl | H | CH3 | OCH3 | CH | |
| O | 0 | H | H | C(Cl)=CHCl | H | OCH3 | OCH3 | CH | |
| O | 0 | H | H | CH=CHC(O)CH3 | H | OCH3 | OCH3 | CH | |
| O | 0 | H | H | CH=CHCN | H | OCH3 | OCH3 | CH | |
| O | 0 | H | H | CH=CHCO2CH3 | H | OCH3 | OCH3 | CH | |
| O | 0 | H | H | CH=CHCH3 | H | CH3 | CH3 | CH | |
| O | 0 | H | H | CH=CHCH3 | H | OCH3 | OCH3 | CH | |
| O | 0 | H | H | CH=CHCH3 | H | CH3 | OCH3 | N | |
| O | 0 | H | H | CH=CHCH3 | H | OCH3 | OCH3 | N | |
| O | 0 | H | H | 2-epoxypropyl | H | CH3 | CH3 | CH | |
| O | 0 | H | H | 2-epoxypropyl | H | Cl | OCH3 | CH | |
| O | 0 | H | H | 2-epoxypropyl | H | OCH3 | OCH3 | CH | |
| O | 0 | H | H | 2-epoxypropyl | H | CH3 | OCH3 | CH | |
| O | 0 | H | H | 2-epoxypropyl | H | OCH3 | OCH3 | N | |
| O | 0 | H | H | 2-epoxybutyl | H | CH3 | CH3 | CH | |
| O | 0 | H | H | 2-epoxybutyl | H | OCH3 | OCH3 | CH | |
| O | 0 | H | H | 2-epoxybutyl | H | Cl | OCH3 | CH | |
| O | 0 | H | H | 2-epoxybutyl | H | CH3 | OCH3 | N | |
| O | 0 | H | H | 2-epoxybutyl | H | OCH3 | OCH3 | N | |
| O | 0 | H | H | (4-t-butylcyclohexyl)methyl | H | OCH3 | OCH3 | CH | |
| O | 0 | H | H | (4-chlorocyclopentyl)methyl | H | OCH3 | OCH3 | CH | |
| O | 0 | H | H | C6H5 | H | CH3 | CH3 | CH | |
| O | 0 | H | H | C6H5 | H | CH3 | OCH3 | CH | |
| O | 0 | H | H | C6H5 | H | OCH3 | OCH3 | CH | |
| O | 0 | H | H | C6H5 | H | CH3 | OCH3 | N | |
| O | 0 | H | H | C6H5 | H | OCH3 | OCH3 | N | |
| O | 0 | H | H | p-NO2C6H4 | H | OCH3 | OCH3 | CH | |
| O | 0 | H | H | p-NO2C6H5 | 4 | CH3 | OCH3 | CH | |
| O | 0 | H | H | p-CNC6H4 | H | OCH3 | OCH3 | CH | 193–194 |
| O | 0 | H | H | p-CNC6H4 | H | CH3 | OCH3 | CH | |
| O | 0 | H | H | p-CH3SO2C6H4 | H | CH3 | OCH3 | CH | |
| O | 0 | H | H | p-CH3SO2C6H4 | H | OCH3 | OCH3 | CH | |
| O | 0 | H | H | p-ClC6H4 | H | CH3 | OCH3 | CH | |
| O | 0 | H | H | p-ClC6H4 | H | OCH3 | OCH3 | CH | |
| O | 0 | H | H | 4-pyrimidinyl | H | CH3 | OCH3 | CH | |
| O | 0 | H | H | 4-pyrimidinyl | H | OCH3 | OCH3 | CH | |
| O | 0 | H | H | 2-pyrimidinyl | H | CH3 | OCH3 | CH | |

TABLE Ia-continued

| W | n | R | R₁ | R₂ | R₃ | X | Y | Z | m.p. (°C.) |
|---|---|---|---|---|---|---|---|---|---|
| O | 0 | H | H | 2-pyrimidinyl | H | OCH₃ | OCH₃ | CH | |
| O | 0 | H | H | 2-thienyl | H | OCH₃ | OCH₃ | CH | |
| O | 0 | H | H | 3-thienyl | H | OCH₃ | OCH₃ | CH | |
| O | 0 | H | H | 2-thiazolyl | H | OCH₃ | OCH₃ | CH | |
| O | 0 | H | H | 1-methyl-1H—imidazol-2-yl | H | OCH₃ | CH₃ | CH | |
| O | 0 | H | H | 2-oxazolyl | H | CH₃ | OCH₃ | CH | |
| O | 0 | H | H | 2-(5-nitrothienyl) | H | CH₃ | OCH₃ | CH | |
| O | 0 | H | H | pyrimidin-2-yl | H | CH₃ | OCH₃ | CH | |
| O | 0 | H | H | 4,6-dimethoxypyrimidin-2-yl | H | CH₃ | OCH₃ | CH | |
| O | 0 | H | H | 2-cyclopentanonyl | H | CH₃ | OCH₃ | CH | |
| O | 0 | H | H | 2-cyclopentanonyl | H | OCH₃ | OCH₃ | CH | |
| O | 0 | H | H | 3-cyclopentanonyl | H | CH₃ | OCH₃ | CH | |
| O | 0 | H | H | 3-cyclopentanonyl | H | OCH₃ | OCH₃ | CH | |
| O | 0 | H | H | 2-cyclohexanonyl | H | CH₃ | OCH₃ | CH | |
| O | 0 | H | H | 2-cyclohexanonyl | H | OCH₃ | OCH₃ | CH | |
| O | 0 | H | H | 3-cyclohexanonyl | H | CH₃ | OCH₃ | CH | |
| O | 0 | H | H | 3-cyclohexanonyl | H | OCH₃ | OCH₃ | CH | |
| O | 0 | H | H | γ-butyrolactone-2-yl | H | CH₃ | OCH₃ | CH | |
| O | 0 | H | H | γ-butyrolactone-2-yl | H | OCH₃ | OCH₃ | CH | 206-211 |
| O | 0 | H | H | γ-butyrolactone-3-yl | H | CH₃ | OCH₃ | CH | |
| O | 0 | H | H | γ-butyrolactone-3-yl | H | OCH₃ | OCH₃ | CH | |
| O | 0 | H | H | SCH₃ | H | CH₃ | OCH₃ | CH | |
| O | 0 | H | H | SCH₃ | H | OCH₃ | OCH₃ | CH | |
| O | 0 | H | H | SCH₂CH₂CH₃ | H | CH₃ | OCH₃ | CH | |
| O | 0 | H | H | SCH₂CH₂CH₃CH | H | OCH₃ | OCH₃ | CH | |
| O | 0 | H | H | S(CH₂)₉CH | H | CH₃ | CH₃ | CH | |
| O | 0 | H | H | SCCl₃ | H | OCH₃ | OCH₃ | CH | |
| O | 0 | H | H | SCCl₃ | H | Cl | OCH₃ | CH | |
| O | 0 | H | H | SCCl₃ | H | CH₃ | OCH₃ | N | |
| O | 0 | H | H | SCCl₃ | H | OCH₃ | OCH₃ | N | |
| O | 0 | H | H | SC₆H₅ | H | CH₃ | CH₃ | CH | |
| O | 0 | H | H | SC₆H₅ | H | CH₃ | OCH₃ | CH | |
| O | 0 | H | H | 4-nitrophenylthio | H | CH₃ | OCH₃ | CH | |
| O | 0 | H | H | 4-nitrophenylthio | H | OCH₃ | OCH₃ | CH | |

TABLE Ia-continued

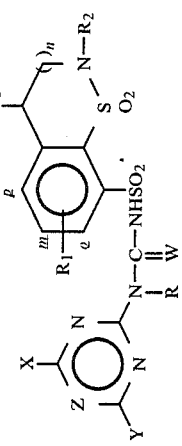

| W | n | R | R₁ | R₂ | R₃ | X | Y | Z | m.p. (°C.) |
|---|---|---|---|----|----|----|----|----|-----------|
| O | 0 | H | H | SO₂CH₃ | H | CH₃ | CH₃ | CH | |
| O | 0 | H | H | SO₂CH₃ | H | Cl | OCH₃ | CH | |
| O | 0 | H | H | SO₂CH₃ | H | CH₃ | OCH₃ | N | |
| O | 0 | H | H | SO₂CH₃ | H | OCH₃ | OCH₃ | N | |
| O | 0 | H | H | SO₂CH₂CH₃ | H | OCH₃ | OCH₃ | CH | |
| O | 0 | H | H | SO₂CH₂CH₃ | H | CH₃ | OCH₃ | CH | |
| O | 0 | H | H | SO₂CH(CH₃)₂ | H | OCH₃ | OCH₃ | CH | |
| O | 0 | H | H | SO₂CH(CH₃)₂ | H | CH₃ | OCH₃ | CH | |
| O | 0 | H | H | phenylsulfonyl | H | OCH₃ | OCH₃ | CH | |
| O | 0 | H | H | phenylsulfonyl | H | CH₃ | OCH₃ | N | |
| O | 0 | H | H | 4-toluenesulfonyl | H | OCH₃ | OCH₃ | N | |
| O | 0 | H | H | OCH₃ | H | CH₃ | CH₃ | N | 227–228 |
| O | 0 | H | H | OCH₃ | H | Cl | OCH₃ | N | 218–220 |
| O | 0 | H | H | OCH₃ | H | CH₃ | OCH₃ | N | 195–197 |
| O | 0 | H | H | OCH₃ | H | OCH₃ | OCH₃ | N | 199–201 |
| O | 0 | H | H | OH | H | CH₃ | OCH₃ | CH | 190–191 |
| O | 0 | H | H | OH | H | OCH₃ | OCH₃ | CH | 203–205 |
| O | 0 | H | H | OCH₂CH₂CH₃ | H | CH₃ | OCH₃ | CH | 185–186 |
| O | 0 | H | H | OCH₂CH₂CH₃ | H | OCH₃ | OCH₃ | CH | 189–190 |
| O | 0 | H | H | C(O)CH₃ | H | Cl | CH₃ | CH | 196–198 |
| O | 0 | H | H | C(O)CH₃ | H | Br | CH₃ | N | 203–205 |
| O | 0 | H | H | C(O)CH₃ | H | CH₃ | OCH₃ | CH | 185–186 |
| O | 0 | H | H | C(O)CH₃ | H | OCH₃ | OCH₃ | CH | 170–171 |
| O | 0 | H | H | C(O)CH₂CH₃ | H | CH₃ | OCH₃ | N | |
| O | 0 | H | H | C(O)CH₂CH₃ | H | Cl | OCH₃ | CH | |
| O | 0 | H | H | C(O)CH₂CH₃ | H | CH₃ | OCH₃ | CH | |
| O | 0 | H | H | C(O)CH₂CH₃ | H | OCH₃ | OCH₃ | CH | |
| O | 0 | H | H | C(O)CH₂CH₂CH₃ | H | CH₃ | OCH₃ | N | |
| O | 0 | H | H | C(O)CH₂CH₂CH₃ | H | Cl | OCH₃ | CH | |
| O | 0 | H | H | C(O)CH₂CH₂CH₃ | H | CH₃ | OCH₃ | CH | |
| O | 0 | H | H | C(O)CH₂CH₂CH₃ | H | OCH₃ | OCH₃ | CH | |
| O | 0 | H | H | C(O)C₆H₅ | H | CH₃ | CH₃ | CH | |
| O | 0 | H | H | C(O)C₆H₅ | H | Cl | OCH₃ | N | |
| O | 0 | H | H | C(O)C₆H₅ | H | CH₃ | OCH₃ | CH | |
| O | 0 | H | H | C(O)C₆H₅ | H | OCH₃ | OCH₃ | CH | |
| O | 0 | H | H | C(O)CH₂C₆H₅ | H | CH₃ | OCH₃ | CH | 88, dec. |
| O | 0 | H | H | C(O)CH₂C₆H₅ | H | OCH₃ | OCH₃ | N | |
| O | 0 | H | H | C(O)thienyl | H | CH₃ | OCH₃ | CH | |

TABLE Ia-continued

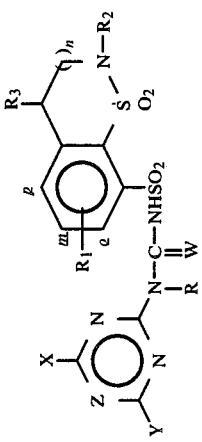

| W | n | R | R₁ | R₂ | R₃ | X | Y | Z | m.p. (°C.) |
|---|---|---|---|---|---|---|---|---|---|
| O | 0 | H | H | C(O)thienyl | H | OCH₃ | OCH₃ | CH | 210–215 |
| O | 0 | H | H | CO₂CH₂CH₃ | H | CH₃ | OCH₃ | CH | 171–173 |
| O | 0 | H | H | CO₂CH₂CH₃ | H | OCH₃ | OCH₃ | CH | 190–195 |
| O | 0 | H | H | CO₂CH₂CH₂CH₃ | H | OCH₃ | OCH₃ | CH | 143–150 |
| O | 0 | H | H | CO₂CH₂CH₂CH₃ | H | CH₃ | OCH₃ | CH | |
| O | 0 | H | H | CO₂CH(CH₃)₂ | H | OCH₃ | OCH₃ | CH | |
| O | 0 | H | H | CO₂CH(CH₃)₂ | H | CH₃ | OCH₃ | CH | |
| O | 0 | H | H | CO₂C(CH₃)₃ | H | OCH₃ | OCH₃ | CH | |
| O | 0 | H | H | CO₂C(CH₃)₃ | H | CH₃ | OCH₃ | CH | |
| O | 0 | H | H | CO₂CH₂CH₂OH | H | OCH₃ | OCH₃ | CH | |
| O | 0 | H | H | CO₂CH₂CH₂OH | H | CH₃ | OCH₃ | CH | |
| O | 0 | H | H | C(O)NHCH₃ | H | OCH₃ | OCH₃ | CH | |
| O | 0 | H | H | C(O)NHCH₃ | H | CH₃ | OCH₃ | CH | |
| O | 0 | H | H | C(O)NHCH₂CH₃ | H | OCH₃ | OCH₃ | CH | |
| O | 0 | H | H | C(O)NHCH₂CH₃ | H | CH₃ | OCH₃ | CH | 202–212 |
| O | 0 | H | H | C(O)NHCH₂CH₂CH₃ | H | OCH₃ | OCH₃ | CH | |
| O | 0 | H | H | C(O)NH₂CH₂CH₂CH₃ | H | CH₃ | OCH₃ | CH | |
| O | 0 | H | H | C(O)N(CH₃)₂ | H | OCH₃ | OCH₃ | CH | |
| O | 0 | H | H | C(O)N(CH₃)₂ | H | CH₃ | OCH₃ | CH | 181–183 |
| O | 0 | H | H | C(O)NH(cyclohexyl) | H | OCH₃ | OCH₃ | CH | |
| O | 0 | H | H | C(O)NH(cyclohexyl) | H | CH₃ | OCH₃ | CH | |
| O | 0 | H | H | C(O)NHC₆H₅ | H | OCH₃ | OCH₃ | CH | |
| O | 0 | H | H | C(O)NHC₆H₅ | H | CH₃ | CH₃ | CH | |
| O | 0 | H | H | (4,6-dimethylpyrimidin-2-yl)aminocarbonyl | H | CH₃ | OCH₃ | CH | 192–194 |
| O | 0 | H | H | (4-methoxy-6-methylpyrimidin-2-yl)aminocarbonyl | H | OCH₃ | OCH₃ | CH | 206–208 |
| O | 0 | H | H | (4,6-dimethoxypyrimidin-2-yl)aminocarbonyl | H | Cl | OCH₃ | CH | |
| O | 0 | H | H | (4-chloro-6-methoxypyrimidin-2-yl)aminocarbonyl | H | CH₃ | OCH₃ | CH | |
| O | 0 | H | H | (4-methoxy-6-methyl-1,3,5-triazin-2-yl)aminocarbonyl | H | OCH₃ | OCH₃ | N | |
| O | 0 | H | H | (4,6-dimethoxy-1,3,5-triazin-2-yl)aminocarbonyl | H | CH₃ | OCH₃ | CH | |
| O | 0 | H | H | CS₂CH₃ | H | CH₃ | OCH₃ | CH | |
| O | 0 | H | H | CS₂CH₃ | H | OCH₃ | OCH₃ | CH | |
| O | 0 | H | H | CS₂CH₂CH₃ | H | CH₃ | OCH₃ | CH | |
| O | 0 | H | H | CS₂CH₂CH₃ | H | OCH₃ | OCH₃ | CH | |
| O | 0 | H | H | CS₂CH₂CH₂CH₃ | H | CH₃ | OCH₃ | CH | |
| O | 0 | H | H | CS₂CH₂CH₂CH₃ | H | OCH₃ | OCH₃ | CH | |

TABLE Ia-continued

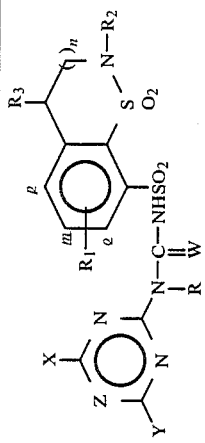

| W | n | R | R₁ | R₂ | R₃ | X | Y | Z | m.p. (°C.) |
|---|---|---|---|---|---|---|---|---|---|
| O | 0 | H | H | NH₂ | H | CH₂ | OCH₃ | CH | |
| O | 0 | H | H | NH₂ | H | OCH₃ | OCH₃ | CH | |
| O | 0 | H | H | NHCH₃ | H | CH₃ | OCH₃ | CH | |
| O | 0 | H | H | NHCH₃ | H | OCH₃ | OCH₃ | CH | |
| O | 0 | H | H | NHCH₂CH₃ | H | CH₃ | OCH₃ | CH | |
| O | 0 | H | H | NHCH₂CH₃ | H | OCH₃ | OCH₃ | CH | |
| O | 0 | H | H | NHC₆H₅ | H | CH₃ | OCH₃ | CH | |
| O | 0 | H | H | NHC₆H₅ | H | OCH₃ | OCH₃ | CH | |
| O | 0 | H | H | 4-chlorobenzyl | H | CH₃ | OCH₃ | CH | |
| O | 0 | H | H | 4-chlorobenzyl | H | OCH₃ | OCH₃ | N | |
| O | 0 | H | H | 4-chlorobenzyl | H | CH₃ | CH₃ | N | |
| O | 0 | H | H | 4-chlorobenzyl | H | OCH₃ | OCH₃ | CH | 194–197 |
| O | 0 | H | H | 4-chlorobenzyl | H | Cl | CH₃ | CH | 193–196 |
| O | 0 | H | H | 4-methylbenzyl | H | CH₃ | OCH₃ | CH | 170–173 |
| O | 0 | H | H | 4-methylbenzyl | H | OCH₃ | OCH₃ | CH | 147–150 |
| O | 0 | H | H | 4-methylbenzyl | H | CH₃ | CH₃ | CH | 154–157 |
| O | 0 | H | H | 4-methylbenzyl | H | OCH₃ | OCH₃ | N | 139–143 |
| O | 0 | H | H | 4-methylbenzyl | H | Cl | OCH₃ | CH | 223–225 |
| O | 0 | H | H | 4-methylbenzyl | H | CH₃ | OCH₃ | CH | 218–219 |
| O | 0 | H | H | 4-nitrobenzyl | H | OCH₃ | OCH₃ | CH | 180–183 |
| O | 0 | H | H | 4-nitrobenzyl | H | CH₃ | CH₃ | CH | 200–203 |
| O | 0 | H | H | 4-nitrobenzyl | H | OCH₃ | OCH₃ | N | 189–192 |
| O | 0 | H | H | 4-nitrobenzyl | H | CH₃ | OCH₃ | CH | 198–200 |
| O | 0 | H | H | 4-nitrobenzyl | H | OCH₃ | OCH₃ | CH | |
| O | 0 | H | H | 3-trifluoromethylbenzyl | H | CH₃ | OCH₃ | CH | |
| O | 0 | H | H | 3-trifluoromethylbenzyl | H | OCH₃ | OCH₃ | CH | |
| O | 0 | H | H | 3-trifluoromethylbenzyl | H | CH₃ | CH₃ | CH | |
| O | 0 | H | H | 3-trifluoromethylbenzyl | H | OCH₃ | OCH₃ | N | |
| O | 0 | H | H | 3-trifluoromethylbenzyl | H | Cl | OCH₃ | CH | |
| O | 0 | H | H | 3-trifluoromethylbenzyl | H | CH₃ | OCH₃ | CH | |
| O | 0 | H | H | 3-methylbenzyl | H | OCH₃ | OCH₃ | CH | |
| O | 0 | H | H | 3-methylbenzyl | H | CH₃ | CH₃ | CH | |
| O | 0 | H | H | 3-methylbenzyl | H | OCH₃ | OCH₃ | N | |
| O | 0 | H | H | 3-methylbenzyl | H | CH₃ | OCH₃ | CH | |
| O | 0 | H | H | 2-methylbenzyl | H | CH₃ | CH₃ | CH | |
| O | 0 | H | H | 2-methylbenzyl | H | CH₃ | OCH₃ | N | |
| O | 0 | H | H | 2-methylbenzyl | H | OCH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | H | 2-methylbenzyl | H | Cl | OCH₃ | CH | |
| O | 0 | H | H | 2-methylbenzyl | H | CH₃ | OCH₃ | N | |
| O | 0 | H | H | 2-methylbenzyl | H | OCH₃ | OCH₃ | N | |
| O | 0 | H | H | OH | H | CH₃ | OCH₃ | CH | |
| O | 0 | H | H | OH | H | CH₃ | CH₃ | CH | |
| O | 0 | H | H | CN | H | CH₃ | OCH₃ | CH | |
| O | 0 | H | H | CN | H | OCH₃ | OCH₃ | CH | |
| O | 0 | H | H | CN | H | Cl | OCH₃ | CH | |
| O | 0 | H | H | CN | H | CH₃ | OCH₃ | N | |
| O | 0 | H | H | CN | H | OCH₃ | OCH₃ | N | |
| O | 0 | H | H | P(O)(OCH₃)₂ | H | CH₃ | CH₃ | CH | |
| O | 0 | H | H | P(O)(OCH₃)₂ | H | CH₃ | OCH₃ | CH | |
| O | 0 | H | H | P(O)(OCH₃)₂ | H | OCH₃ | OCH₃ | CH | |
| O | 0 | H | H | P(O)(OCH₃)₂ | H | Cl | OCH₃ | CH | |
| O | 0 | H | H | P(O)(OCH₃)₂ | H | CH₃ | OCH₃ | N | |
| O | 0 | H | H | P(O)(OCH₃)₂ | H | OCH₃ | OCH₃ | N | |
| O | 0 | H | H | P(O)(OCH₂CH₃)₂ | H | CH₃ | CH₃ | CH | |
| O | 0 | H | H | P(S)(OCH₃)₂ | H | CH₃ | OCH₃ | CH | |
| O | 0 | H | H | P(O)(CH₃)₂ | H | OCH₃ | OCH₃ | CH | |
| O | 0 | H | H | P(S)(CH₃)₂ | H | CH₃ | OCH₃ | CH | |
| O | 0 | H | H | P(O)(SCH₂CH₂CH₂CH₃)₂ | H | OCH₃ | OCH₃ | CH | |
| O | 0 | H | H | Si(CH₃)₃ | H | CH₃ | OCH₃ | CH | |
| O | 0 | H | H | Si(CH₃)₃ | H | OCH₃ | OCH₃ | CH | |
| O | 0 | H | H | Si(CH₃)₃ | H | Cl | OCH₃ | CH | |
| O | 0 | H | H | Si(CH₃)₃ | H | CH₃ | OCH₃ | N | |
| O | 0 | H | H | Si(CH₃)₃ | H | OCH₃ | OCH₃ | N | |
| O | 0 | H | H | Si(CH₃)₂C(CH₃)₃ | H | CH₃ | CH₃ | CH | |
| O | 0 | H | H | Si(CH₃)₂C(CH₃)₃ | H | CH₃ | OCH₃ | CH | |
| O | 0 | H | H | Si(CH₃)₂C(CH₃)₃ | H | OCH₃ | OCH₃ | CH | |
| O | 0 | H | H | Si(CH₃)₂C(CH₃)₃ | H | Cl | OCH₃ | CH | |
| O | 0 | H | H | Si(CH₃)₂C(CH₃)₃ | H | CH₃ | OCH₃ | N | |
| O | 0 | H | H | Si(CH₃)₂C(CH₃)₃ | H | OCH₃ | OCH₃ | N | |
| O | 0 | H | H | Si(CH₃)₂C₆H₅ | H | CH₃ | OCH₃ | CH | |
| O | 0 | H | H | Si(CH₃)₂(CH₂)₉CH₃ | H | CH₃ | OCH₃ | CH | |
| O | 0 | H | H | C(O)CH₃ | H | OCH₃ | OCH₃ | CH | |
| O | 0 | H | H | CO₂CH₃ | H | OCH₃ | OCH₃ | CH | |
| S | 0 | H | H | CH₂CH=CH₂ | H | OCH₃ | OCH₃ | CH | |
| S | 0 | H | H | CH₂CH₂F | H | OCH₃ | OCH₃ | CH | |
| S | 0 | H | H | CH₂C(O)OCH₃ | H | OCH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| S | 0 | H | H | CF₂H | H | OCH₃ | OCH₃ | CH | |
| S | 0 | H | H | SO₂CH₃ | H | OCH₃ | OCH₃ | CH | |
| O | 1 | H | H | OCH₃ | H | OCH₃ | OCH₃ | CH | |
| O | 1 | H | H | C(O)NHCH₃ | H | OCH₃ | OCH₃ | CH | |
| O | 1 | H | H | CS₂CH₃ | H | OCH₃ | OCH₃ | CH | |
| O | 1 | H | H | NH₂ | H | OCH₃ | OCH₃ | CH | |
| O | 1 | H | H | OH | H | OCH₃ | OCH₃ | CH | |
| O | 1 | H | H | P(O)(OCH₃)₂ | H | OCH₃ | OCH₃ | CH | |
| O | 1 | H | H | Si(CH₃)₂C(CH₃)₃ | H | OCH₃ | OCH₃ | CH | |
| O | 1 | H | H | CH₂Cl | H | OCH₃ | OCH₃ | CH | |
| O | 1 | H | H | CH₂CN | H | OCH₃ | OCH₃ | CH | |
| O | 1 | H | H | CH₂F | H | OCH₃ | OCH₃ | CH | |
| O | 1 | H | H | CH₂OCH₃ | H | OCH₃ | OCH₃ | CH | |
| O | 1 | H | H | CH₂SCN | H | OCH₃ | OCH₃ | CH | |
| O | 1 | H | H | CH₂NO₂ | H | OCH₃ | OCH₃ | CH | |
| O | 1 | H | H | CH₂CO₂CH₃ | H | OCH₃ | OCH₃ | CH | |
| O | 1 | H | H | CH₂CH₂Cl | H | OCH₃ | OCH₃ | CH | |
| O | 1 | H | H | CH₂CH₂OH | H | OCH₃ | OCH₃ | CH | |
| O | 1 | H | H | CH₂SO₂CH₃ | H | OCH₃ | OCH₃ | CH | |
| O | 1 | H | H | CH₂SCH₃ | H | OCH₃ | OCH₃ | CH | |
| O | 1 | H | H | CH₂CF₃ | H | OCH₃ | OCH₃ | CH | |
| O | 0 | H | H | C(O)CH₃ | H | OCH₃ | OCH₃ | CH | |
| O | 0 | H | H | C(O)CH₃ | H | H | OCH₃ | CH | |
| O | 0 | H | H | C(O)CH₃ | H | CH₂CH₃ | OCH₃ | CH | |
| O | 0 | H | H | C(O)CH₃ | H | CH₂CH₂CH₃ | OCH₃ | CH | |
| O | 0 | H | H | C(O)CH₃ | H | CH₂CH₂CH₂CH₃ | OCH₃ | CH | |
| O | 0 | H | H | C(O)CH₃ | H | OCH₃ | OCH₃ | CH | |
| O | 0 | H | H | C(O)CH₃ | H | OCH₂CH₃ | OCH₃ | CH | |
| O | 0 | H | H | C(O)CH₃ | H | OCH₂CH₂CH₃ | OCH₃ | CH | |
| O | 0 | H | H | C(O)CH₃ | H | OCH(CH₃)₂ | OCH₃ | CH | |
| O | 0 | H | H | C(O)CH₃ | H | OCH₂CF₃ | OCH₃ | CH | |
| O | 0 | H | H | C(O)CH₃ | H | CH₂Cl | OCH₃ | CH | |
| O | 0 | H | H | C(O)CH₃ | H | CH₂Br | OCH₃ | CH | |
| O | 0 | H | H | C(O)CH₃ | H | CH₂CH₂Cl | OCH₃ | CH | |
| O | 0 | H | H | C(O)CH₃ | H | SCH₃ | OCH₃ | CH | |
| O | 0 | H | H | C(O)CH₃ | H | SCH₂CH₃ | OCH₃ | CH | |
| O | 0 | H | H | C(O)CH₃ | H | SCH₂CH₃Cl | OCH₃ | CH | |
| O | 0 | H | H | C(O)CH₃ | H | F | OCH₃ | CH | |
| O | 0 | H | H | C(O)CH₃ | H | Cl | OCH₃ | CH | |
| O | 0 | H | H | C(O)CH₃ | H | Br | OCH₃ | CH | |
| O | 0 | H | H | C(O)CH₃ | H | OCH₂CH₂F | OCH₃ | CH | |
| O | 0 | H | H | C(O)CH₃ | H | CH₂OCH₃ | OCH₃ | CH | |

TABLE Ia-continued

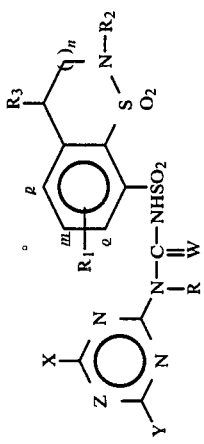

| W | n | R | R₁ | R₂ | R₃ | X | Y | Z | m.p. (°C.) |
|---|---|---|---|---|---|---|---|---|---|
| O | O | H | H | C(O)CH₃ | H | CH₂OCH₂CH₃ | OCH₃ | CH | |
| O | O | H | H | C(O)CH₃ | H | CH₂OCH₂CH₂CH₃ | OCH₃ | CH | |
| O | O | H | H | C(O)CH₃ | H | OCH₂OCH₃ | OCH₃ | CH | |
| O | O | H | H | C(O)CH₃ | H | OCH₂CH₂OCH₃ | OCH₃ | CH | |
| O | O | H | H | C(O)CH₃ | H | NH₂ | OCH₃ | CH | |
| O | O | H | H | C(O)CH₃ | H | NHCH₃ | OCH₃ | CH | |
| O | O | H | H | C(O)CH₃ | H | NHCH₂CH₃ | OCH₃ | CH | |
| O | O | H | H | C(O)CH₃ | H | NHCH(CH₃)₂ | OCH₃ | CH | |
| O | O | H | H | C(O)CH₃ | H | NHCH₂CH₂CH₃ | OCH₃ | CH | |
| O | O | H | H | C(O)CH₃ | H | N(CH₃)₂ | OCH₃ | CH | |
| O | O | H | H | C(O)CH₃ | H | N(CH₃)CH₂CH₃ | OCH₃ | CH | |
| O | O | H | H | C(O)CH₃ | H | N(CH₃)C(CH₃)₂ | OCH₃ | CH | |
| O | O | H | H | C(O)CH₃ | H | cyclopropyl | OCH₃ | CH | |
| O | O | H | H | C(O)CH₃ | H | cyclobutyl | OCH₃ | CH | |
| O | O | H | H | C(O)CH₃ | H | cyclopentyl | OCH₃ | CH | |
| O | O | H | H | C(O)CH₃ | H | OCH₃ | H | CH | |
| O | O | H | H | C(O)CH₃ | H | OCH₃ | OCH₂CH=CH₂ | CH | |
| O | O | H | H | C(O)CH₃ | H | OCH₃ | OCH₂C(CH₃)=CH₂ | CH | |
| O | O | H | H | C(O)CH₃ | H | OCH₃ | OCH₂C≡CH | CH | |
| O | O | H | H | C(O)CH₃ | H | OCH₃ | OCH₂C≡CCH₃ | CH | |
| O | O | H | H | C(O)CH₃ | H | OCH₃ | CH₂SCH₃ | CH | |
| O | O | H | H | C(O)CH₃ | H | OCH₃ | CH₂SCH₂CH₃ | CH | |
| O | O | H | H | C(O)CH₃ | H | OCH₃ | CH₂SC(CH₃)₃ | CH | |
| O | O | H | H | C(O)CH₃ | H | OCH₃ | CH₂CH₂CH₂Cl | CH | |
| O | O | H | H | C(O)CH₃ | H | OCH₃ | N₃ | CH | |
| O | O | H | H | C(O)CH₃ | H | OCH₃ | CN | CH | |
| O | O | H | H | C(O)CH₃ | H | OCH₃ | C(O)CH₃ | CH | |
| O | O | H | H | C(O)CH₃ | H | OCH₃ | CHO | CH | |
| O | O | H | H | C(O)CH₃ | H | OCH₃ | C(O)CH(CH₃)₂ | CH | |
| O | O | H | H | C(O)CH₃ | H | OCH₃ | CH(OCH₃)₂ | CH | |
| O | O | H | H | C(O)CH₃ | H | OCH₃ | CH(OCH₂CH₃)₂ | CH | |
| O | O | H | H | C(O)CH₃ | H | SCH₃ | SCH₃ | CH | |
| O | O | H | H | C(O)CH₃ | H | NHCH₃ | NHCH₃ | CH | |
| O | O | H | m-CH₃ | C(O)CH₃ | H | OCH₃ | OCH₃ | CH | |
| O | O | H | o-CH₃ | C(O)CH₃ | H | OCH₃ | OCH₃ | CH | |
| O | O | H | o-CH₂CH₃ | C(O)CH₃ | H | OCH₃ | OCH₃ | CH | |
| O | O | H | o-CH₂CH₂CH₃ | CH₂CH₂CH₂CH₃ | H | OCH₃ | OCH₃ | CH | |
| O | O | H | o-CH₂CH₂CH₃ | CH₂CH₂CH₂CH₃ | H | OCH₃ | OCH₃ | CH | |
| O | O | H | m-OCH₃ | C(O)CH₃ | H | OCH₃ | OCH₃ | CH | |
| O | O | H | m-OCH₂CH₃ | C(O)CH₃ | H | OCH₃ | OCH₃ | CH | |
| O | O | H | m-OCH₂CH₂CH₃ | C(O)CH₃ | H | OCH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | m-OCH(CH₃)₂ | C(O)CH₃ | H | OCH₃ | OCH₃ | CH | |
| O | 0 | H | o-OCH₃ | C(O)CH₃ | H | OCH₃ | OCH₃ | CH | |
| O | 0 | H | o-OCH₂CH₃ | C(O)CH₃ | H | OCH₃ | OCH₃ | CH | |
| O | 0 | H | m-OCF₂H | C(O)CH₃ | H | OCH₃ | OCH₃ | CH | |
| O | 0 | H | m-OCH₂CH₂F | C(O)CH₃ | H | OCH₃ | OCH₃ | CH | |
| O | 0 | H | m-OCH₂CF₃ | C(O)CH₃ | H | OCH₃ | OCH₃ | CH | |
| O | 0 | H | o—OCH₂CH₂CH₂F | C(O)CH₃ | H | OCH₃ | OCH₃ | CH | |
| O | 0 | H | m-CF₃ | C(O)CH₃ | H | OCH₃ | OCH₃ | CH | |
| O | 0 | H | o-CF₃ | C(O)CH₃ | H | OCH₃ | OCH₃ | CH | |
| O | 0 | H | o-CH₂CH₂Cl | C(O)CH₃ | H | OCH₃ | OCH₃ | CH | |
| O | 0 | H | o-CH₂CH₂CH₂F | C(O)CH₃ | H | OCH₃ | OCH₃ | CH | |
| O | 0 | H | m-SCH₃ | C(O)CH₃ | H | OCH₃ | OCH₃ | CH | |
| O | 0 | H | o-SCH₃ | C(O)CH₃ | H | OCH₃ | OCH₃ | CH | |
| O | 0 | H | o-SCH₂CH₂CH₃ | C(O)CH₃ | H | OCH₃ | OCH₃ | CH | |
| O | 0 | H | o-SCF₃ | C(O)CH₃ | H | OCH₃ | OCH₃ | CH | |
| O | 0 | H | o-SCH₂CH₂CH₂Cl | C(O)CH₃ | H | OCH₃ | OCH₃ | CH | |
| O | 0 | H | o-NH₂ | C(O)CH₃ | H | OCH₃ | OCH₃ | CH | |
| O | 0 | H | m-NHCH₃ | C(O)CH₃ | H | OCH₃ | OCH₃ | CH | |
| O | 0 | H | o-NHCH₃ | C(O)CH₃ | H | OCH₃ | OCH₃ | CH | |
| O | 0 | H | m-NH(CH₃)₂ | C(O)CH₃ | H | OCH₃ | OCH₃ | CH | |
| O | 0 | H | o-NHCH₂CH₃ | C(O)CH₃ | H | OCH₃ | OCH₃ | CH | |
| O | 0 | H | o-NHCH₂CH₂CH₃ | C(O)CH₃ | H | OCH₃ | OCH₃ | CH | |
| O | 0 | H | o-N(CH₃)CH₂CH₂CH₃ | C(O)CH₃ | H | OCH₃ | OCH₃ | CH | |
| O | 0 | H | m-F | C(O)CH₃ | H | OCH₃ | OCH₃ | CH | |
| O | 0 | H | o-F | C(O)CH₃ | H | OCH₃ | OCH₃ | CH | |
| O | 0 | H | p-F | C(O)CH₃ | H | OCH₃ | OCH₃ | CH | |
| O | 0 | H | m-Cl | C(O)CH₃ | H | OCH₃ | OCH₃ | CH | |
| O | 0 | H | o-Cl | C(O)CH₃ | H | OCH₃ | OCH₃ | CH | |
| O | 0 | H | p-Cl | C(O)CH₃ | H | OCH₃ | OCH₃ | CH | |
| O | 0 | H | m-Br | C(O)CH₃ | H | OCH₃ | OCH₃ | CH | |
| O | 0 | H | o-Br | C(O)CH₃ | H | OCH₃ | OCH₃ | CH | |
| O | 0 | H | m-I | C(O)CH₃ | H | OCH₃ | OCH₃ | CH | |
| O | 0 | H | o-NO₂ | C(O)CH₃ | H | OCH₃ | OCH₃ | CH | |
| O | 0 | H | m-CH₃ | C(O)CH₃ | H | CH₃ | OCH₃ | CH | |
| O | 0 | H | o-CH₃ | C(O)CH₃ | H | CH₃ | OCH₃ | CH | |
| O | 0 | H | o-CH₂CH₃ | C(O)CH₃ | H | CH₃ | OCH₃ | CH | |
| O | 0 | H | m-OCH₃ | C(O)CH₃ | H | CH₃ | OCH₃ | CH | |
| O | 0 | H | o-OCH₃ | C(O)CH₃ | H | CH₃ | OCH₃ | CH | |
| O | 0 | H | m-OCH₂CH₃ | C(O)CH₃ | H | CH₃ | OCH₃ | CH | |
| O | 0 | H | m-CF₃ | C(O)CH₃ | H | CH₃ | OCH₃ | CH | |
| O | 0 | H | m-SCH₃ | C(O)CH₃ | H | CH₃ | OCH₃ | CH | |

TABLE Ia-continued

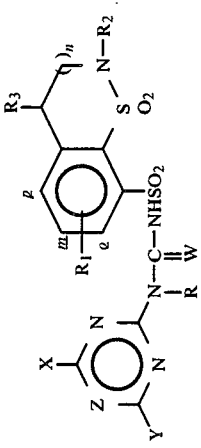

| W | n | R | R$_1$ | R$_2$ | R$_3$ | X | Y | Z | m.p. (°C.) |
|---|---|---|---|---|---|---|---|---|---|
| O | 0 | H | o-SCH$_3$ | C(O)CH$_3$ | H | CH$_3$ | OCH$_3$ | CH | |
| O | 0 | H | m-N(CH$_3$)$_2$ | C(O)CH$_3$ | H | CH$_3$ | OCH$_3$ | CH | |
| O | 0 | H | m-F | C(O)CH$_3$ | H | CH$_3$ | OCH$_3$ | CH | |
| O | 0 | H | o-F | C(O)CH$_3$ | H | CH$_3$ | OCH$_3$ | CH | |
| O | 0 | H | m-Cl | C(O)CH$_3$ | H | CH$_3$ | OCH$_3$ | CH | |
| O | 0 | H | o-Cl | C(O)CH$_3$ | H | CH$_3$ | OCH$_3$ | CH | |
| O | 0 | H | m-Br | C(O)CH$_3$ | H | CH$_3$ | OCH$_3$ | CH | |
| O | 0 | H | m-CH$_3$ | C(O)CH$_2$CH$_3$ | H | CH$_3$ | OCH$_3$ | CH | |
| O | 0 | H | m-CH$_3$ | C(O)CH$_2$CH$_3$ | H | OCH$_3$ | OCH$_3$ | CH | |
| O | 0 | H | m-OCH$_3$ | C(O)CH$_2$CH$_3$ | H | CH$_3$ | OCH$_3$ | CH | |
| O | 0 | H | m-N(CH$_3$)$_2$ | C(O)CH$_2$CH$_3$ | H | OCH$_3$ | OCH$_3$ | CH | |
| O | 0 | H | m-N(CH$_3$)$_2$ | C(O)CH$_2$CH$_3$ | H | CH$_3$ | OCH$_3$ | CH | |
| O | 0 | H | m-F | C(O)CH$_2$CH$_3$ | H | OCH$_3$ | OCH$_3$ | CH | |
| O | 0 | H | m-F | C(O)CH$_2$CH$_3$ | H | CH$_3$ | OCH$_3$ | CH | |
| O | 0 | H | m-Cl | C(O)CH$_2$CH$_3$ | H | OCH$_3$ | OCH$_3$ | CH | |
| O | 0 | H | m-Cl | C(O)CH$_2$CH$_3$ | H | CH$_3$ | OCH$_3$ | CH | |
| O | 0 | H | m-Br | C(O)CH$_2$CH$_3$ | H | OCH$_3$ | OCH$_3$ | CH | |
| O | 0 | H | m-SCH$_3$ | C(O)CH$_2$CH$_3$ | H | CH$_3$ | OCH$_3$ | CH | |
| O | 0 | H | m-SCH$_3$ | C(O)CH$_2$CH$_3$ | H | OCH$_3$ | OCH$_3$ | CH | |
| O | 0 | H | m-CH$_3$ | C(O)CH$_2$CH$_3$ | H | CH$_3$ | OCH$_3$ | CH | |
| O | 0 | H | o-OCH$_3$ | C(O)CH$_2$CH$_3$ | H | OCH$_3$ | OCH$_3$ | CH | |
| O | 0 | H | o-OCH$_3$ | C(O)CH$_2$CH$_3$ | H | CH$_3$ | OCH$_3$ | CH | |
| O | 0 | H | m-CH$_3$ | C(O)CH$_2$CH$_3$ | H | OCH$_3$ | OCH$_3$ | CH | |
| O | 0 | H | m-CH$_3$ | C(O)CH$_2$CH$_3$ | H | CH$_3$ | OCH$_3$ | CH | |
| O | 0 | H | m-OCH$_3$ | C(O)CH$_2$CH$_3$ | H | OCH$_3$ | OCH$_3$ | CH | |
| O | 0 | H | m-N(CH$_3$)$_2$ | C(O)CH$_2$CH$_3$ | H | CH$_3$ | OCH$_3$ | CH | |
| O | 0 | H | m-N(CH$_3$)$_2$ | C(O)CH$_2$CH$_3$ | H | OCH$_3$ | OCH$_3$ | CH | |
| O | 0 | H | m-F | C(O)CH$_2$CH$_3$ | H | CH$_3$ | OCH$_3$ | CH | |
| O | 0 | H | m-Cl | C(O)CH$_2$CH$_3$ | H | OCH$_3$ | OCH$_3$ | CH | |
| O | 0 | H | m-Br | C(O)CH$_2$CH$_3$ | H | CH$_3$ | OCH$_3$ | CH | |
| O | 0 | H | m-SCH$_3$ | C(O)CH$_2$CH$_3$ | H | OCH$_3$ | OCH$_3$ | CH | |
| O | 0 | H | m-SCH$_3$ | C(O)CH$_2$CH$_3$ | H | CH$_3$ | OCH$_3$ | CH | |
| O | 0 | H | m-CH$_3$ | C(O)CH$_2$CH$_3$ | H | OCH$_3$ | OCH$_3$ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | m-CH₃ | C(O)CH₂CH₃ | H | OCH₃ | OCH₃ | CH | |
| O | 0 | H | o-OCH₃ | C(O)CH₂CH₃ | H | CH₃ | OCH₃ | CH | |
| O | 0 | H | o-OCH₃ | C(O)CH₂CH₃ | H | OCH₃ | OCH₃ | CH | |
| O | 0 | H | o-F | C(O)CH₂CH₃ | H | CH₃ | OCH₃ | CH | |
| O | 0 | H | o-F | C(O)CH₂CH₃ | H | OCH₃ | OCH₃ | CH | |
| O | 0 | H | o-Cl | C(O)CH₂CH₃ | H | CH₃ | OCH₃ | CH | |
| O | 0 | H | o-Cl | C(O)CH₂CH₃ | H | OCH₃ | OCH₃ | CH | |
| O | 0 | H | o-Br | C(O)CH₂CH₃ | H | CH₃ | OCH₃ | CH | |
| O | 0 | H | o-Br | C(O)CH₂CH₃ | H | OCH₃ | OCH₃ | CH | |
| O | 0 | H | o-SCH₃ | C(O)CH₂CH₃ | H | CH₃ | OCH₃ | CH | |
| O | 0 | H | o-SCH₃ | C(O)CH₂CH₃ | H | OCH₃ | OCH₃ | CH | |
| O | 0 | H | m-OCH₂CH₃ | C(O)CH₂CH₃ | H | CH₃ | OCH₃ | CH | |
| O | 0 | H | m-OCH₂CH₃ | C(O)CH₂CH₃ | H | OCH₃ | OCH₃ | CH | |
| O | 0 | H | m-CH₃ | CH₂C(O)CH₃ | H | CH₃ | OCH₃ | CH | |
| O | 0 | H | m-CH₃ | CH₂C(O)CH₃ | H | OCH₃ | OCH₃ | CH | |
| O | 0 | H | m-OCH₃ | CH₂C(O)CH₃ | H | CH₃ | OCH₃ | CH | |
| O | 0 | H | m-OCH₃ | CH₂C(O)CH₃ | H | OCH₃ | OCH₃ | CH | |
| O | 0 | H | m-N(CH₃)₂ | CH₂C(O)CH₃ | H | CH₃ | OCH₃ | CH | |
| O | 0 | H | m-N(CH₃)₂ | CH₂C(O)CH₃ | H | OCH₃ | OCH₃ | CH | |
| O | 0 | H | m-F | CH₂C(O)CH₃ | H | CH₃ | OCH₃ | CH | |
| O | 0 | H | m-F | CH₂C(O)CH₃ | H | OCH₃ | OCH₃ | CH | |
| O | 0 | H | m-Cl | CH₂C(O)CH₃ | H | CH₃ | OCH₃ | CH | |
| O | 0 | H | m-Cl | CH₂C(O)CH₃ | H | OCH₃ | OCH₃ | CH | |
| O | 0 | H | m-Br | CH₂C(O)CH₃ | H | CH₃ | OCH₃ | CH | |
| O | 0 | H | m-Br | CH₂C(O)CH₃ | H | OCH₃ | OCH₃ | CH | |
| O | 0 | H | m-SCH₃ | CH₂C(O)CH₃ | H | CH₃ | OCH₃ | CH | |
| O | 0 | H | m-SCH₃ | CH₂C(O)CH₃ | H | OCH₃ | OCH₃ | CH | |
| O | 0 | H | m-CH₃ | C(O)CH₂CH₃ | H | CH₃ | OCH₃ | CH | |
| O | 0 | H | o-OCH₃ | C(O)CH₂CH₃ | H | OCH₃ | OCH₃ | CH | |
| O | 0 | H | o-F | C(O)CH₂CH₃ | H | CH₃ | OCH₃ | CH | |
| O | 0 | H | o-F | C(O)CH₂CH₃ | H | OCH₃ | OCH₃ | CH | |
| O | 0 | H | o-Cl | C(O)CH₂CH₃ | H | CH₃ | OCH₃ | CH | |
| O | 0 | H | o-Cl | C(O)CH₂CH₃ | H | OCH₃ | OCH₃ | CH | |
| O | 0 | H | o-Br | C(O)CH₂CH₃ | H | CH₃ | OCH₃ | CH | |
| O | 0 | H | o-Br | C(O)CH₂CH₃ | H | OCH₃ | OCH₃ | CH | |
| O | 0 | H | o-SCH₃ | C(O)CH₂CH₃ | H | CH₃ | OCH₃ | CH | |
| O | 0 | H | o-SCH₃ | C(O)CH₂CH₃ | H | OCH₃ | OCH₃ | CH | |
| O | 0 | H | m-OCH₂CH₃ | C(O)CH₂CH₃ | H | CH₃ | OCH₃ | CH | |
| O | 0 | H | m-OCH₂CH₃ | C(O)CH₂CH₃ | H | OCH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | m-CH₃ | CH₂OCH₃ | H | CH₃ | OCH₃ | CH | |
| O | 0 | H | m-CH₃ | CH₂OCH₃ | H | OCH₃ | OCH₃ | CH | |
| O | 0 | H | m-OCH₃ | CH₂OCH₃ | H | CH₃ | OCH₃ | CH | |
| O | 0 | H | m-OCH₃ | CH₂OCH₃ | H | OCH₃ | OCH₃ | CH | |
| O | 0 | H | m-N(CH₃)₂ | CH₂OCH₃ | H | CH₃ | OCH₃ | CH | |
| O | 0 | H | m-N(CH₃)₂ | CH₂OCH₃ | H | OCH₃ | OCH₃ | CH | |
| O | 0 | H | m-F | CH₂OCH₃ | H | CH₃ | OCH₃ | CH | |
| O | 0 | H | m-F | CH₂OCH₃ | H | OCH₃ | OCH₃ | CH | |
| O | 0 | H | m-Cl | CH₂OCH₃ | H | CH₃ | OCH₃ | CH | |
| O | 0 | H | m-Cl | CH₂OCH₃ | H | OCH₃ | OCH₃ | CH | |
| O | 0 | H | m-Br | CH₂OCH₃ | H | CH₃ | OCH₃ | CH | |
| O | 0 | H | m-Br | CH₂OCH₃ | H | OCH₃ | OCH₃ | CH | |
| O | 0 | H | m-SCH₃ | CH₂OCH₃ | H | CH₃ | OCH₃ | CH | |
| O | 0 | H | m-SCH₃ | CH₂OCH₃ | H | OCH₃ | OCH₃ | CH | |
| O | 0 | H | o-CH₃ | CH₂OCH₃ | H | CH₃ | OCH₃ | CH | |
| O | 0 | H | o-CH₃ | CH₂OCH₃ | H | OCH₃ | OCH₃ | CH | |
| O | 0 | H | o-OCH₃ | CH₂OCH₃ | H | CH₃ | OCH₃ | CH | |
| O | 0 | H | o-OCH₃ | CH₂OCH₃ | H | OCH₃ | OCH₃ | CH | |
| O | 0 | H | o-F | CH₂OCH₃ | H | CH₃ | OCH₃ | CH | |
| O | 0 | H | o-F | CH₂OCH₃ | H | OCH₃ | OCH₃ | CH | |
| O | 0 | H | o-Cl | CH₂OCH₃ | H | CH₃ | OCH₃ | CH | |
| O | 0 | H | o-Cl | CH₂OCH₃ | H | OCH₃ | OCH₃ | CH | |
| O | 0 | H | o-Br | CH₂OCH₃ | H | CH₃ | OCH₃ | CH | |
| O | 0 | H | o-Br | CH₂OCH₃ | H | OCH₃ | OCH₃ | CH | |
| O | 0 | H | o-SCH₃ | CH₂OCH₃ | H | CH₃ | OCH₃ | CH | |
| O | 0 | H | o-SCH₃ | CH₂OCH₃ | H | OCH₃ | OCH₃ | CH | |
| O | 0 | H | m-OCH₂CH₃ | CH₂OCH₃ | H | CH₃ | OCH₃ | CH | |
| O | 0 | H | m-OCH₂CH₃ | CH₂OCH₃ | H | OCH₃ | OCH₃ | CH | |
| O | 0 | H | m-CH₃ | CO₂CH₃ | H | CH₃ | OCH₃ | CH | |
| O | 0 | H | m-CH₃ | CO₂CH₃ | H | OCH₃ | OCH₃ | CH | |
| O | 0 | H | m-OCH₃ | CO₂CH₃ | H | CH₃ | OCH₃ | CH | |
| O | 0 | H | m-OCH₃ | CO₂CH₃ | H | OCH₃ | OCH₃ | CH | |
| O | 0 | H | m-N(CH₃)₂ | CO₂CH₃ | H | CH₃ | OCH₃ | CH | |
| O | 0 | H | m-N(CH₃)₂ | CO₂CH₃ | H | OCH₃ | OCH₃ | CH | |
| O | 0 | H | m-F | CO₂CH₃ | H | CH₃ | OCH₃ | CH | |
| O | 0 | H | m-F | CO₂CH₃ | H | OCH₃ | OCH₃ | CH | |
| O | 0 | H | m-Cl | CO₂CH₃ | H | CH₃ | OCH₃ | CH | |
| O | 0 | H | m-Cl | CO₂CH₃ | H | OCH₃ | OCH₃ | CH | |
| O | 0 | H | m-Br | CO₂CH₃ | H | CH₃ | OCH₃ | CH | |
| O | 0 | H | m-Br | CO₂CH₃ | H | OCH₃ | OCH₃ | CH | |
| O | 0 | H | m-SCH₃ | CO₂CH₃ | H | CH₃ | OCH₃ | CH | |

TABLE Ia-continued

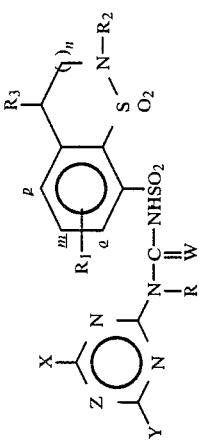

| W | n | R | R₁ | R₂ | R₃ | X | Y | Z | m.p. (°C.) |
|---|---|---|---|---|---|---|---|---|---|
| O | 0 | H | m-SCH₃ | CO₂CH₃ | H | OCH₃ | OCH₃ | CH | |
| O | 0 | H | m-CH₃ | CO₂CH₃ | H | CH₃ | OCH₃ | CH | |
| O | 0 | H | m-CH₃ | CO₂CH₃ | H | OCH₃ | OCH₃ | CH | |
| O | 0 | H | o-OCH₃ | CO₂CH₃ | H | CH₃ | OCH₃ | CH | |
| O | 0 | H | o-OCH₃ | CO₂CH₃ | H | OCH₃ | OCH₃ | CH | |
| O | 0 | H | o-F | CO₂CH₃ | H | CH₃ | OCH₃ | CH | |
| O | 0 | H | o-F | CO₂CH₃ | H | OCH₃ | OCH₃ | CH | |
| O | 0 | H | o-Cl | CO₂CH₃ | H | CH₃ | OCH₃ | CH | |
| O | 0 | H | o-Cl | CO₂CH₃ | H | OCH₃ | OCH₃ | CH | |
| O | 0 | H | o-Br | CO₂CH₃ | H | CH₃ | OCH₃ | CH | |
| O | 0 | H | o-Br | CO₂CH₃ | H | OCH₃ | OCH₃ | CH | |
| O | 0 | H | o-SCH₃ | CO₂CH₃ | H | CH₃ | OCH₃ | CH | |
| O | 0 | H | o-SCH₃ | CO₂CH₃ | H | OCH₃ | OCH₃ | CH | |
| O | 0 | H | m-OCH₂CH₃ | CO₂CH₃ | H | CH₃ | OCH₃ | CH | |
| O | 0 | H | m-OCH₂CH₃ | CO₂CH₃ | H | OCH₃ | OCH₃ | CH | |
| O | 0 | H | m-CH₃ | CN | H | CH₃ | OCH₃ | CH | |
| O | 0 | H | m-CH₃ | CN | H | OCH₃ | OCH₃ | CH | |
| O | 0 | H | m-OCH₃ | CN | H | CH₃ | OCH₃ | CH | |
| O | 0 | H | m-OCH₃ | CN | H | OCH₃ | OCH₃ | CH | |
| O | 0 | H | m-N(CH₃)₂ | CN | H | CH₃ | OCH₃ | CH | |
| O | 0 | H | m-N(CH₃)₂ | CN | H | OCH₃ | OCH₃ | CH | |
| O | 0 | H | m-F | CN | H | CH₃ | OCH₃ | CH | |
| O | 0 | H | m-F | CN | H | OCH₃ | OCH₃ | CH | |
| O | 0 | H | m-Cl | CN | H | CH₃ | OCH₃ | CH | |
| O | 0 | H | m-Cl | CN | H | OCH₃ | OCH₃ | CH | |
| O | 0 | H | m-Br | CN | H | CH₃ | OCH₃ | CH | |
| O | 0 | H | m-Br | CN | H | OCH₃ | OCH₃ | CH | |
| O | 0 | H | m-SCH₃ | CN | H | CH₃ | OCH₃ | CH | |
| O | 0 | H | m-SCH₃ | CN | H | OCH₃ | OCH₃ | CH | |
| O | 0 | H | m-CH₃ | CN | H | CH₃ | OCH₃ | CH | |
| O | 0 | H | m-CH₃ | CN | H | OCH₃ | OCH₃ | CH | |
| O | 0 | H | o-OCH₃ | CN | H | CH₃ | OCH₃ | CH | |
| O | 0 | H | o-OCH₃ | CN | H | OCH₃ | OCH₃ | CH | |
| O | 0 | H | o-F | CN | H | CH₃ | OCH₃ | CH | |
| O | 0 | H | o-F | CN | H | OCH₃ | OCH₃ | CH | |
| O | 0 | H | o-Cl | CN | H | CH₃ | OCH₃ | CH | |
| O | 0 | H | o-Cl | CN | H | OCH₃ | OCH₃ | CH | |
| O | 0 | H | o-Br | CN | H | CH₃ | OCH₃ | CH | |
| O | 0 | H | o-Br | CN | H | OCH₃ | OCH₃ | CH | |
| O | 0 | H | o-SCH₃ | CN | H | CH₃ | OCH₃ | CH | |
| O | 0 | H | o-SCH₃ | CN | H | OCH₃ | OCH₃ | CH | |

TABLE Ia-continued

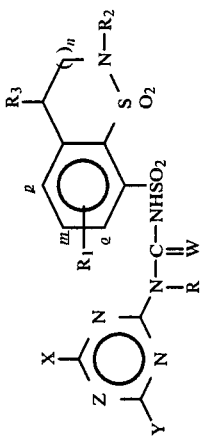

| W | n | R | R₁ | R₂ | R₃ | X | Y | Z | m.p. (°C.) |
|---|---|---|---|---|---|---|---|---|---|
| O | 0 | H | m-OCH₂CH₃ | CN | H | CH₃ | OCH₃ | CH | |
| O | 0 | H | m-OCH₂CH₃ | CN | H | OCH₃ | OCH₃ | CH | |
| O | 0 | H | m-CH₃ | CH₂CN | H | CH₃ | OCH₃ | CH | |
| O | 0 | H | m-CH₃ | CH₂CN | H | OCH₃ | OCH₃ | CH | |
| O | 0 | H | m-OCH₃ | CH₂CN | H | CH₃ | OCH₃ | CH | |
| O | 0 | H | m-OCH₃ | CH₂CN | H | OCH₃ | OCH₃ | CH | |
| O | 0 | H | m-N(CH₃)₂ | CH₂CN | H | CH₃ | OCH₃ | CH | |
| O | 0 | H | m-N(CH₃)₂ | CH₂CN | H | OCH₃ | OCH₃ | CH | |
| O | 0 | H | m-F | CH₂CN | H | CH₃ | OCH₃ | CH | |
| O | 0 | H | m-F | CH₂CN | H | OCH₃ | OCH₃ | CH | |
| O | 0 | H | m-Cl | CH₂CN | H | CH₃ | OCH₃ | CH | |
| O | 0 | H | m-Cl | CH₂CN | H | OCH₃ | OCH₃ | CH | |
| O | 0 | H | m-Br | CH₂CN | H | CH₃ | OCH₃ | CH | |
| O | 0 | H | m-Br | CH₂CN | H | OCH₃ | OCH₃ | CH | |
| O | 0 | H | m-SCH₃ | CH₂CN | H | CH₃ | OCH₃ | CH | |
| O | 0 | H | m-SCH₃ | CH₂CN | H | OCH₃ | OCH₃ | CH | |
| O | 0 | H | m-CH₃ | CH₂CN | H | CH₃ | OCH₃ | CH | |
| O | 0 | H | o-OCH₃ | CH₂CN | H | CH₃ | OCH₃ | CH | |
| O | 0 | H | o-OCH₃ | CH₂CN | H | OCH₃ | OCH₃ | CH | |
| O | 0 | H | o-F | CH₂CN | H | CH₃ | OCH₃ | CH | |
| O | 0 | H | o-F | CH₂CN | H | OCH₃ | OCH₃ | CH | |
| O | 0 | H | o-Cl | CH₂CN | H | CH₃ | OCH₃ | CH | |
| O | 0 | H | o-Cl | CH₂CN | H | OCH₃ | OCH₃ | CH | |
| O | 0 | H | o-Br | CH₂CN | H | CH₃ | OCH₃ | CH | |
| O | 0 | H | o-Br | CH₂CN | H | OCH₃ | OCH₃ | CH | |
| O | 0 | H | o-SCH₃ | CH₂CN | H | CH₃ | OCH₃ | CH | |
| O | 0 | H | o-SCH₃ | CH₂CN | H | OCH₃ | OCH₃ | CH | |
| O | 0 | H | m-OCH₂CH₃ | CH₂CN | H | CH₃ | OCH₃ | CH | |
| O | 0 | H | m-OCH₂CH₃ | CH₂CN | H | OCH₃ | OCH₃ | CH | |
| O | 0 | H | m-CH₃ | CH₂CH=CH₂ | H | CH₃ | OCH₃ | CH | |
| O | 0 | H | m-CH₃ | CH₂CH=CH₂ | H | OCH₃ | OCH₃ | CH | |
| O | 0 | H | m-OCH₃ | CH₂CH=CH₂ | H | CH₃ | OCH₃ | CH | |
| O | 0 | H | m-OCH₃ | CH₂CH=CH₂ | H | OCH₃ | OCH₃ | CH | |
| O | 0 | H | m-N(CH₃)₂ | CH₂CH=CH₂ | H | CH₃ | OCH₃ | CH | |
| O | 0 | H | m-N(CH₃)₂ | CH₂CH=CH₂ | H | OCH₃ | OCH₃ | CH | |
| O | 0 | H | m-F | CH₂CH=CH₂ | H | CH₃ | OCH₃ | CH | |
| O | 0 | H | m-Cl | CH₂CH=CH₂ | H | OCH₃ | OCH₃ | CH | |
| O | 0 | H | m-Cl | CH₂CH=CH₂ | H | CH₃ | OCH₃ | CH | |
| O | 0 | H | m-Br | CH₂CH=CH₂ | H | CH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | m-Br | CH₂CH=CH₂ | H | OCH₃ | OCH₃ | CH | |
| O | 0 | H | m-SCH₃ | CH₂CH=CH₂ | H | CH₃ | OCH₃ | CH | |
| O | 0 | H | m-SCH₃ | CH₂CH=CH₂ | H | OCH₃ | OCH₃ | CH | |
| O | 0 | H | m-CH₃ | CH₂CH=CH₂ | H | CH₃ | OCH₃ | CH | |
| O | 0 | H | m-CH₃ | CH₂CH=CH₂ | H | OCH₃ | OCH₃ | CH | |
| O | 0 | H | o-OCH₃ | CH₂CH=CH₂ | H | CH₃ | OCH₃ | CH | |
| O | 0 | H | o-OCH₃ | CH₂CH=CH₂ | H | OCH₃ | OCH₃ | CH | |
| O | 0 | H | o-F | CH₂CH=CH₂ | H | CH₃ | OCH₃ | CH | |
| O | 0 | H | o-F | CH₂CH=CH₂ | H | OCH₃ | OCH₃ | CH | |
| O | 0 | H | o-Cl | CH₂CH=CH₂ | H | CH₃ | OCH₃ | CH | |
| O | 0 | H | o-Cl | CH₂CH=CH₂ | H | OCH₃ | OCH₃ | CH | |
| O | 0 | H | o-Br | CH₂CH=CH₂ | H | CH₃ | OCH₃ | CH | |
| O | 0 | H | o-Br | CH₂CH=CH₂ | H | OCH₃ | OCH₃ | CH | |
| O | 0 | H | o-SCH₃ | CH₂CH=CH₂ | H | CH₃ | OCH₃ | CH | |
| O | 0 | H | o-SCH₃ | CH₂CH=CH₂ | H | OCH₃ | OCH₃ | CH | |
| O | 0 | H | m-OCH₂CH₃ | CH₂CH=CH₂ | H | CH₃ | OCH₃ | CH | |
| O | 0 | H | m-OCH₂CH₃ | CH₂CH=CH₂ | H | OCH₃ | OCH₃ | CH | |
| O | 0 | H | m-N(CH₃)₂ | CH₂CH=CH₂ | H | CH₃ | OCH₃ | CH | |
| O | 0 | H | m-N(CH₃)₂ | CH₂CH=CH₂ | H | OCH₃ | OCH₃ | CH | |
| O | 0 | H | m-CH₃ | CH₂C≡CH | H | CH₃ | OCH₃ | CH | |
| O | 0 | H | m-CH₃ | CH₂C≡CH | H | OCH₃ | OCH₃ | CH | |
| O | 0 | H | m-OCH₃ | CH₂C≡CH | H | CH₃ | OCH₃ | CH | |
| O | 0 | H | m-OCH₃ | CH₂C≡CH | H | OCH₃ | OCH₃ | CH | |
| O | 0 | H | m-F | CH₂C≡CH | H | CH₃ | OCH₃ | CH | |
| O | 0 | H | m-F | CH₂C≡CH | H | OCH₃ | OCH₃ | CH | |
| O | 0 | H | m-Cl | CH₂C≡CH | H | CH₃ | OCH₃ | CH | |
| O | 0 | H | m-Cl | CH₂C≡CH | H | OCH₃ | OCH₃ | CH | |
| O | 0 | H | m-Br | CH₂C≡CH | H | CH₃ | OCH₃ | CH | |
| O | 0 | H | m-Br | CH₂C≡CH | H | OCH₃ | OCH₃ | CH | |
| O | 0 | H | m-SCH₃ | CH₂C≡CH | H | CH₃ | OCH₃ | CH | |
| O | 0 | H | m-SCH₃ | CH₂C≡CH | H | OCH₃ | OCH₃ | CH | |
| O | 0 | H | m-CH₃ | CH₂C≡CH | H | CH₃ | OCH₃ | CH | |
| O | 0 | H | m-CH₃ | CH₂C≡CH | H | OCH₃ | OCH₃ | CH | |
| O | 0 | H | o-OCH₃ | CH₂C≡CH | H | CH₃ | OCH₃ | CH | |
| O | 0 | H | o-OCH₃ | CH₂C≡CH | H | OCH₃ | OCH₃ | CH | |
| O | 0 | H | o-F | CH₂C≡CH | H | CH₃ | OCH₃ | CH | |
| O | 0 | H | o-F | CH₂C≡CH | H | OCH₃ | OCH₃ | CH | |
| O | 0 | H | o-Cl | CH₂C≡CH | H | CH₃ | OCH₃ | CH | |
| O | 0 | H | o-Cl | CH₂C≡CH | H | OCH₃ | OCH₃ | CH | |
| O | 0 | H | o-Br | CH₂C≡CH | H | CH₃ | OCH₃ | CH | |
| O | 0 | H | o-Br | CH₂C≡CH | H | OCH₃ | OCH₃ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | o-SCH₃ | CH₂C≡CH | H | CH₃ | OCH₃ | CH | |
| O | 0 | H | o-SCH₃ | CH₂C≡CH | H | OCH₃ | OCH₃ | CH | |
| O | 0 | H | m-OCH₂CH₃ | CH₂C≡CH | H | CH₃ | OCH₃ | CH | |
| O | 0 | H | m-OCH₂CH₃ | CH₂C≡CH | H | OCH₃ | OCH₃ | CH | |
| O | 0 | H | m-CH₃ | CH₂CH₂F | H | Cl | OCH₃ | CH | |
| O | 0 | H | m-CH₃ | CH₂CH₂F | H | OCH₃ | OCH₃ | CH | |
| O | 0 | H | m-OCH₃ | CH₂CH₂F | H | Cl | OCH₃ | CH | |
| O | 0 | H | m-OCH₃ | CH₂CH₂F | H | OCH₃ | OCH₃ | CH | |
| O | 0 | H | m-N(CH₃)₂ | CH₂CH₂F | H | Cl | OCH₃ | CH | |
| O | 0 | H | m-N(CH₃)₂ | CH₂CH₂F | H | OCH₃ | OCH₃ | CH | |
| O | 0 | H | m-F | CH₂CH₂F | H | Cl | OCH₃ | CH | |
| O | 0 | H | m-F | CH₂CH₂F | H | OCH₃ | OCH₃ | CH | |
| O | 0 | H | m-Cl | CH₂CH₂F | H | Cl | OCH₃ | CH | |
| O | 0 | H | m-Cl | CH₂CH₂F | H | OCH₃ | OCH₃ | CH | |
| O | 0 | H | m-Br | CH₂CH₂F | H | Cl | OCH₃ | CH | |
| O | 0 | H | m-Br | CH₂CH₂F | H | OCH₃ | OCH₃ | CH | |
| O | 0 | H | m-SCH₃ | CH₂CH₂F | H | Cl | OCH₃ | CH | |
| O | 0 | H | m-SCH₃ | CH₂CH₂F | H | OCH₃ | OCH₃ | CH | |
| O | 0 | H | m-CH₃ | CH₂CH₂F | H | Cl | OCH₃ | CH | |
| O | 0 | H | m-CH₃ | CH₂CH₂F | H | OCH₃ | OCH₃ | CH | |
| O | 0 | H | o-OCH₃ | CH₂CH₂F | H | Cl | OCH₃ | CH | |
| O | 0 | H | o-OCH₃ | CH₂CH₂F | H | OCH₃ | OCH₃ | CH | |
| O | 0 | H | o-F | CH₂CH₂F | H | Cl | OCH₃ | CH | |
| O | 0 | H | o-F | CH₂CH₂F | H | OCH₃ | OCH₃ | CH | |
| O | 0 | H | o-Cl | CH₂CH₂F | H | Cl | OCH₃ | CH | |
| O | 0 | H | o-Cl | CH₂CH₂F | H | OCH₃ | OCH₃ | CH | |
| O | 0 | H | o-Br | CH₂CH₂F | H | Cl | OCH₃ | CH | |
| O | 0 | H | o-Br | CH₂CH₂F | H | OCH₃ | OCH₃ | CH | |
| O | 0 | H | o-SCH₃ | CH₂CH₂F | H | Cl | OCH₃ | CH | |
| O | 0 | H | o-SCH₃ | CH₂CH₂F | H | OCH₃ | OCH₃ | CH | |
| O | 0 | H | m-OCH₂CH₃ | CH₂CH₂F | H | Cl | OCH₃ | CH | |
| O | 0 | H | m-OCH₂CH₃ | CH₂CH₂F | H | OCH₃ | OCH₃ | CH | |
| O | 0 | H | m-CH₃ | CH₂NO₂ | H | CH₃ | OCH₃ | CH | |
| O | 0 | H | m-CH₃ | CH₂NO₂ | H | OCH₃ | OCH₃ | CH | |
| O | 0 | H | m-OCH₃ | CH₂NO₂ | H | CH₃ | OCH₃ | CH | |
| O | 0 | H | m-OCH₃ | CH₂NO₂ | H | OCH₃ | OCH₃ | CH | |
| O | 0 | H | m-N(CH₃)₂ | CH₂NO₂ | H | CH₃ | OCH₃ | CH | |
| O | 0 | H | m-N(CH₃)₂ | CH₂NO₂ | H | OCH₃ | OCH₃ | CH | |
| O | 0 | H | m-F | CH₂NO₂ | H | CH₃ | OCH₃ | CH | |
| O | 0 | H | m-F | CH₂NO₂ | H | OCH₃ | OCH₃ | CH | |
| O | 0 | H | m-Cl | CH₂NO₂ | H | CH₃ | OCH₃ | CH | |

TABLE Ia-continued

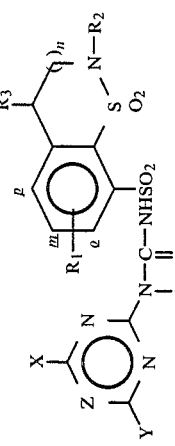

| W | n | R | R₁ | R₂ | R₃ | X | Y | Z | m.p. (°C.) |
|---|---|---|---|---|---|---|---|---|---|
| O | 0 | H | m-Cl | CH₂NO₂ | H | OCH₃ | OCH₃ | CH | |
| O | 0 | H | m-Br | CH₂NO₂ | H | CH₃ | OCH₃ | CH | |
| O | 0 | H | m-Br | CH₂NO₂ | H | OCH₃ | OCH₃ | CH | |
| O | 0 | H | m-SCH₃ | CH₂NO₂ | H | CH₃ | OCH₃ | CH | |
| O | 0 | H | m-SCH₃ | CH₂NO₂ | H | OCH₃ | OCH₃ | CH | |
| O | 0 | H | m-CH₃ | CH₂NO₂ | H | CH₃ | OCH₃ | CH | |
| O | 0 | H | m-CH₃ | CH₂NO₂ | H | OCH₃ | OCH₃ | CH | |
| O | 0 | H | o-OCH₃ | CH₂NO₂ | H | CH₃ | OCH₃ | CH | |
| O | 0 | H | o-OCH₃ | CH₂NO₂ | H | OCH₃ | OCH₃ | CH | |
| O | 0 | H | o-F | CH₂NO₂ | H | CH₃ | OCH₃ | CH | |
| O | 0 | H | o-F | CH₂NO₂ | H | OCH₃ | OCH₃ | CH | |
| O | 0 | H | o-Cl | CH₂NO₂ | H | CH₃ | OCH₃ | CH | |
| O | 0 | H | o-Cl | CH₂NO₂ | H | OCH₃ | OCH₃ | CH | |
| O | 0 | H | o-Br | CH₂NO₂ | H | CH₃ | OCH₃ | CH | |
| O | 0 | H | o-SCH₃ | CH₂NO₂ | H | CH₃ | OCH₃ | CH | |
| O | 0 | H | o-SCH₃ | CH₂NO₂ | H | OCH₃ | OCH₃ | CH | |
| O | 0 | H | m-OCH₂CH₃ | H | H | CH₃ | OCH₃ | CH | |
| O | 0 | H | m-OCH₂CH₃ | H | H | OCH₃ | OCH₃ | CH | |
| O | 0 | H | m-OCH(CH₃)₂ | H | H | OCH₃ | OCH₃ | CH | |
| O | 0 | H | m-OCH₂CH₃ | CH₃ | H | CH₃ | OCH₃ | CH | |
| O | 0 | H | m-OCH₂CH₃ | CH₃ | H | OCH₃ | OCH₃ | CH | |
| O | 0 | H | m-OCH(CH₃)₂ | CH₃ | H | OCH₃ | OCH₃ | CH | |
| O | 0 | H | m-OCH₂CH₃ | CH₂CH₃ | H | CH₃ | OCH₃ | CH | |
| O | 0 | H | m-OCH₂CH₃ | CH₂CH₃ | H | OCH₃ | OCH₃ | CH | |
| O | 0 | H | m-OCH(CH₃)₂ | CH₂CH₃ | H | OCH₃ | OCH₃ | CH | |
| O | 0 | H | m-N(CH₃)₂ | CH₂CH₃ | H | OCH₃ | OCH₃ | CH | |
| O | 0 | H | m-OCH₂CH₃ | CH CH(CH₃)₂ | H | CH₃ | OCH₃ | CH | |
| O | 0 | H | m-OCH₂CH₃ | CH CH(CH₃)₂ | H | OCH₃ | OCH₃ | CH | |
| O | 0 | H | m-OCH(CH₃)₂ | CH CH(CH₃)₂ | H | OCH₃ | OCH₃ | CH | |
| O | 0 | H | m-N(CH₃)₂ | CH CH(CH₃)₂ | H | OCH₃ | OCH₃ | CH | |
| O | 0 | H | m-OCH₂CH₃ | CH₂CH₂CH₂CH₃ | H | CH₃ | OCH₃ | CH | |
| O | 0 | H | m-OCH₂CH₃ | CH₂CH₂CH₂CH₃ | H | OCH₃ | OCH₃ | CH | |
| O | 0 | H | m-OCH(CH₃)₂ | CH₂CH₂CH₂CH₃ | H | OCH₃ | OCH₃ | CH | |
| O | 0 | H | m-N(CH₃)₂ | CH₂CH₂CH₂CH₃ | H | OCH₃ | OCH₃ | CH | |
| O | 0 | H | m-NHCH₃ | CH₂CH₂CH₂CH₃ | H | OCH₃ | OCH₃ | CH | |
| O | 0 | H | m-OCH₂CH₂F | CH₂CH₂CH₂CH₃ | H | OCH₃ | OCH₃ | CH | |
| O | 0 | H | m-SCH₃CH₃ | CH₂C≡CH | H | OCH₃ | OCH₃ | CH | |
| O | 0 | H | H | CH₂C≡CH | H | CH₃ | CH₃ | CH | 206–209 |

TABLE Ia-continued

[Structure: pyrimidine/triazine ring with X, Y, Z substituents connected via N(R)-C(W)-N(R1)- to a phenyl ring with NHSO2 group and -C(R3)H-(CH2)n-N(R2)-S(O2) cyclic sulfonamide]

| W | n | R | R1 | R2 | R3 | X | Y | Z | m.p. (°C.) |
|---|---|---|----|----|----|---|---|---|------------|
| O | 0 | H | H | CH2C≡CH | H | Cl | OCH3 | CH | 198-200 |
| O | 0 | H | H | CH2C≡CH | H | CH3 | OCH3 | N | 188-190 |
| O | 0 | H | H | CH2C≡CH | H | OCH3 | CH3 | CH | 190-192 |
| O | 0 | H | H | CH2CH2OSO2CH3 | H | CH3 | CH3 | CH | |
| O | 0 | H | H | CH2CH2OSO2CH3 | H | CH3 | OCH3 | CH | |
| O | 0 | H | H | CH2CH2OSO2CH3 | H | OCH3 | OCH3 | CH | |
| O | 0 | H | H | CH2CH2OSO2CH3 | H | Cl | OCH3 | CH | |
| O | 0 | H | H | CH2CH2OSO2CH3 | H | CH3 | OCH3 | N | |
| O | 0 | H | H | CH2CH2OSO2CH3 | H | OCH3 | OCH3 | N | |
| O | 0 | H | H | CH2CH=C(CH3)2 | H | CH3 | CH3 | CH | 203-204.5d |
| O | 0 | H | H | CH2CH=C(CH3)2 | H | CH3 | OCH3 | CH | 205-208(d) |
| O | 0 | H | H | CH2CH=C(CH3)2 | H | OCH3 | OCH3 | CH | 224-226(d) |
| O | 0 | H | H | CH2CH=C(CH3)2 | H | Cl | OCH3 | CH | 214-215(d) |
| O | 0 | H | H | CH2CH=C(CH3)2 | H | CH3 | OCH3 | N | 183-185(d) |
| O | 0 | H | H | CH2CH=C(CH3)2 | H | OCH3 | OCH3 | N | 170-173(d) |
| O | 0 | H | H | C(O)CH3 | H | OCH3 | NHCH3 | N | |
| O | 0 | H | H | C(O)CH2CH3 | H | OCH2CH3 | NHCH3 | N | |
| O | 0 | H | H | C(O)CH2CH2CH3 | H | OCH2CH3 | NHCH3 | N | |
| O | 0 | H | H | C(O)C(CH3)3 | H | OCH2CH3 | NHCH3 | N | |
| O | 0 | H | H | CO2CH3 | H | OCH2CH3 | NHCH3 | N | |
| O | 0 | H | H | CO2CH2CH3 | H | OCH2CH3 | NHCH3 | N | |
| O | 0 | H | H | CO2CH2CH2CH3 | H | OCH2CH3 | NHCH3 | N | |
| O | 0 | H | H | CO2CH(CH3)2 | H | OCH2CH3 | NHCH3 | N | |
| O | 0 | H | H | CH2C(O)CH3 | H | OCH2CH3 | NHCH3 | N | |
| O | 0 | H | H | CH2CH=CH2 | H | OCH2CH3 | NHCH3 | N | |
| O | 0 | H | H | CH2C≡CH | H | OCH2CH3 | NHCH3 | N | |
| O | 0 | H | H | CH2CH2F | H | OCH2CH3 | NHCH3 | N | |
| O | 0 | H | H | CH2CH2Cl | H | OCH2CH3 | NHCH3 | N | |
| O | 0 | H | H | CH2CH2Br | H | OCH2CH3 | NHCH3 | N | |
| O | 0 | H | H | CH2CH2CH2F | H | OCH2CH3 | NHCH3 | N | |
| O | 0 | H | H | CH2CF3 | H | OCH2CH3 | NHCH3 | N | |
| O | 0 | H | H | CH2CH2CF3 | H | OCH2CH3 | NHCH3 | N | |
| O | 0 | H | H | CH2CHF2 | H | OCH2CH3 | NHCH3 | N | |
| O | 0 | H | H | CH2CN | H | OCH2CH3 | NHCH3 | N | |
| O | 0 | H | H | CH3OCH3 | H | OCH2CH3 | NHCH3 | N | |
| O | 0 | H | H | CH2Cl | H | OCH2CH3 | NHCH3 | N | |
| O | 0 | H | H | C(O)CH3 | H | OCH3 | CH3 | N | |
| O | 0 | H | H | C(O)CH2CH3 | H | OCH3 | NHCH3 | N | |
| O | 0 | H | H | C(O)CH2CH2CH3 | H | OCH3 | H | CH | |
| O | 0 | H | H | C(O)CH2CH2CH3 | H | OCH3 | H | CH | |
| O | 0 | H | H | C(O)C(CH3)3 | H | OCH3 | H | CH | |

TABLE Ia-continued

| W | n | R | R₁ | R₂ | R₃ | X | Y | Z | m.p. (°C.) |
|---|---|---|----|----|----|---|---|---|------------|
| O | 0 | H | H | CO₂CH₃ | H | OCH₃ | H | CH | |
| O | 0 | H | H | CO₂CH₂CH₃ | H | OCH₃ | H | CH | |
| O | 0 | H | H | CO₂CH₂CH₂CH₃ | H | OCH₃ | H | CH | |
| O | 0 | H | H | CO₂CH(CH₃)₂ | H | OCH₃ | H | CH | |
| O | 0 | H | H | CO₂C(CH₃)₃ | H | OCH₃ | H | CH | |
| O | 0 | H | H | CH₂C(O)OCH₃ | H | OCH₃ | H | CH | |
| O | 0 | H | H | CH₂C(O)OCH₂CH₃ | H | OCH₃ | H | CH | |
| O | 0 | H | H | CH₂CH=CH₂ | H | OCH₃ | H | CH | |
| O | 0 | H | H | CH₂C≡CH | H | OCH₃ | H | CH | |
| O | 0 | H | H | CH₂CH₂F | H | OCH₃ | H | CH | |
| O | 0 | H | H | CH₂CH₂Cl | H | OCH₃ | H | CH | |
| O | 0 | H | H | CH₂CH₂Br | H | OCH₃ | H | CH | |
| O | 0 | H | H | CH₂CH₂CH₂F | H | OCH₃ | H | CH | |
| O | 0 | H | H | CH₂CF₃ | H | OCH₃ | H | CH | |
| O | 0 | H | H | CH₂CHF₂ | H | OCH₃ | H | CH | |
| O | 0 | H | H | CH₂CN | H | OCH₃ | H | CH | |
| O | 0 | H | H | CH₂OCH₃ | H | OCH₃ | H | CH | |
| O | 0 | H | H | CH₂Cl | H | OCH₃ | H | CH | |
| O | 0 | H | H | C(O)CH₃ | H | OCH₃ | H | CH | |
| O | 0 | H | H | C(O)CH₂CH₃ | H | OCH₃ | H | CH | |
| O | 0 | H | H | C(O)CH₂CH₂CH₃ | H | OCH₃ | H | CH | |
| O | 0 | H | H | C(O)C(CH₃)₃ | H | OCH₃ | H | CH | |
| O | 0 | H | H | CO₂CH₃ | H | OCH₃ | OCH₂CH₂F | N |
| O | 0 | H | H | CO₂CH₂CH₃ | H | OCH₃ | OCH₂CH₂F | N |
| O | 0 | H | H | CO₂CH₂CH₂CH₃ | H | OCH₃ | OCH₂CH₂F | N |
| O | 0 | H | H | CO₂CH(CH₃)₂ | H | OCH₃ | OCH₂CH₂F | N |
| O | 0 | H | H | CO₂C(CH₃)₃ | H | OCH₃ | OCH₂CH₂F | N |
| O | 0 | H | H | CH₂C(O)OCH₃ | H | OCH₃ | OCH₂CH₂F | N |
| O | 0 | H | H | CH₂C(O)OCH₂CH₃ | H | OCH₃ | OCH₂CH₂F | N |
| O | 0 | H | H | CH₂CH=CH₂ | H | OCH₃ | OCH₂CH₂F | N |
| O | 0 | H | H | CH₂C≡CH | H | OCH₃ | OCH₂CH₂F | N |
| O | 0 | H | H | CH₂CN | H | OCH₃ | OCH₂CH₂F | N |
| O | 0 | H | H | CH₂OCH₃ | H | OCH₃ | OCH₂CH₂F | N |
| O | 0 | H | H | C(O)CH₃ | H | OCH₃ | OCH₂CH₂F | N |
| O | 0 | H | H | C(O)CH₂CH₃ | H | OCH₃ | OCH₂CH₂F | N |
| O | 0 | H | H | C(O)CH₂CH₂CH₃ | H | OCH₃ | OCH₂CH₂F | N |
| O | 0 | H | H | C(O)C(CH₃)₃ | H | OCH₃ | OCH₂CH₂F | N |
| O | 0 | H | H | CO₂CH₃ | H | OCH₃ | OCH₂CF₃ | N |
| O | 0 | H | H | CO₂CH₂CH₃ | H | OCH₃ | OCH₂CF₃ | N |
| O | 0 | H | H | CO₂CH₂CH₂CH₃ | H | OCH₃ | OCH₂CF₃ | N |

TABLE Ia-continued

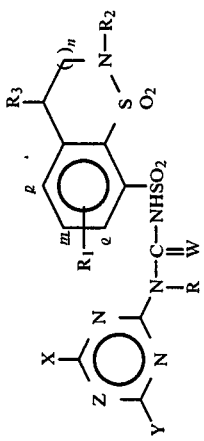

| W | n | R | R₁ | R₂ | R₃ | X | Y | Z | m.p. (°C.) |
|---|---|---|---|---|---|---|---|---|---|
| O | 0 | H | H | $CO_2CH(CH_3)_2$ | H | $OCH_3$ | $OCH_2CF_3$ | N | |
| O | 0 | H | H | $CO_2C(CH_3)_3$ | H | $OCH_3$ | $OCH_2CF_3$ | N | |
| O | 0 | H | H | $CH_2C(O)OCH_3$ | H | $OCH_3$ | $OCH_2CF_3$ | N | |
| O | 0 | H | H | $CH_2C(O)OCH_2CH_3$ | H | $OCH_3$ | $OCH_2CF_3$ | N | |
| O | 0 | H | H | $CH_2CH=CH_2$ | H | $OCH_3$ | $OCH_2CF_3$ | N | |
| O | 0 | H | H | $CH_2C\equiv CH$ | H | $OCH_3$ | $OCH_2CF_3$ | N | |
| O | 0 | H | H | $CH_2CH_2F$ | H | $OCH_3$ | $OCH_2CF_3$ | N | |
| O | 0 | H | H | $CH_2CH_2Cl$ | H | $OCH_3$ | $OCH_2CF_3$ | N | |
| O | 0 | H | H | $CH_2CH_2Br$ | H | $OCH_3$ | $OCH_2CF_3$ | N | |
| O | 0 | H | H | $CH_2CH_2CH_2F$ | H | $OCH_3$ | $OCH_2CF_3$ | N | |
| O | 0 | H | H | $CH_2CF_3$ | H | $OCH_3$ | $OCH_2CF_3$ | N | |
| O | 0 | H | H | $CH_2CH_2CF_3$ | H | $OCH_3$ | $OCH_2CF_3$ | N | |
| O | 0 | H | H | $CH_2CHF_2$ | H | $OCH_3$ | $OCH_2CF_3$ | N | |
| O | 0 | H | H | $CH_2CN$ | H | $OCH_3$ | $OCH_2CF_3$ | N | |
| O | 0 | H | H | $CH_2OCH_3$ | H | $OCH_3$ | $OCH_2CF_3$ | N | |
| O | 0 | H | H | $CH_2Cl$ | H | $OCH_3$ | $OCH_2CF_3$ | N | |
| O | 0 | H | m-$(CH_2)_5CH_3$ | $C(O)CH_3$ | H | $OCH_3$ | $OCH_3$ | CH | |
| O | 0 | H | m-$(CH_2)_3CH(CH_3)_2$ | $C(O)CH_3$ | H | $OCH_3$ | $OCH_3$ | CH | |
| O | 0 | H | m-$(CH_2)_5CF_3$ | $C(O)CH_3$ | H | $OCH_3$ | $OCH_3$ | CH | |
| O | 0 | H | m-$O(CH_2)_5CH_3$ | $C(O)CH_3$ | H | $OCH_3$ | $OCH_3$ | CH | |
| O | 0 | H | m-$S(CH_2)_5CH_3$ | $C(O)CH_3$ | H | $OCH_3$ | $OCH_3$ | CH | |
| O | 0 | H | o-$S(O)(CH_2)_5CH_3$ | $C(O)CH_3$ | H | $OCH_3$ | $OCH_3$ | CH | |
| O | 0 | H | o-$SO_2(CH_2)_5CH_3$ | $C(O)CH_3$ | H | $OCH_3$ | $OCH_3$ | CH | |
| O | 0 | H | m-CN | $C(O)CH_3$ | H | $OCH_3$ | $OCH_3$ | CH | |
| O | 0 | H | m-$O(CH_2)_5CF_3$ | $C(O)CH_3$ | H | $OCH_3$ | $OCH_3$ | CH | |
| O | 0 | H | m-$S(CH_2)_5CF_3$ | $C(O)CH_3$ | H | $OCH_3$ | $OCH_3$ | CH | |
| O | 0 | H | m-$NH(CH_2)_5CH_3$ | $C(O)CH_3$ | H | $OCH_3$ | $OCH_3$ | CH | |
| O | 0 | H | m-$N(CH_3)(CH_2)_5CH_3$ | $C(O)CH_3$ | H | $OCH_3$ | $OCH_3$ | CH | |
| O | 0 | H | o-$SO_2NH_2$ | $C(O)CH_3$ | H | $OCH_3$ | $OCH_3$ | CH | |
| O | 0 | H | o-$SO_2NH(CH_2)_3CH_3$ | $C(O)CH_3$ | H | $OCH_3$ | $OCH_3$ | CH | |
| O | 0 | H | o-$SO_2N(CH_3)_2$ | $C(O)CH_3$ | H | $OCH_3$ | $OCH_3$ | CH | |
| O | 0 | H | o-$SO_2N(CH_3)OCH_3$ | $C(O)CH_3$ | H | $OCH_3$ | $OCH_3$ | CH | |
| O | 0 | H | o-$SO_2N(CH_3)OCH_2CH_3$ | $C(O)CH_3$ | H | $OCH_3$ | $OCH_3$ | CH | |
| O | 0 | H | o-$SO_2N(CH_3)CH_2CN$ | $C(O)CH_3$ | H | $OCH_3$ | $OCH_3$ | CH | |
| O | 0 | H | o-$SO_2NH(CH_2)_3CN$ | $C(O)CH_3$ | H | $OCH_3$ | $OCH_3$ | CH | |
| O | 0 | H | o-$SO_2NHCH_2CH=CH_2$ | $C(O)CH_3$ | H | $OCH_3$ | $OCH_3$ | CH | |
| O | 0 | H | o-azetidinyl-sulfonyl | $C(O)CH_3$ | H | $OCH_3$ | $OCH_3$ | CH | |
| O | 0 | H | o-pyrrolidinyl-sulfonyl | $C(O)CH_3$ | H | $OCH_3$ | $OCH_3$ | CH | |
| O | 0 | H | o-piperidinyl- | $C(O)CH_3$ | H | $OCH_3$ | $OCH_3$ | CH | |

TABLE Ia-continued

| W | n | R | R₁ | R₂ | R₃ | X | Y | Z | m.p. (°C.) |
|---|---|---|---|---|---|---|---|---|---|
| O | 0 | H | o-morpholino-sulfonyl | C(O)CH₃ | H | OCH₃ | OCH₃ | CH | |
| O | 0 | H | m-CH₂OCH₃ | C(O)CH₃ | H | OCH₃ | OCH₃ | CH | |
| O | 0 | H | o-CH₂OCH₃ | C(O)CH₃ | H | OCH₃ | OCH₃ | CH | |
| O | 0 | H | m-(CH₂)₃OCH₃ | C(O)CH₃ | H | OCH₃ | OCH₃ | CH | |
| O | 0 | H | o-CH₂O(CH₂)₂CH₃ | C(O)CH₃ | H | OCH₃ | OCH₃ | CH | |
| O | 0 | H | o-CH₂SCH₃ | C(O)CH₃ | H | OCH₃ | OCH₃ | CH | |
| O | 0 | H | o-CH₂Si(CH₂)₂CH₃ | C(O)CH₃ | H | OCH₃ | OCH₃ | CH | |
| O | 0 | H | o-CH₂S(O)Pr | C(O)CH₃ | H | OCH₃ | OCH₃ | CH | |
| O | 0 | H | o-CH₂SO₂Pr | C(O)CH₃ | H | OCH₃ | OCH₃ | CH | |
| O | 0 | H | m-CH₂SO₂N(CH₃)₂ | C(O)CH₃ | H | OCH₃ | OCH₃ | CH | |
| O | 0 | H | m-CH₂SO₂NHPr | C(O)CH₃ | H | OCH₃ | OCH₃ | CH | |
| O | 0 | H | o-CH₂N(CH₃)₂ | C(O)CH₃ | H | OCH₃ | OCH₃ | CH | |
| O | 0 | H | o-CH₂NHPr | C(O)CH₃ | H | OCH₃ | OCH₃ | CH | |
| O | 0 | H | m-CH₂CH₂N(CH₃)₂ | C(O)CH₃ | H | OCH₃ | OCH₃ | CH | |
| O | 0 | H | m-CH₂NO₂ | C(O)CH₃ | H | OCH₃ | OCH₃ | CH | |
| O | 0 | H | o-(CH₂)₃NO₂ | C(O)CH₃ | H | OCH₃ | OCH₃ | CH | |
| O | 0 | H | m-CH₂CN | C(O)CH₃ | H | OCH₃ | OCH₃ | CH | |
| O | 0 | H | o-(CH₂)₃CN | C(O)CH₃ | H | OCH₃ | OCH₃ | CH | |
| O | 0 | H | o-CH₂CO₂CH₃ | C(O)CH₃ | H | OCH₃ | OCH₃ | CH | |
| O | 0 | H | m-CH₂CO₂Pr | C(O)CH₃ | H | OCH₃ | OCH₃ | CH | |
| O | 0 | H | o-CH₂O(CH₂)₂F | C(O)CH₃ | H | OCH₃ | OCH₃ | CH | |
| O | 0 | H | o-CH₂O(CH₂)₂CF₃ | C(O)CH₃ | H | OCH₃ | OCH₃ | CH | |
| O | 0 | H | o-CH₂OCH₂CF₃ | C(O)CH₃ | H | OCH₃ | OCH₃ | CH | |
| O | 0 | H | o-CH₂O(CH₂)₃Cl | C(O)CH₃ | H | OCH₃ | OCH₃ | CH | |
| O | 0 | H | o-(CH₂)₂S(CH₂)₂Cl | C(O)CH₃ | H | OCH₃ | OCH₃ | CH | |
| O | 0 | H | o-Si(CH₃)₃ | C(O)CH₃ | H | OCH₃ | OCH₃ | CH | |
| O | 0 | H | o-Si(CH₃)₂C(CH₃)₃ | C(O)CH₃ | H | OCH₃ | OCH₃ | CH | |
| O | 0 | H | o-Si(CH₃)₂Ph | C(O)CH₃ | H | OCH₃ | OCH₃ | CH | |
| O | 0 | H | o-CO₂CH₃ | C(O)CH₃ | H | OCH₃ | OCH₃ | CH | |
| O | 0 | H | o-CO₂(CH₂)₂CH₃ | C(O)CH₃ | H | OCH₃ | OCH₃ | CH | |
| O | 0 | H | o-CO₂(CH₂)₂CH=CH₂ | C(O)CH₃ | H | OCH₃ | OCH₃ | CH | |
| O | 0 | H | o-CO₂(CH₂)₂CH=CH₂ | C(O)CH₃ | H | OCH₃ | OCH₃ | CH | |
| O | 0 | H | o-CO₂CH₂C≡CCH₃ | C(O)CH₃ | H | OCH₃ | OCH₃ | CH | |
| O | 0 | H | o-CO₂CH₂CF₃ | C(O)CH₃ | H | OCH₃ | OCH₃ | CH | |
| O | 0 | H | o-CO₂(CH₂)₄Cl | C(O)CH₃ | H | OCH₃ | OCH₃ | CH | |
| O | 0 | H | o-CO₂(CH₂)₂CN | C(O)CH₃ | H | OCH₃ | OCH₃ | CH | |
| O | 0 | H | o-CO₂(CH₂)₃CN | C(O)CH₃ | H | OCH₃ | OCH₃ | CH | |
| O | 0 | H | o-CO₂—cyclopentyl | C(O)CH₃ | H | OCH₃ | OCH₃ | CH | |
| O | 0 | H | o-CO₂—cyclohexyl | C(O)CH₃ | H | OCH₃ | OCH₃ | CH | |

TABLE Ia-continued

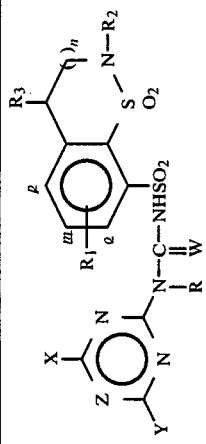

| W | n | R | R₁ | R₂ | R₃ | X | Y | Z | m.p. (°C.) |
|---|---|---|---|---|---|---|---|---|---|
| O | 0 | H | o-CO₂—cyclopropylmethyl | C(O)CH₃ | H | OCH₃ | OCH₃ | CH | |
| O | 0 | H | o-CO₂—cyclohexylmethyl | C(O)CH₃ | H | OCH₃ | OCH₃ | CH | |
| O | 0 | H | o-CO₂(CH₂)₂OCH₃ | C(O)CH₃ | H | OCH₃ | OCH₃ | CH | |
| O | 0 | H | m-CN | CH₃ | H | CH₃ | OCH₃ | CH | |
| O | 0 | H | m-CN | CH₃ | H | OCH₃ | OCH₃ | CH | |
| O | 0 | H | m-CN | CH₃ | H | Cl | OCH₃ | CH | |
| O | 0 | H | o-CN | CH₃ | H | CH₃ | OCH₃ | CH | |
| O | 0 | H | o-CN | CH₃ | H | OCH₃ | OCH₃ | CH | |
| O | 0 | H | o-CN | CH₃ | H | Cl | OCH₃ | CH | |
| O | 0 | H | o-CH₂OCH₃ | CH₃ | H | CH₃ | OCH₃ | CH | |
| O | 0 | H | o-CH₂OCH₃ | CH₃ | H | OCH₃ | OCH₃ | CH | |
| O | 0 | H | o-CH₂OCH₃ | CH₃ | H | Cl | OCH₃ | CH | |
| O | 0 | H | o-Si(CH₃)₃ | CH₃ | H | CH₃ | OCH₃ | CH | |
| O | 0 | H | o-Si(CH₃)₃ | CH₃ | H | OCH₃ | OCH₃ | CH | |
| O | 0 | H | o-Si(CH₃)₃ | CH₃ | H | Cl | OCH₃ | CH | |
| O | 0 | H | o-CH₂SCH₃ | CH₃ | H | CH₃ | OCH₃ | CH | |
| O | 0 | H | o-CH₂SCH₃ | CH₃ | H | OCH₃ | OCH₃ | CH | |
| O | 0 | H | o-CH₂SCH₃ | CH₃ | H | Cl | OCH₃ | CH | |
| O | 0 | H | o-CH₂CN | CH₃ | H | CH₃ | OCH₃ | CH | |
| O | 0 | H | o-CH₂CN | CH₃ | H | OCH₃ | OCH₃ | CH | |
| O | 0 | H | o-CH₂CN | CH₃ | H | Cl | OCH₃ | CH | |
| O | 0 | H | m-CN | CH₂CH₂CH₂CH₃ | H | CH₃ | OCH₃ | CH | |
| O | 0 | H | m-CN | CH₂CH₂CH₂CH₃ | H | OCH₃ | OCH₃ | CH | |
| O | 0 | H | m-CN | CH₂CH₂CH₂CH₃ | H | Cl | OCH₃ | CH | |
| O | 0 | H | o-CN | CH₂CH₂CH₂CH₃ | H | CH₃ | OCH₃ | CH | |
| O | 0 | H | o-CN | CH₂CH₂CH₂CH₃ | H | OCH₃ | OCH₃ | CH | |
| O | 0 | H | o-CN | CH₂CH₂CH₂CH₃ | H | Cl | OCH₃ | CH | |
| O | 0 | H | o-CH₂OCH₃ | CH₂CH₂CH₂CH₃ | H | CH₃ | OCH₃ | CH | |
| O | 0 | H | o-CH₂OCH₃ | CH₂CH₂CH₂CH₃ | H | OCH₃ | OCH₃ | CH | |
| O | 0 | H | o-CH₂OCH₃ | CH₂CH₂CH₂CH₃ | H | Cl | OCH₃ | CH | |
| O | 0 | H | o-Si(CH₃)₃ | CH₂CH₂CH₂CH₃ | H | CH₃ | OCH₃ | CH | |
| O | 0 | H | o-Si(CH₃)₃ | CH₂CH₂CH₂CH₃ | H | OCH₃ | OCH₃ | CH | |
| O | 0 | H | o-Si(CH₃)₃ | CH₂CH₂CH₂CH₃ | H | Cl | OCH₃ | CH | |
| O | 0 | H | o-CH₂SCH₃ | CH₂CH₂CH₂CH₃ | H | CH₃ | OCH₃ | CH | |
| O | 0 | H | o-CH₂SCH₃ | CH₂CH₂CH₂CH₃ | H | OCH₃ | OCH₃ | CH | |
| O | 0 | H | o-CH₂SCH₃ | CH₂CH₂CH₂CH₃ | H | Cl | OCH₃ | CH | |
| O | 0 | H | o-CH₂CN | CH₂CH₂CH₂CH₃ | H | CH₃ | OCH₃ | CH | |
| O | 0 | H | o-CH₂CN | CH₂CH₂CH₂CH₃ | H | OCH₃ | OCH₃ | CH | |
| O | 0 | H | o-CH₂CN | CH₂CH₂CH₂CH₃ | H | Cl | OCH₃ | CH | |
| O | 0 | H | H | (CO)₂OCH₃ | H | CH₃ | CH₃ | CH | |
| O | 0 | H | H | (CO)₂OCH₃ | H | CH₃ | OCH₃ | CH | |

TABLE Ia-continued

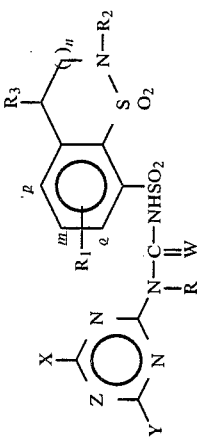

| W | n | R | R₁ | R₂ | R₃ | X | Y | Z | m.p. (°C.) |
|---|---|---|----|----|----|----|----|----|-----------|
| O | O | H | H | (CO)₂OCH₃ | H | OCH₃ | OCH₃ | CH | |
| O | O | H | H | (CO)₂OCH₃ | H | Cl | OCH₃ | CH | |
| O | O | H | H | (CO)₂OCH₃ | H | Br | OCH₃ | CH | |
| O | O | H | H | (CO)₂OCH₃ | H | CH₃ | OCH₃ | N | |
| O | O | H | H | (CO)₂OCH₃ | H | OCH₃ | CH₃ | CH | |
| O | O | H | H | (CO)₂OCH₂CH₃ | H | CH₃ | OCH₃ | CH | |
| O | O | H | H | (CO)₂OCH₂CH₃ | H | CH₃ | OCH₃ | CH | |
| O | O | H | H | (CO)₂OCH₂CH₃ | H | OCH₃ | OCH₃ | CH | |
| O | O | H | H | (CO)₂OCH₂CH₃ | H | Cl | OCH₃ | CH | |
| O | O | H | H | (CO)₂OCH₂CH₃ | H | Br | OCH₃ | CH | |
| O | O | H | H | (CO)₂OCH₂CH₃ | H | CH₃ | OCH₃ | N | |
| O | O | H | H | (CO)₂OCH₂CH₃ | H | OCH₃ | CH₃ | CH | |
| O | O | H | H | (CO)₂OPh | H | OCH₃ | OCH₃ | CH | |
| O | O | H | H | (CO)₂OPh | H | CH₃ | CH₃ | CH | |
| O | O | H | H | CH₂CH₂SeCH₃ | H | OCH₃ | OCH₃ | CH | |
| O | O | H | H | CH₂CH₂SeCH₃ | H | CH₃ | OCH₃ | CH | |
| O | O | H | H | CH₂CH₂SeCH₃ | H | OCH₃ | OCH₃ | CH | |
| O | O | H | H | CH₂CH₂SeCH₃ | H | Cl | OCH₃ | CH | |
| O | O | H | H | CH₂CH₂SeCH₃ | H | Br | OCH₃ | CH | |
| O | O | H | H | CH₂CH₂SeCH₃ | H | CH₃ | OCH₃ | N | |
| O | O | H | H | CH₂CH₂SeCH₃ | H | OCH₃ | CH₃ | CH | |
| O | O | H | H | CH₂CH₂SeCH₂CH₃ | H | CH₃ | OCH₃ | CH | |
| O | O | H | H | CH₂CH₂SeCH₂CH₃ | H | OCH₃ | OCH₃ | CH | |
| O | O | H | H | CH₂SeCH₃ | H | CH₃ | CH₃ | CH | |
| O | O | H | H | CH₂SeCH₃ | H | OCH₃ | OCH₃ | CH | |
| O | O | H | H | CH₂CH₂SePh | H | CH₃ | OCH₃ | CH | |
| O | O | H | H | CH₂CH₂SePh | H | OCH₃ | OCH₃ | CH | |
| O | O | H | H | CH₂CH₂SePh | H | CH₃ | OCH₃ | N | |
| O | O | H | H | CH₂CH₂SePh | H | Cl | OCH₃ | CH | |
| O | O | H | H | CH₂CH₂SePh | H | Br | OCH₃ | CH | |
| O | O | H | H | CH₂CH₂SePh | H | CH₃ | OCH₃ | CH | |
| O | O | H | H | CH₂CH₂SePh | H | OCH₃ | OCH₃ | CH | |
| O | O | H | H | (CO)₂CH₃ | H | CH₃ | OCH₃ | N | |
| O | O | H | H | (CO)₂CH₃ | H | OCH₃ | OCH₃ | N | |
| O | O | H | H | (CO)₂CH₂CH₃ | H | CH₃ | OCH₃ | CH | |
| O | O | H | H | (CO)₂CH₂CH₃ | H | OCH₃ | OCH₃ | CH | |
| O | O | H | H | (CO)₂Ph | H | CH₃ | CH₃ | CH | |
| O | O | H | H | (CO)₂Ph | H | OCH₃ | CH₃ | CH | |
| O | O | H | H | 2-thienoyl | H | CH₃ | OCH₃ | CH | |
| O | O | H | H | 2-thienoyl | H | CH₃ | CH₃ | CH | |
| O | O | H | H | 2-thienoyl | H | OCH₃ | OCH₃ | CH | |

TABLE Ia-continued

| W | n | R | R₁ | R₂ | R₃ | X | Y | Z | m.p. (°C) |
|---|---|---|----|----|----|---|---|---|-----------|
| O | 0 | H | H | 2-thienoyl | H | Cl | OCH₃ | CH | |
| O | 0 | H | H | 2-thienoyl | H | Br | OCH₃ | CH | |
| O | 0 | H | H | 2-thienoyl | H | CH₃ | OCH₃ | N | |
| O | 0 | H | H | 2-thienoyl | H | OCH₃ | OCH₃ | N | |
| O | 0 | H | H | 2-thienoyl | H | CH₃ | CH₃ | CH | |
| O | 0 | H | H | 3-thienoyl | H | CH₃ | OCH₃ | CH | |
| O | 0 | H | H | 3-thienoyl | H | OCH₃ | OCH₃ | CH | |
| O | 0 | H | H | 3-thienoyl | H | Cl | OCH₃ | CH | |
| O | 0 | H | H | 3-thienoyl | H | Br | OCH₃ | CH | |
| O | 0 | H | H | 3-thienoyl | H | CH₃ | OCH₃ | N | |
| O | 0 | H | H | 3-thienoyl | H | OCH₃ | OCH₃ | N | |
| O | 0 | H | H | 3-thienoyl | H | CH₃ | CH₃ | CH | |
| O | 0 | H | H | 2-furoyl | H | CH₃ | OCH₃ | CH | |
| O | 0 | H | H | 2-furoyl | H | OCH₃ | OCH₃ | CH | |
| O | 0 | H | H | 2-furoyl | H | Cl | OCH₃ | CH | |
| O | 0 | H | H | 2-furoyl | H | Br | OCH₃ | CH | |
| O | 0 | H | H | 2-furoyl | H | CH₃ | OCH₃ | N | |
| O | 0 | H | H | 2-furoyl | H | OCH₃ | OCH₃ | N | |
| O | 0 | H | H | 2-furoyl | H | CH₃ | CH₃ | CH | |
| O | 0 | H | H | 3-furoyl | H | CH₃ | OCH₃ | CH | |
| O | 0 | H | H | 3-furoyl | H | OCH₃ | OCH₃ | CH | |
| O | 0 | H | H | 3-furoyl | H | Cl | OCH₃ | CH | |
| O | 0 | H | H | 3-furoyl | H | Br | OCH₃ | CH | |
| O | 0 | H | H | 3-furoyl | H | CH₃ | OCH₃ | N | |
| O | 0 | H | H | 3-furoyl | H | OCH₃ | OCH₃ | N | |
| O | 0 | H | H | 3-furoyl | H | CH₃ | CH₃ | CH | |
| O | 0 | H | H | CH₂CH₂—pyridinium bromide | H | OCH₃ | OCH₃ | CH | |
| O | 0 | H | H | C(O)C(CH₃)₃ | H | CH₃ | CH₃ | CH | 176–178 |
| O | 0 | H | H | C(O)C(CH₃)₃ | H | CH₃ | OCH₃ | CH | 201–202 |
| O | 0 | H | H | C(O)C(CH₃)₃ | H | OCH₃ | OCH₃ | CH | 203–204 |
| O | 0 | H | H | C(O)C(CH₃)₃ | H | Cl | OCH₃ | CH | 199–200 |
| O | 0 | H | H | C(O)C(CH₃)₃ | H | Br | OCH₃ | CH | |
| O | 0 | H | H | C(O)C(CH₃)₃ | H | CH₃ | OCH₃ | N | |
| O | 0 | H | H | C(O)C(CH₃)₃ | H | OCH₃ | OCH₃ | N | |
| O | 0 | H | H | C(O)CH₂CH(CH₃)₂ | H | CH₃ | CH₃ | CH | |
| O | 0 | H | H | C(O)CH₂CH(CH₃)₂ | H | CH₃ | OCH₃ | CH | |
| O | 0 | H | H | C(O)CH₂CH(CH₃)₂ | H | OCH₃ | OCH₃ | CH | |
| O | 0 | H | H | C(O)CH₂CH(CH₃)₂ | H | Cl | OCH₃ | CH | |
| O | 0 | H | H | C(O)CH₂CH(CH₃)₂ | H | Br | OCH₃ | CH | |
| O | 0 | H | H | C(O)CH₂CH(CH₃)₂ | H | CH₃ | OCH₃ | N | |
| O | 0 | H | H | C(O)CH₂CH(CH₃)₂ | H | OCH₃ | OCH₃ | N | |

TABLE Ia-continued

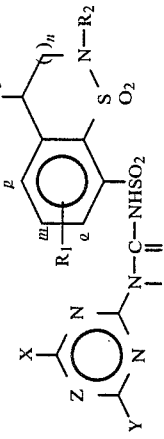

| W | n | R | R₁ | R₂ | R₃ | X | Y | Z | m.p. (°C.) |
|---|---|---|---|---|---|---|---|---|---|
| O | 0 | H | H | C(O)CH(CH₃)₂ | H | CH₃ | OCH₃ | CH | |
| O | 0 | H | H | C(O)CH(CH₃)₂ | H | OCH₃ | OCH₃ | CH | |
| O | 0 | H | H | CH₂C(Br)=CH₂ | H | CH₃ | CH₃ | CH | 220-222 |
| O | 0 | H | H | CH₂C(Br)=CH₂ | H | OCH₃ | OCH₃ | CH | 213-214 |
| O | 0 | H | H | CH₂C(Br)=CH₂ | H | Cl | OCH₃ | CH | 211-213 |
| O | 0 | H | H | CH₂C(Br)=CH₂ | H | Br | OCH₃ | CH | 188-190 |
| O | 0 | H | H | CH₂C(Br)=CH₂ | H | CH₃ | OCH₃ | CH | |
| O | 0 | H | H | CH₂C(Br)=CH₂ | H | OCH₃ | OCH₃ | N | 190-192 |
| O | 0 | H | H | CH=CH₂ | H | CH₃ | CH₃ | N | 184-185 |
| O | 0 | H | H | CH=CH₂ | H | OCH₃ | OCH₃ | CH | |
| O | 0 | H | H | CH=CH₂ | H | CH₃ | OCH₃ | CH | |
| O | 0 | H | H | CH=CH₂ | H | OCH₃ | OCH₃ | CH | |
| O | 0 | H | H | CH=CH₂ | H | Cl | OCH₃ | CH | |
| O | 0 | H | H | CH=CH₂ | H | Br | OCH₃ | N | |
| O | 0 | H | H | CH=CH₂ | H | CH₃ | OCH₃ | N | |
| O | 0 | H | H | CH₂CH₂SO₂CH₃ | H | OCH₃ | OCH₃ | CH | 207-208 |
| O | 0 | H | H | CH₂CH₂SO₂CH₃ | H | CH₃ | CH₃ | CH | 149-150 |
| O | 0 | H | H | CH₂CH₂SO₂CH₃ | H | CH₃ | OCH₃ | CH | 204-205 |
| O | 0 | H | H | CH₂CH₂SO₂CH₃ | H | OCH₃ | OCH₃ | CH | 212-214 |
| O | 0 | H | H | CH₂CH₂SO₂CH₃ | H | Cl | OCH₃ | CH | |
| O | 0 | H | H | CH₂CH₂SO₂CH₃ | H | Br | OCH₃ | N | |
| O | 0 | H | H | CH₂CH₂SO₂CH₃ | H | CH₃ | OCH₃ | N | 197-198 |
| O | 0 | H | H | CH₂CHF₂ | H | OCH₃ | OCH₃ | CH | 195-196 |
| O | 0 | H | H | CH₂CHF₂ | H | CH₃ | CH₃ | CH | |
| O | 0 | H | H | CH₂CHF₂ | H | CH₃ | OCH₃ | CH | |
| O | 0 | H | H | CH₂CHF₂ | H | OCH₃ | OCH₃ | CH | |
| O | 0 | H | H | CH₂CHF₂ | H | Cl | OCH₃ | CH | |
| O | 0 | H | H | CH₂CHCl₂ | H | Br | OCH₃ | N | |
| O | 0 | H | H | CH₂CHCl₂ | H | CH₃ | OCH₃ | N | |
| O | 0 | H | H | CH₂CHCl₂ | H | OCH₃ | OCH₃ | CH | |
| O | 0 | H | H | CH₂CHCl₂ | H | CH₃ | CH₃ | CH | |
| O | 0 | H | H | CH₂CHCl₂ | H | CH₃ | OCH₃ | CH | |
| O | 0 | H | H | CH₂OCH₂CH₃ | H | OCH₃ | OCH₃ | CH | |
| O | 0 | H | H | CH₂OCH₂CH₃ | H | Cl | OCH₃ | CH | |
| O | 0 | H | H | CH₂OCH₂CH₃ | H | Br | OCH₃ | N | |
| O | 0 | H | H | CH₂OCH₂CH₃ | H | CH₃ | OCH₃ | N | |
| O | 0 | H | H | CH₂OCH₂CH₂CH₃ | H | CH₃ | CH₃ | CH | |
| O | 0 | H | H | CH₂OCH₂CH₂CH₃ | H | CH₃ | OCH₃ | CH | |

TABLE Ia-continued

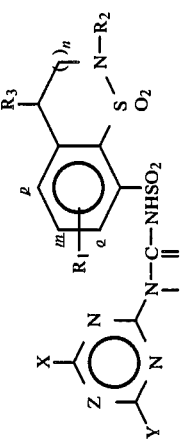

| W | n | R | R₁ | R₂ | R₃ | X | Y | Z | m.p. (°C.) |
|---|---|---|---|---|---|---|---|---|---|
| O | 0 | H | H | CH₂OCH₂CH₂CH₃ | H | OCH₃ | OCH₃ | CH | |
| O | 0 | H | H | CH₂OCH₂CH₂CH₃ | H | Cl | OCH₃ | CH | |
| O | 0 | H | H | CH₂OCH₂CH₂CH₃ | H | CH₃ | OCH₃ | N | |
| O | 0 | H | H | CH₂OCH₂CH₂CH₃ | H | OCH₃ | CH₃ | N | |
| O | 0 | H | H | CH₂OCH(CH₃)₂ | H | CH₃ | CH₃ | CH | |
| O | 0 | H | H | CH₂OCH(CH₃)₂ | H | CH₃ | OCH₃ | CH | |
| O | 0 | H | H | CH₂OCH(CH₃)₂ | H | OCH₃ | OCH₃ | CH | |
| O | 0 | H | H | CH₂OCH(CH₃)₂ | H | Cl | OCH₃ | CH | |
| O | 0 | H | H | CH₂OCH(CH₃)₂ | H | CH₃ | OCH₃ | N | |
| O | 0 | H | H | CH₂OCH(CH₃)₂ | H | OCH₃ | CH₃ | N | |
| O | 0 | H | H | CH₂OC(CH₃)₃ | H | CH₃ | CH₃ | CH | |
| O | 0 | H | H | CH₂OC(CH₃)₃ | H | CH₃ | OCH₃ | CH | |
| O | 0 | H | H | CH₂OC(CH₃)₃ | H | OCH₃ | OCH₃ | CH | |
| O | 0 | H | H | CH₂OC(CH₃)₃ | H | Cl | OCH₃ | CH | |
| O | 0 | H | H | CH₂OC(CH₃)₃ | H | CH₃ | OCH₃ | N | |
| O | 0 | H | H | CH₂OC(CH₃)₃ | H | OCH₃ | CH₃ | N | |
| O | 0 | H | H | CH₂CH₂SPh | H | CH₃ | CH₃ | CH | |
| O | 0 | H | H | CH₂CH₂SPh | H | CH₃ | OCH₃ | CH | |
| O | 0 | H | H | CH₂CH₂SPh | H | OCH₃ | OCH₃ | CH | |
| O | 0 | H | H | CH₂CH₂SPh | H | Cl | OCH₃ | CH | |
| O | 0 | H | H | CH₂CH₂SPh | H | CH₃ | OCH₃ | N | |
| O | 0 | H | H | CH₂CH₂SPh | H | OCH₃ | CH₃ | N | |
| O | 0 | H | H | N(CH₃)₂ | H | CH₃ | CH₃ | CH | |
| O | 0 | H | H | N(CH₃)₂ | H | CH₃ | OCH₃ | CH | |
| O | 0 | H | H | N(CH₃)₂ | H | OCH₃ | OCH₃ | CH | |
| O | 0 | H | H | N(CH₃)₂ | H | Cl | OCH₃ | CH | |
| O | 0 | H | H | N(CH₃)₂ | H | CH₃ | OCH₃ | N | |
| O | 0 | H | H | N(CH₃)₂ | H | OCH₃ | CH₃ | N | |
| O | 0 | H | H | cyclopropyl | H | CH₃ | CH₃ | CH | |
| O | 0 | H | H | cyclopropyl | H | CH₃ | OCH₃ | CH | |
| O | 0 | H | H | cyclopropyl | H | OCH₃ | OCH₃ | CH | |
| O | 0 | H | H | cyclopropyl | H | Cl | OCH₃ | CH | |
| O | 0 | H | H | cyclopropyl | H | CH₃ | OCH₃ | N | |
| O | 0 | H | H | cyclopropyl | H | OCH₃ | CH₃ | N | |
| O | 0 | H | H | CH₂CH(CH₃)OH | H | CH₃ | CH₃ | CH | |
| O | 0 | H | H | CH₂CH(CH₃)OH | H | CH₃ | OCH₃ | CH | |
| O | 0 | H | H | CH₂CH(CH₃)OH | H | OCH₃ | OCH₃ | CH | |
| O | 0 | H | H | CH₂CH(CH₃)OH | H | Cl | OCH₃ | CH | |
| O | 0 | H | H | CH₂CH(CH₃)OH | H | CH₃ | OCH₃ | N | |
| O | 0 | H | H | CH₂CH(CH₃)OH | H | OCH₃ | CH₃ | N | |
| O | 0 | H | H | CH₂CH(CH₃)OC(O)CH₃ | H | CH₃ | CH₃ | CH | |
| O | 0 | H | H | CH₂CH(CH₃)OC(O)CH₃ | H | CH₃ | OCH₃ | CH | |
| O | 0 | H | H | CH₂CH(CH₃)OC(O)CH₃ | H | OCH₃ | OCH₃ | CH | |

TABLE Ia-continued

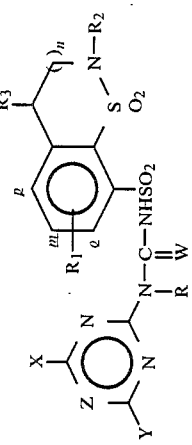

| W | n | R | R1 | R2 | R3 | X | Y | Z | m.p. (°C) |
|---|---|---|----|-----|----|----|----|---|-----------|
| O | 0 | H | H | CH2CH(CH3)OC(O)CH3 | H | Cl | OCH3 | CH | |
| O | 0 | H | H | CH2CH(CH3)OC(O)CH3 | H | CH3 | OCH3 | N | |
| O | 0 | H | H | CH2CH(CH3)OC(O)CH3 | H | OCH3 | OCH3 | N | |
| O | 0 | H | H | CH2CH(CH3)OSO2CH3 | H | CH3 | CH3 | CH | |
| O | 0 | H | H | CH2CH(CH3)OSO2CH3 | H | CH3 | OCH3 | CH | |
| O | 0 | H | H | CH2CH(CH3)OSO2CH3 | H | OCH3 | OCH3 | CH | |
| O | 0 | H | H | CH2CH(CH3)OSO2CH3 | H | Cl | OCH3 | CH | |
| O | 0 | H | H | CH2CH(CH3)OSO2CH3 | H | CH3 | OCH3 | N | |
| O | 0 | H | H | CH2CH(CH3)OSO2CH3 | H | OCH3 | OCH3 | N | |
| O | 0 | H | H | CH2CH2CH2OH | H | CH3 | CH3 | CH | |
| O | 0 | H | H | CH2CH2CH2OH | H | CH3 | OCH3 | CH | |
| O | 0 | H | H | CH2CH2CH2OH | H | OCH3 | OCH3 | CH | |
| O | 0 | H | H | CH2CH2CH2OH | H | Cl | OCH3 | CH | |
| O | 0 | H | H | CH2CH2CH2OH | H | CH3 | OCH3 | N | |
| O | 0 | H | H | CH2CH2CH2OH | H | OCH3 | OCH3 | N | |
| O | 0 | H | H | CH2CH2CH2OC(O)CH3 | H | CH3 | CH3 | CH | |
| O | 0 | H | H | CH2CH2CH2OC(O)CH3 | H | CH3 | OCH3 | CH | |
| O | 0 | H | H | CH2CH2CH2OC(O)CH3 | H | OCH3 | OCH3 | CH | |
| O | 0 | H | H | CH2CH2CH2OC(O)CH3 | H | Cl | OCH3 | CH | |
| O | 0 | H | H | CH2CH2CH2OC(O)CH3 | H | CH3 | OCH3 | N | |
| O | 0 | H | H | CH2CH2CH2OC(O)CH3 | H | OCH3 | OCH3 | N | |
| O | 0 | H | H | CH2CH2CH2OSO2CH3 | H | CH3 | CH3 | CH | |
| O | 0 | H | H | CH2CH2CH2OSO2CH3 | H | CH3 | OCH3 | CH | |
| O | 0 | H | H | CH2CH2CH2OSO2CH3 | H | OCH3 | OCH3 | CH | |
| O | 0 | H | H | CH2CH2CH2OSO2CH3 | H | Cl | OCH3 | CH | 170–173 |
| O | 0 | H | H | CH2CH2CH2OSO2CH3 | H | CH3 | OCH3 | N | 199–201 |
| O | 0 | H | H | CH2CH2CH2OSO2CH3 | H | OCH3 | OCH3 | N | 196–198 |
| O | 0 | H | H | CH2CH(CH2CH3)OH | H | CH3 | CH3 | CH | |
| O | 0 | H | H | CH2CH(CH2CH3)OH | H | CH3 | OCH3 | CH | |
| O | 0 | H | H | CH2CH(CH2CH3)OH | H | OCH3 | OCH3 | CH | |
| O | 0 | H | H | CH2CH(CH2CH3)OH | H | Cl | OCH3 | CH | |

TABLE Ia-continued

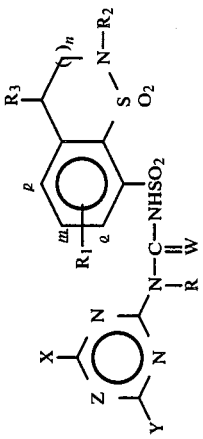

| W | n | R | R1 | R2 | R3 | X | Y | Z | m.p. (°C.) |
|---|---|---|---|---|---|---|---|---|---|
| O | O | H | H | CH2CH(CH2CH3)OH | H | CH3 | OCH3 | N | |
| O | O | H | H | CH2CH(CH2CH3)OH | H | OCH3 | OCH3 | N | |
| O | O | H | H | CH2CH(CH2CH3)OC(O)CH3 | H | CH3 | CH3 | CH | |
| O | O | H | H | CH2CH(CH2CH3)OC(O)CH3 | H | Cl | OCH3 | CH | |
| O | O | H | H | CH2CH(CH2CH3)OC(O)CH3 | H | OCH3 | OCH3 | CH | |
| O | O | H | H | CH2CH(CH2CH3)OC(O)CH3 | H | CH3 | OCH3 | CH | |
| O | O | H | H | CH2CH(CH2CH3)OC(O)CH3 | H | CH3 | OCH3 | N | |
| O | O | H | H | CH2CH(CH2CH3)OC(O)CH3 | H | OCH3 | OCH3 | N | |
| O | O | H | H | CH2CH(CH2CH3)OSO2CH3 | H | CH3 | CH3 | CH | |
| O | O | H | H | CH2CH(CH2CH3)OSO2CH3 | H | Cl | OCH3 | CH | |
| O | O | H | H | CH2CH(CH2CH3)OSO2CH3 | H | OCH3 | OCH3 | CH | |
| O | O | H | H | CH2CH(CH2CH3)OSO2CH3 | H | CH3 | OCH3 | CH | |
| O | O | H | H | CH2CH(CH2CH3)OSO2CH3 | H | CH3 | OCH3 | N | |
| O | O | H | H | CH2CH(CH2CH3)OSO2CH3 | H | OCH3 | OCH3 | N | |
| O | O | H | H | CH2CH2C≡CH | H | CH3 | CH3 | CH | |
| O | O | H | H | CH2CH2C≡CH | H | Cl | OCH3 | CH | |
| O | O | H | H | CH2CH2C≡CH | H | CH3 | OCH3 | CH | |
| O | O | H | H | CH2CH2C≡CH | H | OCH3 | OCH3 | CH | |
| O | O | H | H | CH2C≡C—CH3 | H | CH3 | CH3 | CH | |
| O | O | H | H | CH2C≡C—CH3 | H | Cl | OCH3 | CH | |
| O | O | H | H | CH2C≡C—CH3 | H | CH3 | OCH3 | CH | |
| O | O | H | H | CH2C≡C—CH3 | H | OCH3 | OCH3 | CH | |
| O | O | H | H | CH(CH3)C≡CH | H | CH3 | CH3 | CH | |
| O | O | H | H | CH(CH3)C≡CH | H | Cl | OCH3 | CH | |
| O | O | H | H | CH(CH3)C≡CH | H | CH3 | OCH3 | CH | |
| O | O | H | H | CH(CH3)C≡CH | H | OCH3 | OCH3 | CH | |
| O | O | H | H | 3-epoxybutyl | H | CH3 | CH3 | CH | |
| O | O | H | H | 3-epoxybutyl | H | Cl | OCH3 | CH | |
| O | O | H | H | 3-epoxybutyl | H | CH3 | OCH3 | CH | |
| O | O | H | H | 3-epoxybutyl | H | OCH3 | OCH3 | CH | |
| O | O | H | H | CH2CH2NH2 | H | CH3 | CH3 | CH | |
| O | O | H | H | CH2CH2NH2 | H | Cl | OCH3 | CH | |
| O | O | H | H | CH2CH2NH2 | H | CH3 | OCH3 | CH | |
| O | O | H | H | CH2CH2NH2 | H | CH3 | OCH3 | N | |
| O | O | H | H | CH2CH2NH2 | H | OCH3 | OCH3 | N | |
| O | O | H | H | CH2CH2N(CH3)2 | H | CH3 | CH3 | CH | |
| O | O | H | H | CH2CH2N(CH3)2 | H | CH3 | OCH3 | CH | |
| O | O | H | H | CH2CH2N(CH3)2 | H | OCH3 | OCH3 | CH | |

TABLE Ia-continued

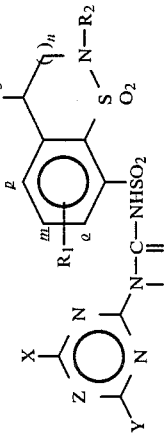

| W | n | R | R₁ | R₂ | R₃ | X | Y | Z | m.p. (°C.) |
|---|---|---|---|---|---|---|---|---|---|
| O | 0 | H | H | CH₂CH₂N(CH₃)₂ | H | Cl | OCH₃ | CH | |
| O | 0 | H | H | CH₂CH₂N(CH₃)₂ | H | CH₃ | OCH₃ | N | |
| O | 0 | H | H | CH₂CH₂N(CH₃)₂ | H | OCH₃ | OCH₃ | N | |
| O | 0 | H | H | CH₂CH₂CH₂N(CH₃)₂ | H | CH₃ | CH₃ | CH | |
| O | 0 | H | H | CH₂CH₂CH₂N(CH₃)₂ | H | CH₃ | OCH₃ | CH | |
| O | 0 | H | H | CH₂CH₂CH₂N(CH₃)₂ | H | OCH₃ | OCH₃ | CH | |
| O | 0 | H | H | CH₂CH₂CH₂N(CH₃)₂ | H | Cl | OCH₃ | CH | |
| O | 0 | H | H | CH₂CH₂CH₂N(CH₃)₂ | H | CH₃ | OCH₃ | N | |
| O | 0 | H | H | CH₂CH₂CH₂N(CH₃)₂ | H | OCH₃ | OCH₃ | N | |
| O | 0 | H | H | CH₂CH₂NHC(O)CH₃ | H | CH₃ | CH₃ | CH | |
| O | 0 | H | H | CH₂CH₂NHC(O)CH₃ | H | CH₃ | OCH₃ | CH | |
| O | 0 | H | H | CH₂CH₂NHC(O)CH₃ | H | Cl | OCH₃ | CH | |
| O | 0 | H | H | CH₂CH₂NHC(O)CH₃ | H | OCH₃ | OCH₃ | CH | |
| O | 0 | H | H | CH₂CH₂NHC(O)CH₃ | H | CH₃ | OCH₃ | N | |
| O | 0 | H | H | CH₂CH₂NHCH₃ | H | CH₃ | CH₃ | CH | |
| O | 0 | H | H | CH₂CH₂NHCH₃ | H | CH₃ | OCH₃ | CH | |
| O | 0 | H | H | CH₂CH₂NHCH₃ | H | Cl | OCH₃ | CH | |
| O | 0 | H | H | CH₂C(CH₃)=NOH | H | CH₃ | CH₃ | CH | |
| O | 0 | H | H | CH₂C(CH₃)=NOH | H | CH₃ | OCH₃ | CH | |
| O | 0 | H | H | CH₂C(CH₃)=NOH | H | Cl | OCH₃ | CH | |
| O | 0 | H | H | CH₂C(CH₃)=NOH | H | OCH₃ | OCH₃ | CH | |
| O | 0 | H | H | CH₂C(CH₃)=NOH | H | CH₃ | OCH₃ | N | |
| O | 0 | H | H | CH₂C(CH₃)=NNH₂ | H | CH₃ | CH₃ | CH | |
| O | 0 | H | H | CH₂C(CH₃)=NNH₂ | H | CH₃ | OCH₃ | CH | |
| O | 0 | H | H | CH₂C(CH₃)=NNH₂ | H | Cl | OCH₃ | CH | |
| O | 0 | H | H | CH₂C(CH₃)=NNH₂ | H | OCH₃ | OCH₃ | CH | |
| O | 0 | H | H | CH₂C(CH₃)=NNH₂ | H | CH₃ | OCH₃ | N | |
| O | 0 | H | H | CH₂C(CH₃)=NNHPh | H | CH₃ | CH₃ | CH | |
| O | 0 | H | H | CH₂C(CH₃)=NNHPh | H | CH₃ | OCH₃ | CH | |
| O | 0 | H | H | CH₂C(CH₃)=NNHPh | H | Cl | OCH₃ | CH | |
| O | 0 | H | H | CH₂C(CH₃)=NNHPh | H | OCH₃ | OCH₃ | CH | |
| O | 0 | H | H | CH₂C(CH₃)=NNHPh | H | CH₃ | OCH₃ | N | |
| O | 0 | H | H | CH₂C(CH₃)=NNHCH₃ | H | CH₃ | CH₃ | CH | |
| O | 0 | H | H | CH₂C(CH₃)=NNHCH₃ | H | CH₃ | OCH₃ | CH | |
| O | 0 | H | H | CH₂C(CH₃)=NNHCH₃ | H | Cl | OCH₃ | CH | |
| O | 0 | H | H | CH₂C(CH₃)=NNHCH₃ | H | OCH₃ | OCH₃ | CH | |
| O | 0 | H | H | CH₂C(CH₃)=NNHCH₃ | H | CH₃ | OCH₃ | N | |
| O | 0 | H | H | CH₂CH₂P(O)(OCH₃)₂ | H | CH₃ | CH₃ | CH | |
| O | 0 | H | H | CH₂CH₂P(O)(OCH₃)₂ | H | CH₃ | OCH₃ | CH | |
| O | 0 | H | H | CH₂CH₂P(O)(OCH₃)₂ | H | OCH₃ | OCH₃ | CH | |
| O | 0 | H | H | CH₂CH₂P(O)(OCH₃)₂ | H | Cl | OCH₃ | CH | |

TABLE Ia-continued

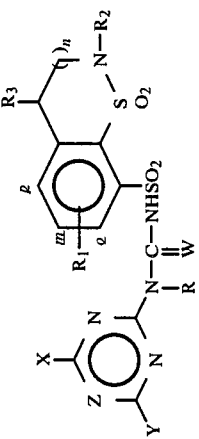

| W | n | R | R₁ | R₂ | R₃ | X | Y | Z | m.p. (°C.) |
|---|---|---|---|---|---|---|---|---|---|
| O | 0 | H | H | CH₂CH₂P(O)(OCH₃)₂ | H | CH₃ | OCH₃ | N | |
| O | 0 | H | H | CH₂CH₂P(O)(OCH₃)₂ | H | OCH₃ | OCH₃ | N | |
| O | 0 | H | H | CH₂SCN | H | CH₃ | CH₃ | CH | |
| O | 0 | H | H | CH₂SCN | H | Cl | OCH₃ | CH | |
| O | 0 | H | H | CH₂SCN | H | OCH₃ | OCH₃ | N | |
| O | 0 | H | H | CH₂SCN | H | CH₃ | OCH₃ | N | |
| O | 0 | H | H | CH₂CO₂CH(CH₃)₂ | H | CH₃ | CH₃ | CH | |
| O | 0 | H | H | CH₂CO₂CH(CH₃)₂ | H | OCH₃ | OCH₃ | CH | |
| O | 0 | H | H | CH₂CO₂CH(CH₃)₂ | H | OCH₃ | OCH₃ | N | |
| O | 0 | H | H | CH₂CO₂CH(CH₃)₂ | H | Cl | OCH₃ | CH | |
| O | 0 | H | H | CH₂CO₂CH(CH₃)₂ | H | CH₃ | OCH₃ | N | |
| O | 0 | H | H | CH₂CO₂CH(CH₃)₂ | H | OCH₃ | CH₃ | CH | |
| O | 0 | H | H | cyclopentanone-3-yl | H | CH₃ | CH₃ | CH | |
| O | 0 | H | H | cyclopentanone-3-yl | H | CH₃ | OCH₃ | CH | |
| O | 0 | H | H | cyclopentanone-3-yl | H | OCH₃ | OCH₃ | CH | |
| O | 0 | H | H | cyclopentanone-3-yl | H | OCH₃ | OCH₃ | N | |
| O | 0 | H | H | cyclopentanone-3-yl | H | Cl | OCH₃ | CH | |
| O | 0 | H | H | cyclopentanone-3-yl | H | CH₃ | OCH₃ | N | |
| O | 0 | H | H | cyclopentanone-3-yl | H | OCH₃ | CH₃ | CH | |
| O | 0 | H | H | cyclohexanone-3-yl | H | CH₃ | CH₃ | CH | |
| O | 0 | H | H | cyclohexanone-3-yl | H | CH₃ | OCH₃ | CH | |
| O | 0 | H | H | cyclohexanone-3-yl | H | OCH₃ | OCH₃ | CH | |
| O | 0 | H | H | cyclohexanone-3-yl | H | OCH₃ | OCH₃ | N | |
| O | 0 | H | H | cyclohexanone-3-yl | H | Cl | OCH₃ | CH | |
| O | 0 | H | H | cyclohexanone-3-yl | H | CH₃ | OCH₃ | N | |
| O | 0 | H | H | cyclohexanone-3-yl | H | OCH₃ | CH₃ | CH | |
| O | 0 | H | H | CH₂CH=CH—C≡CC(CH₃)₃ | H | OCH₃ | OCH₃ | N | |
| O | 0 | H | H | CH₂CH=CH—CH=CH₂ | H | CH₃ | CH₃ | CH | |
| O | 0 | H | H | CH₂CH=CH—CH=CH₂ | H | CH₃ | OCH₃ | CH | |
| O | 0 | H | H | CH₂CH=CH—CH=CH₂ | H | OCH₃ | OCH₃ | CH | |
| O | 0 | H | H | CH₂CH=CH—CH=CH₂ | H | OCH₃ | OCH₃ | N | |
| O | 0 | H | H | CH₂CH=CH—CH=CH₂ | H | Cl | OCH₃ | CH | |
| O | 0 | H | H | CH₂CH=CH—CH=CH₂ | H | CH₃ | OCH₃ | N | |
| O | 0 | H | H | CH₂CH=CH—CH=CH₂ | H | OCH₃ | CH₃ | CH | |
| O | 0 | H | H | CH₂CH₂F | H | CH₃ | CH₃ | CH | |
| O | 0 | H | H | CH₂CH₂F | H | CH₃ | OCH₃ | CH | |
| O | 0 | H | H | CH₂CH₂F | H | OCH₃ | OCH₃ | N | |
| O | 0 | H | m-Cl | C(O)CH₃ | H | CH₃ | CH₃ | CH | |
| O | 0 | H | m-Cl | C(O)CH₃ | H | Cl | OCH₃ | CH | |
| O | 0 | H | m-Cl | C(O)CH₃ | H | CH₃ | OCH₃ | N | |
| O | 0 | H | m-Cl | C(O)CH₃ | H | OCH₃ | OCH₃ | N | |
| O | 0 | H | m-Cl | CH₂CH₂CH₂F | H | OCH₃ | OCH₃ | Z | |
| O | 0 | H | m-Cl | CH₂CH₂CH₂F | H | CH₃ | CH₃ | CH | |

TABLE Ia-continued

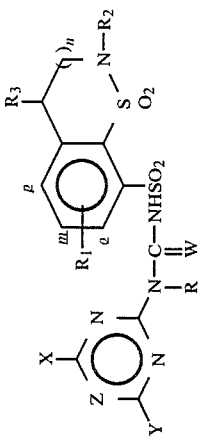

| W | n | R | R₁ | R₂ | R₃ | X | Y | Z | m.p. (°C.) |
|---|---|---|---|---|---|---|---|---|---|
| O | 0 | H | m-Cl | $CH_2CH_2CH_2F$ | H | $CH_3$ | $OCH_3$ | CH | |
| O | 0 | H | m-Cl | $CH_2CH_2CH_2F$ | H | $OCH_3$ | $OCH_3$ | CH | |
| O | 0 | H | m-Cl | $CH_2CH_2CH_2F$ | H | Cl | $OCH_3$ | CH | |
| O | 0 | H | m-Cl | $CH_2CH_2CH_2F$ | H | $CH_3$ | $OCH_3$ | N | |
| O | 0 | H | m-Cl | $CH_2CH_2CH_2F$ | H | $OCH_3$ | $CH_3$ | CH | |
| O | 0 | H | m-Cl | $CH_2CH_2CH_2F$ | H | $CH_3$ | $CH_3$ | CH | |
| O | 0 | H | m-Cl | $CH_2OCH_3$ | H | $CH_3$ | $OCH_3$ | CH | |
| O | 0 | H | m-Cl | $CH_2OCH_3$ | H | $OCH_3$ | $OCH_3$ | CH | |
| O | 0 | H | m-Cl | $CH_2OCH_3$ | H | Cl | $OCH_3$ | CH | |
| O | 0 | H | m-CH₃ | $CH_2CH_2OCH_3$ | H | $CH_3$ | $OCH_3$ | CH | 188–193 |
| O | 0 | H | m-CH₃ | $CH_2CH_2OCH_3$ | H | $OCH_3$ | $OCH_3$ | CH | 119–124 |
| O | 0 | H | m-CH₃ | $CH_2CH_2OCH_3$ | H | Cl | $OCH_3$ | CH | 164–172 |
| O | 0 | H | m-CH₃ | $CH_2CH_2OCH_3$ | H | $CH_3$ | $OCH_3$ | N | 153–158 |
| O | 0 | H | m-CH₃ | $CH_2CH_2OCH_3$ | H | $OCH_3$ | $CH_3$ | CH | |
| O | 0 | H | m-CH₃ | $CH_2CH_2OCH_3$ | H | $CH_3$ | $CH_3$ | CH | |
| O | 0 | H | p-CH₃ | $CH_2CH_2OCH_3$ | H | $CH_3$ | $OCH_3$ | CH | |
| O | 0 | H | p-CH₃ | $CH_2CH_2OCH_3$ | H | $OCH_3$ | $OCH_3$ | CH | |
| O | 0 | H | p-CH₃ | $CH_2CH_2OCH_3$ | H | Cl | $OCH_3$ | CH | |
| O | 0 | H | p-CH₃ | $CH_2CH_2OCH_3$ | H | $CH_3$ | $OCH_3$ | N | |
| O | 0 | H | p-CH₃ | $CH_2CH_2OCH_3$ | H | $OCH_3$ | $CH_3$ | CH | |
| O | 0 | H | p-CH₃ | $CH_2CH_2OCH_3$ | H | $CH_3$ | $CH_3$ | CH | |
| O | 0 | H | m-SCH₃ | $CH_2CH_2F$ | H | $CH_3$ | $OCH_3$ | CH | |
| O | 0 | H | m-SCH₃ | $CH_2CH_2F$ | H | $OCH_3$ | $OCH_3$ | CH | |
| O | 0 | H | m-SCH₃ | $CH_2CH_2F$ | H | Cl | $OCH_3$ | CH | |
| O | 0 | H | m-SCH₃ | $CH_2CH_2F$ | H | $CH_3$ | $OCH_3$ | N | |
| O | 0 | H | m-SO₂CH₃ | $CH_2CH_2F$ | H | $OCH_3$ | $CH_3$ | CH | |
| O | 0 | H | m-SO₂CH₃ | $CH_2CH_2F$ | H | $CH_3$ | $CH_3$ | CH | |
| O | 0 | H | m-SO₂CH₃ | $CH_2CH_2F$ | H | $CH_3$ | $OCH_3$ | CH | |
| O | 0 | H | m-SO₂CH₃ | $CH_2CH_2F$ | H | $OCH_3$ | $OCH_3$ | CH | |
| O | 0 | H | m-SO₂CH₃ | $CH_2CH_2F$ | H | Cl | $OCH_3$ | CH | |
| O | 0 | H | m-SO₂CH₃ | $CH_2CH_2F$ | H | $CH_3$ | $OCH_3$ | N | |
| O | 0 | H | m-SO₂CH₃ | $CH_2CH_2F$ | H | $OCH_3$ | $CH_3$ | CH | |
| O | 0 | H | m-SO₂CH₃ | $CH_2CH_2F$ | H | $CH_3$ | $CH_3$ | CH | |
| O | 0 | H | m-SO₂CH₃ | $C(O)CH_3$ | H | $CH_3$ | $OCH_3$ | CH | |
| O | 0 | H | m-CF₃ | $C(O)CH_3$ | H | $OCH_3$ | $OCH_3$ | CH | |
| O | 0 | H | m-CF₃ | $C(O)CH_3$ | H | Cl | $OCH_3$ | CH | |
| O | 0 | H | m-CF₃ | $C(O)CH_3$ | H | $CH_3$ | $OCH_3$ | N | |
| O | 0 | H | m-CF₃ | $CF_2CF_2H$ | H | $CH_3$ | $OCH_3$ | CH | |
| O | 0 | H | m-CF₃ | $CF_2CF_2H$ | H | $OCH_3$ | $OCH_3$ | CH | |
| O | 0 | H | m-CF₃ | $CF_2CF_2H$ | H | Cl | $OCH_3$ | CH | |
| O | 0 | H | m-CF₃ | $CF_2CF_2H$ | H | $CH_3$ | $OCH_3$ | N | |
| O | 0 | H | H | $CH(CH_3)CH(CH_3)_2$ | H | $CH_3$ | $CH_3$ | CH | 214–216 |
| O | 0 | H | H | $CH(CH_3)CH(CH_3)_2$ | H | $CH_3$ | $OCH_3$ | CH | 230–233 |
| O | 0 | H | H | $CH(CH_3)CH(CH_3)_2$ | H | $OCH_3$ | $OCH_3$ | CH | 228–231 |

TABLE Ia-continued

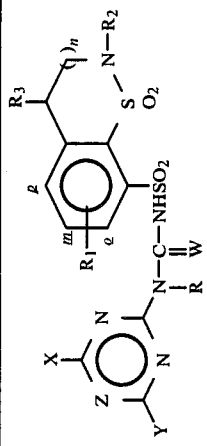

| W | n | R | R₁ | R₂ | R₃ | X | Y | Z | m.p. (°C.) |
|---|---|---|---|---|---|---|---|---|---|
| O | 0 | H | H | CH(CH₃)CH(CH₃)₂ | H | Cl | OCH₃ | CH | 224-272 |
| O | 0 | H | H | CH(CH₃)CH(CH₃)₂ | H | CH₃ | OCH₃ | N | 167-170 |
| O | 0 | H | H | CH(CH₃)CH(CH₃)₂ | H | OCH₃ | OCH₃ | CH | 130-133 |
| O | 0 | H | H | cyclohexyl | H | CH₃ | OCH₃ | CH | 168-171 |
| O | 0 | H | H | cyclohexyl | H | Cl | OCH₃ | N | 224-227 |
| O | 0 | H | H | cyclohexyl | H | CH₃ | OCH₃ | N | 139-142 |
| O | 0 | H | H | cyclopropyl | H | Cl | OCH₃ | CH | 184-187 |
| O | 0 | H | H | cyclopropyl | H | OCH₃ | OCH₃ | N | |
| O | 0 | H | H | cyclopropyl | H | CH₃ | CH₃ | CH | 180-183 |
| O | 0 | H | H | 2-fluorobenzyl | H | CH₃ | OCH₃ | CH | 182-185 |
| O | 0 | H | H | 2-fluorobenzyl | H | Cl | OCH₃ | CH | 180-183 |
| O | 0 | H | H | 2-fluorobenzyl | H | OCH₃ | OCH₃ | CH | 172-174 |
| O | 0 | H | H | 2-fluorobenzyl | H | CH₃ | CH₃ | CH | 173-175 |
| O | 0 | H | H | 2-chlorobenzyl | H | CH₃ | OCH₃ | CH | 194-197 |
| O | 0 | H | H | 2-chlorobenzyl | H | Cl | OCH₃ | CH | 178-180 |
| O | 0 | H | H | 2-chlorobenzyl | H | OCH₃ | OCH₃ | N | 200-203 |
| O | 0 | H | H | 2-chlorobenzyl | H | CH₃ | OCH₃ | CH | 194-197 |
| O | 0 | H | H | 2-bromobenzyl | H | CH₃ | OCH₃ | CH | 180-182 |
| O | 0 | H | H | 2-bromobenzyl | H | Cl | OCH₃ | CH | 163-166 |
| O | 0 | H | H | 2-bromobenzyl | H | CH₃ | CH₃ | CH | |
| O | 0 | H | H | 2-bromobenzyl | H | OCH₃ | OCH₃ | N | |
| O | 0 | H | H | 2-bromobenzyl | H | CH₃ | OCH₃ | CH | |
| O | 0 | H | H | CH₂CH₂CH₂F | H | Cl | OCH₃ | CH | |
| O | 0 | H | m-Cl | CH₂CH₂CH₂F | H | Cl | OCH₃ | CH | |
| O | 0 | H | m-OCH₃ | CH₂CH₂CH₂F | H | Cl | OCH₃ | CH | |
| O | 0 | H | m-SCH₃ | CH₂CH₂CH₂F | H | Cl | OCH₃ | CH | |
| O | 0 | H | m-CN | CH₂CH₂CH₂F | H | Cl | OCH₃ | CH | |
| O | 0 | H | m-F | CH₂CH₂CH₂F | H | Cl | OCH₃ | CH | |
| O | 0 | H | m-CH₃ | CH₂CH₂CH₂F | H | Cl | OCH₃ | CH | |
| O | 0 | H | o-Cl | CH₂CH₂CH₂F | H | Cl | OCH₃ | CH | |
| O | 0 | H | o-OCH₃ | CH₂CH₂CH₂F | H | Cl | OCH₃ | CH | |
| O | 0 | H | o-SCH₃ | CH₂CH₂CH₂F | H | Cl | OCH₃ | CH | |
| O | 0 | H | o-F | CH₂CH₂CH₂F | H | Cl | OCH₃ | CH | |
| O | 0 | H | o-CN | CH₂CH₂CH₂F | H | Cl | OCH₃ | CH | |
| O | 1 | H | H | CH₂CH₂F | H | Cl | OCH₃ | CH | |
| O | 1 | H | H | CH₂CH₂F | H | OCH₃ | OCH₃ | CH | |
| O | 1 | H | H | CH₂CH₂F | H | CH₃ | OCH₃ | CH | |

TABLE Ib

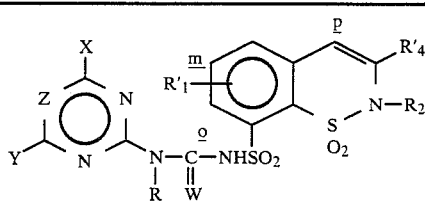

| W | R | R'₁ | R₂ | R'₄ | X | Y | Z | m.p. (°C.) |
|---|---|---|---|---|---|---|---|---|
| O | H | H | CH₂CH₂CH₂CH₂CH₃ | H | CH₃ | OCH₃ | CH | |
| O | H | H | CH₂CH₂CH₂CH₂CH₃ | H | OCH₃ | OCH₃ | CH | |
| O | H | H | CH₂CH₂CH(CH₃)₂ | H | CH₃ | OCH₃ | CH | |
| O | H | H | CH₂CH₂CH(CH₃)₂ | H | OCH₃ | OCH₃ | CH | |
| O | H | H | CH₂CH(CH₃)CH₂CH₃ | H | CH₃ | OCH₃ | CH | |
| O | H | H | CH₂CH(CH₃)CH₂CH₃ | H | OCH₃ | OCH₃ | CH | |
| O | H | H | CH₂CH₂CH₂Cl | H | CH₃ | OCH₃ | CH | |
| O | H | H | CH₂CH₂CH₂Cl | H | OCH₃ | OCH₃ | CH | |
| O | H | H | CH₂CH₂OCH₃ | H | CH₃ | OCH₃ | CH | |
| O | H | H | CH₂CH₂OCH₃ | H | OCH₃ | OCH₃ | CH | |
| O | H | H | CH₂Cl | H | CH₃ | OCH₃ | CH | |
| O | H | H | CH₂CH₂F | H | CH₃ | CH₃ | CH | |
| O | H | H | CH₂CH₂F | H | CH₃ | OCH₃ | CH | |
| O | H | H | CH₂CH₂F | H | OCH₃ | OCH₃ | CH | |
| O | H | H | CH₂CH₂F | H | CH₃ | OCH₃ | N | |
| O | H | H | CH₃ | CH₃ | CH₃ | CH₃ | CH | |
| O | H | H | CH₃ | CH₃ | OCH₃ | OCH₃ | CH | |
| O | H | H | CH₃ | CH₃ | CH₃ | OCH₃ | N | |
| O | H | H | CH₃ | CH₃ | OCH₃ | OCH₃ | N | |
| O | H | H | CH₃ | CH₃ | Cl | OCH₃ | CH | |
| O | H | H | CH₃ | CH₃ | Br | OCH₃ | CH | |
| O | H | H | CH₂CH₃ | CH₃ | CH₃ | OCH₃ | CH | |
| O | H | H | CH₂CH₃ | CH₃ | OCH₃ | OCH₃ | CH | |
| O | H | H | CH₂CH₃ | CH₃ | CH₃ | OCH₃ | N | |
| O | H | H | CH₂CH₂CH₃ | CH₃ | OCH₃ | OCH₃ | CH | |
| O | H | H | CH₃ | CH₂CH₃ | OCH₃ | OCH₃ | CH | |
| O | H | H | CH₃ | CH₂CH₂CH₂CH₃ | OCH₃ | OCH₃ | CH | |
| O | H | o-CH₂CH₃ | CH₃ | H | CH₃ | OCH₃ | CH | |
| O | H | m-CH₂CH₃ | CH₃ | H | OCH₃ | OCH₃ | CH | |
| O | H | m-CH₂CH₃ | CH₃ | H | CH₃ | OCH₃ | N | |
| O | H | o-OCH₂CH₃ | CH₃ | H | CH₃ | OCH₃ | CH | |
| O | H | m-OCH₂CH₃ | CH₃ | H | OCH₃ | OCH₃ | CH | |
| O | H | m-OCH₂CH₃ | CH₃ | H | CH₃ | OCH₃ | N | |
| O | H | H | CH₂CH₂CH₂CH₃ | CH₃ | CH₃ | CH₃ | CH | |
| O | H | H | CH₂CH₂CH₂CH₃ | CH₃ | CH₃ | OCH₃ | CH | |
| O | H | H | CH₂CH₂CH₂CH₃ | CH₃ | OCH₃ | OCH₃ | CH | |
| O | H | H | CH₂CH₂CH₂CH₃ | CH₃ | CH₃ | OCH₃ | N | |
| O | H | H | CH₂CH₂CH₂CH₃ | CH₃ | OCH₃ | OCH₃ | N | |
| O | H | H | CH₂CH₂CH₂CH₃ | CH₃ | Cl | OCH₃ | CH | |
| O | H | H | CH₂CH₂CH₂CH₃ | CH₃ | Br | OCH₃ | CH | |
| O | H | H | CH₂CH(CH₃)₂ | CH₃ | CH₃ | CH₃ | CH | |
| O | H | H | CH₂CH(CH₃)₂ | CH₃ | CH₃ | OCH₃ | CH | |
| O | H | H | CH₂CH(CH₃)₂ | CH₃ | OCH₃ | OCH₃ | CH | |
| O | H | H | CH₂CH(CH₃)₂ | CH₃ | CH₃ | OCH₃ | N | |
| O | H | H | CH₂CH(CH₃)₂ | CH₃ | OCH₃ | OCH₃ | N | |
| O | H | H | CH₂CH(CH₃)₂ | CH₃ | Cl | OCH₃ | CH | |
| O | H | H | CH₂CH(CH₃)₂ | CH₃ | Br | OCH₃ | CH | |
| O | H | H | CH₂CH₂OCH₃ | H | — | OCH₃ | N | |
| O | H | H | CH₂CH₂OCH₃ | H | — | OCH₃ | CH | |
| O | H | o-CH₃ | C(O)CH₃ | H | OCH₃ | OCH₃ | CH | |
| O | H | m-CH₃ | C(O)CH₃ | H | OCH₃ | OCH₃ | CH | |
| O | H | o-CH₂CH₂CH₃ | C(O)CH₃ | H | OCH₃ | OCH₃ | CH | |
| O | H | o-OCH₃ | C(O)CH₃ | H | OCH₃ | OCH₃ | CH | |
| O | H | m-OCH₃ | C(O)CH₃ | H | OCH₃ | OCH₃ | CH | |
| O | H | o-OCH₂CH₂CH₃ | C(O)CH₃ | H | OCH₃ | OCH₃ | CH | |
| O | H | o-OCH₂CH₂CH₂Cl | C(O)CH₃ | H | OCH₃ | OCH₃ | CH | |
| O | H | o-CH₂CH₂Br | C(O)CH₃ | H | OCH₃ | OCH₃ | CH | |
| O | H | m-CH₂CF₃ | C(O)CH₃ | H | OCH₃ | OCH₃ | CH | |
| O | H | o-CF₃ | C(O)CH₃ | H | OCH₃ | OCH₃ | CH | |
| O | H | m-CF₃ | C(O)CH₃ | H | OCH₃ | OCH₃ | CH | |
| O | H | o-CH₂CH₂CH₂F | C(O)CH₃ | H | OCH₃ | OCH₃ | CH | |
| O | H | o-SCH₃ | C(O)CH₃ | H | OCH₃ | OCH₃ | CH | |
| O | H | m-SCH₃ | C(O)CH₃ | H | OCH₃ | OCH₃ | CH | |
| O | H | o-SCH₂CH₂CH₃ | C(O)CH₃ | H | OCH₃ | OCH₃ | CH | |
| O | H | o-SCH₂CH₂CH₂F | C(O)CH₃ | H | OCH₃ | OCH₃ | CH | |
| O | H | o-NH₂ | C(O)CH₃ | H | OCH₃ | OCH₃ | CH | |
| O | H | o-NHCH₃ | C(O)CH₃ | H | OCH₃ | OCH₃ | CH | |
| O | H | m-N(CH₃)₂ | C(O)CH₃ | H | OCH₃ | OCH₃ | CH | |
| O | H | m-NH(CH₂)₂CH₃ | C(O)CH₃ | H | OCH₃ | OCH₃ | CH | |

TABLE Ib-continued

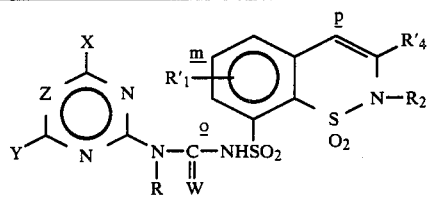

| W | R | R'₁ | R₂ | R'₄ | X | Y | Z | m.p. (°C.) |
|---|---|---|---|---|---|---|---|---|
| O | H | m-N(CH₂CH₂CH₃)₂ | C(O)CH₃ | H | OCH₃ | OCH₃ | CH | |
| O | H | o-Cl | C(O)CH₃ | H | OCH₃ | OCH₃ | CH | |
| O | H | m-Cl | C(O)CH₃ | H | OCH₃ | OCH₃ | CH | |
| O | H | p-Cl | C(O)CH₃ | H | OCH₃ | OCH₃ | CH | |
| O | H | o-F | C(O)CH₃ | H | OCH₃ | OCH₃ | CH | |
| O | H | m-F | C(O)CH₃ | H | OCH₃ | OCH₃ | CH | |
| O | H | p-F | C(O)CH₃ | H | OCH₃ | OCH₃ | CH | |
| O | H | o-Br | C(O)CH₃ | H | OCH₃ | OCH₃ | CH | |
| O | H | m-Br | C(O)CH₃ | H | OCH₃ | OCH₃ | CH | |
| O | H | o-NO₂ | C(O)CH₃ | H | OCH₃ | OCH₃ | CH | |
| O | H | m-NO₂ | C(O)CH₃ | H | OCH₃ | OCH₃ | CH | |

TABLE Ic

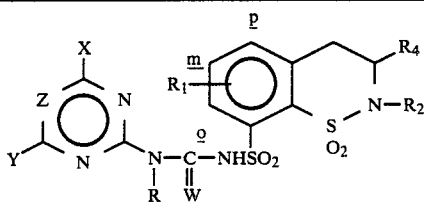

| W | R | R₁ | R₂ | R₄ | X | Y | Z | m.p. (°C.) |
|---|---|---|---|---|---|---|---|---|
| O | H | H | CH₃ | CH₃ | CH₃ | CH₃ | CH | |
| O | H | H | CH₃ | CH₃ | CH₃ | OCH₃ | CH | |
| O | H | H | CH₃ | CH₃ | OCH₃ | OCH₃ | CH | |
| O | H | H | CH₃ | CH₃ | CH₃ | CH₃ | N | |
| O | H | H | CH₃ | CH₃ | CH₃ | OCH₃ | N | |
| O | H | H | CH₃ | CH₃ | OCH₃ | OCH₃ | N | |
| O | H | H | CH₃ | CH₃ | Cl | OCH₃ | CH | |
| O | H | H | CH₃ | CH₃ | Br | OCH₃ | CH | |
| O | H | H | CH₃ | CH₃ | OCH₃ | CH(OCH₃)₂ | CH | |
| O | H | H | CH₃ | CH₂CH₃ | CH₃ | OCH₃ | CH | |
| O | H | H | CH₃ | CH₂CH₃ | OCH₃ | OCH₃ | CH | |
| O | H | H | CH₃ | CH₂CH₃ | CH₃ | OCH₃ | N | |
| O | H | H | CH₃ | CH₂CH₂CH₃ | CH₃ | OCH₃ | CH | |
| O | H | H | CH₃ | CH₂CH₂CH₃ | OCH₃ | OCH₃ | CH | |
| O | H | H | CH₃ | CH₂CH₂CH₃ | CH₃ | OCH₃ | N | |
| O | H | H | CH₃ | CH(CH₃)₂ | OCH₃ | OCH₃ | CH | |
| O | H | H | CH₃ | CH₂CH₂CH₂CH₃ | OCH₃ | OCH₃ | CH | |
| O | H | H | CH₃ | CH₂CH(CH₃)₂ | OCH₃ | OCH₃ | CH | |
| O | H | H | CH₃ | CH(CH₃)CH₂CH₃ | OCH₃ | OCH₃ | CH | |
| O | H | H | CH₂CH₃ | CH₃ | CH₃ | CH₃ | CH | |
| O | H | H | CH₂CH₃ | CH₃ | CH₃ | OCH₃ | CH | |
| O | H | H | CH₂CH₃ | CH₃ | OCH₃ | OCH₃ | CH | |
| O | H | H | CH₂CH₃ | CH₃ | CH₃ | OCH₃ | N | |
| O | H | H | CH₂CH₃ | CH₃ | OCH₃ | OCH₃ | N | |
| O | H | H | CH₂CH₃ | CH₃ | Cl | OCH₃ | CH | |
| O | H | H | CH₂CH₃ | CH₃ | Br | OCH₃ | CH | |
| O | H | H | CH₂CH₂CH₃ | CH₃ | CH₃ | OCH₃ | CH | |
| O | H | H | CH₂CH₂CH₃ | CH₃ | OCH₃ | OCH₃ | CH | |
| O | H | H | CH₂CH₂CH₂CH₃ | CH₃ | CH₃ | CH₃ | CH | |
| O | H | H | CH₂CH₂CH₂CH₃ | CH₃ | CH₃ | OCH₃ | CH | |
| O | H | H | CH₂CH₂CH₂CH₃ | CH₃ | OCH₃ | OCH₃ | CH | |
| O | H | H | CH₂CH₂CH₂CH₃ | CH₃ | CH₃ | OCH₃ | N | |
| O | H | H | CH₂CH₂CH₂CH₃ | CH₃ | OCH₃ | OCH₃ | N | |
| O | H | H | CH₂CH₂CH₂CH₃ | CH₃ | Cl | OCH₃ | CH | |
| O | H | H | CH₂CH₂CH₂CH₃ | CH₃ | Br | OCH₃ | CH | |
| O | H | H | CH₂CH(CH₃)₂ | CH₃ | CH₃ | CH₃ | CH | |
| O | H | H | CH₂CH(CH₃)₂ | CH₃ | CH₃ | OCH₃ | CH | |
| O | H | H | CH₂CH(CH₃)₂ | CH₃ | OCH₃ | OCH₃ | CH | |
| O | H | H | CH₂CH(CH₃)₂ | CH₃ | CH₃ | OCH₃ | N | |
| O | H | H | CH₂CH(CH₃)₂ | CH₃ | OCH₃ | OCH₃ | N | |
| O | H | H | CH₂CH(CH₃)₂ | CH₃ | Cl | OCH₃ | CH | |
| O | H | H | CH₂CH(CH₃)₂ | CH₃ | Br | OCH₃ | CH | |

TABLE Ic-continued

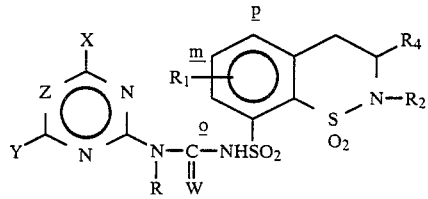

| W | R | R₁ | R₂ | R₄ | X | Y | Z | m.p. (°C.) |
|---|---|----|----|----|---|---|---|------------|
| O | H | H | CH₂CH(CH₃)CH₂CH₃ | H | CH₃ | OCH₃ | CH | |
| O | H | H | CH₂CH(CH₃)CH₂CH₃ | H | OCH₃ | OCH₃ | CH | |
| O | H | H | CH₂CH₂CH₂CH₂CH₃ | H | CH₃ | OCH₃ | CH | |
| O | H | H | CH₂CH₂CH₂CH₂CH₃ | H | OCH₃ | OCH₃ | CH | |
| O | H | H | CH₂CH₂OCH₃ | H | CH₃ | OCH₃ | CH | |
| O | H | H | CH₂CH₂OCH₃ | H | OCH₃ | OCH₃ | CH | |
| O | H | H | CH₂CH₂OCH₂CH₃ | H | CH₃ | OCH₃ | CH | |
| O | H | H | CH₂CH₂OCH₂CH₃ | H | OCH₃ | OCH₃ | CH | |
| O | H | H | CH₂CH₂CH₂Cl | H | CH₃ | OCH₃ | CH | |
| O | H | H | CH₂CH₂CH₂Cl | H | OCH₃ | OCH₃ | CH | |
| O | H | H | CH₂CH₂SCH₃ | H | CH₃ | OCH₃ | CH | |
| O | H | H | CH₂CH₂SCH₃ | H | OCH₃ | OCH₃ | CH | |
| O | H | H | CH₂CH₂CN | H | CH₃ | OCH₃ | CH | |
| O | H | H | CH₂CH₂CN | H | OCH₃ | OCH₃ | CH | |
| O | H | m-Cl | CH₃ | CH₃ | OCH₃ | OCH₃ | CH | |
| O | H | m-Cl | CH₂CH₃ | CH₃ | OCH₃ | OCH₃ | CH | |
| O | H | m-Cl | CH₂CH₂CH₃ | CH₃ | OCH₃ | OCH₃ | CH | |
| O | H | m-Cl | CH₂CH₂CH₂CH₃ | CH₃ | OCH₃ | OCH₃ | CH | |
| O | H | m-Cl | CH₂CH(CH₃)₂ | CH₃ | OCH₃ | OCH₃ | CH | |
| O | H | m-Cl | CH₂CH₂CH₂CH₂CH₃ | CH₃ | OCH₃ | OCH₃ | CH | |
| O | H | m-Cl | CH₂CH(CH₃)CH₂CH₃ | CH₃ | OCH₃ | OCH₃ | CH | |
| O | H | m-Cl | CH₂CH₂OCH₃ | CH₃ | OCH₃ | OCH₃ | CH | |
| O | H | m-Cl | CH₂CH₂OCH₂CH₃ | CH₃ | OCH₃ | OCH₃ | CH | |
| O | H | m-Cl | CH₂CH₂CH₂Cl | CH₃ | OCH₃ | OCH₃ | CH | |
| O | H | m-Br | CH₃ | CH₃ | OCH₃ | OCH₃ | CH | |
| O | H | m-Br | CH₂CH₃ | CH₃ | OCH₃ | OCH₃ | CH | |
| O | H | m-Br | CH₂CH₂CH₃ | CH₃ | OCH₃ | OCH₃ | CH | |
| O | H | m-Br | CH₂CH₂CH₂CH₃ | CH₃ | OCH₃ | OCH₃ | CH | |
| O | H | m-Br | CH₂CH(CH₃)₂ | CH₃ | OCH₃ | OCH₃ | CH | |
| O | H | m-Br | CH₂CH₂CH₂CH₂CH₃ | CH₃ | OCH₃ | OCH₃ | CH | |
| O | H | m-Br | CH₂CH(CH₃)CH₂CH₃ | CH₃ | OCH₃ | OCH₃ | CH | |
| O | H | m-Br | CH₂CH₂OCH₃ | CH₃ | OCH₃ | OCH₃ | CH | |
| O | H | m-Br | CH₂CH₂OCH₂CH₃ | CH₃ | OCH₃ | OCH₃ | CH | |
| O | H | m-Br | CH₂CH₂CH₂Cl | CH₃ | OCH₃ | OCH₃ | CH | |
| O | H | m-CH₃ | CH₃ | CH₃ | OCH₃ | OCH₃ | CH | |
| O | H | m-CH₃ | CH₂CH₃ | CH₃ | OCH₃ | OCH₃ | CH | |
| O | H | m-CH₃ | CH₂CH₂CH₃ | CH₃ | OCH₃ | OCH₃ | CH | |
| O | H | m-CH₃ | CH₂CH₂CH₂CH₃ | CH₃ | OCH₃ | OCH₃ | CH | |
| O | H | m-CH₃ | CH₂CH(CH₃)₂ | CH₃ | OCH₃ | OCH₃ | CH | |
| O | H | m-CH₃ | CH₂CH₂CH₂CH₂CH₃ | CH₃ | OCH₃ | OCH₃ | CH | |
| O | H | m-CH₃ | CH₂CH(CH₃)CH₂CH₃ | CH₃ | OCH₃ | OCH₃ | CH | |
| O | H | m-CH₃ | CH₂CH₂OCH₃ | CH₃ | OCH₃ | OCH₃ | CH | |
| O | H | m-CH₃ | CH₂CH₂OCH₂CH₃ | CH₃ | OCH₃ | OCH₃ | CH | |
| O | H | m-CH₃ | CH₂CH₂CH₂Cl | CH₃ | OCH₃ | OCH₃ | CH | |
| O | H | o-Cl | CH₃ | CH₃ | OCH₃ | OCH₃ | CH | |
| O | H | o-Cl | CH₂CH₃ | CH₃ | OCH₃ | OCH₃ | CH | |
| O | H | o-Cl | CH₂CH₂CH₃ | CH₃ | OCH₃ | OCH₃ | CH | |
| O | H | o-Cl | CH₂CH₂CH₂CH₃ | CH₃ | OCH₃ | OCH₃ | CH | |
| O | H | o-Cl | CH₂CH(CH₃)₂ | CH₃ | OCH₃ | OCH₃ | CH | |
| O | H | o-Cl | CH₂CH₂CH₂CH₂CH₃ | CH₃ | OCH₃ | OCH₃ | CH | |
| O | H | o-Cl | CH₂CH(CH₃)CH₂CH₃ | CH₃ | OCH₃ | OCH₃ | CH | |
| O | H | o-Cl | CH₂CH₂OCH₃ | CH₃ | OCH₃ | OCH₃ | CH | |
| O | H | o-Cl | CH₂CH₂OCH₂CH₃ | CH₃ | OCH₃ | OCH₃ | CH | |
| O | H | o-Cl | CH₂CH₂CH₂Cl | CH₃ | OCH₃ | OCH₃ | CH | |
| O | H | o-CH₃ | CH₃ | CH₃ | OCH₃ | OCH₃ | CH | |
| O | H | o-CH₃ | CH₂CH₃ | CH₃ | OCH₃ | OCH₃ | CH | |
| O | H | o-CH₃ | CH₂CH₂CH₃ | CH₃ | OCH₃ | OCH₃ | CH | |
| O | H | o-CH₃ | CH₂CH₂CH₂CH₃ | CH₃ | OCH₃ | OCH₃ | CH | |
| O | H | o-CH₃ | CH₂CH(CH₃)₂ | CH₃ | OCH₃ | OCH₃ | CH | |
| O | H | o-CH₃ | CH₂CH₂CH₂CH₂CH₃ | CH₃ | OCH₃ | OCH₃ | CH | |
| O | H | o-CH₃ | CH₂CH(CH₃)CH₂CH₃ | CH₃ | OCH₃ | OCH₃ | CH | |
| O | H | o-CH₃ | CH₂CH₂OCH₃ | CH₃ | OCH₃ | OCH₃ | CH | |
| O | H | o-CH₃ | CH₂CH₂OCH₂CH₃ | CH₃ | OCH₃ | OCH₃ | CH | |
| O | H | o-CH₃ | CH₂CH₂CH₂Cl | CH₃ | OCH₃ | OCH₃ | CH | |
| O | H | H | CH₂CH(CH₃)=CH₂ | CH₃ | OCH₃ | OCH₃ | CH | |
| O | H | H | CH₃ | CH₃ | cyclopropyl | OCH₃ | CH | |
| O | H | H | CH₃ | CH₃ | cyclopropyl | OCH₃ | N | |

TABLE Ic-continued

| W | R | $R_1$ | $R_2$ | $R_4$ | X | Y | Z | m.p. (°C.) |
|---|---|---|---|---|---|---|---|---|
| O | H | H | C(O)CH$_3$ | CH$_3$ | OCH$_3$ | OCH$_3$ | CH | |
| O | H | H | C(O)CH$_2$CH$_3$ | CH$_3$ | OCH$_3$ | OCH$_3$ | CH | |
| O | H | H | C(O)CH$_2$CH$_2$CH$_3$ | CH$_3$ | OCH$_3$ | OCH$_3$ | CH | |
| O | H | H | CO$_2$CH$_3$ | CH$_3$ | OCH$_3$ | OCH$_3$ | CH | |
| O | H | H | CO$_2$CH$_2$CH$_3$ | CH$_3$ | OCH$_3$ | OCH$_3$ | CH | |
| O | H | H | CH$_2$CH$_2$F | CH$_3$ | OCH$_3$ | OCH$_3$ | CH | |
| O | H | H | CH$_2$CH$_2$CH$_2$F | CH$_3$ | OCH$_3$ | OCH$_3$ | CH | |
| O | H | H | CH$_2$CH$_2$Cl | CH$_3$ | OCH$_3$ | OCH$_3$ | CH | |
| O | H | H | CH$_2$OCH$_3$ | CH$_3$ | OCH$_3$ | OCH$_3$ | CH | |

TABLE Id

| $W_2$ | $W_1$ | J | n | R | $R_1$ or $R'_1$ | $R_3$ | $R_5$ | $R_6$ | $R_7$ | X | Y | Z | m.p. (°C.) |
|---|---|---|---|---|---|---|---|---|---|---|---|---|---|
| — | S | J-5 | 0 | H | H | H | H | — | — | OCH$_3$ | OCH$_3$ | CH | |
| — | S | J-5 | 0 | H | H | H | CH$_3$ | — | — | OCH$_3$ | OCH$_3$ | CH | |
| — | S | J-5 | 0 | H | H | H | CH$_2$CH$_3$ | — | — | OCH$_3$ | OCH$_3$ | CH | |
| — | S | J-5 | 0 | H | H | H | CH$_2$CH$_2$CH$_3$ | — | — | OCH$_3$ | OCH$_3$ | CH | |
| — | S | J-5 | 0 | H | H | H | CH(CH$_3$)$_2$ | — | — | OCH$_3$ | OCH$_3$ | CH | |
| — | S | J-5 | 0 | H | H | H | CH$_2$CH$_2$CH$_2$CH$_3$ | — | — | OCH$_3$ | OCH$_3$ | CH | |
| — | S | J-5 | 0 | H | H | H | CH$_2$CH(CH$_3$)$_2$ | — | — | OCH$_3$ | OCH$_3$ | CH | |
| — | S | J-5 | 0 | H | H | H | CH(CH$_2$)CH$_2$CH$_3$ | — | — | OCH$_3$ | OCH$_3$ | CH | |
| — | S | J-5 | 0 | H | H | H | C(CH$_3$)$_3$ | — | — | OCH$_3$ | OCH$_3$ | CH | |
| — | S | J-5 | 0 | H | H | H | CH$_3$ | — | — | CH$_3$ | CH$_3$ | CH | |
| — | S | J-5 | 0 | H | H | H | CH$_3$ | — | — | CH$_3$ | OCH$_3$ | CH | |
| — | S | J-5 | 0 | H | H | H | CH$_3$ | — | — | OCH$_3$ | OCH$_3$ | CH | |
| — | S | J-5 | 0 | H | H | H | CH$_3$ | — | — | OCH$_3$ | OCH$_3$ | N | |
| — | S | J-5 | 1 | H | H | H | CH$_3$ | — | — | OCH$_3$ | OCH$_3$ | CH | |
| — | S | J-5 | 1 | H | H | H | CH$_2$CH$_3$ | — | — | OCH$_3$ | OCH$_3$ | CH | |
| — | S | J-5 | 1 | H | H | H | CH$_2$CH$_2$CH$_3$ | — | — | OCH$_3$ | OCH$_3$ | CH | |
| — | S | J-5 | 1 | H | H | H | CH$_2$CH$_2$CH$_2$CH$_3$ | — | — | OCH$_3$ | OCH$_3$ | CH | |
| — | S | J-5 | 1 | H | H | H | CH$_2$CH(CH$_3$)$_2$ | — | — | OCH$_3$ | OCH$_3$ | CH | |
| O | S | J-6 | 0 | H | H | H | — | — | — | CH$_3$ | CH$_3$ | CH | |
| O | S | J-6 | 0 | H | H | H | — | — | — | CH$_3$ | OCH$_3$ | CH | |
| O | S | J-6 | 0 | H | H | H | — | — | — | OCH$_3$ | OCH$_3$ | CH | |
| O | S | J-6 | 0 | H | H | H | — | — | — | CH$_3$ | CH$_3$ | N | |
| O | S | J-6 | 0 | H | H | H | — | — | — | CH$_3$ | OCH$_3$ | N | |
| O | S | J-6 | 0 | H | H | H | — | — | — | OCH$_3$ | OCH$_3$ | N | |
| O | S | J-6 | 0 | H | H | H | — | — | — | Cl | OCH$_3$ | CH | |
| O | S | J-6 | 0 | H | H | H | — | — | — | Br | OCH$_3$ | CH | |
| O | S | J-6 | 1 | H | H | H | — | — | — | CH$_3$ | CH$_3$ | CH | |
| O | S | J-6 | 1 | H | H | H | — | — | — | CH$_3$ | OCH$_3$ | CH | |
| O | S | J-6 | 1 | H | H | H | — | — | — | OCH$_3$ | OCH$_3$ | CH | |
| O | S | J-6 | 1 | H | H | H | — | — | — | CH$_3$ | CH$_3$ | N | |
| O | S | J-6 | 1 | H | H | H | — | — | — | CH$_3$ | OCH$_3$ | N | |
| O | S | J-6 | 1 | H | H | H | — | — | — | OCH$_3$ | OCH$_3$ | N | |
| O | S | J-6 | 1 | H | H | H | — | — | — | Cl | OCH$_3$ | CH | |
| O | S | J-6 | 1 | H | H | H | — | — | — | Br | OCH$_3$ | CH | |
| — | S | J-7 | 0 | H | H | H | H | — | — | OCH$_3$ | OCH$_3$ | CH | |
| — | S | J-7 | 0 | H | H | H | CH$_3$ | — | — | OCH$_3$ | OCH$_3$ | CH | |
| — | S | J-7 | 1 | H | H | H | H | — | — | OCH$_3$ | OCH$_3$ | CH | |
| — | S | J-7 | 1 | H | H | H | CH$_3$ | — | — | OCH$_3$ | OCH$_3$ | CH | |
| — | S | J-8 | — | H | H | — | H | — | — | OCH$_3$ | OCH$_3$ | CH | |
| — | S | J-8 | — | H | H | — | CH$_3$ | — | — | OCH$_3$ | OCH$_3$ | CH | |
| — | S | J-9 | — | H | H | — | H | — | — | OCH$_3$ | OCH$_3$ | CH | |
| — | S | J-9 | — | H | H | — | CH$_3$ | — | — | OCH$_3$ | OCH$_3$ | CH | |
| O | S | J-10 | — | H | H | — | — | H | CH$_3$ | CH$_3$ | CH$_3$ | CH | |
| O | S | J-10 | — | H | H | — | — | H | CH$_3$ | CH$_3$ | OCH$_3$ | CH | |

TABLE Id-continued

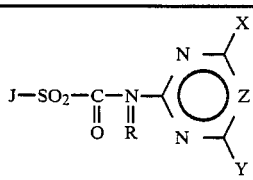

| W₂ | W₁ | J | n | R | R₁ or R'₁ | R₃ | R₅ | R₆ | R₇ | X | Y | Z | m.p. (°C.) |
|---|---|---|---|---|---|---|---|---|---|---|---|---|---|
| O | S | J-10 | — | H | H | — | — | H | CH₃ | OCH₃ | OCH₃ | CH | |
| O | S | J-10 | — | H | H | — | — | H | CH₃ | CH₃ | OCH₃ | N | |
| O | S | J-10 | — | H | H | — | — | H | CH₃ | OCH₃ | OCH₃ | N | |
| O | S | J-10 | — | H | H | — | — | H | CH₃ | Cl | OCH₃ | CH | |
| O | S | J-10 | — | H | H | — | — | H | CH₃ | Br | OCH₃ | CH | |
| O | S | J-10 | — | H | H | — | — | H | CH₂CH₃ | CH₃ | OCH₃ | CH | |
| O | S | J-10 | — | H | H | — | — | H | CH₂CH₃ | OCH₃ | OCH₃ | CH | |
| O | S | J-10 | — | H | H | — | — | H | CH₂CH₂CH₃ | OCH₃ | OCH₃ | CH | |
| O | S | J-10 | — | H | H | — | — | H | CH₂CH₂CH₂CH₃ | OCH₃ | OCH₃ | CH | |
| O | S | J-10 | — | H | H | — | — | CH₃ | CH₃ | OCH₃ | OCH₃ | CH | |
| S | S | J-10 | — | H | H | — | — | H | CH₃ | OCH₃ | OCH₃ | CH | |

TABLE Ie

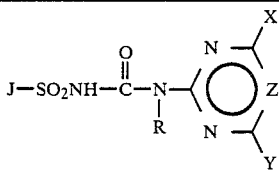

| J | W₂ | m' | n | R | R₁' | R₄ | R₅ | R₆ | X | Y | Z | m.p. (°C.) |
|---|---|---|---|---|---|---|---|---|---|---|---|---|
| J-11 | O | — | 0 | H | H | CH₃ | H | H | OCH₃ | OCH₃ | CH | |
| J-11 | O | — | 0 | H | H | CH₃ | CH₃ | H | OCH₃ | OCH₃ | CH | |
| J-11 | O | — | 1 | H | H | CH₃ | H | H | OCH₃ | OCH₃ | CH | |
| J-11 | O | — | 1 | H | H | CH₃ | H | CH₃ | OCH₃ | OCH₃ | CH | |
| J-11 | S | — | 0 | H | H | CH₃ | H | H | OCH₃ | OCH₃ | CH | |
| J-12 | O | 1 | 0 | H | H | — | H | H | OCH₃ | OCH₃ | CH | |
| J-12 | O | 2 | 0 | H | H | — | H | H | OCH₃ | OCH₃ | CH | |
| J-12 | S | 1 | 0 | H | H | — | H | H | OCH₃ | OCH₃ | CH | |
| J-11 | O | — | 0 | H | H | Butyl | H | H | OCH₃ | OCH₃ | CH | |
| J-11 | O | — | 0 | H | H | CH₃ | Butyl | H | OCH₃ | OCH₃ | CH | |

TABLE IIa

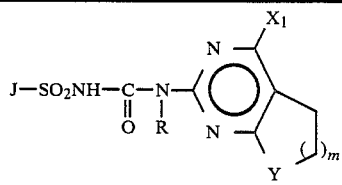

| J | n | R | R₁' or R₁ | R₂ | R₃ | R₄ | X₁ | Y₁ | m | m.p. (°C.) |
|---|---|---|---|---|---|---|---|---|---|---|
| J-1 | O | H | H | CH₂CH₂OCH₃ | H | — | CH₃ | CH₃ | 1 | |
| J-1 | O | H | H | CH₂CH₂OCH₃ | H | — | OCH₃ | CH₂ | 1 | |
| J-1 | O | H | H | CH₂CH₂OCH₃ | H | — | OCH₂CH₃ | CH₂ | 1 | |
| J-1 | O | H | H | CH₂CH₂OCH₃ | H | — | OCF₂H | CH₂ | 1 | |
| J-1 | O | H | H | CH₂CH₂OCH₃ | H | — | CH₃ | O | 1 | |
| J-1 | O | H | H | CH₂CH₂OCH₃ | H | — | OCH₃ | O | 1 | |
| J-1 | O | H | H | CH₂CH₂OCH₃ | H | — | OCH₂CH₃ | O | 1 | |
| J-1 | O | H | H | CH₂CH₂OCH₃ | H | — | OCF₂H | O | 1 | |
| J-1 | O | H | H | CH₂CH₂OCH₃ | H | — | CH₃ | O | 2 | |
| J-1 | O | H | H | CH₂CH₂OCH₃ | H | — | OCH₃ | O | 2 | |
| J-1 | O | H | H | CH₂CH₂OCH₃ | H | — | OCH₂CH₃ | O | 2 | |
| J-1 | O | H | H | CH₂CH₂OCH₂CH₃ | H | — | OCF₂H | O | 2 | |
| J-1 | O | H | H | CH₂CH₂OCH₂CH₃ | H | — | OCH₃ | CH₂ | 1 | |
| J-1 | O | H | H | CH₂CH₂OCH₂CH₃ | H | — | OCH₃ | O | 1 | |
| J-1 | O | H | H | CH₂CH₂OCH₂CH₃ | H | — | OCH₃ | O | 2 | |
| J-1 | O | H | H | CH₂CH₂CH₂CH₂CH₃ | H | — | OCH₃ | CH₂ | 1 | |
| J-1 | O | H | H | CH₂CH₂CH₂CH₂CH₃ | H | — | OCH₃ | O | 1 | |

TABLE IIa-continued

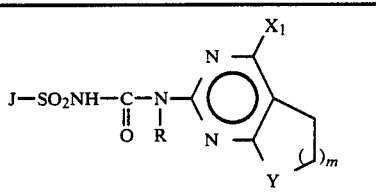

| J | n | R | $R_1'$ or $R_1$ | $R_2$ | $R_3$ | $R_4$ | $X_1$ | $Y_1$ | m | m.p. (°C.) |
|---|---|---|---|---|---|---|---|---|---|---|
| J-1 | O | H | H | $CH_2CH_2CH_2CH_2CH_3$ | H | — | $OCH_3$ | O | 2 | |
| J-1 | O | H | H | $CH_2CH(CH_3)CH_2CH_3$ | H | — | $OCH_3$ | $CH_2$ | 1 | |
| J-1 | O | H | H | $CH_2CH(CH_3)CH_2CH_3$ | H | — | $OCH_3$ | O | 1 | |
| J-1 | O | H | H | $CH_2Ch(CH_3)CH_2CH_3$ | H | — | $OCH_3$ | O | 2 | |
| J-1 | O | H | H | $CH_2CH_2CH_2Cl$ | H | — | $OCH_3$ | $CH_2$ | 1 | |
| J-1 | O | H | H | $CH_2CH_2CH_2Cl$ | H | — | $OCH_3$ | O | 1 | |
| J-1 | O | H | H | $CH_2CH_2CH_2Cl$ | H | — | $OCH_3$ | O | 2 | |
| J-1 | O | H | H | $CH_2C(CH_3)=CH_2$ | H | — | $OCH_3$ | $CH_2$ | 1 | |
| J-1 | O | H | H | $CH_2C(CH_3)=CH_2$ | H | — | $OCH_3$ | O | 1 | |
| J-1 | O | H | H | $CH_2C(CH_3)=CH_2$ | H | — | $OCH_3$ | O | 2 | |
| J-1 | O | H | o-$CH_2CH_3$ | $CH_3$ | H | — | $OCH_3$ | $CH_2$ | 1 | |
| J-1 | O | H | o-$CH_2CH_3$ | $CH_3$ | H | — | $OCH_3$ | O | 1 | |
| J-1 | O | H | o-$CH_2CH_3$ | $CH_3$ | H | — | $OCH_3$ | O | 2 | |
| J-1 | O | H | o-$OCH_2CH_3$ | $CH_3$ | H | — | $OCH_3$ | $CH_2$ | 1 | |
| J-1 | O | H | o-$OCH_2CH_3$ | $CH_3$ | H | — | $OCH_3$ | O | 1 | |
| J-1 | O | H | o-$OCH_2CH_3$ | $CH_3$ | H | — | $OCH_3$ | O | 2 | |
| J-1 | O | H | H | $CH_2CH_2OCH_3$ | H | — | $OCH_3$ | O | 1 | |
| J-1 | O | H | H | $CH_2CH_2OCH_3$ | H | — | $OCH_3$ | O | 2 | |
| J-1 | O | H | H | $CH_2CH_2OCH_2CH_3$ | H | — | $OCH_3$ | O | 1 | |
| J-1 | O | H | H | $CH_2CH_2OCH_2CH_3$ | H | — | $OCH_3$ | O | 2 | |
| J-1 | O | H | H | $CH_2CH_2CH_2CH_2CH_3$ | H | — | $OCH_3$ | O | 1 | |
| J-1 | O | H | H | $CH_2CH_2CH_2CH_2CH_3$ | H | — | $OCH_3$ | O | 2 | |
| J-1 | O | H | H | $CH_2CH(CH_3)CH_2CH_3$ | H | — | $OCH_3$ | O | 1 | |
| J-1 | O | H | H | $CH_2CH(CH_3)CH_2CH_3$ | H | — | $OCH_3$ | O | 2 | |
| J-1 | O | H | H | $CH_2CH_2CH_2Cl$ | H | — | $OCH_3$ | O | 1 | |
| J-1 | O | H | H | $CH_2CH_2CH_2Cl$ | H | — | $OCH_3$ | O | 2 | |
| J-1 | O | H | H | $CH_2C(CH_3)=CH_2$ | H | — | $OCH_3$ | O | 1 | |
| J-1 | O | H | H | $CH_2C(CH_3)=CH_2$ | H | — | $OCH_3$ | O | 2 | |
| J-4 | — | H | H | H | — | $CH_3$ | $OCH_3$ | O | 1 | |
| J-4 | — | H | H | $CH_3$ | — | $CH_3$ | $OCH_3$ | O | 1 | |
| J-4 | — | H | H | $CH_2CH_3$ | — | $CH_3$ | $OCH_3$ | O | 1 | |
| J-4 | H | H | $CH_2CH_2CH_3$ | — | | $CH_3$ | $OCH_3$ | O | 1 | |
| J-4 | — | H | H | $CH_2CH_2CH_2CH_3$ | — | $CH_3$ | $OCH_3$ | O | 1 | |
| J-4 | — | H | H | $CH_2CH(CH_3)_2$ | — | $CH_3$ | $OCH_3$ | O | 1 | |
| J-2 | — | H | H | $CH_2CH_2OCH_3$ | — | $CH_3$ | $OCH_3$ | O | 1 | |
| J-2 | — | H | H | $CH_2CH(CH_3)CH_2CH_3$ | — | $CH_3$ | $OCH_3$ | O | 1 | |
| J-2 | — | H | H | $CH_2CH_2CH_2Cl$ | — | $CH_3$ | $OCH_3$ | O | 1 | |
| J-2 | — | H | H | $CH_2C(CH_3)=CH_2$ | — | $CH_3$ | $OCH_3$ | O | 1 | |
| J-3 | — | H | H | $CH_3$ | — | $CH_3$ | $OCH_3$ | O | 1 | |
| J-3 | — | H | H | $CH_2CH_3$ | — | $CH_3$ | $OCH_3$ | O | 1 | |
| J-3 | — | H | H | $CH_2CH_2CH_3$ | — | $CH_3$ | $OCH_3$ | O | 1 | |
| J-3 | — | H | H | $CH_2CH_2CH_2CH_3$ | — | $CH_3$ | $OCH_3$ | O | 1 | |
| J-3 | — | H | H | $CH_2CH(CH_3)_2$ | — | $CH_3$ | $OCH_3$ | O | 1 | |
| J-1 | O | H | o-$CH_2CH_3$ | $CH_2CH_3$ | H | — | $OCH_3$ | O | 1 | |
| J-1 | O | H | o-$CH_2CH_3$ | $CH_2CH_2CH_3$ | H | — | $OCH_3$ | O | 1 | |
| J-1 | O | H | m-$CH_2CH_3$ | $CH_2CH_2CH_2CH_3$ | H | — | $OCH_3$ | O | 1 | |
| J-1 | O | H | m-$CH_2CH_3$ | $CH_2CH(CH_3)_2$ | H | — | $OCH_3$ | O | 1 | |
| J-1 | O | H | m-$CH_2CH_3$ | H | H | — | $OCH_3$ | O | 1 | |
| J-1 | O | H | m-$OCH_2CH_3$ | H | H | — | $OCH_3$ | O | 1 | |
| J-1 | O | H | m-$OCH_2CH_3$ | $CH_3$ | H | — | $OCH_3$ | O | 1 | |
| J-1 | O | H | m-$OCH_2CH_3$ | $CH_2CH_3$ | H | — | $OCH_3$ | O | 1 | |
| J-1 | O | H | m-$OCH_2CH_3$ | $CH_2CH_2CH_3$ | H | — | $OCH_3$ | O | 1 | |
| J-1 | O | H | o-$OCH_2CH_3$ | $CH_2CH_2CH_3$ | H | — | $OCH_3$ | O | 1 | |
| J-1 | O | H | o-$OCH_2CH_3$ | $CH_2CH(CH_3)_2$ | H | — | $OCH_3$ | O | 1 | |

*symbols o and m refer to ortho and meta to sulfonylurea bridge respectively.

TABLE IIb

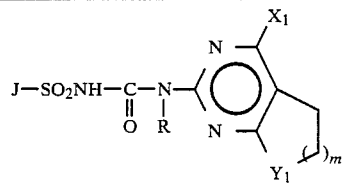

| W₂ | W₁ | J | n | R | R₁ or R₁' | R₃ | R₅ | R₆ | R₇ | X₁ | Y₁ | m | m.p. (°C.) |
|---|---|---|---|---|---|---|---|---|---|---|---|---|---|
| — | S | J-5 | 0 | H | H | H | H | — | — | OCH₃ | O | 1 | |
| — | S | J-5 | 0 | H | H | H | H | — | — | OCH₃ | O | 2 | |
| — | S | J-5 | 0 | H | H | H | CH₃ | — | — | OCH₃ | O | 1 | |
| — | S | J-5 | 0 | H | H | H | CH₃ | — | — | OCH₃ | O | 2 | |
| — | S | J-5 | 1 | H | H | H | CH₃ | — | — | OCH₃ | O | 1 | |
| — | S | J-5 | 1 | H | H | H | CH₃ | — | — | OCH₃ | O | 2 | |
| O | S | J-6 | 0 | H | H | H | — | — | — | OCH₃ | O | 1 | |
| O | S | J-6 | 0 | H | H | H | — | — | — | OCH₃ | O | 2 | |
| O | S | J-6 | 1 | H | H | H | — | — | — | OCH₃ | O | 1 | |
| O | S | J-6 | 1 | H | H | H | — | — | — | OCH₃ | O | 2 | |
| — | S | J-7 | 0 | H | H | H | H | — | — | OCH₃ | O | 1 | |
| — | S | J-7 | 0 | H | H | H | H | — | — | OCH₃ | O | 2 | |
| — | S | J-7 | 0 | H | H | H | CH₃ | — | — | OCH₃ | O | 1 | |
| — | S | J-7 | 0 | H | H | H | CH₃ | — | — | OCH₃ | O | 2 | |
| — | S | J-7 | 1 | H | H | H | CH₃ | — | — | OCH₃ | O | 1 | |
| — | S | J-7 | 1 | H | H | H | CH₃ | — | — | OCH₃ | O | 2 | |
| — | S | J-8 | — | H | H | — | CH₃ | — | — | OCH₃ | O | 1 | |
| — | S | J-8 | — | H | H | — | CH₃ | — | — | OCH₃ | O | 2 | |
| — | S | J-9 | — | H | H | — | CH₃ | — | — | OCH₃ | O | 1 | |
| — | S | J-9 | — | H | H | — | CH₃ | — | — | OCH₃ | O | 2 | |
| O | S | J-10 | — | H | H | — | — | H | CH₃ | OCH₃ | O | 1 | |
| O | S | J-10 | — | H | H | — | — | H | CH₃ | OCH₃ | O | 2 | |
| O | S | J-10 | — | H | H | — | — | H | CH₂CH₃ | OCH₃ | O | 1 | |
| O | S | J-10 | — | H | H | — | — | H | CH₂CH₃ | OCH₃ | O | 2 | |
| O | S | J-10 | — | H | H | — | — | CH₃ | CH₃ | OCH₃ | O | 1 | |
| O | S | J-10 | — | H | H | — | — | CH₃ | CH₃ | OCH₃ | O | 2 | |
| O | S | J-6 | 1 | H | H | H | — | — | — | CH₃ | CH₂ | 1 | |
| O | S | J-6 | 1 | H | H | H | — | — | — | CH₃ | O | 2 | |
| O | S | J-6 | 1 | H | H | H | — | — | — | OCH₃ | CH₂ | 1 | |
| O | S | J-6 | 1 | H | H | H | — | — | — | OCH₂CH₃ | CH₂ | 1 | |
| O | S | J-6 | 1 | H | H | H | — | — | — | OCH₂CH₃ | O | 1 | |
| O | S | J-6 | 1 | H | H | H | — | — | — | OCH₂CH₃ | O | 2 | |
| O | S | J-6 | 1 | H | H | H | — | — | — | OCF₂H | CH₂ | 1 | |
| O | S | J-6 | 1 | H | H | H | — | — | — | OCF₂H | O | 1 | |
| O | S | J-6 | 1 | H | H | H | — | — | — | OCF₂H | O | 2 | |
| S | S | J-6 | 1 | H | H | H | — | — | — | OCH₃ | O | 1 | |

TABLE IIc

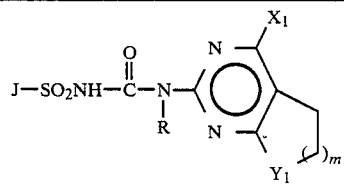

| J | W₂ | m' | n | R | R₁' | R₄ | R₅ | R₆ | X₁ | Y₁ | m | m.p. (°C.) |
|---|---|---|---|---|---|---|---|---|---|---|---|---|
| J-11 | O | — | 0 | H | H | CH₃ | H | H | OCH₃ | O | 1 | |
| J-11 | O | — | 1 | H | H | CH₃ | H | H | OCH₃ | O | 1 | |
| J-11 | S | — | 0 | H | H | CH₃ | H | H | OCH₃ | O | 1 | |
| J-11 | S | — | 1 | H | H | CH₃ | H | H | OCH₃ | O | 1 | |
| J-12 | O | 1 | 0 | H | H | — | H | H | OCH₃ | O | 1 | |
| J-12 | O | 2 | 0 | H | H | — | H | H | OCH₃ | O | 1 | |
| J-12 | S | 1 | 0 | H | H | — | H | H | OCH₃ | O | 1 | |
| J-12 | S | 2 | 0 | H | H | — | H | H | OCH₃ | O | 1 | |
| J-12 | O | 1 | 1 | H | H | — | H | H | OCH₃ | O | 1 | |
| J-12 | O | 2 | 1 | H | H | — | H | H | OCH₃ | O | 1 | |
| J-12 | S | 1 | 1 | H | H | — | H | H | OCH₃ | O | 1 | |
| J-12 | S | 2 | 1 | H | H | — | H | H | OCH₃ | O | 1 | |

TABLE IIIa

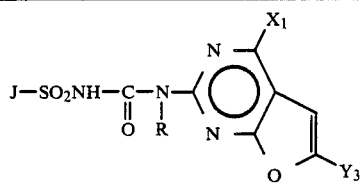

| J | n | R | $R_1^*$ or $R_1'^*$ | $R_2$ | $R_3$ | $R_4$ | $X_1$ | $Y_3$ | m.p. (°C.) |
|---|---|---|---|---|---|---|---|---|---|
| J-1 | 0 | H | H | $CH_2CH_2OCH_3$ | H | — | $CH_3$ | $CH_3$ | |
| J-1 | 0 | H | H | $CH_2CH_2OCH_3$ | H | — | $OCH_3$ | H | |
| J-1 | 0 | H | H | $CH_2CH_2OCH_3$ | H | — | $OCH_3$ | $CH_3$ | |
| J-1 | 0 | H | H | $CH_2CH_2OCH_3$ | H | — | $OCH_2CH_3$ | $CH_3$ | |
| J-1 | 0 | H | H | $CH_2CH_2OCH_3$ | H | — | $OCF_2H$ | $CH_3$ | |
| J-1 | 0 | H | H | $CH_2CH_2OCH_2CH_3$ | H | — | $OCH_3$ | $CH_3$ | |
| J-1 | 0 | H | H | $CH_2CH_2CH_2CH_3$ | H | — | $OCH_3$ | $CH_3$ | |
| J-1 | 0 | H | H | $CH_2CH(CH_3)CH_2CH_3$ | H | — | $OCH_3$ | $CH_3$ | |
| J-1 | 0 | H | H | $CH_2CH_2CH_2Cl$ | H | — | $OCH_3$ | $CH_3$ | |
| J-1 | 0 | H | H | $CH_3C(CH_3)=CH_2$ | H | — | $OCH_3$ | $CH_3$ | |
| J-1 | 0 | H | o-$CH_2CH_3$ | $CH_3$ | H | — | $OCH_3$ | $CH_3$ | |
| J-1 | 0 | H | o-$CH_2CH_3$ | $CH_2CH_3$ | H | — | $OCH_3$ | $CH_3$ | |
| J-1 | 0 | H | o-$CH_2CH_3$ | $CH_2CH_2CH_3$ | H | — | $OCH_3$ | $CH_3$ | |
| J-1 | 0 | H | m-$CH_2CH_3$ | $CH_2CH_2CH_3$ | H | — | $OCH_3$ | $CH_3$ | |
| J-1 | 0 | H | m-$CH_2CH_3$ | $CH_2CH(CH_3)_2$ | H | — | $OCH_3$ | $CH_3$ | |
| J-1 | 0 | H | m-$CH_2CH_3$ | H | H | — | $OCH_3$ | $CH_3$ | |
| J-1 | 0 | H | o-$OCH_2CH_3$ | H | H | — | $OCH_3$ | $CH_3$ | |
| J-1 | 0 | H | o-$OCH_2CH_3$ | $CH_3$ | H | — | $OCH_3$ | $CH_3$ | |
| J-1 | 0 | H | o-$OCH_2CH_3$ | $CH_2CH_3$ | H | — | $OCH_3$ | $CH_3$ | |
| J-1 | 0 | H | m-$OCH_2CH_3$ | $CH_2CH_2CH_3$ | H | — | $OCH_3$ | $CH_3$ | |
| J-1 | 0 | H | m-$OCH_2CH_3$ | $CH_2CH_2CH_2CH_3$ | H | — | $OCH_3$ | $CH_3$ | |
| J-1 | 0 | H | m-$OCH_2CH_3$ | $CH_2CH(CH_3)_2$ | H | — | $OCH_3$ | $CH_3$ | |
| J-1 | 1 | H | H | $CH_2CH_2OCH_3$ | H | — | $OCH_3$ | $CH_3$ | |
| J-1 | 1 | H | H | $CH_2CH_2OCH_2CH_3$ | H | — | $OCH_3$ | $CH_3$ | |
| J-1 | 1 | H | H | $CH_2CH_2CH_2CH_3$ | H | — | $OCH_3$ | $CH_3$ | |
| J-1 | 1 | H | H | $CH_2CH(CH_3)CH_2CH_3$ | H | — | $OCH_3$ | $CH_3$ | |
| J-1 | 1 | H | H | $CH_2CH_2CH_2Cl$ | H | — | $OCH_3$ | $CH_3$ | |
| J-1 | 1 | H | H | $CH_2C(CH_3)=CH_2$ | H | — | $OCH_3$ | $CH_3$ | |
| J-2 | — | H | H | $CH_2CH_2OCH_3$ | — | — | $OCH_3$ | $CH_3$ | |
| J-2 | — | H | H | $CH_2CH_2OCH_2CH_3$ | — | — | $OCH_3$ | $CH_3$ | |
| J-2 | — | H | H | $CH_2CH_2CH_2CH_3$ | — | — | $OCH_3$ | $CH_3$ | |
| J-2 | — | H | H | $CH_2CH(CH_3)CH_2CH_3$ | — | — | $OCH_3$ | $CH_3$ | |
| J-2 | — | H | H | $CH_2CH_2CH_2Cl$ | — | — | $OCH_3$ | $CH_3$ | |
| J-2 | — | H | H | $CH_2C(CH_3)=CH_2$ | — | — | $OCH_3$ | $CH_3$ | |
| J-3 | — | H | H | H | — | $CH_3$ | $OCH_3$ | $CH_3$ | |
| J-3 | — | H | H | $CH_3$ | — | $CH_3$ | $OCH_3$ | $CH_3$ | |
| J-3 | — | H | H | $CH_2CH_3$ | — | $CH_3$ | $OCH_3$ | $CH_3$ | |
| J-3 | — | H | H | $CH_2CH_2CH_3$ | — | $CH_3$ | $OCH_3$ | $CH_3$ | |
| J-3 | — | H | H | $CH_2CH_2CH_2CH_3$ | — | $CH_3$ | $OCH_3$ | $CH_3$ | |
| J-3 | — | H | H | $CH_2CH(CH_3)_2$ | — | $CH_3$ | $OCH_3$ | $CH_3$ | |
| J-3 | — | H | H | $CH_2CH_2CH_2CH_2CH_3$ | — | $CH_3$ | $OCH_3$ | $CH_3$ | |
| J-3 | — | H | H | $CH_2CH(CH_3)CH_2CH_3$ | — | $CH_3$ | $OCH_3$ | $CH_3$ | |
| J-3 | — | H | H | $CH_2CH_2OCH_3$ | — | $CH_3$ | $OCH_3$ | $CH_3$ | |
| J-3 | — | H | H | $CH_2CH_2CH_2Cl$ | — | $CH_3$ | $OCH_3$ | $CH_3$ | |
| J-4 | — | H | H | H | — | $CH_3$ | $OCH_3$ | $CH_3$ | |
| J-4 | — | H | H | $CH_3$ | — | $CH_3$ | $OCH_3$ | $CH_3$ | |
| J-4 | — | H | H | $CH_2CH_3$ | — | $CH_3$ | $OCH_3$ | $CH_3$ | |
| J-4 | — | H | H | $CH_2CH_2CH_3$ | — | $CH_3$ | $OCH_3$ | $CH_3$ | |
| J-4 | — | H | H | $CH_2CH_2CH_2CH_3$ | — | $CH_3$ | $OCH_3$ | $CH_3$ | |
| J-4 | — | H | H | $CH_2CH(CH_3)_2$ | — | $CH_3$ | $OCH_3$ | $CH_3$ | |
| J-4 | — | H | H | $CH_2CH_2CH_2CH_2CH_3$ | — | $CH_3$ | $OCH_3$ | $CH_3$ | |
| J-4 | — | H | H | $CH_2CH(CH_3)CH_2CH_3$ | — | $CH_3$ | $OCH_3$ | $CH_3$ | |
| J-4 | — | H | H | $CH_2CH_2CH_2Cl$ | — | $CH_3$ | $OCH_3$ | $CH_3$ | |
| J-4 | — | H | H | $CH_2CH_2OCH_3$ | — | $CH_3$ | $OCH_3$ | $CH_3$ | |

*symbols o and m refer to ortho and meta to the sulfonylurea bridge respectively.

TABLE IIIb

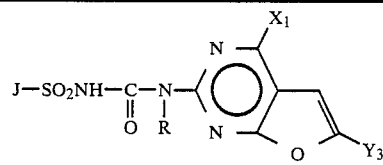

| W₂ | W₁ | J | n | R | R₁ or R₁' | R₃ | R₅ | R₆ | R₇ | X₁ | Y₃ | m.p. (°C.) |
|---|---|---|---|---|---|---|---|---|---|---|---|---|
| — | S | J-5 | 0 | H | H | H | CH₃ | — | — | OCH₃ | CH₃ | |
| — | S | J-5 | 1 | H | H | H | CH₃ | — | — | OCH₃ | CH₃ | |
| O | S | J-6 | 0 | H | H | H | — | — | — | OCH₃ | CH₃ | |
| O | S | J-6 | 1 | H | H | H | — | — | — | OCH₃ | CH₃ | |
| — | S | J-7 | 0 | H | H | H | CH₃ | — | — | OCH₃ | CH₃ | |
| — | S | J-7 | 1 | H | H | H | CH₃ | — | — | OCH₃ | CH₃ | |
| — | S | J-8 | — | H | H | H | CH₃ | — | — | OCH₃ | CH₃ | |
| — | S | J-9 | — | H | H | H | CH₃ | — | — | OCH₃ | CH₃ | |
| O | S | J-10 | — | H | H | H | — | H | CH₃ | OCH₃ | CH₃ | |
| O | S | J-10 | — | H | H | H | — | H | CH₂CH₃ | OCH₃ | CH₃ | |
| O | S | J-6 | 1 | H | H | H | — | — | — | OCH₃ | H | |
| O | S | J-6 | 1 | H | H | H | — | — | — | CH₃ | H | |
| O | S | J-6 | 1 | H | H | H | — | — | — | OCH₂CH₃ | H | |
| O | S | J-6 | 1 | H | H | H | — | — | — | OCF₂H | H | |
| O | S | J-6 | 1 | H | H | H | — | — | — | CH₃ | CH₃ | |
| O | S | J-6 | 1 | H | H | H | — | — | — | OCH₂CH₃ | CH₃ | |
| O | S | J-6 | 1 | H | H | H | — | — | — | OCF₂H | CH₃ | |

TABLE IIIc

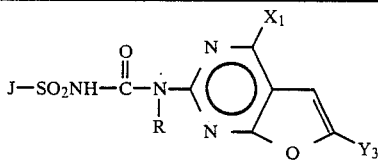

| J | W₂ | m' | n | R | R₁' | R₄ | R₅ | R₆ | X₁ | Y₃ | m.p. (°C.) |
|---|---|---|---|---|---|---|---|---|---|---|---|
| J-11 | O | — | 0 | H | H | CH₃ | H | H | OCH₃ | CH₃ | |
| J-11 | O | — | 1 | H | H | CH₃ | H | H | OCH₃ | CH₃ | |
| J-11 | S | — | 0 | H | H | CH₃ | H | H | OCH₃ | CH₃ | |
| J-11 | S | — | 1 | H | H | CH₃ | H | H | OCH₃ | CH₃ | |

TABLE IIIc-continued

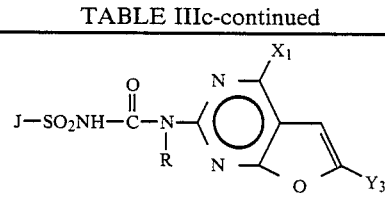

| J | W₂ | m' | n | R | R₁' | R₄ | R₅ | R₆ | X₁ | Y₃ | m.p. (°C.) |
|---|---|---|---|---|---|---|---|---|---|---|---|
| J-12 | O | 1 | 0 | H | H | — | H | H | OCH₃ | CH₃ | |
| J-12 | O | 2 | 0 | H | H | — | H | H | OCH₃ | CH₃ | |
| J-12 | O | 1 | 1 | H | H | — | H | H | OCH₃ | CH₃ | |
| J-12 | O | 2 | 1 | H | H | — | H | H | OCH₃ | CH₃ | |

TABLE IVa

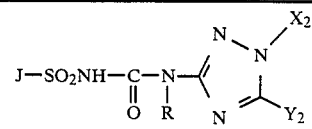

| J | n | R | R₁* or R₁'* | R₂ | R₃ | R₄ | X₂ | Y₂ | m.p. (°C.) |
|---|---|---|---|---|---|---|---|---|---|
| J-1 | 0 | H | H | CH₂CH₂OCH₃ | H | — | CH₃ | OCH₃ | |
| J-1 | 0 | H | H | CH₂CH₂OCH₃ | H | — | CH₂CH₃ | OCH₃ | |
| J-1 | 0 | H | H | CH₂CH₂OCH₃ | H | — | CH₂CF₃ | OCH₃ | |
| J-1 | 0 | H | H | CH₂CH₂OCH₃ | H | — | CH₃ | OCH₂CH₃ | |
| J-1 | 0 | H | H | CH₂CH₂OCH₃ | H | — | CH₃ | SCH₃ | |
| J-1 | 0 | H | H | CH₂CH₂OCH₃ | H | — | CH₃ | SCH₂CH₃ | |
| J-1 | 0 | H | H | CH₂CH₂OCH₃ | H | — | CH₃ | CH₃ | |
| J-1 | 0 | H | H | CH₂CH₂OCH₃ | H | — | CH₃ | CH₂CH₃ | |
| J-1 | 0 | H | H | CH₂CH₂CH₂CH₂CH₃ | H | — | CH₃ | OCH₃ | |
| J-1 | 0 | H | H | CH₂CH(CH₃)CH₂CH₃ | H | — | CH₃ | OCH₃ | |
| J-1 | 0 | H | H | CH₂CH₂CH₂Cl | H | — | CH₃ | OCH₃ | |
| J-1 | 0 | H | o-CH₂CH₃ | H | H | — | CH₃ | OCH₃ | |
| J-1 | 0 | H | o-CH₂CH₃ | CH₃ | H | — | CH₃ | OCH₃ | |
| J-1 | 0 | H | o-CH₂CH₃ | CH₂CH₃ | H | — | CH₃ | OCH₃ | |
| J-1 | 0 | H | o-CH₂CH₃ | CH₂CH₂CH₃ | H | — | CH₃ | OCH₃ | |
| J-1 | 0 | H | o-CH₂CH₃ | CH₂CH₂CH₂CH₃ | H | — | CH₃ | OCH₃ | |
| J-1 | 0 | H | o-CH₂CH₃ | CH₂CH(CH₃)₂ | H | — | CH₃ | OCH₃ | |
| J-1 | 1 | H | H | CH₂CH₂OCH₃ | H | — | CH₃ | OCH₃ | |
| J-1 | 1 | H | H | CH₂CH₂CH₂CH₂CH₃ | H | — | CH₃ | OCH₃ | |
| J-1 | 1 | H | H | CH₂CH(CH₃)CH₂CH₃ | H | — | CH₃ | OCH₃ | |
| J-1 | 1 | H | H | CH₂CH₂CH₂Cl | H | — | CH₃ | OCH₃ | |
| J-2 | — | H | H | CH₂CH₂OCH₃ | — | — | CH₃ | OCH₃ | |

TABLE IVa-continued

J—SO$_2$NH—C(=O)—N(R)—[triazole with X$_2$, Y$_2$]

| J | n | R | R$_1$* or R$_1$'* | R$_2$ | R$_3$ | R$_4$ | X$_2$ | Y$_2$ | m.p. (°C.) |
|---|---|---|---|---|---|---|---|---|---|
| J-2 | — | H | H | CH$_2$CH$_2$CH$_2$CH$_2$CH$_3$ | — | — | CH$_3$ | OCH$_3$ | |
| J-2 | — | H | H | CH$_2$CH(CH$_3$)CH$_2$CH$_3$ | — | — | CH$_3$ | OCH$_3$ | |
| J-2 | — | H | H | CH$_2$CH$_2$CH$_2$Cl | — | — | CH$_3$ | OCH$_3$ | |
| J-3 | — | H | H | CH$_3$ | — | CH$_3$ | CH$_3$ | OCH$_3$ | |
| J-3 | — | H | H | CH$_2$CH$_3$ | — | CH$_3$ | CH$_3$ | OCH$_3$ | |
| J-3 | — | H | H | CH$_2$CH$_2$CH$_3$ | — | CH$_3$ | CH$_3$ | OCH$_3$ | |
| J-3 | — | H | H | CH$_2$CH$_2$CH$_2$CH$_3$ | — | CH$_3$ | CH$_3$ | OCH$_3$ | |
| J-3 | — | H | H | CH$_2$CH(CH$_3$)$_2$ | — | CH$_3$ | CH$_3$ | OCH$_3$ | |
| J-3 | — | H | H | CH$_2$CH$_2$OCH$_3$ | — | CH$_3$ | CH$_3$ | OCH$_3$ | |
| J-3 | — | H | H | CH$_2$CH$_2$CH$_2$CH$_2$CH$_3$ | — | CH$_3$ | CH$_3$ | OCH$_3$ | |
| J-3 | — | H | H | CH$_2$CH(CH$_3$)CH$_2$CH$_3$ | — | CH$_3$ | CH$_3$ | OCH$_3$ | |
| J-3 | — | H | H | CH$_2$CH$_2$CH$_2$Cl | — | CH$_3$ | CH$_3$ | OCH$_3$ | |
| J-4 | — | H | H | CH$_3$ | — | CH$_3$ | CH$_3$ | OCH$_3$ | |
| J-4 | — | H | H | CH$_2$CH$_3$ | — | CH$_3$ | CH$_3$ | OCH$_3$ | |
| J-4 | — | H | H | CH$_2$CH$_2$CH$_3$ | — | CH$_3$ | CH$_3$ | OCH$_3$ | |
| J-4 | — | H | H | CH$_2$CH$_2$CH$_2$CH$_3$ | — | CH$_3$ | CH$_3$ | OCH$_3$ | |
| J-4 | — | H | H | CH$_2$CH(CH$_3$)$_2$ | — | CH$_3$ | CH$_3$ | OCH$_3$ | |
| J-4 | — | H | H | CH$_2$CH$_2$OCH$_3$ | — | CH$_3$ | CH$_3$ | OCH$_3$ | |
| J-4 | — | H | H | CH$_2$CH$_2$CH$_2$CH$_2$CH$_3$ | — | CH$_3$ | CH$_3$ | OCH$_3$ | |
| J-4 | — | H | H | CH$_2$CH(CH$_3$)CH$_2$CH$_3$ | — | CH$_3$ | CH$_3$ | OCH$_3$ | |
| J-4 | — | H | H | CH$_2$CH$_2$CH$_2$Cl | — | CH$_3$ | CH$_3$ | OCH$_3$ | |

*symbols o and m refer to ortho and meta to sulfonylurea bridge respectively.

TABLE IVb

J—SO$_2$NH—C(=O)—N(R)—[ring with X$_2$, Y$_2$]

| W$_2$ | W$_1$ | J | n | R | R$_1$ or R$_1$' | R$_3$ | R$_5$ | R$_6$ | R$_7$ | X$_2$ | Y$_2$ | m.p. (°C.) |
|---|---|---|---|---|---|---|---|---|---|---|---|---|
| — | S | J-5 | 0 | H | H | H | CH$_3$ | — | — | CH$_3$ | OCH$_3$ | |
| — | S | J-5 | 1 | H | H | H | CH$_3$ | — | — | CH$_3$ | OCH$_3$ | |
| O | S | J-6 | 0 | H | H | H | — | — | — | CH$_3$ | OCH$_3$ | |
| O | S | J-6 | 1 | H | H | H | — | — | — | CH$_3$ | OCH$_3$ | |
| — | S | J-7 | 0 | H | H | H | CH$_3$ | — | — | CH$_3$ | OCH$_3$ | |
| — | S | J-7 | 1 | H | H | H | CH$_3$ | — | — | CH$_3$ | OCH$_3$ | |
| — | S | J-8 | — | H | H | H | CH$_3$ | — | — | CH$_3$ | OCH$_3$ | |
| — | S | J-9 | — | H | H | H | CH$_3$ | — | — | CH$_3$ | OCH$_3$ | |
| O | S | J-10 | — | H | H | H | — | H | CH$_3$ | CH$_3$ | OCH$_3$ | |
| O | S | J-10 | — | H | H | H | — | H | CH$_2$CH$_3$ | CH$_3$ | OCH$_3$ | |
| O | S | J-6 | 1 | H | H | H | — | — | — | CH$_3$ | OCH$_2$CH$_3$ | |
| O | S | J-6 | 1 | H | H | H | — | — | — | CH$_3$ | SCH$_3$ | |
| O | S | J-6 | 1 | H | H | H | — | — | — | CH$_3$ | SCH$_2$CH$_3$ | |
| O | S | J-6 | 1 | H | H | H | — | — | — | CH$_3$ | CH$_3$ | |
| O | S | J-6 | 1 | H | H | H | — | — | — | CH$_3$ | CH$_2$CH$_3$ | |
| O | S | J-6 | 1 | H | H | H | — | — | — | CH$_2$CH$_3$ | OCH$_3$ | |
| O | S | J-6 | 1 | H | H | H | — | — | — | CH$_2$CF$_3$ | OCH$_3$ | |

TABLE IVc

J—SO$_2$NH—C(=O)—N(R)—[ring with X$_2$, Y$_2$]

| J | W$_2$ | m' | n | R | R$_1$' | R$_4$ | R$_5$ | R$_6$ | X$_2$ | Y$_2$ | m.p. (°C.) |
|---|---|---|---|---|---|---|---|---|---|---|---|
| J-11 | O | — | 0 | H | H | CH$_3$ | H | H | CH$_3$ | OCH$_3$ | |
| J-11 | O | — | 1 | H | H | CH$_3$ | H | H | CH$_3$ | OCH$_3$ | |
| J-11 | S | — | 0 | H | H | CH$_3$ | H | H | CH$_3$ | OCH$_3$ | |
| J-11 | S | — | 1 | H | H | CH$_3$ | H | H | CH$_3$ | OCH$_3$ | |
| J-12 | O | 1 | 0 | H | H | — | H | H | CH$_3$ | OCH$_3$ | |
| J-12 | O | 1 | 1 | H | H | — | H | H | CH$_3$ | OCH$_3$ | |
| J-12 | O | 2 | 0 | H | H | — | H | H | CH$_3$ | OCH$_3$ | |
| J-12 | O | 2 | 1 | H | H | — | H | H | CH$_3$ | OCH$_3$ | |

TABLE Va

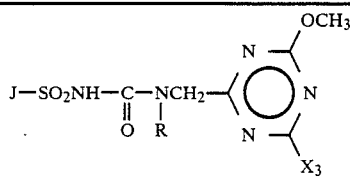

| J | n | R | R₁ or R₁' | R₂ | R₃ | R₄ | X₃ | m.p. (°C.) |
|---|---|---|---|---|---|---|---|---|
| J-1 | 0 | H | H | CH₂CH₂OCH₃ | H | — | CH₃ | |
| J-1 | 0 | H | H | CH₂CH₂OCH₃ | H | — | OCH₃ | |
| J-1 | 0 | H | H | CH₂CH₂CH₂CH₂CH₃ | H | — | OCH₃ | |
| J-1 | 0 | H | H | CH₂CH₂CH₂Cl | H | — | OCH₃ | |
| J-1 | 1 | H | H | CH₂CH₂OCH₃ | H | — | OCH₃ | |
| J-1 | 1 | H | H | CH₂CH₂CH₂CH₂CH₃ | H | — | OCH₃ | |
| J-1 | 1 | H | H | CH₂CH₂CH₂Cl | H | — | OCH₃ | |
| J-2 | — | H | H | CH₂CH₂OCH₃ | — | — | OCH₃ | |
| J-2 | — | H | H | CH₂CH₂CH₂CH₂CH₃ | — | — | OCH₃ | |
| J-2 | — | H | H | CH₂CH₂CH₂Cl | — | — | OCH₃ | |
| J-3 | — | H | H | CH₂CH₂OCH₃ | — | CH₃ | OCH₃ | |
| J-3 | — | H | H | CH₂CH₂CH₂CH₂CH₃ | — | CH₃ | OCH₃ | |
| J-3 | — | H | H | CH₂CH₂CH₂Cl | — | CH₃ | OCH₃ | |
| J-3 | — | H | H | CH₃ | — | CH₃ | OCH₃ | |
| J-3 | — | H | H | CH₂CH₃ | — | CH₃ | OCH₃ | |
| J-3 | — | H | H | CH₂CH₂CH₃ | — | CH₃ | OCH₃ | |
| J-3 | — | H | H | CH₂CH₂CH₂CH₃ | — | CH₃ | OCH₃ | |
| J-3 | — | H | H | CH₂CH(CH₃)₂ | — | CH₃ | OCH₃ | |
| J-4 | — | H | H | CH₂CH₂OCH₃ | — | CH₃ | OCH₃ | |
| J-4 | — | H | H | CH₂CH₂CH₂CH₂CH₃ | — | CH₃ | OCH₃ | |
| J-4 | — | H | H | CH₂CH₂CH₂Cl | — | CH₃ | OCH₃ | |
| J-4 | — | H | H | H | — | CH₃ | OCH₃ | |
| J-4 | — | H | H | CH₃ | — | CH₃ | OCH₃ | |
| J-4 | — | H | H | CH₂CH₃ | — | CH₃ | OCH₃ | |
| J-4 | — | H | H | CH₂CH₂CH₃ | — | CH₃ | OCH₃ | |
| J-4 | — | H | H | CH₂CH₂CH₂CH₃ | — | CH₃ | OCH₃ | |
| J-4 | — | H | H | CH₂CH(CH₃)₂ | — | CH₃ | OCH₃ | |

TABLE Vb

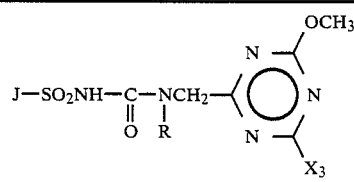

| W₂ | W₁ | J | n | R | R₁ or R₁' | R₃ | R₅ | R₆ | R₇ | X₃ | m.p. (°C.) |
|---|---|---|---|---|---|---|---|---|---|---|---|
| — | S | J-5 | 0 | H | H | H | CH₃ | — | — | CH₃ | |
| — | S | J-5 | 0 | H | H | H | CH₃ | — | — | OCH₃ | |
| — | S | J-5 | 1 | H | H | H | CH₃ | — | — | CH₃ | |
| — | S | J-5 | 1 | H | H | H | CH₃ | — | — | OCH₃ | |
| O | S | J-6 | 0 | H | H | H | — | — | — | CH₃ | |
| O | S | J-6 | 0 | H | H | H | — | — | — | OCH₃ | |
| O | S | J-6 | 1 | H | H | H | — | — | — | CH₃ | |
| O | S | J-6 | 1 | H | H | H | — | — | — | OCH₃ | |
| — | S | J-7 | 0 | H | H | H | CH₃ | — | — | CH₃ | |
| — | S | J-7 | 0 | H | H | H | CH₃ | — | — | OCH₃ | |
| — | S | J-7 | 1 | H | H | H | CH₃ | — | — | CH₃ | |
| — | S | J-7 | 1 | H | H | H | CH₃ | — | — | OCH₃ | |
| — | S | J-8 | — | H | H | — | CH₃ | — | — | CH₃ | |
| — | S | J-8 | — | H | H | — | CH₃ | — | — | OCH₃ | |
| — | S | J-9 | — | H | H | — | CH₃ | — | — | CH₃ | |
| — | S | J-9 | — | H | H | — | CH₃ | — | — | OCH₃ | |
| O | S | J-10 | — | H | H | — | — | H | CH₃ | CH₃ | |
| O | S | J-6 | — | H | H | — | — | H | CH₃ | OCH₃ | |
| O | S | J-10 | — | H | H | — | — | H | CH₂CH₃ | CH₃ | |
| O | S | J-10 | — | H | H | — | — | H | CH₂CH₃ | OCH₃ | |

TABLE Vc

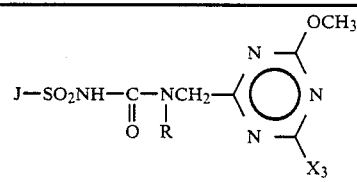

| J | W₂ | m' | n | R | R₁' | R₄ | R₅ | R₆ | X₃ | m.p. (°C.) |
|---|---|---|---|---|---|---|---|---|---|---|
| J-11 | O | — | 0 | H | H | CH₃ | H | H | OCH₃ | |
| J-11 | O | — | 1 | H | H | CH₃ | H | H | OCH₃ | |
| J-11 | S | — | 0 | H | H | CH₃ | H | H | OCH₃ | |
| J-11 | S | — | 1 | H | H | CH₃ | H | H | OCH₃ | |
| J-12 | O | 1 | 0 | H | H | — | H | H | OCH₃ | |
| J-12 | O | 1 | 1 | H | H | — | H | H | OCH₃ | |
| J-12 | O | 2 | 0 | H | H | — | H | H | OCH₃ | |
| J-12 | O | 2 | 1 | H | H | — | H | H | OCH₃ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 5% to about 99% solid or liquid inert diluent(s). More specifically, they will contain these ingredients in the following approximate proportions:

TABLE VI

| Active Ingredient | Weight Percent* Diluent(s) | Surfactant(s) |
|---|---|---|
| Wettable Powders 20–90 | 0–74 | 1–10 |
| Oil Suspensions, Emulsions, Solution (including Emulsifiable Concentrates) 5–50 | 40–95 | 0–15 |
| Aqueous Suspension 10–50 | 40–84 | 1–20 |
| Dusts 1–25 | 70–99 | 0–5 |
| Granules and Pellets 1–95 | 5–99 | 0–15 |
| High Strength Compositions 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommend uses. All formations can contain minor amounts of additives to reduce foaming, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, New York, 1963, pp. 8–59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 10

| Wettable Powder | |
|---|---|
| 2,3-dihydro-N—[(4,6-dimethoxypyrimidin-2-yl)aminocarbonyl]-2-(2-methoxyethyl)-1,2-benzisothiazole-7-sulfonamide, 1,1-dioxdde | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

| Granule | |
|---|---|
| Wettable Powder of Example 10 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 12

| Extruded Pellet | |
|---|---|
| 2,3-dihydro-N—[(4,6-dimethoxypyrimidin-2-yl)aminocarbonyl]-2-(2-methoxyethyl)-1,2-benzisothiazole-7-sulfonamide, 1,1-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

| Low Strength Granule | |
|---|---|
| 2,3-dihydro-N—[(4,6-dimethoxypyrimidin-2-yl)aminocarbonyl]-2-(3-methylbutyl)-1,2-benzisothiazole-7-sulfonamide, 1,1-dioxide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| 2,3-dihydro-N—[(4,6-dimethoxypyrimidin-2-yl)aminocarbonyl]-2-(2-methoxyethyl)-1,2-benzisothiazole-7-sulfonamide, 1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Oil Suspension | |
|---|---|
| 2,3-dihydro-N—[(4,6-dimethoxypyrimidin-2-yl)aminocarbonyl]-2-(3-methylbutyl)-1,2-benzisothiazole-7-sulfonamide, 1,1-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water

EXAMPLE 16

| Granule | |
|---|---|
| 2,3-dihydro-N—[(4,6-dimethoxypyrimidin-2-yl)aminocarbonyl]-2-(2-methoxyethyl)-1,2-benzisothiazole-7-sulfonamide, 1,1-dioxide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 17

| High Strength Concentrate | |
|---|---|
| 2,3-dihydro-N—[(4,6-dimethoxypyrimidin-2-yl)aminocarbonyl]-2-(2-methoxyethyl)-1,2-benzisothiazole-7-sulfonamide, 1,1-dioxide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 18

| Wettable Powder | |
|---|---|
| 2,3-dihydro-N—[(4,6-dimethoxypyrimidin-2-yl)aminocarbonyl]-2-(3-methylbutyl)-1,2-benzisothiazole-7-sulfonamide, 1,1-dioxide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 19

| Wettable Powder | |
|---|---|
| 2,3-dihydro-N—[(4,6-dimethoxypyrimidin-2-yl)aminocarbonyl]-2-(3-methylbutyl)-1,2-benzisothiazole-7-sulfonamide, 1,1-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and the packaged.

EXAMPLE 20

| Dust | |
|---|---|
| 2,3-dihydro-N—[(4,6-dimethoxypyrimidin-2-yl)aminocarbonyl]-2-(3-methylbutyl)-1,2-benzisothiazole-7-sulfonamide, 1,1-dioxide | 10% |
| attapulgite | 10% |
| talc | 80% |

The active ingredient is blended with attapulgite and then passed through a hammer mill to produce particles substantially all below 200 microns. The ground concentrate is then blended with powdered talc until homogeneous.

EXAMPLE 21

| Solution | |
|---|---|
| 2,3-dihydro-N—[(4,6-dimethoxypyrimidin-2-yl)aminocarbonyl]-2-(3-methylbutyl)-1,2-benzisothiazole-7-sulfonamide, 1,1-dioxide | 30% |
| dimethylformamide | 70% |

The ingredients are combined and stirred to produce a solution, which can be used for low volume applications.

Solutions of compounds of Formula I with J=J-5 to J-10 should be avoided due to the instability of the compounds when dissolved.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. Alternatively, the subject compounds are useful to modify plant growth. Certain of the compounds can be used to control weeds in crops such as wheat. The related compounds where J is J₁, n is O, R₁=R₃=H and R₂ is isobutyl show excellent control of wild oats both pre- and postemergence and are also useful for preemergence and postemergence control of grassy weeds in broadlead crops such as cotton and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria sp.), barnyard-grass (Echinochloa crusgalli), wild oats (Avena fatua), sicklepod (Cassia obtusifolia), morningglory (Ipomoea sp.), cocklebur (Xanthium sp.), sorghum, corn, soybean, surgarbeet, rice, wheat and purple nutsedge (Cyperus rotundus) tubers, and in certain cases, cotton were planted and treated pre-emergence with the test chemicals dissolved in a non-phytotoxic solvent. At the same time, these crop and weed species, along with cotton and bush bean, were treated post-emergence with a soil foliage application. At the time of treatment, the plants ranged in height from 2 to 19 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:
  C=chlorosis or necrosis;
  E=emergence inhibition;
  G=growth retardation;
  H=formative effects;
  L=lodging;
  U=unusual pigmentation;
  X=axillary stimulation; and
  6Y abscised buds or flowers.

The data show that most of the compounds tested are highly active herbicides with growth modifying properties and that some of the compounds tested provide selective weed control in crops such as wheat, cotton and soybeans. It will be noted that all compounds were tested at the low rate of 50 g/ha. It is expected that compounds such as 10, 17, 19, 23, 25, 28, 34 and 35 will show improved activity at higher rates.

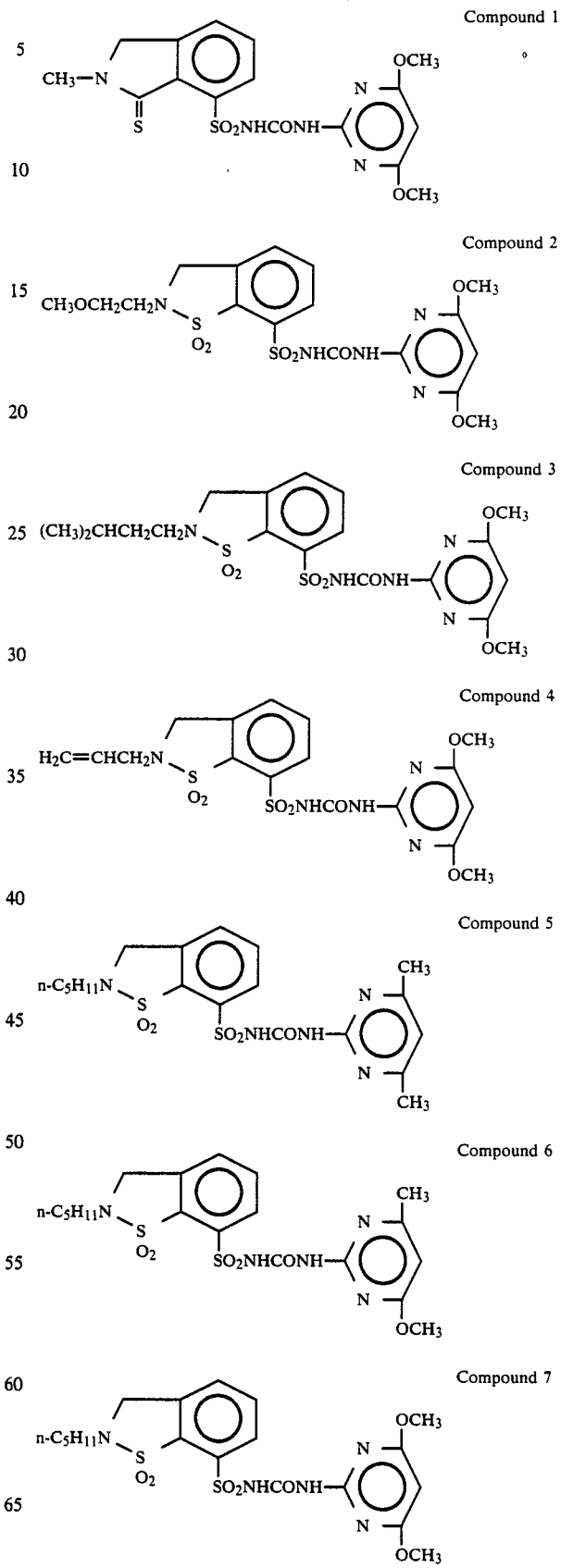

-continued
Compounds
Compound 8
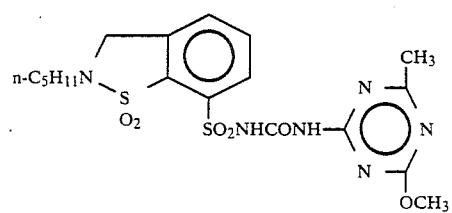
Compound 9
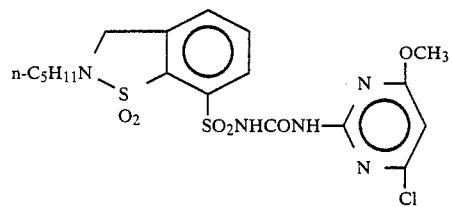
Compound 10
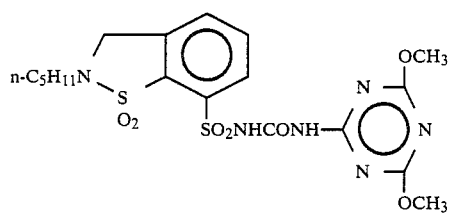
Compound 11
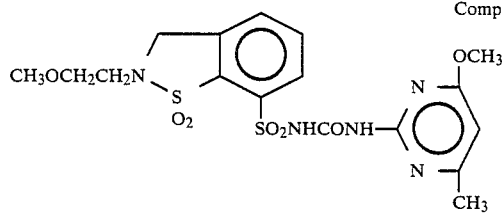
Compound 12
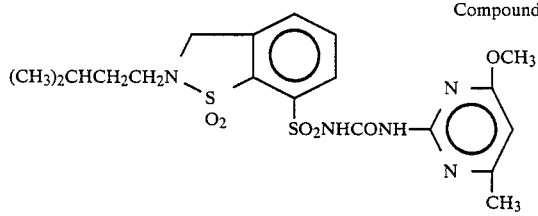
Compound 13
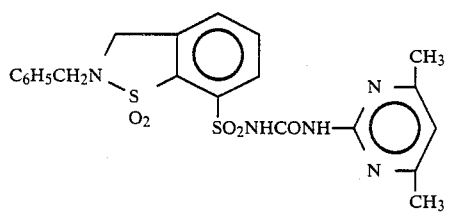
Compound 14
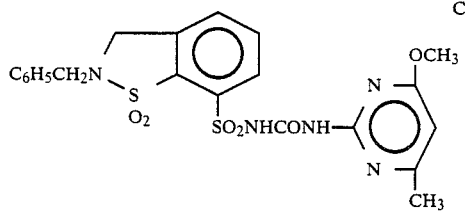
-continued
Compounds
Compound 15
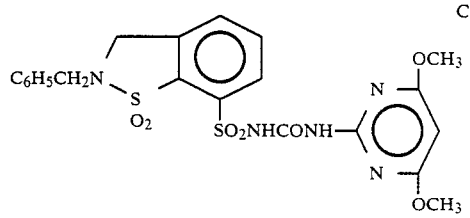
Compound 16
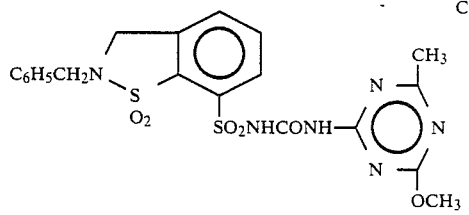
Compound 17
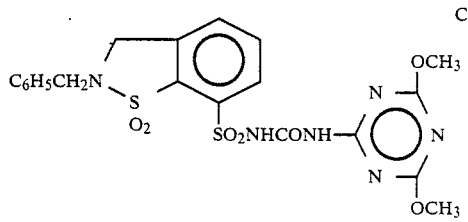
Compound 18
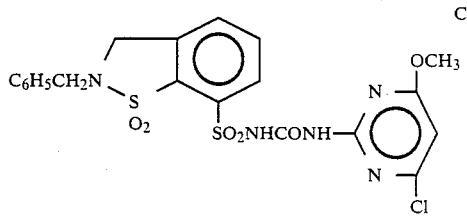
Compound 19
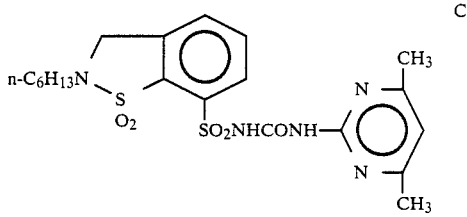
Compound 20
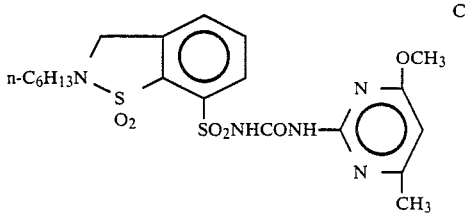
Compound 21
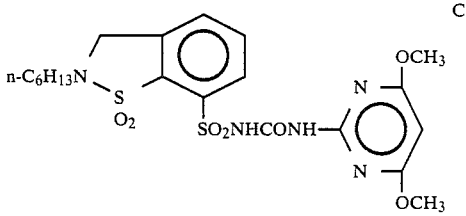

-continued
Compounds
Compound 22
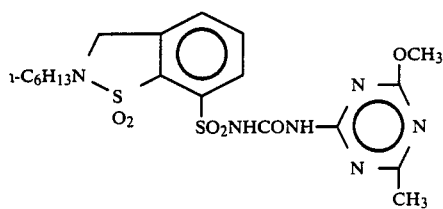
Compound 23
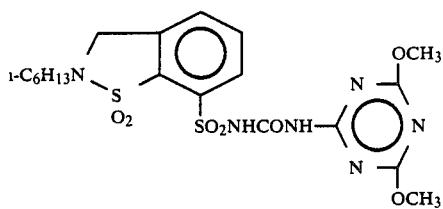
Compound 24
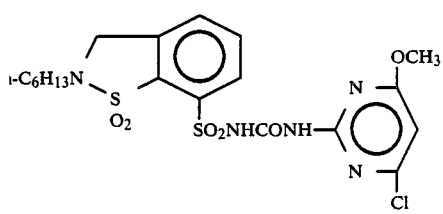
Compound 25
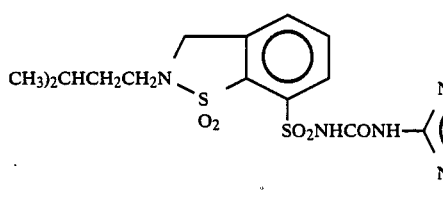
Compound 26
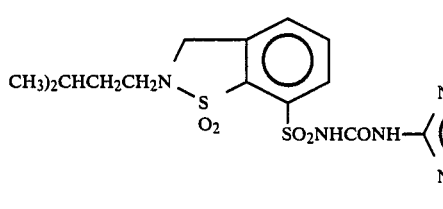
Compound 27
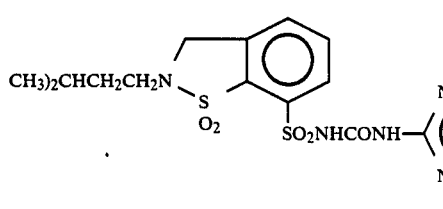
Compound 28
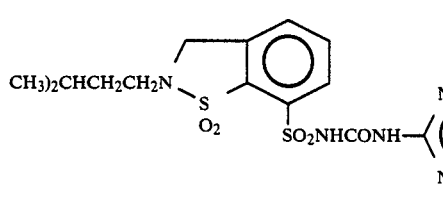
-continued
Compounds
Compound 29
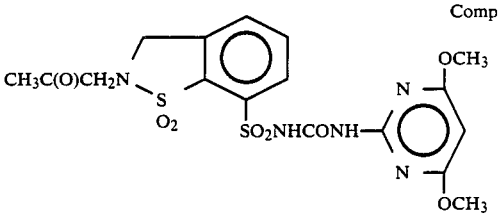
Compound 30
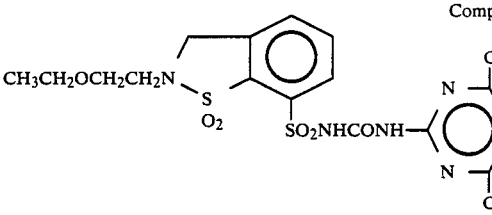
Compound 31
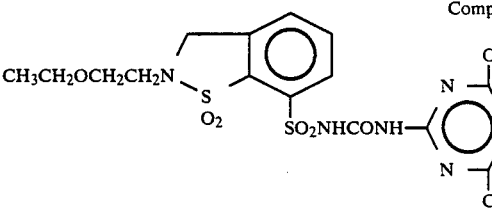
Compound 32
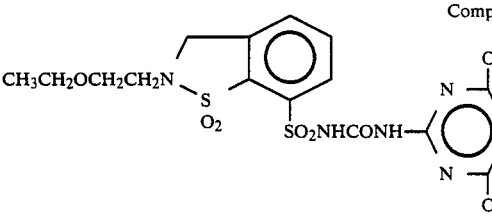
Compound 33
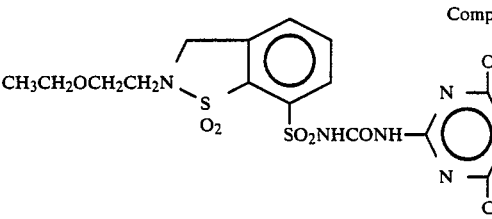
Compound 34
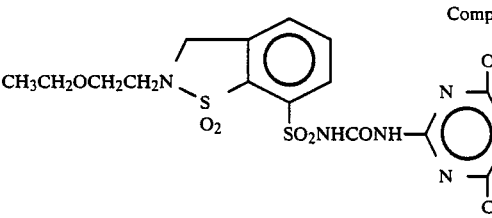
Compound 35
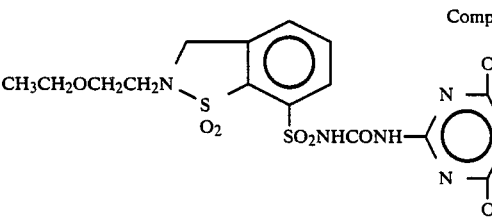

-continued
Compounds
Compound 36
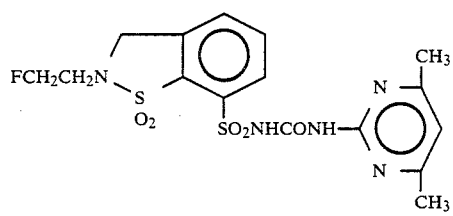
Compound 37
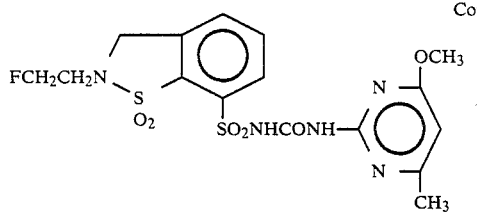
Compound 38
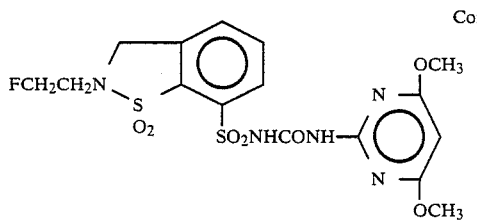
Compound 39
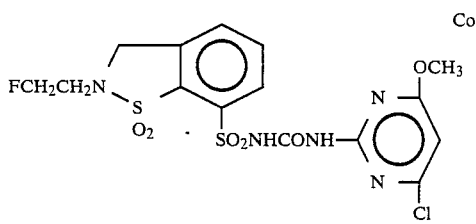
Compound 40
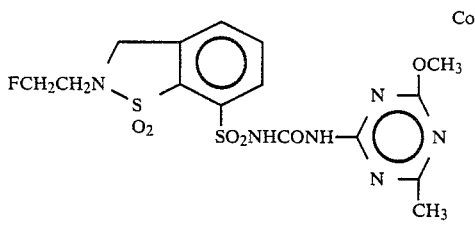
Compound 41
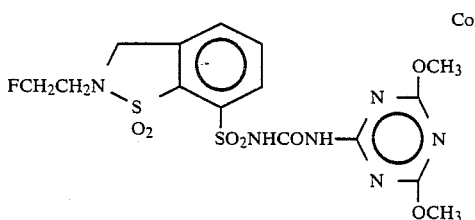
Compound 42
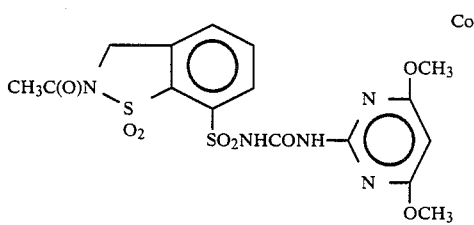
-continued
Compounds
Compound 43
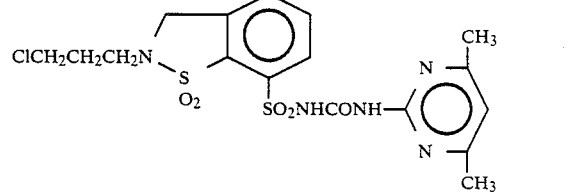
Compound 44
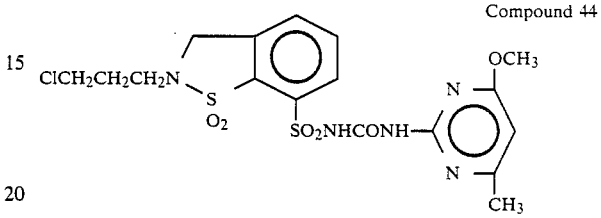
Compound 45
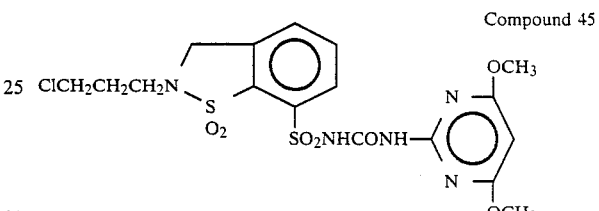
Compound 46
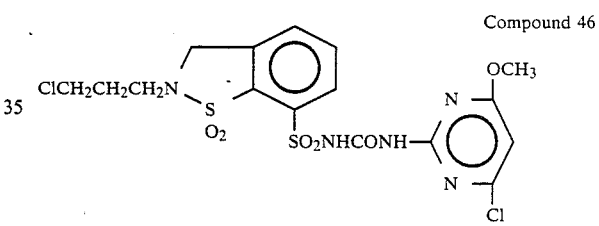
Compound 47
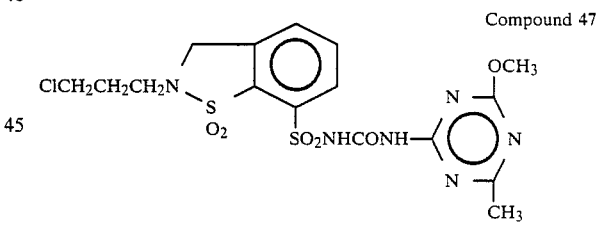
Compound 48
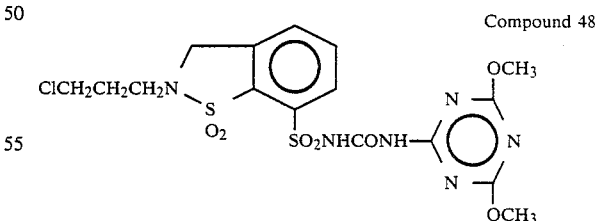
Compound 49
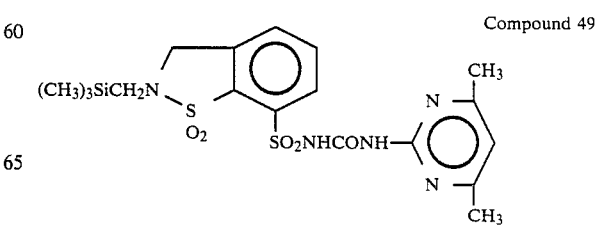

-continued
Compounds
Compound 50
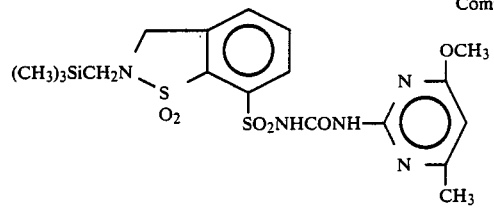
Compound 51
-continued
Compounds
Compound 52
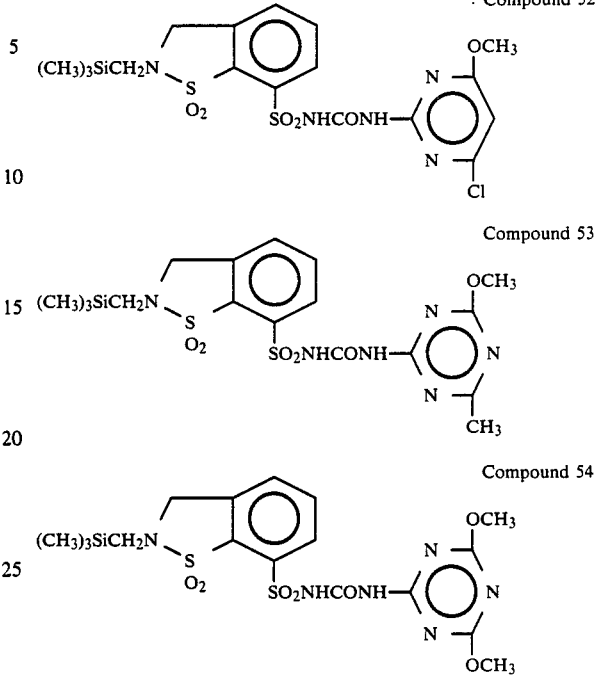
Compound 53
Compound 54

TABLE A

| TYPE TEST | RATE G/HA | COTTON | SORGHUM | CORN | SOYBEAN | WHEAT | WILD OATS | RICE | BARNYARD-GRASS | CRAB-GRASS | MORNING-GLORY | COCKLEBUR | SICKLEPOD | NUTSEDGE | SUGAR-BEETS |
|---|---|---|---|---|---|---|---|---|---|---|---|---|---|---|---|
| | | | | | | | | Compound 1 | | | | | | | |
| POST | 50 | 2C 4G | 3C 9G | 2C 8H | 2C 7H 1C | 5G | 4G | 3C 9G 1C | 2C 9H | 2G | 2C 3H 3G | 3C 5G | 3C 5G | 2G | 2C 8G |
| PRE | 50 | 0 | 0 | 0 | | 0 | 0 | | | 0 | | 5G | | 0 | 0 |
| | | | | | | | | Compound 2 | | | | | | | |
| POST | 50 | 3C 8H | 2C 9H | 2C 9G 4C | 4C | 5G | 2C 9G 10E | 5C 9G 4C | 5C 10C | 5c 9G 9G | 3C 9G 9H | 2C 5H 2C | 2G 10E 8G | 8G | 9C |
| PRE 50 | | 4C 8G | 4C 9H | 9C 7G | 9C 7G | 9C | | 9H | | | | | | 9C | |
| | | | | | | | | Compound 3 | | | | | | | |
| POST | 50 | 4C 8G | 5C 9H 9G | 3C 9G 4U 9H | 5C 9G 3C 7G | 2G | 2C 5G 2C 7G | 9C 10E 3C 9G | 5C 9H 9C | 2C 7G 2C 5G | 9C | 3C 8H 8H | 5C 9G 8G | 4C 9G 10E | 3C 7G 9G |
| PRE | 50 | | | | | | | | | | 9G | | | | |
| | | | | | | | | Compound 4 | | | | | | | |
| POST | 50 | 9C 2C 9G | 9C 10H | 9C 5C 9H | 9C 4C 9H | 9C 10H | 9C 9C | 9C 10E 9H | 9C 9H | 10C 6C 9G | 10C 9C | 9C 8H | 9C 9G | 9C 10E 10E | 10C 9C |
| PRE | 50 | | | | | | | | | | | | | | |
| | | | | | | | | Compound 5 | | | | | | | |
| POST | 50 | 0 | 3C 7H 4G | 2C 2H 5G | 0 | 0 | 2C 4G 2C 5G | 2C 4G 3c 8G | 3C 8H 0 | 4G | 1C 2G 2C | 0 | 1C | 0 | 3G |
| PRE | 50 | 0 | | | 0 | 0 | | | | 0 | | 0 | 0 | 0 | 0 |
| | | | | | | | | Compound 6 | | | | | | | |
| POST | 50 | 4C 7G 2G | 5C 9H 9G | 4C 8G 2C 5G | 4C 8G 2C | 2G | 4C 7G 2C 8H | 9C 10E | 5C 9H 4H | 6G 2C 8G 5C 9G | 3C 8G 6G | 2C 8G 5G | 5C 9G 2G | 8G | 2C 3G 4G |
| PRE | 50 | 4C 9G 8G | 4C 9H 3C 9G | 5C 9G 2C 8G | 4C 8G 3C 8G | 2G | 4C 8G 9H | 9G 10E | 6G 9G 9H | 5C 9G 2C 9G | 10C 9G | 3C 8G 5G | 9C 2G | 4C 9G 10E | 4C 9C 9G |
| | | | | | | | | Compound 8 | | | | | | | |
| POST | 50 | 1C | 2C 6H 2C 4G | 3C 8H 2C 7G | 0 1C | 0 | 0 3G | 6G 8H | 0 1C | 0 2G | 2C 3H 2C | 2C 5H 1H | 0 0 | 3G 0 | 3G 0 |
| PRE | 50 | 0 | | | | | | | | | | | | | |
| | | | | | | | | Compound 9 | | | | | | | |
| POST | 50 | 4C 6G 2G | 3C 9G 3C 9H | 3C 9H 2C 9G | 3H 2C | 0 3G | 0 3G | 4C 9G 10E 3C 8H | | 3C 6G 3G | 3C 7H 2C 9G | 3C 3G | 2G 3G | 2C 9C | 2C 3G |
| PRE | 50 | | | | | | | | | | | | | | |
| | | | | | | | | Compound 10 | | | | | | | |
| POST | 50 | 0 | 0 | 0 | 0 | 0 | 0 | 0 | 0 | 0 | 2G 0 | 0 | 0 | 0 | 0 |
| PRE | 50 | 0 | 0 | 0 | 0 | 0 | 0 | 0 | | 0 | | 0 | 0 | 0 | 0 |
| | | | | | | | | Compound 11 | | | | | | | |
| POST | | 4C 9H | 3C 9G | 2U 9G | 5C 9G | 6C 9G | 9C | 9C 10C | | 9C | 5C 8H | 4C 8H | 3C 3H | 2C 5G | 5C 9G |

TABLE A-continued

| TYPE TEST | RATE G/HA | COTTON | SORGHUM | CORN | SOYBEAN | WHEAT | WILD OATS | RICE | BARNYARD-GRASS | CRAB-GRASS | MORNING-GLORY | COCKLEBUR | SICKLEPOD | NUTSEDGE | SUGAR-BEETS |
|---|---|---|---|---|---|---|---|---|---|---|---|---|---|---|---|
| PRE | 50 | 5G | 3C 8G | 2C 9G | 3C 7G | 0 | 6C 9G | 5C 9H | 5C 6G | 4C 9G | 8G | 7H | 2G | 0 | 3C 7G |
| | | | | | | | | Compound 12 | | | | | | | |
| POST | 50 | 2G | 4C 9H | 4C 9H | 5C 9G | 0C | 3C 8G | 5C 9G 10E | 3C 8H 4C 6G | 2G | 5C 9H 2C 8G | 3C 6H 6H | 52C 9H 2C 4G | 2C 5G 5G | 0 |
| PRE | 50 | 2G 9S | 3C 9G | 2C 8G | 2C 4G | 0 0 | 4C 9G | 10E | | 2G | | | | | 0 |
| | | | | | | | | Compound 13 | | | | | | | |
| POST | 50 | 0 | 2G | 2C 9H 2C 5G | 3C 9G 1C | 7G | 7G | 3C 9G 2C 9H | 0 | 0 | 3C 7G 0 | 3C 9H 7G | 3C 5H 0 | 0 | 3H |
| PRE | 50 | 0 | 0 | | | 0 | 0 | | 0 | 0 | 0 | 0 | 0 | 0 | 8H |
| | | | | | | | | Compound 14 | | | | | | | |
| POST | 50 | 8H | 5C 9G 3C 8G | 4C 9H 3C 9G | 5C 9G 6H | 8G | 1C | 5C 9G 10E | 3C 9H 3C 7H | 2C 5G 2C 8G | 4C 9G 8G | 4C 9H 9H | 6C 9G 2G | 2C 9G 8G | 9C |
| PRE | 50 | 3G | | | | 8G | 3C 8G | | | | | | | | 5C 9G |
| | | | | | | | | Compound 15 | | | | | | | |
| POST | 50 | 9H | 6C 9G 4C 9G | 10C 3C 9G | 5C 9G 3C 7H | 7G 4C 9G | 5G 4C 8G | 5C 9G 10E | 4C 9H 5C 9H | 3C 9G 2C 7G | 10C 8H | 10C 9H | 9C 7G | 2C 9G 10E | 9C |
| PRE | 50 | 8G | | | | | | | | | | | | | 5C 9G |
| | | | | | | | | Compound 16 | | | | | | | |
| POST | 50 | 0 | 0 | 2H 4H 4G | 2H | 0 | 0 | 5G | 0 | 0 | 2C | 2C 3H | | 0 | 2H |
| PRE | 50 | 0 | 6G | 0 | 1C | 5G | 0 | 9G | 0 | 0 | 0 | 0 | 0 | 0 | 7G |
| | | | | | | | | Compound 17 | | | | | | | |
| POST | 50 | 0 | 0 | 0 0 | 0 0 | 0 0 | 0 0 | 0 0 | 0 0 | 0 0 | 0 0 | 0 1H | | 0 0 | 0 3H |
| PRE | 50 | 0 | 0 | | | | | | | | | | | | |
| | | | | | | | | Compound 18 | | | | | | | |
| POST | 50 | 8H | 4C 9G | 3C 9G | 3C 9H 1C 3G | 3G | 0 | 4C 8G 10E | 4C 9H 5C 9H | 0 | 4C 8G 5G | 5G 9H | 2C | 0 | 9C |
| PRE | 50 | 0 | 6C 9H | | | 6G | 6G | 7H | 1C | | | | 0 | 10E | 4C 9G |
| | | | | | | | | Compound 19 | | | | | | | |
| POST | 50 | 0 | 0 | 0 0 | 0 | 0 | 0 | 0 | 0 | 0 | 0 | 0 | 0 | 0 | 0 |
| PRE | 50 | 0 | 0 | | 0 | 0 | 0 | 0 | 0 | 0 | 0 | 0 | 0 | 0 | 0 |
| | | | | | | | | Compound 20 | | | | | | | |
| POST | 50 | 3C 8H | 3C 8H | 5C 9G 0 | 5C 9G 0 | 2G | 0 | 6C 9G 0 | 2C 9H 0 | 2G | 5c 9G 0 | 2C 7G 0 | 3C 7G 0 | 2C 7G 0 | 3C 7H |
| PRE | 50 | 0 | 0 | | | 0 | 0 | | | 0 | | | | | 0 |
| | | | | | | | | Compound 21 | | | | | | | |
| POST | 50 | 3C 9G | 3C 7H 2G | 3C 9H 2C 8G | 4C 9G 2C 7G | 0 | 0 | 5C 9G 8G | 3C 9H 2H | 3C 9G 0 | 9C 9G | 2C 6H 4G | 2C 8G 0 | 2C 8G 0 | 9C |
| PRE | 50 | 0 | | | | 0 | 0 | | | | | | | | 8G |
| | | | | | | | | Compound 22 | | | | | | | |

TABLE A-continued

| TYPE TEST | RATE G/HA | COTTON | SORGHUM | CORN | SOYBEAN | WHEAT | WILD OATS | RICE | BARNYARD-GRASS | CRAB-GRASS | MORNING-GLORY | COCKLEBUR | SICKLEPOD | NUTSEDGE | SUGAR-BEETS |
|---|---|---|---|---|---|---|---|---|---|---|---|---|---|---|---|
| POST | 50 | 3G | 0 | 2C 7H 0 | 0 | 0 | 0 | 2G | 0 | 0 | 0 | 0 | 0 | 0 | 3H |
| PRE | 50 | 0 | 0 | 0 | 0 | 0 | 0 | 0 | 0 | 0 | 0 | 0 | 0 | 0 | 0 |
| | | | | | | | | Compound 23 | | | | | | | |
| POST | 50 | 0 | 0 | 0 | 0 | 0 | 0 | 0 | 0 | 0 | 0 | 0 | 0 | 0 | 0 |
| PRE | 50 | 0 | 0 | 0 | 0 | 0 | 0 | 0 | 0 | 0 | 0 | — | 0 | 0 | 0 |
| | | | | | | | | Compound 24 | | | | | | | |
| POST | 50 | 3C 8H | 2G | 3C 9H 2C 7G | 0 | 3G | 0 | 6C 9G 9H | 3C 9H 0 | 2G | 2C 7H 2G | 3G | 0 | 5G | 0 |
| PRE | 50 | 0 | 3C 9G | | 0 | 0 | 0 | 0 | 0 | 0 | 0 | 0 | 0 | 0 | 0 |
| | | | | | | | | Compound 25 | | | | | | | |
| POST PRE | 50 50 | 0 0 | 0 0 | 0 0 | 0 0 | 0 0 | 0 0 | 0 0 | 0 0 | 0 0 | 0 — | 0 — | — 0 | 0 0 | 0 0 |
| | | | | | | | | Compound 26 | | | | | | | |
| POST | 50 | 2C 4G | 3C 8H 3C 9H | 3C 8H 3C 8G | 0 | 0 | 1C | 3C 9G 10E 9H | 3C 9H 3C | 1C | 2C 5H 2C | 0 | — | 2C 5G 5G | 0 |
| PRE | 50 | 0 | | | 1C | 0 | 0 | | | 3G 6H | | 5G | — | | 2H |
| | | | | | | | | Compound 27 | | | | | | | |
| POST | 50 | 0 | 3C 8H | 3C 7H 2G | 1C | 0 | 0 | 3C 6G 0 | 3C 5H 0 | 0 | 3G | 0 | — | 0 | 0 |
| PRE | 50 | 0 | 0 | 0 | 0 | 0 | 0 | 0 | 0 | 0 | 0 | 0 | — | 0 | 0 |
| | | | | | | | | Compound 28 | | | | | | | |
| POST PRE | 50 50 | 0 0 | 0 0 | 0 0 | 0 0 | 0 0 | 0 0 | 0 0 | 0 0 | 0 0 | 0 0 | 1H 0 | — — | 0 0 | 0 0 |
| | | | | | | | | Compound 29 | | | | | | | |
| POST | 50 | 5C 9G 2C 9G | 5C 9G 9G | 10C 9G | 4C 9G 3C 8H | 9C 2C 8G | 9C 2G 4G | 5C 9G 9H | 10C 2C 5G | 9C 2C 7G | 10C 8G | 10C 5H | — — | 9C 10E | 10C 4C 9G |
| PRE | 50 | | | | | | | | | | | | — | | |
| | | | | | | | | Compound 30 | | | | | | | |
| POST | 50 | 1C | 2G | 3C 7H 0 | 2C 2H 0 | 5G | 2C 4G 0 | 1C 2G | 2C 5G | 0 | 3G | 0 | — | 0 | 0 |
| PRE | 50 | 0 | 0 | 0 | 0 | 0 | 0 | 0 | 0 | 0 | 0 | 0 | — | 0 | 0 |
| | | | | | | | | Compound 31 | | | | | | | |
| POST | 50 | 3C 8H 2G | 4C 9H 2C 7H | 5C 9G 2C 7H | 5C 9G 7G | 8G 2G | 5C 9G 2C 7G | 5C 9G 6G | 10C 0 | 2C 8G 5G | 3C 7H 3C 6G | 3C 8H 9H | — — | 2C 9G 0 | 3C 7H 2C 5G |
| PRE | 50 | | | | | | | | | | | | — | | |
| | | | | | | | | Compound 32 | | | | | | | |
| POST | 50 | 4C 9G 7G | 9C 9H | 10C 4C 9G | 4C 9G 4C 7G | 6C 9G 9C | 6C 9G 9C | 9C 9H | 9C 3C 5H | 9C 3C 9G | 10C 9C | 5C 9H 8H | — — | 4C 9G 9G | 10C 4C 9G |
| PRE | 50 | | | | | | | | | | | | — | | |
| | | | | | | | | Compound 33 | | | | | | | |
| POST | 50 | 2C 5G | 5C 9H | 9C | 1H | 1C 2G | 3C 7G | 5C 9G | 10C | 9C | 2C 3H | 3G | — | 0 | 3C 7G |

TABLE A-continued

| TYPE TEST | RATE G/HA | COTTON | SORGHUM | CORN | SOYBEAN | WHEAT | WILD OATS | RICE | BARNYARD-GRASS | CRAB-GRASS | MORNING-GLORY | COCKLEBUR | SICKLEPOD | NUTSEDGE | SUGAR-BEETS |
|---|---|---|---|---|---|---|---|---|---|---|---|---|---|---|---|
| PRE | 50 | 0 | 3C 9H | 2C 8H | 2C 2G | 2G | 2C 5G | 3C 8H | 3C 8H | 2C 4G | 3C 5G | 0 | — | 0 | 5H |
| | | | | | | | | Compound 34 | | | | | | | |
| POST | 50 | 0 | 0 | 0 | 0 | 0 | 0 | 0 | 0 | 0 | 0 | 0 | — | 0 | 0 |
| PRE | 50 | 0 | 0 | 0 | 0 | 0 | 0 | 0 | 0 | 0 | 0 | 0 | — | 0 | 0 |
| | | | | | | | | Compound 35 | | | | | | | |
| POST | 50 | 0 | 0 | 0 | 0 | 0 | 0 | 0 | 0 | 0 | 0 | 0 | — | 0 | 0 |
| PRE | 50 | 0 | 0 | 0 | 0 | 0 | 0 | 0 | 0 | 0 | 0 | 0 | — | 0 | 0 |
| | | | | | | | | Compound 36 | | | | | | | |
| POST | 50 | 5C 9H 5G | 4C 9H 2C | 2C 9H 2G | 2C 4H 0 | 3C 9G 5G | 9C | 5C 9G 0 | 3C 8H 5G | 3H | 3G | — | 0 | 3C 3H 0 |
| PRE | 50 | 0 | 0 | 0 | 0 | 0 | 7G | 0 | 0 | 0 | 0 | — | 0 | |
| | | | | | | | | Compound 37 | | | | | | | |
| POST | 50 | 5C 9H 8G | 9C | 10C | 5C 9G 3C 7G | 9C | 10C | 9C | 5C 9H | 9C | 10C | 5C 9H | — | 4C 9G 10E | 10C |
| PRE | 50 | 4C 8H | 5C 9H | 5C 9H | 4C 8H | 7C 9H | 9C | 5C 9H | 10H | 10H | 3C 7H | 9H 9H | — | | 6C 9G |
| | | | | | | | | Compound 38 | | | | | | | |
| POST | 50 | 0 | 10C | 10C | 9C | 9C | 9C | 9C | 10C | 5C 9G | 9C | — | 9C | 10C |
| PRE | 50 | 0 | 5C 9H | 10H | 4C 8H | 6G | 10C | 10H 9C | 10H | | | — | 10E | 6C 9G |
| | | | | | | | | Compound 39 | | | | | | | |
| POST | 50 | 4C 8H | 9C | 10C | 3H 6G 5X 3C 4G | 4C 9G | 2C 9G 2C 5G | 5C 9H | 7C 9H | 5C 9G | 4C 8H | — | 2C 5G | 5C 9H |
| PRE | 50 | 0 | 9C | 5C 9H | | 6G | | 10C | 3C 7G | 2C 7G | 2H | — | 4G | 2C 5H |
| | | | | | | | | Compound 40 | | | | | | | |
| POST | 50 | 0 | 4C 8H 2C 3G | 6C 9H 2C 5G | 1C 3G 0 | 5C 9G 7G | 4C 9G 3G | 4C 9G 2C 3G | 0 | 3C 7H | 2G | — | 3G | 2C 5H 3H |
| PRE | 50 | 0 | 0 | 3G | 0 | 2C 8G 0 | 3C 8G 0 | 3C 9G 0 | 0 | 0 | — | — | 0 | |
| | | | | | | | | Compound 41 | | | | | | | |
| POST | 50 | 0 | 4G | 3C 8H 0 | 3G | 2C 8G 0 | 3C 8G 0 | 3C 9G 0 | 0 | 0 | 0 | — | 0 | 0 |
| PRE | 50 | 0 | 0 | 0 | 0 | 0 | 0 | | 0 | 0 | 0 | — | 0 | 0 |
| | | | | | | | | Compound 42 | | | | | | | |
| POST | 50 | 10C 9G | 9C 7C 9H | 10C 10E | 9C 9H | 10C 9H | 10C 9C | 9C 10E | 10C 10C | 10C 10C | 10C 9H | — | 10C 10E | 10C 10C |
| PRE | 50 | 0 | | 3C 8H 3G | 6G | 6C 9G 0 | 10C | 9C | 3C 8G 0 | 0 | 0 | — | 0 | 4H |
| | | | | | | | | Compound 43 | | | | | | | |
| POST | 50 | 0 | 2C 4H 4G | | 0 | 0 | 2C 6G | 2C 7G | 0 | 0 | 0 | — | 0 | 0 |
| | | | | | | | | Compound 44 | | | | | | | |
| POST | 50 | 3C | 9C | 10C | 3C | 3C | 10C | 9C | 9C | 4C | 4C | — | 3C | 3C |

TABLE A-continued

| TYPE TEST | RATE G/HA | COTTON | SORGHUM | CORN | SOYBEAN | WHEAT | WILD OATS | RICE | BARNYARD-GRASS | CRAB-GRASS | MORNING-GLORY | COCKLEBUR | SICKLEPOD | NUTSEDGE | SUGAR BEETS |
|---|---|---|---|---|---|---|---|---|---|---|---|---|---|---|---|
| | | | | | | | | | | | | | | | |
| PRE | 50 | 8H 5G | 4C 9H | 3C 9G | 8H 2C 4H | 9G 2G | 9C | 10E | 3C 9H | 4C 9H | 8H 3C 6H | 9H — | — | 8G 3C 5G | 8H 4C 9H |
| | | | | | | | | Compound 45 | | | | | | | |
| POST | 50 | 5C 9G 9G | 9C | 10C | 10C | 9C | 10C | 9C | 9C | 10C | 10C | 10C | — | 9C | 9C |
| PRE | 50 | 9G | 9H | 9G | 2C 7G | 8G | 9C | 10E | 4C 9H | 10C | 9G | 8H | — | 10E | 5C 9G |
| | | | | | | | | Compound 46 | | | | | | | |
| POST | 50 | 0 | | 10C | 7G | 3G | 6C | 9C | 9C | 9C | 2C 5H 3G | 2C 7G 2G | — | 2C 3G 10E | 4H |
| PRE | 50 | 0 | 3C 9H | 2C 8G | 0 | 3G | 7G | 10E | 3C 9H | 3C 9G | | | — | | 5G |
| | | | | | | | | Compound 47 | | | | | | | |
| POST | 50 | 0 | 9H | 3C 9H 2C 4G | 1H | 2C 6G 0 | 9C 9H 2G | 4C 3C | 4C 3C | 0 | 0 | 2G | — | 0 | 3H |
| PRE | 50 | 0 | 0 | 3C 7H 0 | 0 | 2G 0 | 5C 9G 0 | 2G | 0 | 0 | 0 | 0 | — | 0 | 0 |
| | | | | | | | | Compound 48 | | | | | | | |
| POST | 50 | 0 | 2C 5H 0 | 0 | 0 | 4C 9G 7G | 5C 9G 3C 9G | 8G 0 | 0 | 0 | 0 | 1H | — | 0 | 0 |
| PRE | 50 | 4G | 4C 8H 2G | 5C 9H 5G | 2H 5G 0 | 9G | 9C | 5C 9G 8H | 3C 9H | 5G | 3C 8H 3C | 0 | — | 2c 8G 0 | 3C 7H |
| | | | | | | | | Compound 49 | | | | | | | |
| POST | 50 | 9C | 6C 9G 4C 9H | 9C | 4C 9G 3C 7G | 5C 9G 6C 9H | 9C | 9C | 5C 9G 9H | 5C 9G 5C 9G | 5C 9G 9H | 4C 9H — | — | 4C 9G 9G | 10C |
| PRE | 50 | 3G | 9C | 9G | 4C 9G 3C 8G | 5C 9G 6C 9H | 9C | 5C 9G 9H | 5C 9H | 10C | 10C | 10C | — | 10E | 9G |
| | | | | | | | | Compound 50 | | | | | | | |
| POST | 50 | 9C | 9C | 10C | 4C 9G 3C 8G | 2C 6G 3C 7G | 7C 9H | 6C 9G 10E | 7C 9H | 7C 9H | 10C | 10C | — | 9C | 9C |
| PRE | 50 | 9H | 6C 9H | 5C 9H | 6H | 2C 6G 3C 7G | 3C 7G 3C 8G | 9C | 7C 9H | 9C | 10C | 8H | — | 10E | 10C |
| | | | | | | | | Compound 51 | | | | | | | |
| POST | 50 | 6G | 9C | 9C | 2C 5G | 2C 6G 3C 7G | 3C 7G 3C 8G | 10C | 6C 9H | 3C 7G | 8H | 5H | — | 3C 8G 3C 9H | 5C 9G |
| PRE | 50 | 9H | 9C | 9C | 6H | 2C 6G 3C 7G | 2C 5G 3G | 9C | 10C | 3C 7G | 10C | 1H | — | 0 | 1H |
| | | | | | | | | Compound 52 | | | | | | | |
| POST | 50 | 0 | 3C 8H 6G | 3C 9H 0 | 0 5G | 2G | 2C 5G | 2C 9G 0 | 6C 9H | 0 | 0 | — | 0 | 2G | 0 |
| PRE 50 | | 0 | 3C 9H | 3C 9H | 0 | 2G | 2C 5G | 9G | 4H | 0 | 0 | — | 0 | 0 | 0 |
| | | | | | | | | Compound 53 | | | | | | | |
| POST | | 2G | 2C 3H | | | | | | | | | | | | |
| | | | | | | | | Compound 54 | | | | | | | |

TEST B

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Amena fatua*), cheatgrass (*Bromus secalinus*), blackgrass (*Alopecurus myosuroides*), annual bluegrass (*Poa annua*), green foxtail (*Setaria viridis*), rapeseed (*Brassica napus*), and Italian ryegrass (*Lolium multiflorum*). The other pan was planted with seeds of Russian thistle (*Salsola kali*), speedwell (*Veronica persica*), kochia (*Kochia scoparia*), shepard's purse (*Capsella bursa-pastoris*), *Matricaria inodora*, black nightshade (*Solanum nigrum*), and wild buckwheat (*Polygonum convolvulus*). The above two pans were treated preemergence. At the same time two pans in which the above plant species were growing were treated post-emergence. Plant height at the time of treatment ranged from 1-15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table B.

TABLE B

| TYPE TEST | RATE G/HA | WHEAT | BARLEY | WILDOATS | CHEAT-GRASS | BLACK-GRASS | BLUE-GRASS | FOXTAIL | RYE-GRASS | CIAB-GRASS | RAPE-SEED |
|---|---|---|---|---|---|---|---|---|---|---|---|
| | | | | | Compound 2 | | | | | | |
| POST | 125 | 10C | 10C | 10C | 9G | 10C | 10C | 10C | 10C | 10C | |
| PRE | 125 | 8G | 9G | 9G | 10C | 9G | 8G | 10C | 10C | 9G | |
| POST | 64 | 8G | 10C | 10C | 8G | 10C | 10C | 10C | 10C | 10C | |
| PRE | 64 | 7G | 7G | 9G | 9G | 9G | 9G | 9G | 8G | 5G | |
| POST | 32 | 3G | 10C | 7C | 7G | 9G | 10C | 10C | 7G | 10C | |
| PRE | 32 | 6G | 6G | 8G | 8G | 7G | 7G | 7G | 7G | 0 | |
| POST | 16 | 0 | 10C | 10C | 7G | 9G | 10C | 10C | 6G | 9G | |
| PRE | 16 | 4G | 4G | 6G | 7G | 4G | 7G | 2g | 4G | 0 | |
| POST | 8 | 0 | 9G | 8G | 0 | 3G | 4G | 9G | 4G | 9G | |
| PRE | 8 | 0 | 2G | 4G | 3G | 4G | 4G | 0 | 2G | 0 | |

| TYPE TEST | RATE G/HA | MATRICARDIA INODORA | GALIUM | THISTLE | SHEPARDS-PURSE | KOCHIA | NIGHT-SHADE | SPEED-WELL | BUCK-WHEAT | SUGAR-BEETS |
|---|---|---|---|---|---|---|---|---|---|---|
| | | | | | Compound 2 | | | | | |
| POST | 125 | 6G | 10C | 10C | 9G | 8G | 10C | 0 | 7G | 9G |
| PRE | 125 | 8G | 10C | 0 | 9G | 9G | 8G | 0 | 9G | 10C |
| POST | 64 | 5G | 10C | 10C | 8G | 8G | 8G | 0 | 7G | 9G |
| PRE | 64 | 7G | 9G | 0 | 9G | 6G | 8G | 0 | 9G | 10C |
| POST | 32 | 2G | 7G | 10C | 9G | 5G | 6G | 0 | 0 | 9G |
| PRE | 32 | 7G | 7G | 0 | 9G | 0 | 7G | 0 | 5G | 9G |
| POST | 16 | 0 | 5G | 10C | 9G | 0 | 0 | 0 | 0 | 9G |
| PRE | 16 | 6G | 6G | 0 | 7G | 0 | 5G | 0 | 0 | 5G |
| POST | 8 | 0 | 4G | 7G | 8g | 0 | 0 | 0 | 0 | 3G |
| PRE | 8 | 3G | 4G | 0 | 6G | 0 | 2G | 0 | 0 | 4G |

| TYPE TEST | RATE G/HA | WHEAT | BARLEY | WILDOATS | CHEAT-GRASS | BLACK-GRASS | BLUE-GRASS | FOXTAIL | RYE-GRASS | CIAB-GRASS | RAPE-SEED |
|---|---|---|---|---|---|---|---|---|---|---|---|
| | | | | | Compound 3 | | | | | | |
| POST | 125 | 0 | 0 | 0 | 0 | 5G | 3G | 7G | 0 | 10C | |
| PRE | 125 | 0 | 0 | 0 | 0 | 0 | 0 | 0 | 0 | 0 | |
| POST | 64 | 0 | 0 | 0 | 0 | 4G | 0 | 6G | 0 | 8G | |
| PRE | 64 | 0 | 0 | 0 | 0 | 0 | 0 | 0 | 0 | 0 | |
| POST | 32 | 0 | 0 | 0 | 0 | 0 | 0 | 0 | 0 | 7G | |
| PRE | 32 | 0 | 0 | 0 | 0 | 0 | 0 | 0 | 0 | 0 | |
| POST | 16 | 0 | 0 | 0 | 0 | 0 | 0 | 0 | 0 | 4G | |
| PRE | 16 | 0 | 0 | 0 | 0 | 0 | 0 | 0 | 0 | 0 | |
| POST | 8 | 0 | 0 | 0 | 0 | 0 | 0 | 0 | 0 | 2G | |
| PRE | 8 | 0 | 0 | 0 | 0 | 0 | 0 | 0 | 0 | 0 | |

| TYPE TEST | RATE G/HA | MATRICARDIA INODORA | GALUIM | THISTLE | SHEPARDS-PURSE | KOCHIA | NIGHT-SHADE | SPEED-WELL | BUCK-WHEAT | SUGAR-BEETS |
|---|---|---|---|---|---|---|---|---|---|---|
| | | | | | Compound 3 | | | | | |
| POST | 125 | 5G | 10C | 10C | 7G | 10C | 0 | 0 | 6G | 0 |
| PRE | 125 | 7G | 8G | 4G | 9G | 7G | 8G | 0 | 0 | 4G |
| POST | 64 | 0 | 6G | 9G | 7G | 3G | 0 | 0 | 0 | 0 |
| PRE | 64 | 7G | 2G | 4G | 6G | 7G | 6G | 0 | 0 | 0 |
| POST | 32 | 0 | 4G | 8G | 6G | 0 | 0 | 0 | 0 | 0 |
| PRE | 32 | 6G | 2G | 3G | 4G | 5G | 4G | 0 | 0 | 0 |
| POST | 16 | 0 | 0 | 7G | 6G | 0 | 0 | 0 | 0 | 0 |
| PRE | 16 | 4G | 0 | 0 | 3G | 0 | 0 | 0 | 0 | 0 |
| POST | 8 | 0 | 0 | 3G | 5G | 0 | 0 | 0 | 0 | 0 |
| PRE | 8 | 0 | 0 | 0 | 0 | 0 | 0 | 0 | 0 | 0 |

What is claimed is:

1. A compound of the formula

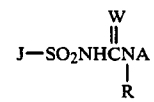

wherein

J is

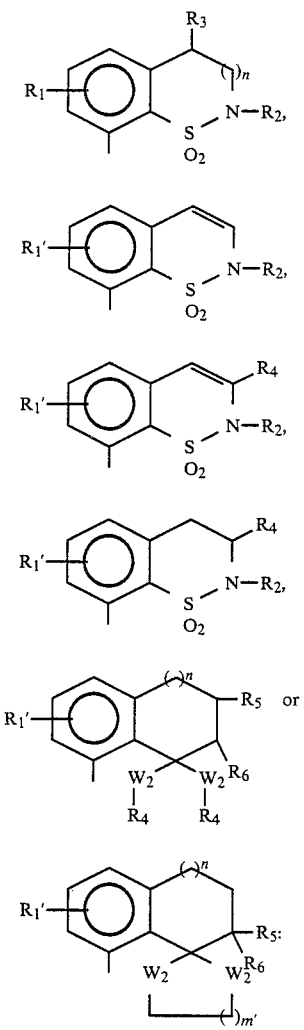

n is 0 or 1;
W is O or S;
$W_2$ is O or S;
R is H or $CH_3$;
$R_1$ is H, $C_1-C_6$ alkyl, $C_1-C_6$ haloalkyl, halogen, nitro, $C_1-C_6$ alkoxy, $SO_2NR_aR_b$, $C_1-C_6$ alkylthio, $C_1-C_6$ alkylsulfinyl, $C_1-C_6$ alkylsulfonyl, CN, $CO_2R_c$, $C_1-C_6$ haloalkoxy, $C_1-C_6$ haloalkylthio, $NH_2$, $C_1-C_6$ alkylamino, di($C_1-C_6$ alkyl)amino, $Si(CH_3)_2(C_1-C_4$ alkyl), $Si(CH_3)_2$-phenyl or $C_1-C_3$ alkyl substituted with $C_1-C_3$ alkoxy, $C_1-C_3$ alkylthio, $C_1-C_3$ alkylsulfinyl, $C_1-C_3$ alkylsulfonyl, $SO_2NR_dR_e$, $NO_2$, CN, $CO_2R_f$, $C_1-C_3$ haloalkoxy or $C_1-C_3$ haloalkylthio;
$R_a$ is H, $C_1-C_4$ alkyl, $C_1-C_3$ cyanoalkyl, methoxy or ethoxy;
$R_b$ is H, $C_1-C_4$ alkyl or $C_3-C_4$ alkenyl; or $R_a$ and $R_b$ may be taken together as $-(CH_2)_3-$, $-(CH_2)_4-$, $-(CH_2)_5-$ or $-CH_2CH_2OCH_2CH_2-$;
$R_c$ is $C_1-C_4$ alkyl, $C_3-C_4$ alkenyl, $C_3-C_4$ alkynyl, $C_2-C_4$ haloalkyl, $C_2-C_3$ cyanoalkyl, $C_5-C_6$ cycloalkyl, $C_4-C_7$ cycloalkylalkyl or $C_2-C_4$ alkoxyalkyl;
$R_d$ is $C_1-C_3$ alkyl;
$R_e$ is H or $C_1-C_3$ alkyl;
$R_f$ is $C_1-C_3$ alkyl;
$R_1'$ is H, $C_1-C_3$ alkyl, $C_1-C_3$ alkoxy, $C_1-C_3$ haloalkoxy, $C_1-C_3$ haloalkyl, $C_1-C_3$ alkylthio, $C_1-C_3$ haloalkylthio, amino, $C_1-C_3$ alkylamino, di($C_1-C_3$ alkyl)amino, halogen or $NO_2$;
$R_2$ is H, $R_{11}$, $SR_{11}'$, $SO_2R_{11}$, $OR_{11}'$; $C(O)R_{11}$, $C(O)OR_{11}'$, $(C(O))_2OR_{11}$, $(CO)_2R_{11}$, $C(O)NR_{12}R_{18}$, $C(O)NRA$, $C(S)SR_{11}'$, $NH_2$, $NR_{12}R_{18}$, OH, CN, $P(O)R_{13}R_{14}$, $P(S)R_{13}R_{14}$, $Si(CH_3)_2R_{15}$, L or C(O)L;
$R_3$ is H or $CH_3$;
$R_4$ is $C_1-C_4$ alkyl;
$R_5$ is H or $C_1-C_4$ alkyl;
$R_6$ is H or $CH_3$;
A is

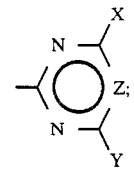

X is H, $C_1-C_4$ alkyl, $C_1-C_4$ alkoxy, $C_1-C_4$ haloalkoxy, $C_1-C_4$ haloalkyl, $C_1-C_4$ haloalkylthio, $C_1-C_4$ alkylthio, F, Cl, Br, $C_2-C_5$ alkoxyalkyl, $C_2-C_5$ alkoxyalkoxy, amino, $C_1-C_3$ alkylamino, amino, di($C_1-C_3$ alkyl)amino or $C_3-C_5$ cycloalkyl;
Y is H, $C_1-C_4$ alkyl, $C_1-C_4$ alkoxy, $C_1-C_4$ haloalkoxy, $C_1-C_4$ haloalkylthio, $C_1-C_4$ alkylthio, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_1-C_4$ haloalkyl, azido, cyano, $$\underset{R_8}{\overset{O}{\underset{\|}{C}}}, -\underset{R_8}{\overset{Q_1R_9}{\underset{|}{C}}}-, -\underset{R_8}{\overset{Q_1}{\underset{|}{C}}}\underset{Q_2}{\overset{(CH_2)_m}{\diagdown}}, -CR_8\underset{Q_2}{\overset{Q_1}{\diagdown}}CH_3$$

or $N(OCH_3)CH_3$;
m is 2 or 3;
$Q_1$ and $Q_2$ are independently O or S;
$R_8$ is H or $C_1-C_3$ alkyl;
$R_9$ and $R_{10}$ are independently $C_1-C_3$ alkyl;
Z is N;
$R_{11}$ is $C_1-C_{10}$ alkyl, $C_3-C_{10}$ alkoxyalkoxyalkyl, $C_2-C_{10}$ alkenyl, $C_4-C_{10}$ alkenylalkenyl, $C_3-C_{10}$ epoxyalkyl, $C_2-C_{10}$ alkynyl, $C_4-C_{10}$ alkynylalkynyl, $C_4-C_{10}$ alkynylalkenyl, $C_3-C_6$ cycloalkyl, $C_4-C_7$ cycloalkylalkyl or

[benzene ring with $R_{16}$ substituent];

when $R_{11}$ is $C_3-C_6$ cycloalkyl or $C_4-C_7$ cycloalkylalkyl it may optionally be substituted by $C_1-C_4$ alkyl, 1 to 3 atoms of Cl or F or 1 Br; when $R_{11}$ is $C_1-C_{10}$ alkyl, $C_2-C_{10}$ alkenyl or $C_2-C_{10}$ alkynyl it may optionally be substituted by one or more halogens and/or by $(R_{17})_{m'}$, where m' is 2, the values of $R_{17}$ may be identical or different;
$R_{11}'$ is $C_1-C_{10}$ alkyl, $C_3-C_{10}$ alkoxyalkoxyalkyl, $C_3-C_{10}$ alkenyl, $C_5-C_{10}$ alkenylalkenyl, $C_3-C_{10}$ epoxyalkyl, $C_3$-$C_{10}$ alkynyl, $C_5$-$C_{10}$ alkynylalkynyl, $C_5$-$C_{10}$ alkynylalkenyl, $C_3$-$C_6$ cycloalkyl, $C_4$-$C_7$ cycloalkylalkyl or

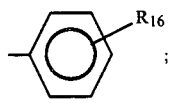

when $R_{11}'$ is $C_3$-$C_6$ cycloalkyl or $C_4$-$C_7$ cycloalkylalkyl it may be optionally substituted by $C_1$-$C_4$ alkyl, 1 to 3 atoms of Cl or F or 1 Br; when $R_{11}'$ is $C_1$-$C_{10}$ alkyl, $C_3$-$C_{10}$ alkenyl or $C_3$-$C_{10}$ alkynyl, it may optionally be substituted by one or more halogens and/or by $(R_{17})_{m'}$, where when m' is 2, the values of $R_{17}$ may be identical or different;

m' is 1 or 2;

$R_{12}$ is H or $C_1$-$C_4$ alkyl;

$R_{13}$ and $R_{14}$ are independently $C_1$-$C_4$ alkyl, $C_1$-$C_4$ alkoxy or $C_1$-$C_4$ alkylthio;

$R_{15}$ is $C_1$-$C_{10}$ alkyl, benzyl or

$R_{16}$ is H, F, Cl, Br, $CH_3$, $OCH_3$, $NO_2$, CN, $SCH_3$, $SO_2CH_3$ or $CF_3$;

$R_{17}$ is $OR_{18}$, $OC(O)R_{18}$, $P^+R_9R_{10}R_{15}$, $P^+(C_6H_5)_3$, $OC(O)NR_{12}R_{18}$, $OSO_2R_{18}'$, $OP(O)R_{13}R_{14}$, $P(O)R_{13}R_{14}$, $OP(S)R_{13}R_{14}$, $P(S)R_{13}R_{14}$, $OSi(CH_3)_2R_{15}$, $Si(CH_3)_2R_{15}$, $SR_{18}$, $SOR_{18}$, $SO_2R_{18}$, SCN, CN, $SP(O)R_{13}R_{14}$, $SP(S)R_{13}R_{14}$, $N^+R_{12}R_{15}R_{18}$, $NR_{12}R_{18}$, $NR_{12}C(O)R_{18}$, $NR_{12}C(O)OR_{18}$, $NR_{12}C(O)NR_{12}R_{18}$, $NR_{12}SO_2R_{18}'$, $NR_{12}P(O)_{13}R_{14}$, $NR_{12}P(S)R_{13}R_{14}$, $NO_2$, $C(O)R_{18}$, $C(O)OR_{18}$, $C(O)NR_{12}R_{18}$, $SeR_{18}$, naphthyl, L,

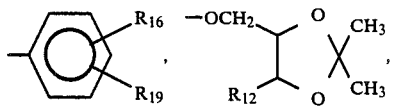

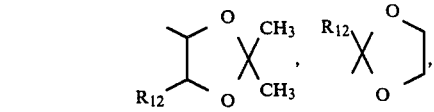

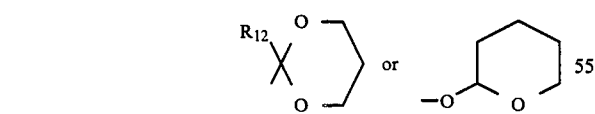

$R_{18}$ is H, $C_1$-$C_{10}$ alkyl, $C_1$-$C_{10}$ haloalkyl, $C_2$-$C_{10}$ alkenyl, $C_2$-$C_{10}$ alkynyl, $C_3$-$C_6$ cycloalkyl or

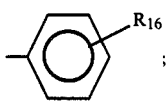

$R_{18}'$ is $C_1$-$C_{10}$ alkyl, $C_1$-$C_{10}$ haloalkyl, $C_3$-$C_{10}$ alkenyl, $C_3$-$C_{10}$ alkynyl, $C_3$-$C_6$ cycloalkyl or

$R_{19}$ is H, F, Cl, Br, $CH_3$,

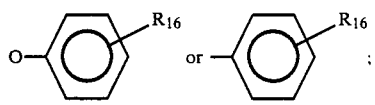

and

L is a pyridinyl, thienyl, furanyl, 4,5-dihydrofuranyl, pyrrolyl, oxazolyl, 4,5-dihydrooxazolyl, thiazolyl, isoxazolyl, oxadiazolyl, pyrazolyl, triazolyl, imidazolyl, 4,5-dihydroimidazolyl, thiadiazolyl, morpholinyl, triazinyl, 1,3-dioxolanyl, tetrahydropyranyl or pyrimidinyl, and these heterocycles may optionally be substituted by 1-4 $CH_3$, 1-2 $OCH_3$, $SCH_3$, Cl, $N(CH_3)_2$ or CN or L is a 5- or 6-membered lactone, lactam or cycloalkanone which may optionally be substituted by 1-4 $C_3$ groups;

provided that (a) when W is S, then R is H, J is $J_1$, $J_2$, $J_3$ or $J_4$; and Y is $CH_3$, $OCH_3$, $OC_2H_5$, $CH_2OCH_3$, $C_2H_5$, $CF_3$, $SCH_3$, $OCH_2CH=CH_2$, $OCH_2\equiv CH$, $OCH_2CF_3$, $OCH_2CH_2OCH_3$, $CH(OCH_3)_2$ or

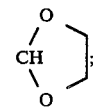

(b) when $R_3$ is $CH_3$, the n is O;

(c) when J is J-1 or J-2 and $R_2$ is H or $C_1$-$C_4$ alkyl, then $R_1$ and $R_1'$ are other than H, F, Cl, Br, $CH_3$, $OCH_3$, $CF_3$, $OCF_2H$, or $SCH_3$ or X is other than $CH_3$, $OCH_3$, $OCH_2CH_3$, F, CL, Br, $OCF_2$ H, $CH_2Cl$, $CH_2Br$, $CH_2F$, cyclopropyl or $CF_3$ or Y is $C_3$-$C_4$ alkyl, $C_3$-$C_4$ alkoxy, $C_4$ haloalkoxy, $C_4$ haloalkylthio, $C_3$-$C_5$ alkoxyalkyl, $C_4$-$C_5$ alkoxyalkoxy, $C_2$-$C_3$ alkylamino, di($C_2$-$C_3$ alkyl)amino, $C_4$ alkenyloxy, $C_4$ alkynyloxy, $C_3$-$C_5$ alkylthioalkyl, $C_2$-$C_4$ haloalkyl, $C_2$-$C_4$ alkynyl, $C(O)R_8$ or $N(OCH_3)CH_3$;

(d) the total number of carbon atoms in $R_2$ does not exceed 13;

(e) when X is $C_3$-$C_5$ cycloalkyl, then Y is $CH_3$, $CH_2CH_3$, $OCH_3$, $OCH_2CH_3$, $CH_2OCH_3OCF_2H$, $SCF_2H$, $OCH_2CF_3$, $CF_3$, $OCH_2CH=CH_2$, $OCH_2C\equiv CH$, $NHCH_3$, $N(CH_3)_2$ or $CH(OCH_3)_2$;

(f) when $R_1$ or $R_1'$ is para to the sulfonylurea bridge then $R_1$ or $R_1'$ are H, $CH_3$, F, Cl, Br or $OCH_3$; and (g) when X or Y is $OCH_2CH_2F$ or $OCH_2CHF_2$ then $R_2$ is other than $C_5$ alkyl, $CH_3OCH_2CH_2$, $C_2H_5OCH_2CH_2$ or $C_1$-$C_4$ alkyl substituted with 1-3 atoms of F, Cl or Br;

(h) when X or Y is $OCH_2CH_2F$, $OCH_2CHF_2$ or $OCH_2CF_3$, then the other is not di($C_1$-$C_3$ alkyl)amino $C_1$-$C_3$ alkylamino or $N(OCH_3)CH_3$;

(i) X or Y is not $OCF_2H$; and (j) when $R_{17}$ and the bridging nitrogen of a cyclic sulfonamide are attached to the same carbon, then $R_{17}$ is other than OH, SH, $OC(O)R_{18}$, OC- (O)NR$_{12}$R$_{18}$, OSO$_2$R$_{18}'$, OP(O)R$_{13}$R$_{14}$, OSi(CH$_3$)$_2$R$_{15}$, SP(O)R$_{13}$R$_{14}$, SP(S)R$_{13}$R$_{14}$, NR$_{12}$R$_{18}$ or N$^+$R$_{12}$R$_{15}$R$_{18}$;

and their agriculturally suitable salts.

2. Compounds of claim 1 wherein J is J-1 or J-4.
3. Compounds of claim 1 wherein J is J-2 or J-3.
4. Compounds of claim 1 wherein J is J-11 or J-12.
5. Compounds of claim 2 wherein W is O;

R is H;

X is CH$_3$, OCH$_3$, OCH$_2$CH$_3$, CH$_2$F, CF$_3$ or cyclopropyl;

Y is H, CH$_3$, OCH$_3$, OC$_2$H$_5$, CH$_2$OCH$_3$, NH$_2$, NHCH$_3$, N(OCH$_3$)CH$_3$, N(CH$_3$)$_2$, C$_2$H$_5$, CF$_3$, SCH$_3$, OCH$_2$CH=CH$_2$, OCH$_2$C≡CH, OCH$_2$CF$_3$, CN, N$_3$, OCH$_2$CH$_2$OCH$_3$, CH$_2$SCH$_3$,

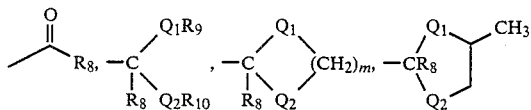

or N(OCH$_3$)CH$_3$.

6. Compounds of claim 5 wherein

R$_1$ is hydrogen, chlorine C$_1$-C$_3$ alkyl, C$_1$-C$_3$ alkoxy, C$_1$-C$_3$ haloalkoxy, C$_1$-C$_3$ haloalkyl, C$_1$-C$_3$ alkylthio, C$_1$-C$_3$ haloalkylthio, amino, C$_1$-C$_3$ alkylsulfinyl, C$_1$-C$_3$ alkylsulfonyl, CN, NH$_2$, C$_1$-C$_3$ alkylamino, di(C$_1$-C$_3$ alkylamino) or C$_1$-C$_2$ alkyl substituted with C$_1$-C$_2$ alkoxy, C$_1$-C$_2$ alkylthio, C$_1$-C$_2$ haloalkoxy, C$_1$-C$_2$ haloalkylthio, CN or NO$_2$.

7. Compounds of claim 6 wherein

R$_2$ is C$_1$-C$_6$ alkyl, C$_1$-C$_6$ alkylcarbonyl, C$_1$-C$_6$ alkoxycarbonyl, C$_1$-C$_6$ alkyl substituted by 1–3 atoms of F, Cl or 1 Br, or by 1 or 2 groups selected from C$_1$-C$_2$ alkoxy, CN, C$_1$-C$_2$ alkoxycarbonyl, C$_1$-C$_2$ alkylcarbonyl, OH, C$_1$-C$_2$ alkylthio C$_1$-C$_2$ alkylsulfonyl, C$_1$-C$_2$ alkylsulfonyloxy or C$_1$-C$_2$ alkylcarbonyloxy, C$_3$-C$_4$ alkenyl, C$_3$-C$_4$ haloalkenyl, C$_3$-C$_4$ alkynyl, C$_4$ alkynyl substituted by 1 atom of F or Cl, phenyl or phenyl substituted with Cl, CF$_3$, NO$_2$, CN or SO$_2$CH$_3$; and R$_4$ is CH$_3$.

8. Compounds of claim 7 wherein

Y is CH$_3$, C$_2$H$_5$, OCH$_3$, CH$_2$OCH$_3$ or CH(OCH$_3$)$_2$.

9. Compounds of claim 8 wherein R$_1$ and R$_1'$ are H, Cl, C$_1$-C$_2$ alkyl, C$_1$-C$_2$ alkoxy or C$_1$-C$_2$ alkylthio.

10. Compounds of claim 9 wherein J is J-1.

11. Compounds of claim 10 wherein

R$_1$ is H; and

R$_2$ is C$_1$-C$_3$ alkylcarbonyl or C$_1$-C$_3$ alkoxycarbonyl.

12. Compounds of claim 3 wherein

W is O;

R$_1$ is H;

X is CH$_3$, OCH$_3$, OCH$_2$CH$_3$, CH$_2$F, CF$_3$ or cyclopropyl;

Y is H, CH$_3$, OCH$_3$, OC$_2$H$_5$, CH$_2$OCH$_3$, NH$_2$, NHCH$_3$, N(OCH$_3$)CH$_3$, N(CH$_3$)$_2$, C$_2$H$_5$, CF$_3$, SCH$_3$, OCH$_2$CH=CH$_2$, OCH$_2$C≡CH, OCH$_2$CF$_3$, CN, N$_3$, OCH$_2$CH$_2$OCH$_3$, CH$_2$SCH$_3$,

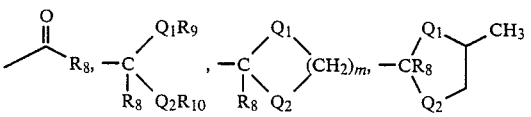

or;

R$_2$ is C$_1$-C$_6$ alkyl, C$_1$-C$_6$ alkylcarbonyl, C$_1$-C$_6$ alkoxycarbonyl, C$_1$-C$_6$ alkyl substituted by 1–3 atoms of F, Cl or 1 Br, or by 1 or 2 groups selected from C$_1$-C$_2$ alkoxy, CN, C$_1$-C$_2$ alkoxycarbonyl, C$_1$-C$_2$ alkylcarbonyl, OH, C$_1$-C$_2$ alkylthio C$_1$-C$_2$ alkylsulfonyl, C$_1$-C$_2$ alkylsulfonyloxy or C$_1$-C$_2$ alkylcarbonyloxy, C$_3$-C$_4$ alkenyl, C$_3$-C$_4$ haloalkenyl, C$_3$-C$_4$ alkynyl, C$_4$ alkynyl substituted by 1 atom of F or Cl, phenyl or phenyl substituted with Cl, CF$_3$, NO$_2$, CN or SO$_2$CH$_3$;

R$_1'$ is H, Cl, C$_1$-C$_2$ alkyl, C$_1$-C$_2$ alkoxy or C$_1$-C$_2$ alkylthio.

13. Compounds of claim 12 wherein

Y is CH$_3$, C$_2$H$_5$, OCH$_3$, CH$_2$OCH$_3$ or CH(OCH$_3$)$_2$.

14. Compounds of claim 4 wherein

W is O;

R$_1$ is H;

R$_1'$ is H;

A is A-1;

X is CH$_3$, OCH$_3$, OCH$_2$CH$_3$, CH$_2$F or cyclopropyl; and

Y is CH$_3$, C$_2$H$_5$, OCH$_3$, CH$_2$OCH$_3$ or CH(OCH$_3$)$_2$.

15. The compound of claim 1 which is 2,3-dihydro-N-[(4-methoxy-6-methyl-1,3,5-triazin-2-yl)aminocarbonyl]-2-(2-fluoroethyl)-1,2benzisothiazole-7-sulfonamide, 1,1-dioxide.

16. A composition suitable for controlling the growth of undesired vegetation which comprises an effective amount of a compound of claim 1 and at least one of the following: surfactant, solid or liquid diluent.

17. A composition suitable for controlling the growth of undesired vegetation which comprises an effective amount of a compound of claim 2 and at least one of the following: surfactant, solid or liquid diluent.

18. A composition suitable for controlling the growth of undesired vegetation which comprises an effective amount of a compound of claim 3 and at least one of the following: surfactant, solid or liquid diluent.

19. A composition suitable for controlling the growth of undesired vegetation which comprises an effective amount of a compound of claim 4 and at least one of the following: surfactant, solid or liquid diluent.

20. A composition suitable for controlling the growth of undesired vegetation which comprises an effective amount of a compound of claim 5 and at least one of the following: surfactant, solid or liquid diluent.

21. A composition suitable for controlling the growth of undesired vegetation which comprises an effective amount of a compound of claim 6 and at least one of the following: surfactant, solid or liquid diluent.

22. A composition suitable for controlling the growth of undesired vegetation which comprises an effective amount of a compound of claim 7 and at least one of the following: surfactant, solid or liquid diluent.

23. A composition suitable for controlling the growth of undesired vegetation which comprises an effective amount of a compound of claim 8 and at least one of the following: surfactant, solid or liquid diluent.

24. A composition suitable for controlling the growth of undesired vegetation which comprises an effective amount of a compound of claim 9 and at least one of the following: surfactant, solid or liquid diluent.

25. A composition suitable for controlling the growth of undesired vegetation which comprises an effective amount of a compound of claim 10 and at least one of the following: surfactant, solid or liquid diluent.

26. A method for controlling the growth of undesired vegetation which comprises applying to the locus to be protected an effective amount of a compound of claim 1.

27. A method for controlling the growth of undesired vegetation which comprises applying to the locus to be protected an effective amount of a compound of claim 2.

28. A method for controlling the growth of undesired vegetation which comprises applying to the locus to be protected an effective amount of a compound of claim 3.

29. A method for controlling the growth of undesired vegetation which comprises applying to the locus to be protected an effective amount of a compound of claim 4.

30. A method for controlling the growth of undesired vegetation which comprises applying to the locus to be protected an effective amount of a compound of claim 5.

31. A method for controlling the growth of undesired vegetation which comprises applying to the locus to be protected an effective amount of a compound of claim 6.

32. A method for controlling the growth of undesired vegetation which comprises applying to the locus to be protected an effective amount of a compound of claim 7.

33. A method for controlling the growth of undesired vegetation which comprises applying to the locus to be protected an effective amount of a compound of claim 8.

34. A method for controlling the growth of undesired vegetation which comprises applying to the locus to be protected an effective amount of a compound of claim 9.

35. A method for controlling the growth of undesired vegetation which comprises applying to the locus to be protected an effective amount of a compound of claim 10.

* * * * *

UNITED STATES PATENT AND TRADEMARK OFFICE
CERTIFICATE OF CORRECTION

PATENT NO. : 4,842,639

DATED : June 27, 1989

INVENTOR(S) : Robert James Pasteris

It is certified that error appears in the above-identified patent and that said Letters Patent is hereby corrected as shown below:

Column 205, lines 28-34, " 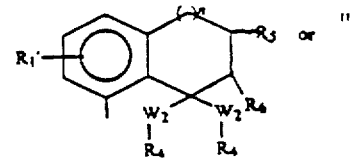 or "

should read -- 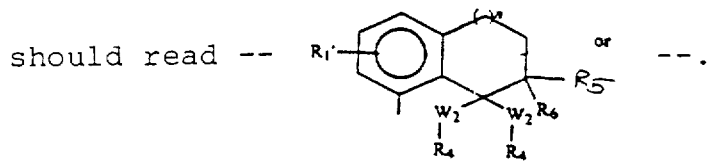 --.

Column 206, line 6, "$R_2$ is H, $R_{11}$," should read --$R_2$ is H, $R'_{11}$,--;

line 7 "$(C(O))_2OR_{11}$, $(CO)_2R_{11}$," should read --$(C(O))_2OR'_{11}$, $(CO)_2R'_{11}$,--.

line 27, "thio, F, Cl, Br, $C_2$-$C_5$ alkoxyalkyl, $C_2$-$C_5$ alkox-" should read --thio, $C_2$-$C_5$ alkoxyalkyl, $C_2$-$C_5$ alkox- --.

UNITED STATES PATENT AND TRADEMARK OFFICE
CERTIFICATE OF CORRECTION

PATENT NO. : 4,842,639

DATED : June 27, 1989

INVENTOR(S) : Robert James Pasteris

It is certified that error appears in the above-identified patent and that said Letters Patent is hereby corrected as shown below:

Column 207, line 34, "$SOR_{18}$," should read --$SOR'_{18}$,--.

line 35, "$SO_2R_{18}$," should read --$SO_2R'_{18}$,--.

line 36, "$N+R_{12}R_{15}R_{18}$," should read --$N+R_{12}R_{15}R'_{18}$,--.

Column 208, line 25, "1-4 $C_3$ groups;" should read --1-4 $CH_3$ groups;--.

line 42, "$CH_3$, $OCH_3$, $OCH_2CH_3$, F, CL, Br, $OCF_2H$," should read --$CH_3$, $OCH_3$, $OCH_2CH_3$,--.

line 53, "$CH_2CH_3$, $OCH_3$, $OCH_2CH_3$, $CH_2OCH_3OCF_2H$," should read --$CH_2CH_3$, $OCH_3$, $OCH_2CH_3$, $CH_2OCH_3$,--.

line 65, "X or Y" should read --X and/or Y--.

UNITED STATES PATENT AND TRADEMARK OFFICE
CERTIFICATE OF CORRECTION

PATENT NO. : 4,842,639

DATED : June 27, 1989

INVENTOR(S) : Robert James Pasteris

It is certified that error appears in the above-identified patent and that said Letters Patent is hereby corrected as shown below:

Column 209, line 26, "$R_1$ is hydrogen, chlorine $C_1$-$C_3$ alkyl, $C_1$-$C_3$ alkoxy," should read --$R_1$ is hydrogen, chlorine, $C_1$-$C_3$ alkyl, $C_1$-$C_3$ alkoxy,--.

Signed and Sealed this

Fourteenth Day of July, 1992

Attest:

DOUGLAS B. COMER

Attesting Officer

Acting Commissioner of Patents and Trademarks